US012344606B2

(12) United States Patent
Zawadzka et al.

(10) Patent No.: US 12,344,606 B2
(45) Date of Patent: Jul. 1, 2025

(54) NEXT-GENERATION MODULATORS OF STIMULATOR OF INTERFERON GENES (STING)

(71) Applicant: RYVU THERAPEUTICS S.A., Cracow (PL)

(72) Inventors: Magdalena Izabela Zawadzka, Gdansk (PL); Luigi Piero Stasi, Cracow (PL); Maciej Krzysztof Rogacki, Cracow (PL); Grzegorz Wojciech Cwiertnia, Kamesznica (PL); Lukasz Piotr Dudek, Cracow (PL); Monika Patrycja Dobrzanska, Wroclaw (PL); Grzegorz Witold Topolnicki, Piekary Slaskie (PL); Agnieszka Justyna Gibas, Cracow (PL); Anna Rajda, Gliwice (PL); Sylwia Sudol, Cracow (PL); Karolina Maria Gluza, Wroclaw (PL); Charles-Henry Fabritius, Poznan (PL)

(73) Assignee: Ryvu Therapeutics S.A., Cracow (PL)

(*) Notice: Subject to any disclaimer, the term of this patent is extended or adjusted under 35 U.S.C. 154(b) by 708 days.

(21) Appl. No.: 17/618,007

(22) PCT Filed: Jun. 12, 2020

(86) PCT No.: PCT/EP2020/066370
§ 371 (c)(1),
(2) Date: Dec. 10, 2021

(87) PCT Pub. No.: WO2020/249773
PCT Pub. Date: Dec. 17, 2020

(65) Prior Publication Data
US 2022/0251082 A1    Aug. 11, 2022

(30) Foreign Application Priority Data

Jun. 12, 2019 (EP) .................................... 19460034
Dec. 11, 2019 (EP) .................................... 19460067

(51) Int. Cl.
| *C07D 471/04* | (2006.01) |
| *A61P 35/00* | (2006.01) |
| *C07D 401/14* | (2006.01) |
| *C07D 405/14* | (2006.01) |
| *C07D 413/14* | (2006.01) |
| *C07D 417/14* | (2006.01) |

(52) U.S. Cl.
CPC ............ *C07D 471/04* (2013.01); *A61P 35/00* (2018.01); *C07D 401/14* (2013.01); *C07D 405/14* (2013.01); *C07D 413/14* (2013.01); *C07D 417/14* (2013.01)

(58) Field of Classification Search
CPC .. C07D 471/04; C07D 401/14; C07D 405/14; C07D 413/14; C07D 417/14; A61P 35/00
See application file for complete search history.

(56) References Cited

U.S. PATENT DOCUMENTS

| 3,410,851 A | 11/1968 | Stauffer |
| 2008/0139558 A1 | 6/2008 | Smith et al. |
| 2011/0212946 A1 | 9/2011 | Barrow et al. |
| 2022/0402898 A1* | 12/2022 | Dobrzanska ......... C07D 473/00 |
| 2023/0055741 A1* | 2/2023 | Zawadzka ............ C07D 471/04 |
| 2023/0076506 A1* | 3/2023 | Zawadzka ............... A61P 37/08 |

FOREIGN PATENT DOCUMENTS

| GB | 2563642 A | 12/2018 |
| WO | WO-2004042083 A2 | 5/2004 |
| WO | WO-2007128568 A1 | 11/2007 |
| WO | WO-2019023635 A1 | 1/2019 |
| WO | WO-2019182886 A1 | 9/2019 |
| WO | WO-2019238786 A1 | 12/2019 |

OTHER PUBLICATIONS

Wang, T.; et al. "Salts, Cocrystals, and Ionic Cocrystals of a "Simple" Tautomeric Compound" 2018, Crystal Growth and Design, vol. 18, pp. 6973-6983. (Year: 2018).*
An, X.; et al. "An Analysis of the Expression and Association with Immune Cell Infiltration of the cGAS/STING Pathway in Pan-Cancer" 2019, Molecular Therapy: Nucleic Acids, vol. 14, pp. 80-89 (published with Mar. 2019 issue). (Year: 2019).*
Bakhoum, S. F.; et al. "Chromosomal instability drives metastasis through a cytosolic DNA response" 2018, Nature, vol. 553, pp. 467-472. (Year: 2018).*
Aguzzi, A.; et al. "The immunobiology of prion diseases" 2013, Nature Reviews Immunology, vol. 13, p. 888-902. (Year: 2011).*
Guo, F.; et al. "STING Agonists Induce an Innate Antiviral Immune Response against Hepatitis B Virus" 2015, Antimicrobial Agents and Chemotherapy, vol. 59, pp. 1273-1281. (Year: 2015).*

(Continued)

*Primary Examiner* — Eric Olson
*Assistant Examiner* — Benjamin M Brandsen
(74) *Attorney, Agent, or Firm* — Knobbe, Martens, Olson & Bear, LLP

(57) ABSTRACT

The present invention relates to compounds of formula (I) and salts, stereoisomers, tautomers or N-oxides thereof that are useful as modulators of STING (Stimulator of Interferon Genes). The present invention further relates to the compounds of formula (I) for use as a medicament and to a pharmaceutical composition comprising said compounds.

11 Claims, 4 Drawing Sheets

(56) References Cited

OTHER PUBLICATIONS

Madhun, A. S.; et al. "Intranasal c-di-GMP-adjuvanted plant-derived HS influenza vaccine induces multifunctional Th1 CD4+ cells and strong mucosal and systemic antibody responses in mice" 2011, Vaccine, vol. 29, pp. 4973-4982. (Year: 2011).*

Zhang, Z.; et al. "Peptide nanotube loaded with a STING agonist, c-di-GMP, enhance cancer immunotherapy against melanoma" 2023, Nano Research, vol. 16, pp. 5206-5215. (Year: 2023).*

Demaria, O.; et al. "STING activation of tumor endothelial cells initiates spontaneous and therapeutic antitumor immunity" 2015, Proceedings of the National Academy of Sciences, vol. 112, pp. 15408-15413. (Year: 2015).*

Aguirre, S., et al., "DENV Inhibits Type I IFN Production in Infected Cells by Cleaving Human STING," PloS Pathog, 8(10):e1002934, Plos, United States (2012).

Chen, X., et al., "SARS coronavirus papain-like protease inhibits the type I interferon signaling pathway through interaction with the STING-TRAF3-TBK1 complex," Protein Cell 5(5):369-381, Oxford University Press , United Kingdom (2014).

Cirulli, E., et al., "Exome sequencing in amyotrophic lateral sclerosis identifies risk genes and pathways," Science 347(6229):1436-1441, American Association for the Advancement of Science, United States (2015).

Collins, A.C., et al., "Cyclic GMP-AMP Synthase Is an Innate Immune DNA Sensor for *Mycobacterium tuberculosis*," Cell Host Microbe 17(6):820-828, Cell Press, United States (2015).

Corrales, L., and Gajewski, T.F., "Molecular Pathways: Targeting the Stimulator of Interferon Genes (STING) in the Immunotherapy of Cancer," Clin. Cancer Res. 21(21):4774-4779, American Association for Cancer Research, United States (Nov. 2015).

Corrales, L., et al., "Direct Activation of STING in the Tumor Microenvironment Leads to Potent and Systemic Tumor Regression and Immunity," Cell Rep. 11(7):1018-1030, Cell Press, United States (May 2015).

Corrales, L., et al., "Extremely potent immunotherapeutic activity of a STING agonist in the B16 melanoma model in vivo," J. Immunother. Cancer 2013, 1 (Suppl 1):O15, BMJ Publishing Group Ltd, United Kingdom (2013).

Crow, Y.J., et al., "Mutations in the gene encoding the 3'-5' DNA exonuclease TREX1 cause Aicardi-Goutières syndrome at the AGS1 locus," Nat. Genet. 38(8):917-920, Springer, Germany (2006).

Ding, Q., et al., "Hepatitis C virus NS4B blocks the interaction of STING and TBK1 to evade host innate immunity," J. Hepatol. 59(1):52-58, Elsevier, Netherlands (2013).

Dubensky, T.W., et al., "Rationale, progress and development of vaccines utilizing STING-activating cyclic dinucleotide adjuvants," Ther. Adv. Vaccines 1(4):131-143, Sage Publications, United States (2013).

Freischmidt, A., et al., "Haploinsufficiency of TBK1 causes familial ALS and fronto-temporal dementia," Nat. Neurosci. 18(5):631-636, Springer, Germany (2015).

Fu, J., et al., "STING agonist formulated cancer vaccines can cure established tumors resistant to PD-1 blockade," Sci. Transl. Med. 7(283):283ra52, American Association for the Advancement of Science, United States (2015).

Gao, D., et al., "Cyclic GMP-AMP synthase is an innate immune sensor of HIV and other retroviruses," Science 341(6148):903-906, American Association for the Advancement of Science, United States (2013).

Gao, P., et al., "Cyclic [G(2',5')pA(3',5')p] is the metazoan second messenger produced by DNA-activated cyclic GMP-AMP synthase," Cell 153:1094-1107, Cell Press, United States (2013).

Herzner, A.-M., et al., "Sequence-specific activation of the DNA sensor cGAS by Y-form DNA structures as found in primary HIV-1 cDNA," Nat. Immunol. 16(10):1025-1033, Springer, Germany (2015).

Holm, C., et al., "Influenza A virus targets a cGAS-independent STING pathway that controls enveloped RNA viruses," Nat Comm. 7:10680, Springer, Netherlands (2016).

Huber, J.P., et al., "Cutting Edge: Type I IFN Reverses Human Th2 Commitment and Stability by Suppressing GATA3," J. Immunol. 185:813-817, American Association of Immunologists, United States (2010).

International Search Report and Written Opinion for International Application No. PCT/EP2020/066370, European Patent Office, Netherlands, mailed on Aug. 28, 2020, 8 pages.

Ishikawa, H., and Barber, G.N., "STING is an endoplasmic reticulum adaptor that facilitates innate immune signaling," Nature 455:674-678, Springer, Netherlands (2008).

Ishikawa, H., et al., "STING regulates intracellular DNA-mediated, type I interferon-dependent innate immunity," Nature 461(7265):788-792, Springer, Netherlands (2009).

Jin, L., et al., "MPYS Is Required for IFN Response Factor 3 Activation and Type I IFN Production in the Response of Cultured Phagocytes to Bacterial Second Messengers Cyclic-di-AMP and Cyclic-di-GMP," J. Immunol. 187(5):2595-2601, American Association of Immunologists, United States (2011).

Lau, L., et al., "DNA tumor virus oncogenes antagonize the cGAS-STING DNA-sensing pathway," Science 350(6260):568-571, American Association for the Advancement of Science, Untied States (2015).

Lemos, H., et al., "Activation of the Stimulator of Interferon Genes (STING) Adaptor Attenuates Experimental Autoimmune Encephalitis," J. Immunol. 192(12):5571-5578, American Association of Immunologists, United States (2014).

Liu, Y., et al., "RIG-I-Mediated STING Upregulation Restricts Herpes Simplex Virus 1 Infection," J. Virol. 90(20):9406-9419, American Society for Microbiology, United States (2016).

Ma, Z., and Damania, B., "The cGAS-STING Defense Pathway and Its Counteraction by Viruses," Cell Host & Microbe 19(2):150-158, Cell Press, United States (2016).

Ma, Z., et al., "Modulation of the cGAS-STING DNA sensing pathway by gammaherpesviruses," PNAS 112(31):E4306-E4315, National Academy of Sciences, Untied States (2015).

McNab, F., et al., "Type I interferons in infectious disease," Nat. Rev. Immunol. 15(2):87-103, Springer, Germany (2015).

Moisan, J., et al., "TLR7 ligand prevents allergen-induced airway hyperresponsiveness and eosinophilia in allergic asthma by a MYD88-dependent and MK2-independent pathway," Am. J. Physiol. Lung Cell Mol. Physiol. 290:L987-L995, American Physiological Society, United States (2005).

Nitta, S., et al., "Hepatitis C virus NS4B protein targets STING and abrogates RIG-I-mediated type I interferon-dependent innate immunity," Hepatology 57(1):46-58, Wiley, United States (2013).

Persing, D.H., et al., "Taking toll: lipid A mimetics as adjuvants and immunomodulators," Trends Microbiol. 10(10 Suppl):S32-S37, Elsevier, Netherlands (2002).

Prantner, D., et al., "Stimulator of IFN gene is critical for induction of IFN-β during *Chlamydia muridarum* infection," J. Immunol. 184(5):2551-2560, American Association of Immunologists, United States (2010).

Rakoff-Nahoum, S., et al., "Recognition of commensal microflora by toll-like receptors is required for intestinal homeostasis," Cell 118(2):229-241, Cell Press, United States (2004).

Sharma, S., et al., "Innate immune recognition of an AT-rich stem-loop DNA motif in the *Plasmodium falciparum* genome," Immunity 35(2):194-207, Cell Press, United States (2011).

Stetson, D.B., et al., "Trex1 prevents cell-intrinsic initiation of autoimmunity," Cell 134(4):587-598, Cell Press, United States (2008).

Storek, K.M., et al., "cGAS and Ifi204 Cooperate To Produce Type I IFNs in Response to *Francisella* Infection," J. Immunol. 194(7):3236-3245, American Association of Immunologists, United States (2015).

Sun, L., et al., "Coronavirus Papain-like Proteases Negatively Regulate Antiviral Innate Immune Response through Disruption of STING-Mediated Signaling," PloS One 7(2): e30802, PLOS, United States (2012).

Sun, L., et al., "Cyclic GMP-AMP synthase is a cytosolic DNA sensor that activates the type I interferon pathway," Science 339:786-791, American Association for the Advancement of Science, United States (2013).

(56) References Cited

OTHER PUBLICATIONS

Wasserman, R., et al., "*Mycobacterium tuberculosis* Differentially Activates cGAS- and Inflammasome-Dependent Intracellular Immune Responses through ESX-1," Cell Host Microbe 17(6):799-810, Cell Press, United States (2015).

Watson, R.O., et al., "The Cytosolic Sensor cGAS Detects *Mycobacterium tuberculosis* DNA to Induce Type I Interferons and Activate Autophagy," Cell Host Microbe 17(6):811-819, Cell Press, United States (2015).

Woo, S.-R., et al., "The STING pathway and the T cell-inflamed tumor microenvironment," Trends Immunol. 36(4):250-256, Elsevier, Netherlands (2015).

Wu, J., et al., "Inhibition of cGAS DNA Sensing by a Herpesvirus Virion Protein," Cell Host Microbe 18(3):333-344, Cell Press, United States (2015).

Zitvogel, L., et al., "Type I interferons in anticancer immunity," Nature Reviews Immunology 15(7):405-414, Springer, Germany (2015).

Abdel-Aal, M.A.A., et al., "Towards anticancer fluoroquinolones: A review article," Arch Pharm Chem Life Sci. 352(7):e1800376, Deutsche Pharmazeutische Gesellschaft, Germany (Jun. 2019), 19 pages.

Bargh, J.D., et al., "Cleavable linkers in antibody-drug conjugates," Chem. Soc. Rev. 10.1039/c8cs00676h, Royal Society of Chemistry, United Kingdom, (Jul. 2019), 14 pages.

Beck, A., et al., "Strategies and challenges for the next generation of antibody-drug conjugates," Nature Reviews Drug Discovery 16(5):315-337, Springer Nature, Germany (May 2017).

Database Registry [online], Chemical Abstracts Service, Database Accession No. 1011381-60-4, Columbus, Ohio, United States (Apr. 1, 2008), 11 pages, assessed Aug. 7, 2018.

Database Registry [online], Chemical Abstracts Service, Database Accession No. 1244927-19-2, Columbus, Ohio, United States (Oct. 3, 2010), 3 pages, assessed Aug. 7, 2018.

File Registry on STN, Document No. 70:77793 (1969), 2 pages.

Misra, P.S., et al., "Synthesis of 2-phenyl benzimidazole derivatives and their Schiff bases as possible antimicrobial agents," Rasayan J. Chem. 3(1):51-54, Rasayan Journal of Chemistry, India (Mar. 2010).

Mousavizadeh, A., et al., "Cell targeting peptides as smart ligands for targeting of therapeutic or diagnostic agents: a systematic review," Colloids Surfaces B. 158:507-517, Elsevier, Netherlands (Oct. 2017).

Orava, E.W., et al., "Delivering cargoes into cancer cells using DNA aptamers targeting internalized surface portals," Biochimica Biophys. Acta 1798:2190-2200, Elsevier, Netherlands (Dec. 2010).

Pedley, R.B., et al., "The potential for enhanced tumour localisation by poly(ethylene glycol) modification of anti-CEA antibody," Br. J. Cancer 70:1126-1130, Macmillan Press Ltd, Great Britain (Dec. 1994).

Polakis, P., "Antibody Drug Conjugates for Cancer Therapy," Pharmacol. Revs. 68(1):3-19, American Society for Pharmacology and Experimental Therapeutics, United States (Jan. 2016).

Todorov, A.R., et al., "Tautomeric Switching and Metal-Cation Sensing of Ligand-Equipped 4-Hydroxy-/4-oxo-1,4-dihydroquinolines," Chemistry: A European Journal 18(23):7269-7277, Wiley-VCH, Germany (Jun. 2012).

Turner, A., et al., "Comparative biodistributions of indium-111-labelled macrocycle chimeric B72.3 antibody conjugates in tumour-bearing mice," Br. J. Cancer 70:35-41, Macmillan Press Ltd, Great Britain (Jul. 1994).

Zhang, B., et al., "Molecular Design, Synthesis and Biological Research of Novel Pyridyl Acridones as Potent DNA-binding and Apoptosis-inducing Agents," European Journal of Medicinal Chemistry 93:214-226, Elsevier Masson SAS, France (Mar. 2015).

\* cited by examiner

Vehicle

Example 1, 2 mg/kg iv, E5Dx3

Figure 1(iii)
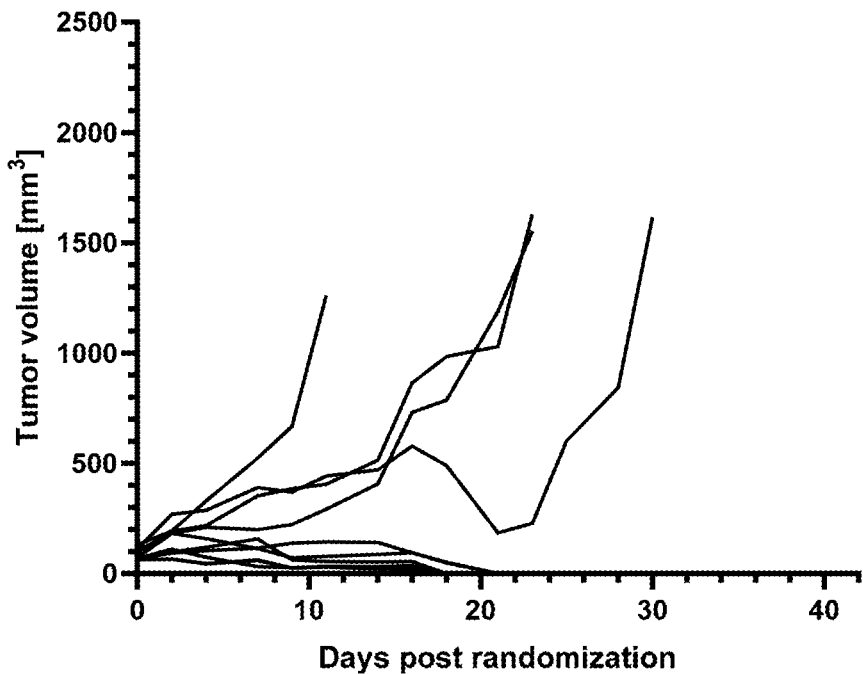

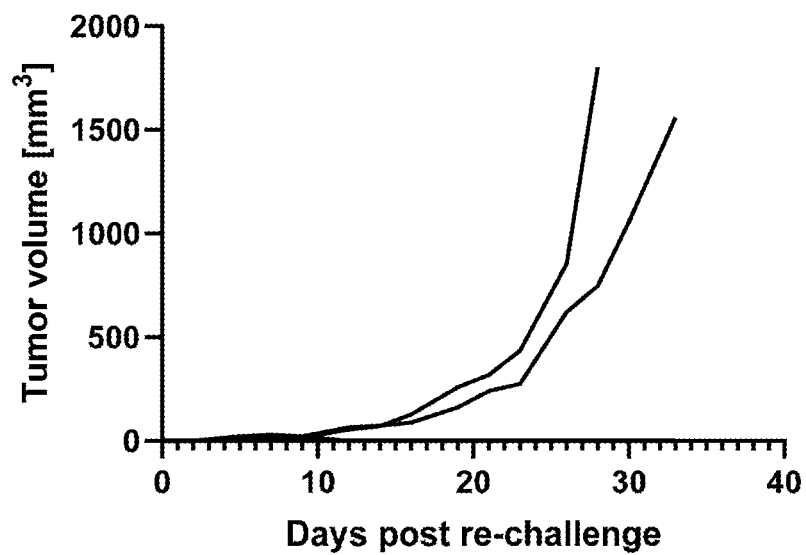
Figure 3(iii)

NEXT-GENERATION MODULATORS OF STIMULATOR OF INTERFERON GENES (STING)

FIELD OF THE INVENTION

The present invention relates to compounds of formula (I) and salts, stereoisomers, tautomers or N-oxides thereof that are useful as modulators of STING (Stimulator of Interferon Genes). The present invention further relates to the compounds of formula (I) for use as a medicament and to a pharmaceutical composition comprising said compounds.

BACKGROUND OF THE INVENTION

The cellular innate immune system is essential for recognizing pathogen infection and for establishing effective host defense. The adaptor protein STING (Stimulator of Interferon Genes), also known as TMEM 173, MPYS, MITA and ERIS, has been identified as a central signaling molecule in the innate immune response to cytosolic nucleic acids (H. Ishikawa, G. N. Barber, Nature, 2008, vol. 455, pp. 674-678). STING inter alia induces type I interferon (IFN) production when cells are infected with intracellular pathogens, such as viruses, mycobacteria and intracellular parasites.

Activation of STING promotes IRF3 and NFκB-dependent signaling leading in consequence to production of proinflammatory cytokines and interferons, including type I and type III interferons and TNF α of particular importance in cancer immunotherapy. STING is responsible for sensing of cytoplasmic nucleic acids and their derivatives called cyclic dinucleotides (CDN), both of pathogen or host origin (e.g. double stranded DNA from bacteria or viruses and cytoplasmic self-DNA).

Endogenous STING direct agonist 2',3'-cGAMP (2',3'-cyclic guanosine monophosphate-adenosine monophosphate) is produced in mammalian cells by enzyme cGAS (cyclic GMP-AMP synthase, MB21D1 or C6orfl50) (P. Gao et al., Cell, 2013, 153, pp. 1094-1107, Wu et al. Science, 2013, 339, pp. 786-791) and has proven activity in modulating STING-dependent pathway, together with its derivatives (L. Corrales et al., J Immunother Cancer, 2013, 1(Suppl 1): O15, L. Corrales et al., Cell Rep., 2015, May 19; 11(7), pp. 1018-30, S-R. Woo et al., Trends Immunol., 2015, 36 (4), 250, J. Fu et al., Sci. Trans. Med., Vol. 7, Issue 283, pp. 283ra52).

Recent evidence supports findings that once STING is activated by CDN within tumor microenvironment, preferably in tumor-resident dendritic cells, it promotes type I IFN and TNFα release which results in immunity-mediated anti-tumor response. STING-dependent activation of antigen-presenting cells (APC) efficiently drives highly specific T-cell priming against neoantigens (L. Corrales and T F. Gajewski, Clin Cancer Res, 2015, 21 (21), pp. 4774-9). STING activation not only provides generation of tumor-specific killer T cells, which directly eradicate tumors, but also results in vaccine-like long-lasting immunity protecting from cancer recurrence.

Thus, synthetic STING agonists are of special interest as potential anticancer agents. The activation or inhibition of type I interferon production is an important strategy for the treatment or prevention of human diseases including viral infections and autoimmune disease. It has been found that compounds activating or inhibiting type I interferon production may be useful not only in infectious disease innate immunity, but also in cancer (L. Zitvogel et al., Nature Reviews Immunology, 2015, vol. 15(7), pp. 405-414), allergic diseases (J. Moisan et al., Am. J. Physiol. Lung Cell Mol. Physiol., 2006, vol. 290, L987-995), neurodegenerative diseases such as amyotrophic lateral sclerosis and multiple sclerosis (H. Lemos et al., J. Immunol, 2014, vol. 192(12), pp. 5571-8; E. Cirulli et al., Science, 2015, vol. 347(6229), pp. 1436-41; A. Freischmidt et al., Nat. Neurosci., vol. 18(5), 631-6), other inflammatory conditions such as irritable bowel disease (S. Rakoff-Nahoum, Cell, 2004, 23, 118(2), pp. 229-41), and as vaccine adjuvants (Persing et al., Trends Microbiol. 2002, 10(10 Suppl), S32-7; Dubensky et al, Therapeutic Advances in Vaccines, published online Sep. 5, 2013).

STING is essential for antimicrobial host defense, including protection against a range of DNA and RNA viruses and bacteria (reviewed in Barber et al., Nat. Rev. Immunol., 2015, vol. 15(2), pp. 87-103, Ma and Damania, Cell Host & Microbe, 2016, vol. 19(2), pp. 150-158). Herpesviridae, Flaviviridae, Coronaviridae, Papillomaviridae, Adenoviridae, Hepadnaviridae, ortho- and paramyxoviridae and rhabdoviridae have evolved mechanisms to inhibit STING mediated Type I interferon production and evade host immune control (Holm et al., Nat Comm., 2016, vol. 7, p. 10680; Ma et al., PNAS2015, vol. 112(31) E4306-E4315; Wu et al., Cell Host Microbe, 2015, vol. 18(3), pp. 333-44; Liu et al., J Virol, 2016, vol. 90(20), pp. 9406-19; Chen et al., Protein Cell 2014, vol. 5(5), pp. 369-81; Lau et al., Science, 2013, vol. 350(6260), pp. 568-71; Ding et al., J Hepatol, 2013, vol. 59(1), pp. 52-8; Nitta et al., Hepatology, 2013, vol. 57(1), pp. 46-58; Sun et al., PloS One, 2012, vol. 7(2), e30802; Aguirre et al., PloS Pathog, 2012, vol. 8(10), e1002934; Ishikawa et al., Nature, 2009, vol. 461(7265), pp. 788-92). Thus, small molecule activation of STING is considered to be beneficial for treatment of these infectious diseases.

In contrast, increased and prolonged type I IFN production is associated with a variety of chronic infections, including Mycobacteria (Collins et al., Cell Host Microbe, 2015, vol. 17(6), pp. 820-8; Wassermann et al., Cell Host Microbe, 2015, vol. 17(6), pp. 799-810; Watson et al., Cell Host Microbe, 2015, vol. 17(6), pp. 811-9), Franciscella (Storek et al., J Immunol., 2015, vol. 194(7), pp. 3236-45; Jin et al., J Immunol., 2011, vol. 187(5), pp. 2595-601), Chlamydia (Prantner et al., J Immunol, 2010, vol. 184(5), pp. 2551-60), *Plasmodium* (Sharma et al., Immunity, 2011, vol. 35(2), pp. 194-207), and HIV (Herzner et al., Nat Immunol, 2015, vol. 16(10), pp. 1025-33; Gao et al., Science, 2013, vol. 341(6148), pp. 903-6). Similarly, excess type I interferon production is found among patients with complex forms of autoimmune disease. Genetic evidence in humans and support from studies in animal models support the hypothesis that inhibition of STING results in reduced type I interferon that drives autoimmune disease (Y. J. Crow et al., Nat. Genet., 2006, vol. 38(8), pp. 38917-920, D. B. Stetson et al., Cell, 2008, pp. 134587-598). Therefore, inhibitors of STING provide a treatment to patients with chronic type I interferon and proinflammatory cytokine production associated with infections or complex autoimmune diseases. Allergic diseases are associated with a Th2-based immune-response to allergens. Th2 responses are associated with raised levels of IgE, which, via its effects on mast cells, promotes a hypersensitivity to allergens, resulting in the symptoms seen, for example, in allergic rhinitis and asthma. In healthy individuals the immune-response to allergens is more balanced with a mixed Th2/Th1 and regulatory T cell response. Induction of Type 1 interferons have been shown to result in reduction of Th2-type cytokines in the local environment and promote Th1/Treg responses. In this context, induction of type 1 interferons by, for example, activation of STING, may offer benefit in treatment of allergic diseases such as asthma and allergic rhinitis (J. P. Huber et al., J Immunol, 2010, vol. 185, pp. 813-817).

In view of the above, compounds modulating STING are useful for treating one or more diseases selected from the group consisting of inflammatory, allergic, and autoimmune diseases, infectious diseases, cancer, pre-cancerous syndromes, and/or as immunogenic composition or vaccine adjuvants. Of particular relevance is the immunotherapy of cancer and viral infections, in particular prostate cancer, renal carcinoma, melanoma, pancreatic cancer, cervical cancer, ovarian cancer, colon cancer, head and neck cancer, lung cancer, fibrosarcoma, breast cancer and hepatitis B. Furthermore, activation of local immune response to the lesions is considered to be preferably an intratumoral or systemic therapeutic approach.

Accordingly, there is a need for compounds modulating the activity of STING, and accordingly, provide a therapeutic impact in the treatment of diseases, in which the modulation of STING is beneficial.

OBJECTS AND SUMMARY OF THE INVENTION

It is therefore an object of the present invention to provide compounds, which modulate STING, in particular, compounds, which act as STING agonists, thereby activating STING. In particular, there is an interest in providing compounds, which have high activity as STING agonists.

It is another object of the present invention to provide compounds, which are suitable for use as a medicament. It is another object of the present invention to provide compounds, which are suitable for use in the treatment of one or more diseases, which are linked to STING modulation. It is yet another object to provide compounds, which are suitable for use in the treatment of one or more diseases selected from the group consisting of inflammatory diseases, allergic diseases, autoimmune diseases, infectious diseases, cancer, and pre-cancerous syndromes. In particular, it is an object to provide compounds, which are suitable for the treatment of cancer, in particular prostate cancer, lung cancer, breast cancer, head and neck cancer, bladder cancer, and/or melanoma. It is yet another object to provide compounds, which are suitable for use in immunogenic compositions and as vaccine adjuvants.

The above objects can be achieved by the compounds of formula (I) as defined herein as well as pharmaceutical compositions comprising the same, and by the medical uses thereof.

The inventors of the present invention inter alia surprisingly found that the compounds of formula (I) as defined herein modulate STING, in particular act as STING agonists. Accordingly, the compounds of formula (I) can be used as a medicament, in particular for the treatment of one or more diseases selected from the group consisting of inflammatory diseases, allergic diseases, autoimmune diseases, infectious diseases, cancer, and pre-cancerous syndromes. In particular, the compounds of formula (I) are suitable for the treatment of cancer, in particular prostate cancer, lung cancer, breast cancer, head and neck cancer, bladder cancer, and/or melanoma. Further, the compounds of formula (I) are suitable for use in immunogenic compositions and as vaccine adjuvants.

In a first aspect, the present invention therefore relates to a compound of formula (I)

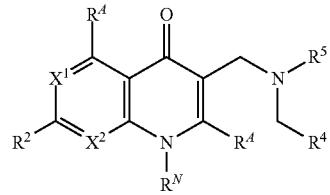

or a salt, stereoisomer, tautomer, or N-oxide thereof, wherein
$X^1$ is $CR^1$ or N;
$X^2$ is $CR^3$ or N;
$R^1$, $R^2$ and $R^3$ are independently H, OH, CN, halogen, $C_1$-$C_4$-alkyl, $C_1$-$C_4$-alkoxy, aryloxy, benzyloxy, $C(=O)R^E$, $NR^FC(=O)R^E$, $NR^F$—($C_1$-$C_4$-alkylene)-C$(=O)R^E$, or 4- to 6-membered saturated, partially or fully unsaturated, or aromatic carbocyclyl, carbocyclyl-$C_1$-$C_2$-alkyl, heterocyclyl, heterocyclyloxy, or heterocyclyl-$C_1$-$C_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;
$R^4$ is a 5- or 6-membered aromatic carbocyclic or heterocyclic ring, or a 9- or 10-membered aromatic carbobicyclic or heterobicyclic ring, wherein the heterocyclic or heterobicyclic ring comprises at least one nitrogen atom and optionally one or more, same or different additional heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more same or different substituents $R^X$;
$R^5$ is a 5- or 6-membered saturated heterocyclic ring, wherein said heterocyclic ring comprises one or more, same or different heteroatoms selected from O, N or S, wherein said N and/or S-atoms are independently oxidized or non-oxidized, and wherein each substitutable carbon or heteroatom is independently unsubstituted or substituted with one or more, same or different substituents $R^Y$;
and wherein
$R^N$ is H, HO(C=O)—$C_1$-$C_4$-alkyl, or a 3- or 4-membered saturated carbocyclyl or heterocyclyl, wherein said heterocyclic ring comprises one or more, same or different heteroatoms selected from O, N or S, wherein said N and/or S-atoms are independently oxidized or non-oxidized, and wherein each substitutable carbon or heteroatom in the aforementioned groups is independently unsubstituted or substituted with one or more, same or different substituents $R^X$;
$R^A$ is H, halogen, CN, OH, $C_1$-$C_3$-alkyl, $C_1$-$C_3$-alkoxy, or 3- to 6-membered saturated, partially or fully unsaturated, or aromatic carbocyclyl, or heterocyclyl, wherein the aforementioned heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

$R^C$ and $R^D$ are independently H, or $C_1$-$C_2$-alkyl; or $R^C$ and $R^D$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^E$ is H, $C_1$-$C_2$-alkyl, phenyl, benzyl, $OR^G$, or $NR^H R^I$; or a 5- or 6-membered saturated, partially or fully unsaturated heterocyclyl, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^F$;

$R^F$ is H, $C_1$-$C_2$-alkyl, $C_3$-$C_6$-cycloalkyl, phenyl, benzyl, or $C(=O)NR^H R^I$;

$R^G$ is H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N-atoms are independently oxidized or non-oxidized;

$R^H$ and $R^I$ are independently H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N-atoms are independently oxidized or non-oxidized; or $R^H$ and $R^I$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^X$ is halogen, CN, $NO_2$, $C_1$-$C_2$-alkyl, $C_1$-$C_2$-haloalkyl, $C_1$-$C_2$-alkoxy, $C(=O)R^E$, or two $R^X$ form =O, or two $R^X$ together with the carbon atom to which they are bonded form a 3- to 5-membered saturated, partially or fully unsaturated, or aromatic carbocyclic ring;

$R^Y$ is halogen, CN, OH, $C_1$-$C_2$-alkyl, $C_1$-$C_2$-alkyl-OH, $C_3$-$C_6$-cycloalkyl, $C_1$-$C_2$-alkoxy, $NR^C R^D$, $S(=O)_2$ $NR^C R^D$, $C(=O)R^E$, or 5- or 6-membered saturated, partially or fully unsaturated, or aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$; or two $R^Y$ form =O; or two $R^Y$ attached to identical or neighboring carbon atoms may form a 3-membered carbocyclic ring.

In a further aspect, the present invention relates to a compound of formula (I)

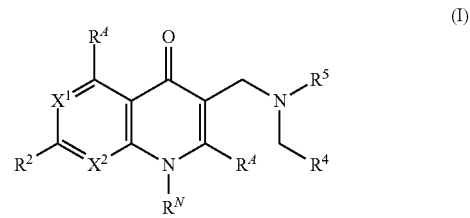

or a salt, stereoisomer, tautomer, or N-oxide thereof, wherein $X^1$ is $CR^1$ or N;

$X^2$ is $CR^3$ or N;

$R^1$, $R^2$ and $R^3$ are independently H, OH, CN, halogen, $C_1$-$C_4$-alkyl, $C_1$-$C_4$-alkoxy, aryloxy, benzyloxy, $C(=O)R^E$, $NR^F C(=O)R^E$, $NR^F$—($C_1$-$C_4$-alkylene)-C $(=O)R^E$, or 4- to 6-membered saturated, partially or fully unsaturated, or aromatic carbocyclyl, carbocyclyl-$C_1$-$C_2$-alkyl, heterocyclyl, heterocyclyloxy or heterocyclyl-$C_1$-$C_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

$R^4$ is a 5- or 6-membered aromatic carbocyclic or heterocyclic ring, or a 9- or 10-membered aromatic carbobicyclic or heterobicyclic ring, wherein the heterocyclic or heterobicyclic ring comprises at least one nitrogen atom and optionally one or more, same or different additional heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more same or different substituents $R^X$;

$R^5$ is a 5- or 6-membered saturated heterocyclic ring, wherein said heterocyclic ring comprises one or more, same or different heteroatoms selected from O, N or S, wherein said N and/or S-atoms are independently oxidized or non-oxidized, and wherein each substitutable carbon or heteroatom is independently unsubstituted or substituted with one or more, same or different substituents $R^Y$;

and wherein $R^N$ is H, $CH_3$, HO(C=O)—$C_1$-$C_4$-alkyl, or a 3- or 4-membered saturated carbocyclyl or heterocyclyl, wherein said heterocyclic ring comprises one or more, same or different heteroatoms selected from O, N or S, wherein said N and/or S-atoms are independently oxidized or non-oxidized, and wherein each substitutable carbon or heteroatom in the aforementioned groups is independently unsubstituted or substituted with one or more, same or different substituents $R^X$;

$R^A$ is H, halogen, CN, OH, $C_1$-$C_3$-alkyl, $C_1$-$C_3$-alkoxy, or 3- to 6-membered saturated, partially or fully unsaturated, or aromatic carbocyclyl, or heterocyclyl, wherein the aforementioned heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

$R^C$ and $R^D$ are independently H, or $C_1$-$C_2$-alkyl; or $R^C$ and $R^D$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^E$ is H, $C_1$-$C_2$-alkyl, phenyl, benzyl, $OR^G$, or $NR^H R^I$; or a 5- or 6-membered saturated, partially or fully unsaturated heterocyclyl, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^F$;

$R^F$ is H, $C_1$-$C_2$-alkyl, $C_3$-$C_6$-cycloalkyl, phenyl, benzyl, or $C(=O)NR^H R^I$;

$R^G$ is H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N-atoms are independently oxidized or non-oxidized;

$R^H$ and $R^I$ are independently H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N-atoms are independently oxidized or non-oxidized; or $R^H$ and $R^I$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^X$ is halogen, CN, $NO_2$, $C_1$-$C_2$-alkyl, $C_1$-$C_2$-alkoxy, $C(=O)R^E$, or two $R^X$ form $=O$;

$R^Y$ is halogen, CN, OH, $C_1$-$C_2$-alkyl, $C_1$-$C_2$-alkyl-OH, $C_3$-$C_6$-cycloalkyl, $C_1$-$C_2$-alkoxy, $NR^C R^D$, $S(=O)_2 NR^C R^D$, $C(=O)R^E$, or 5- or 6-membered saturated, partially or fully unsaturated, or aromatic carbocyclyl, carbocyclyl-$C_1$-$C_2$-alkyl, heterocyclyl, and heterocyclyl-$C_1$-$C_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$; or two $R^Y$ form $=O$; or two $R^Y$ attached to identical or neighboring carbon atoms may form a 3-membered carbocyclic ring.

The following embodiment are relevant in connection with the above aspects.

In a preferred embodiment, $R^A$ is H.

In one preferred embodiment, $R^N$ is H, $CH_3$ or cyclopropyl, preferably $CH_3$.

In another preferred embodiment, $R^N$ is cyclopropyl.

In another preferred embodiment, $R^1$, $R^2$ and $R^3$ are H.

In another preferred embodiment, $R^5$ is a 6-membered saturated heterocyclic ring, wherein said heterocyclic ring comprises one or more, same or different heteroatoms selected from O, N or S, wherein said N and/or S-atoms are independently oxidized or non-oxidized, and wherein each substitutable carbon or heteroatom is independently unsubstituted or substituted with one or more, same or different substituents $R^Y$.

In a more preferred embodiment, $R^5$ is piperidine, wherein each substitutable carbon or heteroatom in the piperidine ring is independently unsubstituted or substituted by one or more, same or different substituents $R^Y$.

In another more preferred embodiment, $R^5$ is piperidine, wherein each substitutable carbon atom in the piperidine ring is independently unsubstituted or substituted by one or more, same or different substituents $R^Y$; and wherein the nitrogen atom in the piperidine ring is preferably substituted with $R^Y$ being pyridinyl.

In another more preferred embodiment, $R^5$ is piperidine, wherein each substitutable carbon atom in the piperidine ring is independently unsubstituted or substituted by one or more, same or different substituents $R^Y$; and wherein the nitrogen atom in the piperidine ring is substituted with $R^Y$ being pyridinyl, which is unsubstituted or substituted with one or more, same or different substituents $R^X$, wherein $R^X$ is preferably methyl.

In a preferred embodiment, $R^4$ is pyridinyl, wherein each substitutable carbon atom in the cyclic ring is independently unsubstituted or substituted by one or more, same or different substituents $R^X$.

In another preferred embodiment, $X^1$ is $CR^1$; and $X^2$ is $CR^3$;

and wherein $R^1$ and $R^3$ are preferably H.

In one preferred embodiment, $R^X$ is halogen, CN, $C_1$-$C_2$-alkyl, or $C_1$-$C_2$-alkoxy.

In another preferred embodiment, $R^X$ is $NO_2$, $C(=O)R^E$, or two $R^X$ form $=O$.

In a preferred embodiment, $R^Y$ is halogen, CN, OH, $C_1$-$C_2$-alkyl, or 5- or 6-membered saturated, partially or fully unsaturated, or aromatic carbocyclyl, carbocyclyl-$C_1$-$C_2$-alkyl, heterocyclyl, and heterocyclyl-$C_1$-$C_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents R<sup>-x</sup>.

In one more preferred embodiment, the compound according to formula (I) is selected from the group consisting of 3-({[(2-methoxypyridin-4-yl)methyl][(3S)-1-(pyridin-3-yl)piperidin-3-yl]amino}methyl)-1-methyl-1,4-dihydroquinolin-4-one, 1-methyl-3-({[(2-methylpyridin-4-yl)methyl][1-(pyridin-3-yl)piperidin-3-yl]amino}methyl)-1,4-dihydroquinolin-4-one, 3-({[(2-methoxypyridin-4-yl)methyl][1-(pyridazin-3-yl)piperidin-3-yl]amino}methyl)-1-methyl-1,4-dihydroquinolin-4-one, 3-({[(2-methoxypyridin-4-yl)methyl][1-(pyrazin-2-yl)piperidin-3-yl]amino}methyl)-1-methyl-1,4-dihydroquinolin-4-one, 1-methyl-3-({[(2-methylpyridin-4-yl)methyl][(3S)-1-(pyridin-3-yl)piperidin-3-yl]amino}methyl)-1,4-dihydroquinolin-4-one, 3-({[(2-methoxypyridin-4-yl)methyl][(3S)-1-(pyridin-3-yl)piperidin-3-yl]amino}methyl)-1,4-dihydroquinolin-4-one, 1-methyl-3-({[(3S)-1-(6-methylpyridin-3-yl)piperidin-3-yl][(2-methylpyridin-4-yl)methyl]amino}methyl)-1,4-dihydroquinolin-4-one, 3-({[(3S)-1-(2-methoxypyrimidin-5-yl)piperidin-3-yl][(2-methylpyridin-4-yl)methyl]amino}methyl)-1-methyl-1,4-dihydroquinolin-4-one, 1-cyclopropyl-6-fluoro-3-({[(2-methoxypyridin-4-yl)methyl][(3S)-1-(pyridin-3-yl)piperidin-3-yl]amino}methyl)-7-(4-methylpiperazin-1-yl)-1,4-dihydroquinolin-4-one, 1-cyclopropyl-6-fluoro-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-methoxypyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-methylpyridin-4-yl)methyl][(3S)-1-(pyridin-3-yl)piperidin-3-yl]amino}methyl)-1,4-dihydroquinolin-4-one, 1-methyl-3-({[(2-methylpyridin-4-yl)methyl][(3S)-1-(pyridin-2-yl)piperidin-3-yl]amino}methyl)-1,4-dihydroquinolin-4-one, 1-methyl-3-({[(2-methylpyridin-4-yl)methyl][(3S)-1-(6-nitropyridin-3-yl)piperidin-3-yl]amino}methyl)-1,4-dihydroquinolin-4-one, 3-({[(3S)-1-(3-bromopyridin-4-yl)piperidin-3-yl][(2-methylpyridin-4-yl)methyl]amino}methyl)-1-methyl-1,4-dihydroquinolin-4-one, 3-({[(3S)-1-(6-fluoropyridin-3-yl)piperidin-3-yl][(2-methylpyridin-4-yl)methyl]amino}methyl)-1-methyl-1,4-dihydroquinolin-4-one, 3-({[(3S)-1-(6-chloropyrimidin-4-yl)piperidin-3-yl][(2-methylpyridin-4-yl)methyl]amino}methyl)-1-methyl-1,4-dihydroquinolin-4-one, 1-methyl-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one, 3-({[(3S)-1-(2-chloropyrimidin-4-yl)piperidin-3-yl][(2-methylpyridin-4-yl)methyl]amino}methyl)-1-methyl-1,4-dihydroquinolin-4-one, 3-({[(3S)-1-(2-methoxypyridin-4-yl)piperidin-3-yl][(2-methylpyridin-4-yl)methyl]amino}methyl)-1-methyl-1,4-dihydroquinolin-4-one, 3-({[(2-ethylpyridin-4-yl)methyl][1-(pyridin-3-yl)piperidin-3-yl]amino}methyl)-1-methyl-1,4-dihydroquinolin-4-one, 1-methyl-3-({[(2-methylpyridin-4-yl)methyl][(3S)-1-(6-oxo-1,6-dihydropyrimidin-4-yl)piperidin-3-yl]amino}methyl)-1,4-dihydroquinolin-4-one, 7-bromo-1-methyl-3-({[(2-methylpyridin-4-yl)methyl][(3S)-1-(pyridin-3-yl)piperidin-3-yl]amino}methyl)-1,4-dihydroquinolin-4-one, 3-({[(3R,4/i)-4-hydroxy-1-(pyridin-3-yl)piperidin-3-yl][(2-methylpyridin-4-yl)methyl]amino}methyl)-1-methyl-1,4-dihydroquinolin-4-one, 7-chloro-6-fluoro-1-methyl-3-({[(2-methylpyridin-4-yl)methyl][(3S)-1-(pyridin-3-yl)piperidin-3-yl]amino}methyl)-1,4-dihydroquinolin-4-one, 3-({[(3S,5S)-5-fluoro-1-(pyridin-3-yl)piperidin-3-yl][(2-methylpyridin-4-yl)methyl]amino}methyl)-1-methyl-1,4-dihydroquinolin-4-one, 1-methyl-3-({[(3S,5R)-5-methyl-1-(pyridin-3-yl)piperidin-3-yl][(2-methylpyridin-4-yl)methyl]amino}methyl)-1,4-dihydroquinolin-4-one, 7-chloro-1-cyclopropyl-6-fluoro-3-({[(2-methoxypyridin-4-yl)methyl][(3S)-1-(pyridin-3-yl)piperidin-3-yl]amino}methyl)-1,4-dihydroquinolin-4-one, methyl 1-[1-methyl-3-({[(2-methylpyridin-4-yl)methyl][(3S)-1-(pyridin-3-yl)piperidin-3-yl]amino}methyl)-4-oxo-1,4-dihydroquinolin-7-yl]piperidine-4-carboxylate, 1-methyl-3-({[(2-methylpyridin-4-yl)methyl][(3S)-1-(2-oxo-1,2-dihydropyridin-4-yl)piperidin-3-yl]amino}methyl)-1,4-dihydroquinolin-4-one, 1-cyclopropyl-6,7-difluoro-3-({[(2-methoxypyridin-4-yl)methyl][(3S)-1-(6-methylpyridin-3-yl)piperidin-3-yl]amino}methyl)-1,4-dihydroquinolin-4-one, 7-chloro-1-cyclopropyl-6-fluoro-3-({[(2-methylpyridin-4-yl)methyl][(3S)-1-(pyridin-3-yl)piperidin-3-yl]amino}methyl)-1,4-dihydroquinolin-4-one, 3-({[(2-methoxypyridin-4-yl)methyl][(3S)-1-(pyridin-3-yl)piperidin-3-yl]amino}methyl)-1,4-dihydroquinolin-4-one, 3-({[(2-methylpyridin-4-yl)methyl][(3S)-1-(pyridin-3-yl)piperidin-3-yl]amino}methyl)-1,4-dihydroquinolin-4-one, 7-bromo-1-methyl-3-({[(3S)-1-(6-methylpyridin-3-yl)piperidin-3-yl][(2-methylpyridin-4-yl)methyl]amino}methyl)-1,4-dihydroquinolin-4-one, 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one, 1-cyclopropyl-6-fluoro-7-methoxy-3-({[(3S)-1-(6-methylpyridin-3-yl)piperidin-3-yl][(2-methylpyridin-4-yl)methyl]amino}methyl)-1,4-dihydro-1,8-naphthyridin-4-one, 3-({[(3S)-1-(5-bromopyrimidin-2-yl)piperidin-3-yl][(2-methylpyridin-4-yl)methyl]amino}methyl)-1-methyl-1,4-dihydroquinolin-4-one 3-({[5,5-difluoro-1-(pyridin-3-yl)piperidin-3-yl][(2-methylpyridin-4-yl)methyl]amino}methyl)-1-methyl-1,4-dihydroquinolin-4-one, 1-methyl-3-({[(2-methylpyridin-4-yl)methyl][(3S)-1-(2-nitropyridin-3-yl)piperidin-3-yl]amino}methyl)-1,4-dihydroquinolin-4-one, 3-({[(2,6-dimethylpyridin-4-yl)methyl][(3S)-1-(pyridine-3-yl)piperidin-3-yl]amino}methyl)-1-methyl-1,4-dihydroquinolin-4-one, 1-methyl-3-({[(3S)-1-(pyridin-3-yl)piperidin-3-yl][(pyridin-4-yl)methyl]amino}methyl)-1,4-dihydroquinolin-4-one, 1-methyl-3-({[(3S)-1-(1-methyl-2-oxo-1,2-dihydropyridin-4-yl)piperidin-3-yl][(2-methylpyridin-4-yl)methyl]amino}methyl)-1,4-dihydroquinolin-4-one, 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydro-1,8-naphthyridin-4-one, 1-cyclopropyl-6-fluoro-7-hydroxy-3-({[(3S)-1-(6-methylpyridin-3-yl)piperidin-3-yl][(2-methylpyridin-4-yl)methyl]amino}methyl)-1,4-dihydro-1,8-naphthyridin-4-one, 1-cyclopropyl-6-fluoro-7-methoxy-3-({[(3S)-1-(6-methylpyridin-3-yl)piperidin-3-yl][(2-methylpyridin-4-yl)methyl]amino}methyl)-1,4-dihydroquinolin-4-one, 1-cyclopropyl-6-fluoro-7-[(3R)-3-methylpiperazin-1-yl]-3-({[(3S)-1-(6-methylpyridin-3-yl)piperidin-3-yl][(2-methylpyridin-4-yl)methyl]amino}methyl)-1,4-dihydroquinolin-4-one, 1-cyclopropyl-6-fluoro-3-({[(3S)-1-(6-methylpyridin-3-yl)piperidin-3-yl][(2-methylpyridin-4-yl)methyl]amino}methyl)-7-(piperazin-1-yl)-1,4-dihydroquinolin-4-one, 1-cyclopropyl-7-[4-(2,2-difluoroethyl)piperazin-1-yl]-6-fluoro-3-({[(3S)-1-(6-methylpyridin-3-yl)piperidin-3-yl][(2-methylpyridin-4-yl)methyl]amino}methyl)-1,4-dihydroquinolin-4-one, 1-methyl-3-({[(3S)-1-(6-methylpyridin-3-yl)piperidin-3-yl][(2-methylpyridin-4-yl)methyl]amino}methyl)-7-(2-oxopiperazin-1-yl)-1,4-dihydroquinolin-4-one, 3-({[(3S)-1-

(6-methylpyridin-3-yl)piperidin-3-yl][(2-methylpyridin-4-yl)methyl]amino}methyl)-1-(oxetan-3-yl)-1,4-dihydroquinolin-4-one, 2-[3-({[(3S)-1-(6-Methylpyridin-3-yl)piperidin-3-yl][(2-methylpyridin-4-yl)methyl]amino}methyl)-4-oxo-1,4-dihydroquinolin-1-yl]acetic acid, and 1-cyclopropyl-7-{4,7-diazaspiro[2.5]octan-7-yl}-6-fluoro-3-({[(3S)-1-(6-methylpyridin-3-yl)piperidin-3-yl][(2-methylpyridin-4-yl)methyl]amino}methyl)-1,4-dihydroquinolin-4-one.

In another more preferred embodiment, the compound according to formula (I) is a compound selected from the group consisting of 3-({[(2-methoxypyridin-4-yl)methyl][(3S)-1-(pyridin-3-yl)piperidin-3-yl]amino}methyl)-1-methyl-1,4-dihydroquinolin-4-one, 1-methyl-3-({[(2-methylpyridin-4-yl)methyl][1-(pyridin-3-yl)piperidin-3-yl]amino}methyl)-1,4-dihydroquinolin-4-one, 3-({[(2-methoxypyridin-4-yl)methyl][1-(pyridazin-3-yl)piperidin-3-yl]amino}methyl)-1-methyl-1,4-dihydroquinolin-4-one, 3-({[(2-methoxypyridin-4-yl)methyl][1-(pyrazin-2-yl)piperidin-3-yl]amino}methyl)-1-methyl-1,4-dihydroquinolin-4-one, 1-methyl-3-({[(2-methylpyridin-4-yl)methyl][(3S)-1-(pyridin-3-yl)piperidin-3-yl]amino}methyl)-1,4-dihydroquinolin-4-one, 3-({[(2-methoxypyridin-4-yl)methyl][(3S)-1-(pyridin-3-yl)piperidin-3-yl]amino}methyl)-1,4-dihydroquinolin-4-one, 1-methyl-3-({[(3S)-1-(6-methylpyridin-3-yl)piperidin-3-yl][(2-methylpyridin-4-yl)methyl]amino}methyl)-1,4-dihydroquinolin-4-one, 3-({[(3S)-1-(2-methoxypyrimidin-5-yl)piperidin-3-yl][(2-methylpyridin-4-yl)methyl]amino}methyl)-1-methyl-1,4-dihydroquinolin-4-one, 1-cyclopropyl-6-fluoro-3-({[(2-methoxypyridin-4-yl)methyl][(3S)-1-(pyridin-3-yl)piperidin-3-yl]amino}methyl)-7-(4-methylpiperazin-1-yl)-1,4-dihydroquinolin-4-one, 1-cyclopropyl-6-fluoro-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-methoxypyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-methylpyridin-4-yl)methyl][(3S)-1-(pyridin-3-yl)piperidin-3-yl]amino}methyl)-1,4-dihydroquinolin-4-one, 1-methyl-3-({[(2-methylpyridin-4-yl)methyl][(3S)-1-(pyridin-2-yl)piperidin-3-yl]amino}methyl)-1,4-dihydroquinolin-4-one, 1-methyl-3-({[(2-methylpyridin-4-yl)methyl][(3S)-1-(6-nitropyridin-3-yl)piperidin-3-yl]amino}methyl)-1,4-dihydroquinolin-4-one, 3-({[(3S)-1-(3-bromopyridin-4-yl)piperidin-3-yl][(2-methylpyridin-4-yl)methyl]amino}methyl)-1-methyl-1,4-dihydroquinolin-4-one, 3-({[(3S)-1-(6-fluoropyridin-3-yl)piperidin-3-yl][(2-methylpyridin-4-yl)methyl]amino}methyl)-1-methyl-1,4-dihydroquinolin-4-one, 3-({[(3S)-1-(6-chloropyrimidin-4-yl)piperidin-3-yl][(2-methylpyridin-4-yl)methyl]amino}methyl)-1-methyl-1,4-dihydroquinolin-4-one, 1-methyl-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one, 3-({[(3S)-1-(2-chloropyrimidin-4-yl)piperidin-3-yl][(2-methylpyridin-4-yl)methyl]amino}methyl)-1-methyl-1,4-dihydroquinolin-4-one, 3-({[(3S)-1-(2-methoxypyridin-4-yl)piperidin-3-yl][(2-methylpyridin-4-yl)methyl]amino}methyl)-1-methyl-1,4-dihydroquinolin-4-one, 3-({[(2-ethylpyridin-4-yl)methyl][1-(pyridin-3-yl)piperidin-3-yl]amino}methyl)-1-methyl-1,4-dihydroquinolin-4-one, 1-methyl-3-({[(2-methylpyridin-4-yl)methyl][(3S)-1-(6-oxo-1,6-dihydropyrimidin-4-yl)piperidin-3-yl]amino}methyl)-1,4-dihydroquinolin-4-one, 7-bromo-1-methyl-3-({[(2-methylpyridin-4-yl)methyl][(3S)-1-(pyridin-3-yl)piperidin-3-yl]amino}methyl)-1,4-dihydroquinolin-4-one, 3-({[(3R,4R)-4-hydroxy-1-(pyridin-3-yl)piperidin-3-yl][(2-methylpyridin-4-yl)methyl]amino}methyl)-1-methyl-1,4-dihydroquinolin-4-one, 7-chloro-6-fluoro-1-methyl-3-({[(2-methylpyridin-4-yl)methyl][(3S)-1-(pyridin-3-yl)piperidin-3-yl]amino}methyl)-1,4-dihydroquinolin-4-one, 3-({[(3S,5S)-5-fluoro-1-(pyridin-3-yl)piperidin-3-yl][(2-methylpyridin-4-yl)methyl]amino}methyl)-1-methyl-1,4-dihydroquinolin-4-one, 1-methyl-3-({[(3S,5R)-5-methyl-1-(pyridin-3-yl)piperidin-3-yl][(2-methylpyridin-4-yl)methyl]amino}methyl)-1,4-dihydroquinolin-4-one, 7-chloro-1-cyclopropyl-6-fluoro-3-({[(2-methoxypyridin-4-yl)methyl][(3S)-1-(pyridin-3-yl)piperidin-3-yl]amino}methyl)-1,4-dihydroquinolin-4-one, methyl 1-[1-methyl-3-({[(2-methylpyridin-4-yl)methyl][(3S)-1-(pyridin-3-yl)piperidin-3-yl]amino}methyl)-4-oxo-1,4-dihydroquinolin-7-yl]piperidine-4-carboxylate, 1-methyl-3-({[(2-methylpyridin-4-yl)methyl][(3S)-1-(2-oxo-1,2-dihydropyridin-4-yl)piperidin-3-yl]amino}methyl)-1,4-dihydroquinolin-4-one, 1-cyclopropyl-6,7-difluoro-3-({[(2-methoxypyridin-4-yl)methyl][(3S)-1-(6-methylpyridin-3-yl)piperidin-3-yl]amino}methyl)-1,4-dihydroquinolin-4-one, 7-chloro-1-cyclopropyl-6-fluoro-3-({[(2-methylpyridin-4-yl)methyl][(3S)-1-(pyridin-3-yl)piperidin-3-yl]amino}methyl)-1,4-dihydroquinolin-4-one, 3-({[(2-methoxypyridin-4-yl)methyl][(3S)-1-(pyridin-3-yl)piperidin-3-yl]amino}methyl)-1,4-dihydroquinolin-4-one, 3-({[(2-methylpyridin-4-yl)methyl][(3S)-1-(pyridin-3-yl)piperidin-3-yl]amino}methyl)-1,4-dihydroquinolin-4-one, 7-bromo-1-methyl-3-({[(3S)-1-(6-methylpyridin-3-yl)piperidin-3-yl][(2-methylpyridin-4-yl)methyl]amino}methyl)-1,4-dihydroquinolin-4-one, 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one, and 1-cyclopropyl-6-fluoro-7-methoxy-3-({[(3S)-1-(6-methylpyridin-3-yl)piperidin-3-yl][(2-methylpyridin-4-yl)methyl]amino}methyl)-1,4-dihydro-1,8-naphthyridin-4-one.

In another more preferred embodiment, the compound according to formula (I) is a compound selected from the group consisting of 3-({[(2-methoxypyridin-4-yl)methyl][(3S)-1-(pyridin-3-yl)piperidin-3-yl]amino}methyl)-1-methyl-1,4-dihydroquinolin-4-one, 1-methyl-3-({[(2-methylpyridin-4-yl)methyl][1-(pyridin-3-yl)piperidin-3-yl]amino}methyl)-1,4-dihydroquinolin-4-one, 3-({[(2-methoxypyridin-4-yl)methyl][1-(pyridazin-3-yl)piperidin-3-yl]amino}methyl)-1-methyl-1,4-dihydroquinolin-4-one, 3-({[(2-methoxypyridin-4-yl)methyl][1-(pyrazin-2-yl)piperidin-3-yl]amino}methyl)-1-methyl-1,4-dihydroquinolin-4-one, 1-methyl-3-({[(2-methylpyridin-4-yl)methyl][(3S)-1-(pyridin-3-yl)piperidin-3-yl]amino}methyl)-1,4-dihydroquinolin-4-one, 3-({[(2-methoxypyridin-4-yl)methyl][(3S)-1-(pyridin-3-yl)piperidin-3-yl]amino}methyl)-1,4-dihydroquinolin-4-one, 1-methyl-3-({[(3S)-1-(6-methylpyridin-3-yl)piperidin-3-yl][(2-methylpyridin-4-yl)methyl]amino}methyl)-1,4-dihydroquinolin-4-one, 3-({[(3S)-1-(2-methoxypyrimidin-5-yl)piperidin-3-yl][(2-methylpyridin-4-yl)methyl]amino}methyl)-1-methyl-1,4-dihydroquinolin-4-one, 1-cyclopropyl-6-fluoro-3-({[(2-methoxypyridin-4-yl)methyl][(3S)-1-(pyridin-3-yl)piperidin-3-yl]amino}methyl)-7-(4-methylpiperazin-1-yl)-1,4-dihydroquinolin-4-one, 1-cyclopropyl-6-fluoro-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-methoxypyridin-4-yl)methyl][(3S)-1-(pyridin-3-yl)

piperidin-3-yl]amino}methyl)-1,4-dihydroquinolin-4-one, 1-cyclopropyl-6,7-difluoro-3-({[(2-methylpyridin-4-yl)methyl][(3S)-1-(pyridin-3-yl)piperidin-3-yl]amino}methyl)-1,4-dihydroquinolin-4-one, 1-methyl-3-({[(2-methylpyridin-4-yl)methyl][(3S)-1-(pyridin-2-yl)piperidin-3-yl]amino}methyl)-1,4-dihydroquinolin-4-one, 1-methyl-3-({[(2-methylpyridin-4-yl)methyl][(3S)-1-(6-nitropyridin-3-yl)piperidin-3-yl]amino}methyl)-1,4-dihydroquinolin-4-one, 3-({[(3S)-1-(3-bromopyridin-4-yl)piperidin-3-yl][(2-methylpyridin-4-yl)methyl]amino}methyl)-1-methyl-1,4-dihydroquinolin-4-one, 3-({[(3S)-1-(6-fluoropyridin-3-yl)piperidin-3-yl][(2-methylpyridin-4-yl)methyl]amino}methyl)-1-methyl-1,4-dihydroquinolin-4-one, 3-({[(3S)-1-(6-chloropyrimidin-4-yl)piperidin-3-yl][(2-methylpyridin-4-yl)methyl]amino}methyl)-1-methyl-1,4-dihydroquinolin-4-one, 1-methyl-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one, 3-({[(3S)-1-(2-chloropyrimidin-4-yl)piperidin-3-yl][(2-methylpyridin-4-yl)methyl]amino}methyl)-1-methyl-1,4-dihydroquinolin-4-one, 3-({[(3S)-1-(2-methoxypyridin-4-yl)piperidin-3-yl][(2-methylpyridin-4-yl)methyl]amino}methyl)-1-methyl-1,4-dihydroquinolin-4-one, 3-({[(2-ethylpyridin-4-yl)methyl][1-(pyridin-3-yl)piperidin-3-yl]amino}methyl)-1-methyl-1,4-dihydroquinolin-4-one, 1-methyl-3-({[(2-methylpyridin-4-yl)methyl][(3S)-1-(6-oxo-1,6-dihydropyrimidin-4-yl)piperidin-3-yl]amino}methyl)-1,4-dihydroquinolin-4-one, 7-bromo-1-methyl-3-({[(2-methylpyridin-4-yl)methyl][(3S)-1-(pyridin-3-yl)piperidin-3-yl]amino}methyl)-1,4-dihydroquinolin-4-one, 3-({[(3R,4R)-4-hydroxy-1-(pyridin-3-yl)piperidin-3-yl][(2-methylpyridin-4-yl)methyl]amino}methyl)-1-methyl-1,4-dihydroquinolin-4-one, 7-chloro-6-fluoro-1-methyl-3-({[(2-methylpyridin-4-yl)methyl][(3S)-1-(pyridin-3-yl)piperidin-3-yl]amino}methyl)-1,4-dihydroquinolin-4-one, 3-({[(3S,5S)-5-fluoro-1-(pyridin-3-yl)piperidin-3-yl][(2-methylpyridin-4-yl)methyl]amino}methyl)-1-methyl-1,4-dihydroquinolin-4-one, 1-methyl-3-({[(3S,5R)-5-methyl-1-(pyridin-3-yl)piperidin-3-yl][(2-methylpyridin-4-yl)methyl]amino}methyl)-1,4-dihydroquinolin-4-one, 7-chloro-1-cyclopropyl-6-fluoro-3-({[(2-methoxypyridin-4-yl)methyl][(3S)-1-(pyridin-3-yl)piperidin-3-yl]amino}methyl)-1,4-dihydroquinolin-4-one, methyl 1-[1-methyl-3-({[(2-methylpyridin-4-yl)methyl][(3S)-1-(pyridin-3-yl)piperidin-3-yl]amino}methyl)-4-oxo-1,4-dihydroquinolin-7-yl]piperidine-4-carboxylate, 1-methyl-3-({[(2-methylpyridin-4-yl)methyl][(36)-1-(2-oxo-1,2-dihydropyridin-4-yl)piperidin-3-yl]amino}methyl)-1,4-dihydroquinolin-4-one and 1-cyclopropyl-6,7-difluoro-3-({[(2-methoxypyridin-4-yl)methyl][(3S)-1-(6-methylpyridin-3-yl)piperidin-3-yl]amino}methyl)-1,4-dihydroquinolin-4-one.

In one even more preferred embodiment, the compound according to formula (I) is selected from the group consisting of 3-({[(2-methoxypyridin-4-yl)methyl][(3S)-1-(pyridin-3-yl)piperidin-3-yl]amino}methyl)-1-methyl-1,4-dihydroquinolin-4-one, 1-methyl-3-({[(2-methylpyridin-4-yl)methyl][(3S)-1-(pyridin-3-yl)piperidin-3-yl]amino}methyl)-1,4-dihydroquinolin-4-one, 1-methyl-3-({[(3S)-1-(6-methylpyridin-3-yl)piperidin-3-yl][(2-methylpyridin-4-yl)methyl]amino}methyl)-1,4-dihydroquinolin-4-one, 1-cyclopropyl-6-fluoro-3-({[(2-methoxypyridin-4-yl)methyl][(3S)-1-(pyridin-3-yl)piperidin-3-yl]amino}methyl)-7-(4-methylpiperazin-1-yl)-1,4-dihydroquinolin-4-one, 1-cyclopropyl-6-fluoro-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-

[(3S)-1-(pyridin-3-yl)piperidin-3-yl]amino}methyl)-1,4-dihydroquinolin-4-one, 1-cyclopropyl-6,7-difluoro-3-({[(2-methoxypyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-methylpyridin-4-yl)methyl][(3S)-1-(pyridin-3-yl)piperidin-3-yl]amino}methyl)-1,4-dihydroquinolin-4-one, 1-methyl-7-(4-methylpiperazin-1-yl)-3-({[(2-methylpyridin-4-yl)methyl][(3,5)-1-(pyridin-3-yl)piperidin-3-yl]amino}methyl)-1,4-dihydroquinolin-4-one, 7-bromo-1-methyl-3-({[(2-methylpyridin-4-yl)methyl][(3S)-1-(pyridin-3-yl)piperidin-3-yl]amino}methyl)-1,4-dihydroquinolin-4-one, 7-chloro-6-fluoro-1-methyl-3-({[(2-methylpyridin-4-yl)methyl][(3S)-1-(pyridin-3-yl)piperidin-3-yl]amino}methyl)-1,4-dihydroquinolin-4-one, 3-({[(3S,5S)-5-fluoro-1-(pyridin-3-yl)piperidin-3-yl][(2-methylpyridin-4-yl)methyl]amino}methyl)-1-methyl-1,4-dihydroquinolin-4-one, 7-chloro-1-cyclopropyl-6-fluoro-3-({[(2-methoxypyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-methoxypyridin-4-yl)methyl][(3S)-1-(6-methylpyridin-3-yl)piperidin-3-yl]amino}methyl)-1,4-dihydroquinolin-4-one, 7-chloro-1-cyclopropyl-6-fluoro-3-({[(2-methoxypyridin-4-yl)methyl][(3S)-1-(pyridin-3-yl)piperidin-3-yl]amino}methyl)-1,4-dihydroquinolin-4-one, 3-({[(2-methoxypyridin-4-yl)methyl][(3S)-1-(pyridin-3-yl)piperidin-3-yl]amino}methyl)-1,4-dihydroquinolin-4-one, 3-({[(2-methylpyridin-4-yl)methyl][(3S)-1-(pyridin-3-yl)piperidin-3-yl]amino}methyl)-1,4-dihydroquinolin-4-one, 7-bromo-1-methyl-3-({[(3S)-1-(6-methylpyridin-3-yl)piperidin-3-yl][(2-methylpyridin-4-yl)methyl]amino}methyl)-1,4-dihydroquinolin-4-one, 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one, 1-cyclopropyl-6-fluoro-7-methoxy-3-({[(3S)-1-(6-methylpyridin-3-yl)piperidin-3-yl][(2-methylpyridin-4-yl)methyl]amino}methyl)-1,4-dihydro-1,8-naphthyridin-4-one, 1-cyclopropyl-6-fluoro-7-methoxy-3-({[(3S)-1-(6-methylpyridin-3-yl)piperidin-3-yl][(2-methylpyridin-4-yl)methyl]amino}methyl)-1,4-dihydroquinolin-4-one 1-cyclopropyl-6-fluoro-7-[(3R)-3-methylpiperazin-1-yl]-3-({[(3S)-1-(6-methylpyridin-3-yl)piperidin-3-yl][(2-methylpyridin-4-yl)methyl]amino}methyl)-1,4-dihydroquinolin-4-one, 1-cyclopropyl-6-fluoro-3-({[(3S)-1-(6-methylpyridin-3-yl)piperidin-3-yl][(2-methylpyridin-4-yl)methyl]amino}methyl)-7-(piperazin-1-yl)-1,4-dihydroquinolin-4-one, and 1-cyclopropyl-7-{4,7-diazaspiro[2.5]octan-7-yl}-6-fluoro-3-({[(3S)-1-(6-methylpyridin-3-yl)piperidin-3-yl][(2-methylpyridin-4-yl)methyl]amino}methyl)-1,4-dihydroquinolin-4-one.

In another even more preferred embodiment, the compound according to formula (I) is selected from the group consisting of 3-({[(2-methoxypyridin-4-yl)methyl][(3S)-1-(pyridin-3-yl)piperidin-3-yl]amino}methyl)-1-methyl-1,4-dihydroquinolin-4-one, 1-methyl-3-({[(2-methylpyridin-4-yl)methyl][(3S)-1-(pyridin-3-yl)piperidin-3-yl]amino}methyl)-1,4-dihydroquinolin-4-one, 1-methyl-3-({[(3S)-1-(6-methylpyridin-3-yl)piperidin-3-yl][(2-methylpyridin-4-yl)methyl]amino}methyl)-1,4-dihydroquinolin-4-one, 1-cyclopropyl-6-fluoro-3-({[(2-methoxypyridin-4-yl)methyl][(3S)-1-(pyridin-3-yl)piperidin-3-yl]amino}methyl)-7-(4-methylpiperazin-1-yl)-1,4-dihydroquinolin-4-one, 1-cyclopropyl-6-fluoro-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2- methoxypyridin-4-yl)methyl][(3S)-1-(pyridin-3-yl)
piperidin-3-yl]amino}methyl)-1,4-dihydroquinolin-4-one,
1-cyclopropyl-6,7-difluoro-3-({[(2-methylpyridin-4-yl)
methyl][(3S)-1-(pyridin-3-yl)piperidin-3-yl]
amino}methyl)-1,4-dihydroquinolin-4-one, 1-methyl-7-(4-
methylpiperazin-1-yl)-3-({[(2-methylpyridin-4-yl)methyl]
[(3S)-1-(pyridin-3-yl)piperidin-3-yl]amino}methyl)-1,4-
dihydroquinolin-4-one, 7-bromo-1-methyl-3-({[(2-
methylpyridin-4-yl)methyl][(3S)-1-(pyridin-3-yl)piperidin-
3-yl]amino}methyl)-1,4-dihydroquinolin-4-one, 7-chloro-
6-fluoro-1-methyl-3-({[(2-methylpyridin-4-yl)methyl]
[(3S)-1-(pyridin-3-yl)piperidin-3-yl]amino}methyl)-1,4-
dihydroquinolin-4-one, 3-({[(3S,5S)-5-fluoro-1-(pyridin-3-
yl)piperidin-3-yl][(2-methylpyridin-4-yl)methyl]
amino}methyl)-1-methyl-1,4-dihydroquinolin-4-one,
7-chloro-1-cyclopropyl-6-fluoro-3-({[(2-methoxypyridin-4-
yl)methyl][(3S)-1-(pyridin-3-yl)piperidin-3-yl]
amino}methyl)-1,4-dihydroquinolin-4-one, 1-cyclopropyl-
6,7-difluoro-3-({[(2-methoxypyridin-4-yl)methyl][(3S)-1-
(6-methylpyridin-3-yl)piperidin-3-yl]amino}methyl)-1,4-
dihydroquinolin-4-one, 7-chloro-1-cyclopropyl-6-fluoro-3-
({[(2-methylpyridin-4-yl)methyl][(3S)-1-(pyridin-3-yl)
piperidin-3-yl]amino}methyl)-1,4-dihydroquinolin-4-one,
3-({[(2-methoxypyridin-4-yl)methyl][(3S)-1-(pyridin-3-yl)
piperidin-3-yl]amino}methyl)-1,4-dihydroquinolin-4-one,
3-({[(2-methylpyridin-4-yl)methyl][(3S)-1-(pyridin-3-yl)
piperidin-3-yl]amino}methyl)-1,4-dihydroquinolin-4-one,
7-bromo-1-methyl-3-({[(3S)-1-(6-methylpyridin-3-yl)pip-
eridin-3-yl][(2-methylpyridin-4-yl)methyl]amino}methyl)-
1,4-dihydroquinolin-4-one, 7-chloro-1-cyclopropyl-6-
fluoro-3-({[(3S)-1-(6-methylpyridin-3-yl)piperidin-3-yl]
[(2-methylpyridin-4-yl)methyl]amino}methyl)-1,4-
dihydroquinolin-4-one, 1-cyclopropyl-6-fluoro-7-methoxy-
3-({[(3S)-1-(6-methylpyridin-3-yl)piperidin-3-yl][(2-
methylpyridin-4-yl)methyl]amino}methyl)-1,4-dihydro-1,
8-naphthyridin-4-one.

In another even more preferred embodiment, the compound according to formula (I) is selected from the group consisting of 3-({[(2-methoxypyridin-4-yl)methyl][(3S)-1-(pyridin-3-yl)piperidin-3-yl]amino}methyl)-1-methyl-1,4-dihydroquinolin-4-one, 1-methyl-3-({[(2-methylpyridin-4-yl)methyl][(3S)-1-(pyridin-3-yl)piperidin-3-yl]amino}methyl)-1,4-dihydroquinolin-4-one, 1-methyl-3-({[(3S)-1-(6-methylpyridin-3-yl)piperidin-3-yl][(2-methylpyridin-4-yl)methyl]amino}methyl)-1,4-dihydroquinolin-4-one, 1-cyclopropyl-6-fluoro-3-({[(2-methoxypyridin-4-yl)methyl][(3S)-1-(pyridin-3-yl)piperidin-3-yl]amino}methyl)-7-(4-methylpiperazin-1-yl)-1,4-dihydroquinolin-4-one, 1-cyclopropyl-6-fluoro-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-methoxypyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-methylpyridin-4-yl)methyl][(3S)-1-(pyridin-3-yl)piperidin-3-yl]amino}methyl)-1,4-dihydroquinolin-4-one, 1-methyl-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one, 7-bromo-1-methyl-3-({[(2-methylpyridin-4-yl)methyl][(3S)-1-(pyridin-3-yl)piperidin-3-yl]amino}methyl)-1,4-dihydroquinolin-4-one, 7-chloro-6-fluoro-1-methyl-3-({[(2-methylpyridin-4-yl)methyl][(3S)-1-(pyridin-3-yl)piperidin-3-yl]amino}methyl)-1,4-dihydroquinolin-4-one, 3-({[(3S,5S)-5-fluoro-1-(pyridin-3-yl)piperidin-3-yl][(2-methylpyridin-4-yl)methyl]amino}methyl)-1-methyl-1,4-dihydroquinolin-4-one, 7-chloro-1-cyclopropyl-6-fluoro-3-({[(2-methoxypyridin-4-yl)methyl][(3S)-1-(pyridin-3-yl)piperidin-3-yl]amino}methyl)-1,4-dihydroquinolin-4-one and 1-cyclopropyl-6,7-difluoro-3-({[(2-methoxypyridin-4-yl)methyl][(3S)-1-(6-methylpyridin-3-yl)piperidin-3-yl]amino}methyl)-1,4-dihydroquinolin-4-one.

In yet another one more preferred embodiment, the compound according to formula (I) is selected from the group consisting of 1-methyl-3-({[(3S)-1-(5-methyl-1,3,4-oxadiazol-2-yl)piperidin-3-yl][(2-methylpyridin-4-yl)methyl]amino}methyl)-1,4-dihydroquinolin-4-one, 3-({[(3S)-1-(2-chloropyrimidin-4-yl)piperidin-3-yl][(2-methylpyridin-4-yl)methyl]amino}methyl)-1-methyl-1,4-dihydroquinolin-4-one, 1-methyl-3-({[(3S)-1-(pyridin-3-yl)piperidin-3-yl][(1,2-thiazol-5-yl)methyl]amino}methyl)-1,4-dihydroquinolin-4-one, 7-chloro-1-cyclopropyl-3-({[(3S)-1-(6-methylpyridin-3-yl)piperidin-3-yl][(2-methylpyridin-4-yl)methyl]amino}methyl)-1,4-dihydro-1,6-naphthyridin-4-one, 7-(cyclohex-1-en-1-yl)-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one, 3-({[(3S)-1-(6-methylpyridin-3-yl)piperidin-3-yl][(2-methylpyridin-4-yl)methyl]amino}methyl)-1,4-dihydroquinolin-4-one, 1-cyclopropyl-6-fluoro-7-hydroxy-3-({[(3S)-1-(6-methylpyridin-3-yl)piperidin-3-yl][(2-methylpyridin-4-yl)methyl]amino}methyl)-1,4-dihydroquinolin-4-one, 8-bromo-1-methyl-3-({[(3S)-1-(6-methylpyridin-3-yl)piperidin-3-yl][(2-methylpyridin-4-yl)methyl]amino}methyl)-1,4-dihydroquinolin-4-one, 7-chloro-6-fluoro-3-({[(3S)-1-(6-methylpyridin-3-yl)piperidin-3-yl][(2-methylpyridin-4-yl)methyl]amino}methyl)-1-(propan-2-yl)-1,4-dihydro-1,8-naphthyridin-4-one, 6-fluoro-7-methoxy-3-({[(3S)-1-(6-methylpyridin-3-yl)piperidin-3-yl][(2-methylpyridin-4-yl)methyl]amino}methyl)-1-(propan-2-yl)-1,4-dihydro-1,8-naphthyridin-4-one, 3-({[(1,3-dimethyl-1H-pyrazol-5-yl)methyl][(3S)-1-(pyridin-3-yl)piperidin-3-yl]amino}methyl)-1-methyl-1,4-dihydroquinolin-4-one, and 1-cyclopropyl-3-({[(3S)-1-(6-methylpyridin-3-yl)piperidin-3-yl][(2-methylpyridin-4-yl)methyl]amino}methyl)-7-(morpholin-3-yl)-1,4-dihydroquinolin-4-one;

and is preferably a compound selected from the group consisting of 3-({[(3S)-1-(6-methylpyridin-3-yl)piperidin-3-yl][(2-methylpyridin-4-yl)methyl]amino}methyl)-1,4-dihydroquinolin-4-one, 1-cyclopropyl-6-fluoro-7-hydroxy-3-({[(3S)-1-(6-methylpyridin-3-yl)piperidin-3-yl][(2-methylpyridin-4-yl)methyl]amino}methyl)-1,4-dihydroquinolin-4-one, 6-fluoro-7-methoxy-3-({[(3S)-1-(6-methylpyridin-3-yl)piperidin-3-yl][(2-methylpyridin-4-yl)methyl]amino}methyl)-1-(propan-2-yl)-1,4-dihydro-1,8-naphthyridin-4-one, and 1-cyclopropyl-3-({[(3S)-1-(6-methylpyridin-3-yl)piperidin-3-yl][(2-methylpyridin-4-yl)methyl]amino}methyl)-7-(morpholin-3-yl)-1,4-dihydroquinolin-4-one.

In a further aspect, the present invention relates to a compound of formula (I)

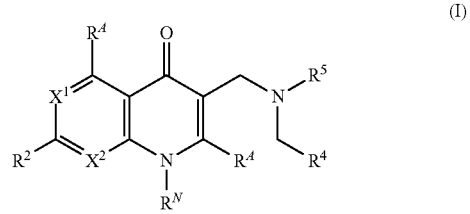

(I)

or a salt, stereoisomer, tautomer, or N-oxide thereof, wherein $X^1$ is $CR^1$;

$X^2$ is $CR^3$;

$R^1$, $R^2$ and $R^3$ are independently H, OH, CN, halogen, $C_1$-$C_4$-alkyl, $C_1$-$C_4$-alkoxy, aryloxy, benzyloxy, $C(=O)R^E$, $NR^FC(=O)R^E$, or 5- to 6-membered saturated, partially or fully unsaturated, or aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

$R^4$ is a 5- or 6-membered aromatic carbocyclic or heterocyclic ring, or a 9- or 10-membered aromatic carbobicyclic or heterobicyclic ring, wherein the heterocyclic or heterobicyclic ring comprises at least one nitrogen atom and optionally one or more, same or different additional heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more same or different substituents $R^X$;

$R^5$ is a 5- or 6-membered saturated heterocyclic ring, wherein said heterocyclic ring comprises one or more, same or different heteroatoms selected from O, N or S, wherein said N and/or S-atoms are independently oxidized or non-oxidized, and wherein each substitutable carbon or heteroatom is independently unsubstituted or substituted with one or more, same or different substituents $R^Y$;

and wherein $R^N$ is H, $CH_3$ or cyclopropyl;

$R^A$ is H, halogen, CN, OH, $C_1$-$C_3$-alkyl, $C_1$-$C_3$-alkoxy, or 3- to 6-membered saturated, partially or fully unsaturated, or aromatic carbocyclyl, or heterocyclyl, wherein the aforementioned heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

$R^C$ and $R^D$ are independently H, or $C_1$-$C_2$-alkyl; or $R^C$ and $R^D$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^E$ is H, $C_1$-$C_2$-alkyl, phenyl, benzyl, $OR^G$, or $NR^HR^I$;

$R^F$ is H, $C_1$-$C_2$-alkyl, $C_3$-$C_6$-cycloalkyl, phenyl, or benzyl;

$R^G$ is H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N-atoms are independently oxidized or non-oxidized;

$R^H$ and $R^I$ are independently H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N-atoms are independently oxidized or non-oxidized; or $R^H$ and $R^I$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^X$ is halogen, CN, $C_1$-$C_2$-alkyl, or $C_1$-$C_2$-alkoxy;

$R^Y$ is halogen, CN, OH, $C_1$-$C_2$-alkyl, $C_3$-$C_6$-cycloalkyl, $C_1$-$C_2$-alkoxy, $NR^CR^D$, $S(=O)_2NR^CR^D$, $C(=O)R^E$, or 5- or 6-membered saturated, partially or fully unsaturated, or aromatic carbocyclyl, carbocyclyl-$C_1$-$C_2$-alkyl, heterocyclyl, and heterocyclyl-$C_1$-$C_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$.

In a preferred embodiment, $R^A$ is H.

In another preferred embodiment, $R^N$ is H, $CH_3$ or cyclopropyl, preferably $CH_3$.

In another preferred embodiment, $R^1$, $R^2$ and $R^3$ are H.

In another preferred embodiment, $R^5$ is a 6-membered saturated heterocyclic ring, wherein said heterocyclic ring comprises one or more, same or different heteroatoms selected from O, N or S, wherein said N and/or S-atoms are independently oxidized or non-oxidized, and wherein each substitutable carbon or heteroatom is independently unsubstituted or substituted with one or more, same or different substituents $R^Y$.

In a more preferred embodiment, $R^5$ is piperidine, wherein each substitutable carbon or heteroatom in the piperidine ring is independently unsubstituted or substituted by one or more, same or different substituents $R^Y$.

In another more preferred embodiment, $R^5$ is piperidine, wherein each substitutable carbon atom in the piperidine ring is independently unsubstituted or substituted by one or more, same or different substituents $R^Y$; and wherein the nitrogen atom in the piperidine ring is preferably substituted with $R^Y$ being pyridinyl.

In another more preferred embodiment, $R^5$ is piperidine, wherein each substitutable carbon atom in the piperidine ring is independently unsubstituted or substituted by one or more, same or different substituents $R^Y$; and wherein the nitrogen atom in the piperidine ring is substituted with $R^Y$ being pyridinyl, which is unsubstituted or substituted with one or more, same or different substituents $R^X$, wherein $R^X$ is preferably methyl.

In a preferred embodiment, $R^4$ is pyridinyl, wherein each substitutable carbon atom in the cyclic ring is independently unsubstituted or substituted by one or more, same or different substituents $R^X$.

In a further aspect, the present invention relates to a pharmaceutical composition comprising a pharmaceutically effective amount of the compound of formula (I) as defined herein, and optionally a pharmaceutically acceptable carrier, diluent or excipient.

In yet another aspect, the present invention relates to a compound of formula (I) as defined herein or a pharmaceutical composition comprising the same as defined herein for use in medicine. In particular, the present invention relates to a compound of formula (I) as defined herein or a pharmaceutical composition comprising the same as defined herein for use in modulating STING, in particular activating STING.

In yet another aspect, the present invention relates to a compound of formula (I) as defined herein or a pharmaceutical composition comprising the same as defined herein for use in a method of treating a disease, in which the modulation of STING, in particular the activation of STING, is beneficial.

In one embodiment, the compound of the present invention or a pharmaceutical composition comprising the same is for use in the treatment of a disease selected from the group consisting of cancer, pre-cancerous syndromes, and infectious diseases; or for use in an immunogenic composition or as vaccine adjuvant.

In another embodiment, the compound of the present invention or a pharmaceutical composition comprising the same is for use in the treatment of a disease selected from the group consisting of inflammatory diseases, allergic diseases, and autoimmune diseases.

In a further aspect, the present invention relates to methods of treatment comprising the administration of a compound of formula (I) as defined herein or a pharmaceutical composition comprising the same as defined herein to a human or animal body.

DETAILED DESCRIPTION

Figure 1I:
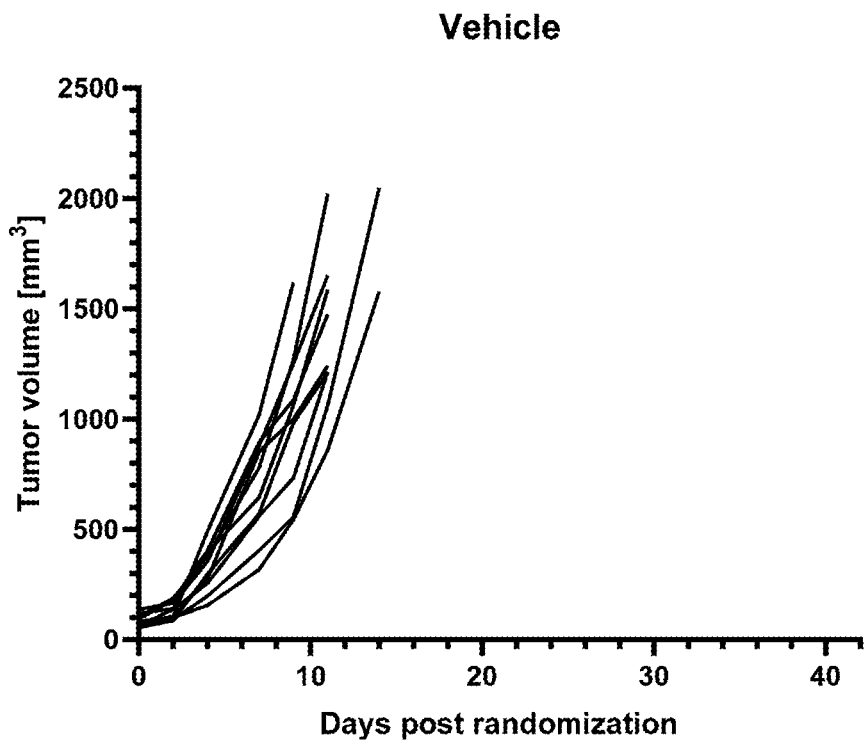
FIGS. 1(i) to (iii) show the in vivo anti-tumor efficacy of a compound according to Example 1 in CT26 murine colon carcinoma allograft in Balb/C female mice by depicting the tumor volume over time at different doses of the compound according to Example 1 in comparison to the vehicle.

In the following, preferred embodiments of the substituents in the above formula (I) are described in further detail.

It is to be understood that each preferred embodiment is relevant on its own as well as in combination with other preferred embodiments. Furthermore, it is to be understood that the preferences in each case also apply to the salts, stereoisomers, tautomers, and N-oxides of the compounds of the invention.

As indicated above, the present invention relates to a compound of formula (I)

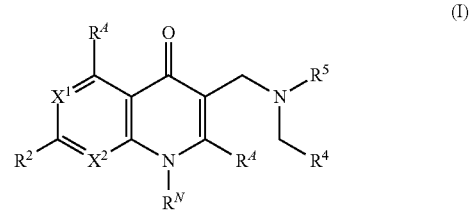

wherein
$X^1$ is $CR^1$ or N, and
$X^2$ is $CR^3$ or N.

Accordingly, the compound of formula (I) may therefore be a compound of formula (Ia), (Ib), (Ic) or (Id) as shown below:

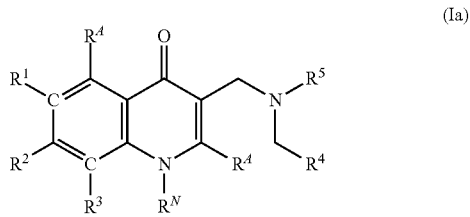

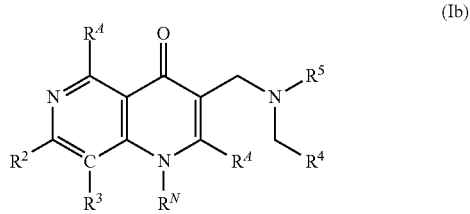

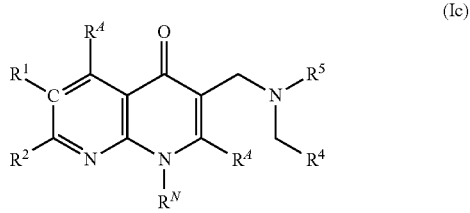

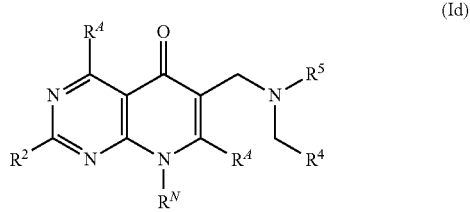

In connection with the compounds according to formula (Ia), (Ib), (Ic) and (Id), it is to be understood that the substituents $R^1$, $R^2$, $R^3$, $R^4$, $R^5$, $R^A$ and $R^N$ are as defined above in formula (I). Further preferred embodiments regarding these substituents are provided further below.

In a preferred embodiment, the compound of formula (I) is a compound of formula (Ia), (Ib) or (Ic). In a particularly preferred embodiment, the compound of formula (I) is a compound of formula (Ia), wherein the 6-membered ring that is fused to the 6-membered ring that contains the =O substituent is a 6-membered aromatic carbocyclic ring. Thus, the compound of formula (I) is preferably a compound of formula (Ia)

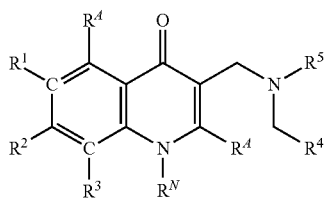

(Ia)

wherein the substituents $R^1$, $R^2$, $R^3$, $R^4$, $R^5$, $R^A$ and $R^N$ are as defined in formula (I) above, in particular wherein the substituents $R^1$, $R^2$ and $R^3$ are independently H, OH, CN, halogen, $C_1$-$C_4$-alkyl, $C_1$-$C_4$-alkoxy, aryloxy, benzyloxy, $C(=O)R^E$, $NR^F C(=O)R^E$, $NR^F$—$(C_1$-$C_4$-alkylene)-$C(=O)R^E$, or 4- to 6-membered saturated, partially or fully unsaturated, or aromatic carbocyclyl, carbocyclyl-$C_1$-$C_2$-alkyl, heterocyclyl, heterocyclyloxy or heterocyclyl-$C_1$-$C_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$.

In connection with the substituents $R^1$, $R^2$ and $R^3$ it is to be understood that $R^E$, $R^F$ and $R^X$ preferably have the meanings as defined above for the compound of formula (I).

In connection with the compounds of formula (I), as well as in connection with the compounds of formula (Ia), (Ib), (Ic) and (Id), especially in connection with the compounds of formula (Ia), (Ib) and (Ic), in particular with the compounds according to formula (Ia), the following preferred embodiments regarding the remaining substituents $R^1$, $R^2$, $R^3$, $R^4$, $R^5$, $R^A$ and $R^N$ are relevant.

As indicated above, in connection with the compounds of the present invention, $R^A$ is H, halogen, CN, OH, $C_1$-$C_3$-alkyl, $C_1$-$C_3$-alkoxy, or 3- to 6-membered saturated, partially or fully unsaturated, or aromatic carbocyclyl, or heterocyclyl, wherein the aforementioned heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

In a preferred embodiment,
$R^A$ is H, halogen, CN, or $C_1$-$C_3$-alkyl.
In another preferred embodiment,
$R^A$ is H, F, Cl, Br, or $C_1$-$C_3$-alkyl.
In a more preferred embodiment,
$R^A$ is H.

In one particular preferred embodiment, the compound according to formula (I) refers to a compound according to formula (Ia), wherein $X^1$ and $X^2$ are $CR^1$ and $CR^3$, and wherein $R^A$ is H. Such compounds may be represented by the following general formula (Ia*)

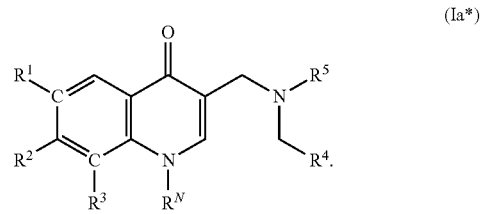

(Ia*)

In connection with the compounds according to formula (Ia*) it is to be understood that $R^1$, $R^2$, $R^3$, $R^4$, $R^5$ and $R^N$ are preferably as defined above.

Further, in connection with the compounds of the present invention, it is preferred that $R^N$ is H, $C_1$-$C_4$-alkyl, HO(C=O)—$C_1$-$C_4$-alkyl, or a 3- or 4-membered saturated carbocyclyl or heterocyclyl, wherein said heterocyclic ring comprises one or more, same or different heteroatoms selected from O, N or S, wherein said N and/or S-atoms are independently oxidized or non-oxidized, and wherein each substitutable carbon or heteroatom in the aforementioned groups is independently unsubstituted or substituted with one or more, same or different substituents $R^X$.

In particular, $R^N$ is H, $CH_3$, HO(C=O)—$C_1$-$C_4$-alkyl, or a 3- or 4-membered saturated carbocyclyl or heterocyclyl, wherein said heterocyclic ring comprises one or more, same or different heteroatoms selected from O, N or S, wherein said N and/or S-atoms are independently oxidized or non-oxidized, and wherein each substitutable carbon or heteroatom in the aforementioned groups is independently unsubstituted or substituted with one or more, same or different substituents $R^X$.

If $R^N$ is HO(C=O)—$C_1$-$C_4$-alkyl, or a 3- or 4-membered saturated carbocyclyl or heterocyclyl, $R^N$ is preferably any one of the following groups

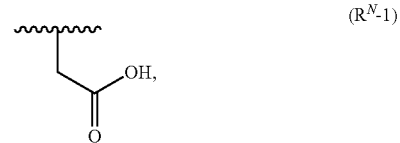

($R^N$-1)

($R^N$-2)

($R^N$-3)

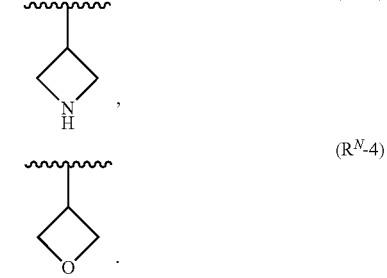

($R^N$-4)

In a preferred embodiment, $R^N$ is H, $CH_3$, or a 3- or 4-membered saturated carbocyclyl or heterocyclyl, wherein said heterocyclic ring comprises one or more, same or different heteroatoms selected from O, N or S, wherein said N and/or S-atoms are independently oxidized or non-oxidized, and wherein each substitutable carbon or heteroatom in the aforementioned groups is independently unsubstituted or substituted with one or more, same or different substituents $R^X$.

If $R^N$ is a 3- or 4-membered saturated carbocyclyl or heterocyclyl, $R^N$ is preferably any one of the following groups

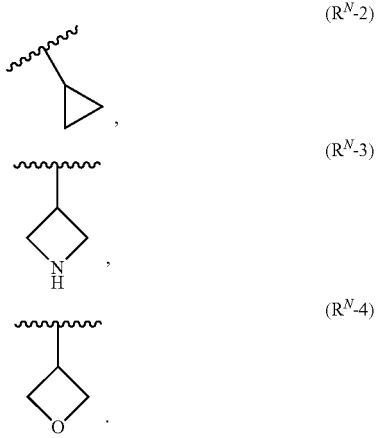

In a more preferred embodiment, $R^N$ is H, $CH_3$, or a 3-membered saturated carbocyclyl or heterocyclyl, wherein said heterocyclic ring comprises one or more, same or different heteroatoms selected from O, N or S, wherein said N and/or S-atoms are independently oxidized or non-oxidized, and wherein each substitutable carbon or heteroatom in the aforementioned groups is independently unsubstituted or substituted with one or more, same or different substituents $R^X$.

In another more preferred embodiment $R^N$ is H, $CH_3$, or a 3-membered saturated carbocyclyl, in particular cyclopropyl according to formula $R^N$-2.

In a more preferred embodiment, $R^N$ is H, $CH_3$ or cyclopropyl.

In a particularly preferred embodiment, $R^N$ is $CH_3$.

In another particularly preferred embodiment, $R^N$ is cyclopropyl.

Further, in connection with the compounds of the present invention, in particular in connection with the compounds according to formula (Ia) or (Ic), it is preferred that $R^1$ is H, OH, CN, halogen, $C_1$-$C_4$-alkyl, $C_1$-$C_4$-alkoxy, aryloxy, benzyloxy, C(=O)$R^E$, $NR^F$C(=O)$R^E$, $NR^F$—($C_1$-$C_4$-alkylene)-C(=O)$R^E$, or 4- to 6-membered saturated, partially or fully unsaturated, or aromatic carbocyclyl, carbocyclyl-$C_1$-$C_2$-alkyl, heterocyclyl, heterocyclyloxy or heterocyclyl-$C_1$-$C_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$.

In a preferred embodiment, $R^1$ is H, halogen, $C_1$-$C_4$-alkyl, or 4- to 6-membered saturated, partially or fully unsaturated, or aromatic carbocyclyl, carbocyclyl-$C_1$-$C_2$-alkyl, heterocyclyl, heterocyclyloxy or heterocyclyl-$C_1$-$C_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$.

In a more preferred embodiment, $R^1$ is H, F, Cl, Br, or $C_1$-$C_2$-alkyl.

In a particularly preferred embodiment, $R^1$ is H or F.

In connection with the above embodiments, it is to be understood that the remaining substituents $R^E$, $R^F$ and $R^X$ are preferably as defined above.

Further, in connection with the compounds of the present invention, it is preferred that $R^2$ is H, OH, CN, halogen, $C_1$-$C_4$-alkyl, $C_1$-$C_4$-alkoxy, aryloxy, benzyloxy, C(=O)$R^E$, $NR^F$C(=O)$R^E$, $NR^F$—($C_1$-$C_4$-alkylene)-C(=O)$R^E$, or 4- to 6-membered saturated, partially or fully unsaturated, or aromatic carbocyclyl, carbocyclyl-$C_1$-$C_2$-alkyl, heterocyclyl, heterocyclyloxy or heterocyclyl-$C_1$-$C_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$.

In a preferred embodiment, $R^2$ is H, halogen, $C_1$-$C_4$-alkyl, $C_1$-$C_4$-alkoxy, $NR^F$—($C_1$-$C_4$-alkylene)-C(=O)$R^E$, or 4- to 6-membered saturated, partially or fully unsaturated, or aromatic carbocyclyl, carbocyclyl-$C_1$-$C_2$-alkyl, heterocyclyl, heterocyclyloxy or heterocyclyl-$C_1$-$C_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$.

In a more preferred embodiment, $R^2$ is H, F, Br, Cl, $C_1$-$C_2$-alkoxy, $NR^F$—($C_1$-$C_4$-alkylene)-C(=O)$R^E$, or a 4- to 6-membered saturated heterocyclyl, or heterocyclyloxy, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$.

If $R^2$ is $NR^F$—($C_1$-$C_4$-alkylene)-C(=O)$R^E$, or a 4- to 6-membered saturated heterocyclyl, or heterocyclyloxy, $R^2$ is preferably any one of the following groups or any one of the following groups As can be seen from the formulae (R²-1) (R²-8), preferred R^X groups in connection with R² include CH₃, or C(=O)R^E. Furthermore, it is to be understood that the remaining substituents R^E and R^F are preferably as defined above. In connection with the above formulae (R²-1) (R²-8), it is to be understood that R² may optionally carry one or more, same or different further substituents R^X.

As can be seen from the formulae (R²-1) (R²-12), preferred R$^X$ groups in connection with R² include CH$_3$, C$_1$-C$_2$-haloalkyl, C(=O)CH$_3$, or the option that two R$^X$ together with the carbon atom to which they are bonded form a 3-membered saturated, partially or fully unsaturated, or aromatic carbocyclic ring. In connection with the above formulae (R²-1)-(R²-12), it is to be understood that R² may optionally carry one or more, same or different further substituents R$^X$.

In a more preferred embodiment,

R² is H, F, Br, Cl, or a 6-membered saturated heterocyclyl, wherein said heterocyclic ring comprises one or more nitrogen atoms as heteroatoms and wherein each substitutable carbon or heteroatom in the aforementioned groups is independently unsubstituted or substituted with one or more, same or different substituents R$^X$.

If R² is a 6-membered saturated heterocyclyl, R² is preferably any one of the following groups

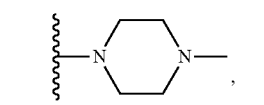
(R²-1)

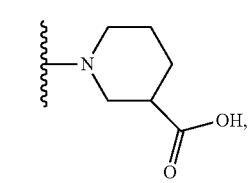
(R²-3)

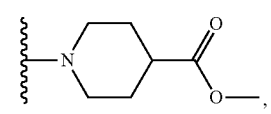
(R²-4)

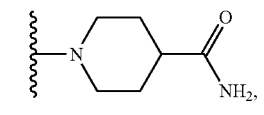
(R²-5)

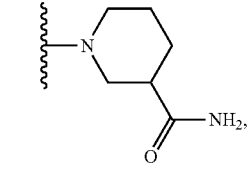
(R²-6)

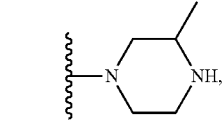
(R²-9)

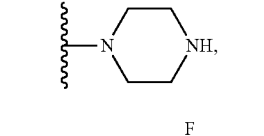
(R²-10)

(R²-11)

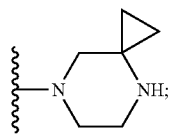
(R²-12)

or any one of the following groups

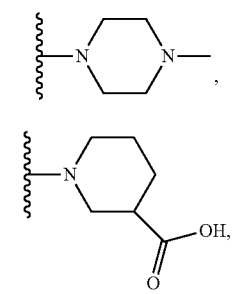
(R²-1)

(R²-3)

(R²-4)

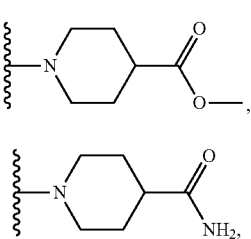
(R²-5)

(R²-6)

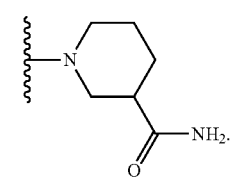

As can be seen from the formulae (R²-1)-(R²-6), preferred R$^X$ groups in connection with R² include CH$_3$, or C(=O)R$^E$, wherein R$^E$ is as defined above. As can be seen from the formulae (R²-1)-(R²-12), preferred R$^X$ groups in connection with R² include CH$_3$, C$_1$-C$_2$-haloalkyl, C(=O)CH$_3$, or the option that two R$^X$ together with the carbon atom to which they are bonded form a 3-membered saturated, partially or fully unsaturated, or aromatic carbocyclic ring. In connection with the above formulae (R²-1)-(R²-12) or formulae (R²-1)-(R²-6) it is to be understood that R² may optionally carry one or more, same or different further substituents R$^X$.

In one particularly preferred embodiment,

R² is H, F, Cl, Br, or any one of the following 6-membered saturated heterocyclyl groups

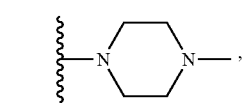
(R²-1)

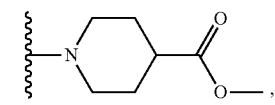
(R²-4)

-continued

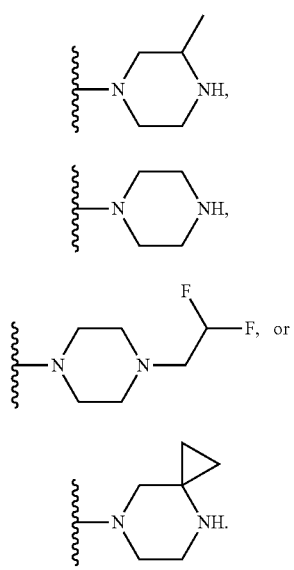

As can be seen from the formulae (R$^2$-1), (R$^2$-4), and (R$^2$-9) to (R$^2$-12), preferred R$^X$ groups in connection with R$^2$ include CH$_3$, C$_1$-C$_2$-haloalkyl, C(=O)CH$_3$, or the option that two R$^X$ together with the carbon atom to which they are bonded form a 3-membered saturated, partially or fully unsaturated, or aromatic carbocyclic ring. In connection with the above formulae (R$^2$-1), (R$^2$-4), and (R$^2$-7) to (R$^2$-10), it is to be understood that R$^2$ may optionally carry one or more, same or different further substituents R$^X$.

In another particularly preferred embodiment,
R$^2$ is H, F, Cl, Br, or any one of the following 6-membered saturated heterocyclyl groups

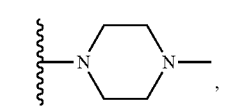

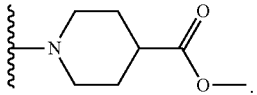

As can be seen from the formulae (R$^2$-1) and (R$^2$-4), preferred R$^X$ groups in connection with R$^2$ include CH$_3$, or C(=O)CH$_3$. In connection with the above formulae (R$^2$-1) and (R$^2$-4), it is to be understood that R$^2$ may optionally carry one or more, same or different further substituents R$^X$.

Further, in connection with the compounds of the present invention, in particular in connection with the compounds according formula (Ia) or (Ib),
R$^3$ is H, OH, CN, halogen, C$_1$-C$_4$-alkyl, C$_1$-C$_4$-alkoxy, aryloxy, benzyloxy, C(=O)R$^E$, NR$^F$C(=O)R$^E$, NR$^F$—(C$_1$-C$_4$-alkylene)-C(=O)R$^E$, or 4- to 6-membered saturated, partially or fully unsaturated, or aromatic carbocyclyl, carbocyclyl-C$_1$-C$_2$-alkyl, heterocyclyl, heterocyclyloxy or heterocyclyl-C$_1$-C$_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents R$^X$.

In a preferred embodiment,
R$^3$ is H, halogen, C$_1$-C$_4$-alkyl, or 4- to 6-membered saturated, partially or fully unsaturated, or aromatic carbocyclyl, carbocyclyl-C$_1$-C$_2$-alkyl, heterocyclyl, heterocyclyloxy or heterocyclyl-C$_1$-C$_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents R$^X$.

In a more preferred embodiment,
R$^3$ is H, halogen or C$_1$-C$_4$-alkyl.
In another more preferred embodiment,
R$^3$ is H, F, Cl, Br, or CH$_3$.
In a particularly preferred embodiment,
R$^3$ is H.

Further, in connection with the compounds of the present invention
R$^4$ is a 5- or 6-membered aromatic carbocyclic or heterocyclic ring, or a 9- or 10-membered aromatic carbobicyclic or heterobicyclic ring, wherein the heterocyclic or heterobicyclic ring comprises at least one nitrogen atom and optionally one or more, same or different additional heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more same or different substituents R$^X$.

In a preferred embodiment,
R$^4$ is a 6-membered aromatic carbocyclic or heterocyclic ring, wherein the heterocyclic ring comprises at least one nitrogen atom and optionally one or more, same or different additional heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more same or different substituents R$^X$.

In a more preferred embodiment,
R$^4$ is a 6-membered aromatic heterocyclic ring, wherein the heterocyclic ring comprises at least one nitrogen atom and optionally one or more, same or different additional heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more, same or different substituents R$^X$.

Preferably, the 6-membered aromatic heterocyclic ring comprises one or more nitrogen atoms as heteroatoms.
In a particularly preferred embodiment,
R$^4$ is pyridinyl, wherein each substitutable carbon or heteroatom in the cyclic ring is independently unsubstituted or substituted by one or more, same or different substituents R$^X$. Preferably, R$^4$ is any one of the following substituted pyridinyl rings

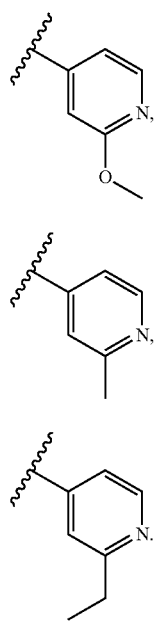

Thus, preferred R$^X$ groups in connection with R$^4$ include CH$_3$, CH$_2$CH$_3$, or C$_1$-alkoxy.

In a particularly preferred embodiment,

R$^4$ is methylpyridinyl.

Particularly preferably,

R$^4$ is:

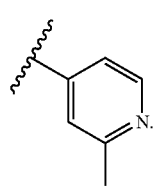

Further, in connection with the compounds of the present invention,

R$^5$ is a 5- or 6-membered saturated heterocyclic ring, wherein said heterocyclic ring comprises one or more, same or different heteroatoms selected from O, N or S, wherein said N and/or S-atoms are independently oxidized or non-oxidized, and wherein each substitutable carbon or heteroatom is independently unsubstituted or substituted with one or more, same or different substituents R$^Y$.

In one preferred embodiment,

R$^5$ is a 5- or 6-membered saturated heterocyclic ring, wherein said heterocyclic ring comprises one or more nitrogen atoms, wherein said N-atoms are independently oxidized or non-oxidized, and wherein each substitutable carbon or heteroatom is independently unsubstituted or substituted with one or more, same or different substituents R$^Y$.

In another preferred embodiment, R$^5$ refers to any one of the following unsubstituted or substituted rings

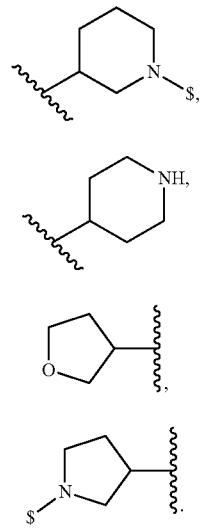

With regard to the above formulae (R$^5$-1)-(R$^5$-4), it is to be understood that the curled line indicates the connection to the remainder of the molecule and $ indicates the connection to the substituent R$^Y$. Particularly preferably R$^5$ is R$^5$-1.

Furthermore, it is to be understood that each substitutable carbon or heteroatom in the above displayed formulae (R$^5$-1)-(R$^5$-4) may optionally carry one or more, same or different (further) substituents R$^Y$.

Preferably,

R$^Y$ is halogen, CN, OH, C$_1$-C$_2$-alkyl, C$_1$-C$_2$-alkyl-OH, C$_3$-C$_5$-cycloalkyl, C$_1$-C$_2$-alkoxy, NR$^C$R$^D$, S(=O)$_2$R$^F$, C(=O)R$^E$, or 5- or 6-membered saturated, partially or fully unsaturated, or aromatic carbocyclyl, carbocyclyl-C$_1$-C$_2$-alkyl, heterocyclyl, and heterocyclyl-C$_1$-C$_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents R$^X$; or two R$^Y$ form =O; or two R$^Y$ attached to identical or neighboring carbon atoms may form a 3-membered carbocyclic ring.

If R$^Y$ is C(=O)R$^E$, or a 5- or 6-membered saturated, partially or fully unsaturated, or aromatic heterocyclyl, R$^Y$ is preferably any one of the following unsubstituted or substituted groups

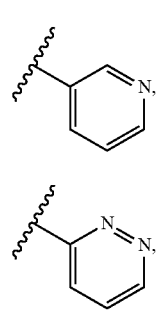

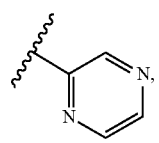 (R$^Y$-3)

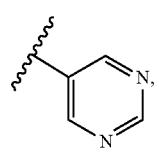 (R$^Y$-4)

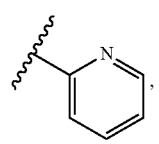 (R$^Y$-5)

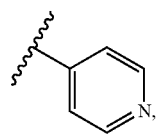 (R$^Y$-6)

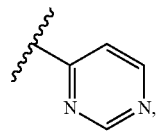 (R$^Y$-7)

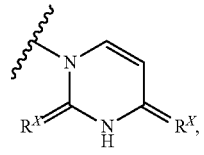 (R$^Y$-8)

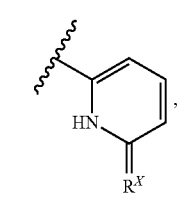 (R$^Y$-9)

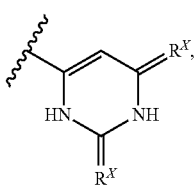 (R$^Y$-10)

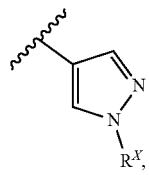 (R$^Y$-11)

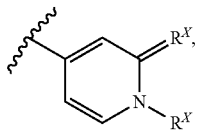 (R$^Y$-12)

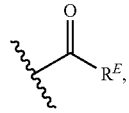 (R$^Y$-13)

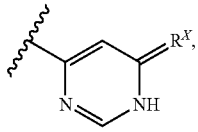 (R$^Y$-14)

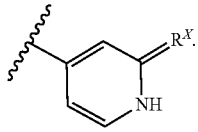 (R$^Y$-15)

In connection with the above substituted groups (R$^Y$-1)-(R$^Y$-15), it is to be understood that each substitutable carbon or heteroatom may optionally carry one or more, same or different (further) substituents R$^X$.

Furthermore, it is to be understood that the remaining substituents R$^C$, R$^D$, R$^E$ and R$^X$ are preferably as defined above.

In a preferred embodiment,

R$^5$ is a 6-membered saturated heterocyclic ring, wherein said heterocyclic ring comprises one or more, same or different heteroatoms selected from O, N or S, wherein said N and/or S-atoms are independently oxidized or non-oxidized, and wherein each substitutable carbon or heteroatom is independently unsubstituted or substituted with one or more, same or different substituents R$^Y$.

In this connection, it is to be understood that R$^Y$ is preferably as defined above.

In another preferred embodiment, R$^5$ is any one of (R$^5$-1)-(R$^5$-4).

In connection with the above embodiment, it is to be understood that each substitutable carbon or heteroatom in the above-mentioned rings is independently unsubstituted or substituted with one or more, same or different substituents R$^Y$, as defined above.

Furthermore, it is to be understood that preferably R$^Y$ is OH, halogen, C$_1$-C$_2$-alkyl, C$_1$-C$_2$-alkyl-OH, C(=O)R$^E$, a 5- or 6-membered partially unsaturated, or aromatic heterocyclyl, wherein the aforementioned heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents R$^X$; or two R$^Y$ form =O; or two R$^Y$ attached to identical or neighboring carbon atoms may form a 3-membered carbocyclic ring.

Preferably, the aforementioned heterocyclic rings comprise one or more nitrogen atoms as heteroatoms.

Furthermore, it is to be understood that the remaining substituents $R^E$ and $R^X$ are preferably as defined above.

In a particularly preferred embodiment, $R^5$ is piperidine, wherein each substitutable carbon or heteroatom in the piperidine ring is independently unsubstituted or substituted by one or more, same or different substituents $R^Y$.

In connection with the above particularly preferred embodiment, it is to be understood that preferably $R^Y$ is OH, halogen, $C_1$-$C_2$-alkyl, C(=O)$R^E$, or a 5- or 6-membered partially unsaturated, or aromatic heterocyclyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$; or two $R^Y$ form =O; or two $R^Y$ attached to identical or neighboring carbon atoms may form a 3-membered carbocyclic ring.

Preferably, the heterocyclic rings comprise one or more nitrogen atoms as heteroatoms.

Furthermore, it is to be understood that the remaining substituents $R^E$ and $R^X$ are as defined above.

In particular, $R^5$, which is further substituted with one or more, same or different substituents $R^Y$ as defined above, is any one of the following structural formulae

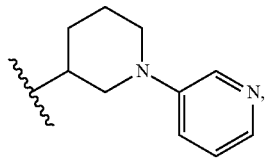
(R$^{5Y}$-1)

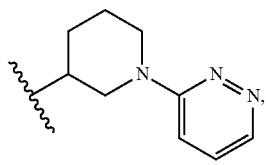
(R$^{5Y}$-2)

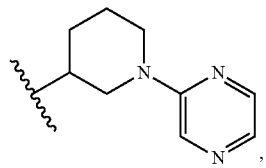
(R$^{5Y}$-3)

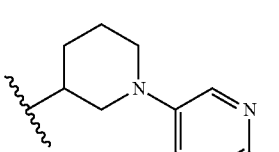
(R$^{5Y}$-4)

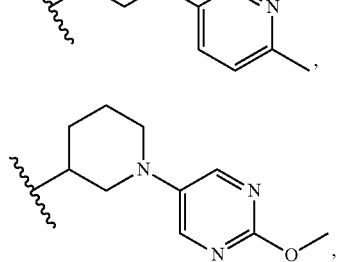
(R$^{5Y}$-5)

-continued

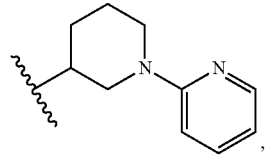
(R$^{5Y}$-6)

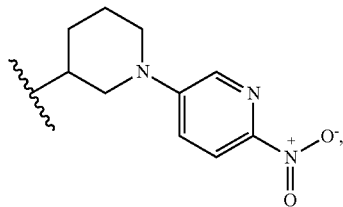
(R$^{5Y}$-7)

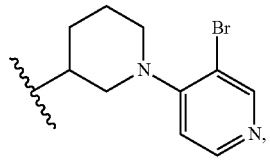
(R$^{5Y}$-8)

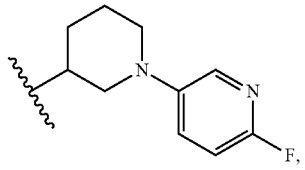
(R$^{5Y}$-9)

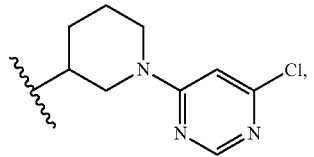
(R$^{5Y}$-10)

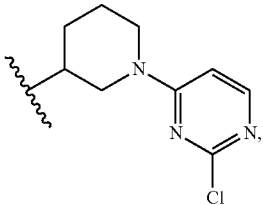
(R$^{5Y}$-11)

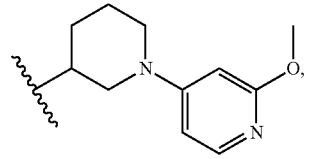
(R$^{5Y}$-12)

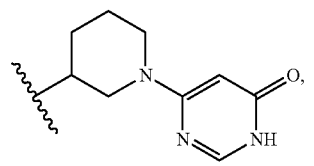
(R$^{5Y}$-13)

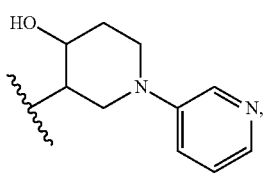
(R^{5Y}-14)
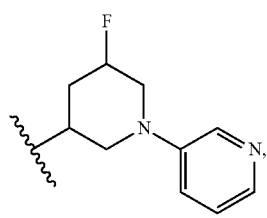
(R^{5Y}-15)
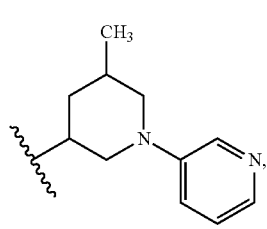
(R^{5Y}-16)
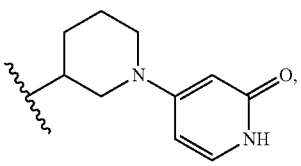
(R^{5Y}-17)
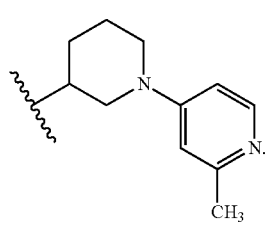
(R^{5Y}-18)
or any one of the following structural formulae
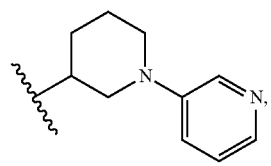
(R^{5Y}-1)
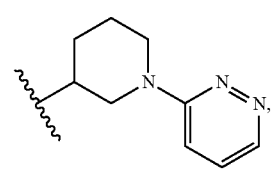
(R^{5Y}-2)
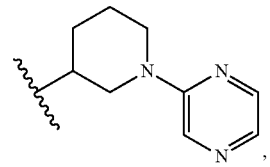
(R^{5Y}-3)
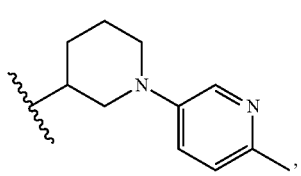
(R^{5Y}-4)
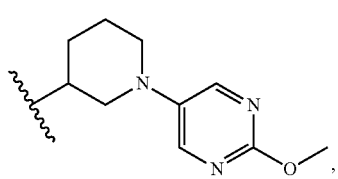
(R^{5Y}-5)
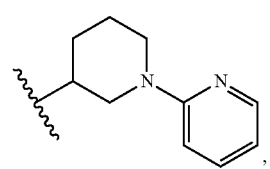
(R^{5Y}-6)
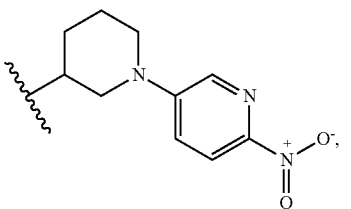
(R^{5Y}-7)
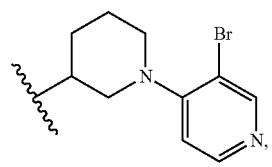
(R^{5Y}-8)
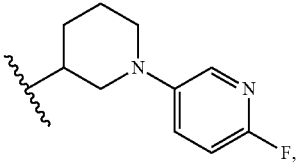
(R^{5Y}-9)
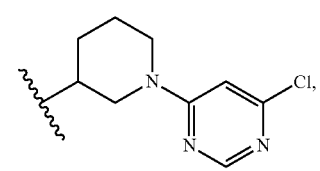
(R^{5Y}-10)

ents $R^Y$; and wherein the nitrogen atom in the piperidine ring is preferably substituted with $R^Y$ being pyridinyl.

In this connection it is to be understood that if one or more substituents $R^Y$ on each substitutable carbon atom of the piperidine ring are present, $R^Y$ is preferably as defined above.

In another particularly preferred embodiment, $R^5$ is piperidine, wherein each substitutable carbon atom in the piperidine ring is independently unsubstituted or substituted by one or more, same or different substituents $R^Y$; and wherein the nitrogen atom in the piperidine ring is preferably substituted with $R^Y$ being pyridinyl, which is unsubstituted or substituted with one or more, same or different substituents $R^X$, wherein $R^X$ is preferably methyl.

In another particularly preferred embodiment, the $R^5$ group is any one of the following groups:

It is especially preferred that the $R^5$ group is

In this connection, it becomes evident that $R^Y$ may optionally carry one or more, same or different substituents $R^X$. Preferred $R^X$ groups in this connection include $CH_3$, F, Cl, Br, $NO_2$, $C_1$-alkoxy, or two $R^X$ form =O.

In another particularly preferred embodiment, $R^5$ is piperidine, wherein each substitutable carbon atom in the piperidine ring is independently unsubstituted or substituted by one or more, same or different substitu- Thus, particularly preferred compounds of the invention are compounds of formula (Ia*) as compiled in the tables below.

Table 1
Compounds of the formula (Ia*), in which $R^3$ is H, $R^1$ is H, $R^4$ is $R^4$-1, $R^N$ is H and $R^2$ and $R^5$ correspond in each case to one row of Table A.

Table 2
Compounds of the formula (Ia*), in which $R^3$ is H, $R^1$ is F, $R^4$ is $R^4$-1, $R^N$ is H and $R^2$ and $R^5$ correspond in each case to one row of Table A.

Table 3
Compounds of the formula (Ia*), in which $R^3$ is H, $R^1$ is H, $R^4$ is $R^4$-2, $R^N$ is H and $R^2$ and $R^5$ correspond in each case to one row of Table A.

Table 4
Compounds of the formula (Ia*), in which $R^3$ is H, $R^1$ is F, $R^4$ is $R^4$-2, $R^N$ is H and $R^2$ and $R^5$ correspond in each case to one row of Table A.

Table 5
Compounds of the formula (Ia*), in which $R^3$ is H, $R^1$ is H, $R^4$ is $R^4$-3, $R^N$ is H and $R^2$ and $R^5$ correspond in each case to one row of Table A.

Table 6
Compounds of the formula (Ia*), in which $R^3$ is H, $R^1$ is F, $R^4$ is $R^4$-3, $R^N$ is H and $R^2$ and $R^5$ correspond in each case to one row of Table A.

Table 7
Compounds of the formula (Ia*), in which $R^3$ is H, $R^1$ is H, $R^4$ is $R^4$-1, $R^N$ is $CH_3$ and $R^2$ and $R^5$ correspond in each case to one row of Table A.

Table 8
Compounds of the formula (Ia*), in which $R^3$ is H, $R^1$ is F, $R^4$ is $R^4$-1, $R^N$ is $CH_3$ and $R^2$ and $R^5$ correspond in each case to one row of Table A.

Table 9
Compounds of the formula (Ia*), in which $R^3$ is H, $R^1$ is H, $R^4$ is $R^4$-2, $R^N$ is $CH_3$ and $R^2$ and $R^5$ correspond in each case to one row of Table A.

Table 10
Compounds of the formula (Ia*), in which $R^3$ is H, $R^1$ is F, $R^4$ is $R^4$-2, $R^N$ is $CH_3$ and $R^2$ and $R^5$ correspond in each case to one row of Table A.

Table 11
Compounds of the formula (Ia*), in which $R^3$ is H, $R^1$ is H, $R^4$ is $R^4$-3, $R^N$ is $CH_3$ and $R^2$ and $R^5$ correspond in each case to one row of Table A.

Table 12
Compounds of the formula (Ia*), in which $R^3$ is H, $R^1$ is F, $R^4$ is $R^4$-3, $R^N$ is $CH_3$ and $R^2$ and $R^5$ correspond in each case to one row of Table A.

Table 13
Compounds of the formula (Ia*), in which $R^3$ is H, $R^1$ is H, $R^4$ is $R^4$-1, $R^N$ is cyclopropyl and $R^2$ and $R^5$ correspond in each case to one row of Table A.

Table 14
Compounds of the formula (Ia*), in which $R^3$ is H, $R^1$ is F, $R^4$ is $R^4$-1, $R^N$ is cyclopropyl and $R^2$ and $R^5$ correspond in each case to one row of Table A.

Table 15
Compounds of the formula (Ia*), in which $R^3$ is H, $R^1$ is H, $R^4$ is $R^4$-2, $R^N$ is cyclopropyl and $R^2$ and $R^5$ correspond in each case to one row of Table A.

Table 16
Compounds of the formula (Ia*), in which $R^3$ is H, $R^1$ is F, $R^4$ is $R^4$-2, $R^N$ is cyclopropyl and $R^2$ and $R^5$ correspond in each case to one row of Table A.

Table 17
Compounds of the formula (Ia*), in which $R^3$ is H, $R^1$ is H, $R^4$ is $R^4$-3, $R^N$ is cyclopropyl and $R^2$ and $R^5$ correspond in each case to one row of Table A.

Table 18
Compounds of the formula (Ia*), in which $R^3$ is H, $R^1$ is F, $R^4$ is $R^4$-3, $R^N$ is cyclopropyl and $R^2$ and $R^5$ correspond in each case to one row of Table A.

TABLE A

| No. | $R^2$ | $R^5$ |
| --- | --- | --- |
| A-1 | H | $R^{5Y}$-1 |
| A-2 | H | $R^{5Y}$-2 |
| A-3 | H | $R^{5Y}$-3 |
| A-4 | H | $R^{5Y}$-4 |
| A-5 | H | $R^{5Y}$-5 |
| A-6 | H | $R^{5Y}$-6 |
| A-7 | H | $R^{5Y}$-7 |
| A-8 | H | $R^{5Y}$-8 |
| A-9 | H | $R^{5Y}$-9 |
| A-10 | H | $R^{5Y}$-10 |
| A-11 | H | $R^{5Y}$-11 |
| A-12 | H | $R^{5Y}$-12 |
| A-13 | H | $R^{5Y}$-13 |
| A-14 | H | $R^{5Y}$-14 |
| A-15 | H | $R^{5Y}$-15 |
| A-16 | H | $R^{5Y}$-16 |
| A-17 | H | $R^{5Y}$-17 |
| A-18 | F | $R^{5Y}$-1 |
| A-19 | F | $R^{5Y}$-2 |
| A-20 | F | $R^{5Y}$-3 |
| A-21 | F | $R^{5Y}$-4 |
| A-22 | F | $R^{5Y}$-5 |
| A-23 | F | $R^{5Y}$-6 |
| A-24 | F | $R^{5Y}$-7 |
| A-25 | F | $R^{5Y}$-8 |
| A-26 | F | $R^{5Y}$-9 |
| A-27 | F | $R^{5Y}$-10 |
| A-28 | F | $R^{5Y}$-11 |
| A-29 | F | $R^{5Y}$-12 |
| A-30 | F | $R^{5Y}$-13 |
| A-31 | F | $R^{5Y}$-14 |
| A-32 | F | $R^{5Y}$-15 |
| A-33 | F | $R^{5Y}$-16 |
| A-34 | F | $R^{5Y}$-17 |
| A-35 | Cl | $R^{5Y}$-1 |
| A-36 | Cl | $R^{5Y}$-2 |
| A-37 | Cl | $R^{5Y}$-3 |
| A-38 | Cl | $R^{5Y}$-4 |
| A-39 | Cl | $R^{5Y}$-5 |
| A-40 | Cl | $R^{5Y}$-6 |
| A-41 | Cl | $R^{5Y}$-7 |
| A-42 | Cl | $R^{5Y}$-8 |
| A-43 | Cl | $R^{5Y}$-9 |
| A-44 | Cl | $R^{5Y}$-10 |
| A-45 | Cl | $R^{5Y}$-11 |
| A-46 | Cl | $R^{5Y}$-12 |
| A-47 | Cl | $R^{5Y}$-13 |
| A-48 | Cl | $R^{5Y}$-14 |
| A-49 | Cl | $R^{5Y}$-15 |
| A-50 | Cl | $R^{5Y}$-16 |
| A-51 | Cl | $R^{5Y}$-17 |
| A-52 | Br | $R^{5Y}$-1 |
| A-53 | Br | $R^{5Y}$-2 |
| A-54 | Br | $R^{5Y}$-3 |
| A-55 | Br | $R^{5Y}$-4 |
| A-56 | Br | $R^{5Y}$-5 |
| A-57 | Br | $R^{5Y}$-6 |
| A-58 | Br | $R^{5Y}$-7 |
| A-59 | Br | $R^{5Y}$-8 |
| A-60 | Br | $R^{5Y}$-9 |
| A-61 | Br | $R^{5Y}$-11 |
| A-62 | Br | $R^{5Y}$-11 |
| A-63 | Br | $R^{5Y}$-12 |
| A-64 | Br | $R^{5Y}$-13 |
| A-65 | Br | $R^{5Y}$-14 |
| A-66 | Br | $R^{5Y}$-15 |
| A-67 | Br | $R^{5Y}$-16 |
| A-68 | Br | $R^{5Y}$-17 |
| A-69 | $OCH_3$ | $R^{5Y}$-1 |
| A-70 | $OCH_3$ | $R^{5Y}$-2 |
| A-71 | $OCH_3$ | $R^{5Y}$-3 |
| A-72 | $OCH_3$ | $R^{5Y}$-4 |

TABLE A-continued

| No. | R² | R⁵ |
|---|---|---|
| A-73 | OCH₃ | R⁵ʸ-5 |
| A-74 | OCH₃ | R⁵ʸ-6 |
| A-75 | OCH₃ | R⁵ʸ-7 |
| A-76 | OCH₃ | R⁵ʸ-8 |
| A-77 | OCH₃ | R⁵ʸ-9 |
| A-78 | OCH₃ | R⁵ʸ-10 |
| A-79 | OCH₃ | R⁵ʸ-11 |
| A-80 | OCH₃ | R⁵ʸ-12 |
| A-81 | OCH₃ | R⁵ʸ-13 |
| A-82 | OCH₃ | R⁵ʸ-14 |
| A-83 | OCH₃ | R⁵ʸ-15 |
| A-84 | OCH₃ | R⁵ʸ-16 |
| A-85 | OCH₃ | R⁵ʸ-17 |
| A-86 | R²-1 | R⁵ʸ-1 |
| A-87 | R²-1 | R⁵ʸ-2 |
| A-88 | R²-1 | R⁵ʸ-3 |
| A-89 | R²-1 | R⁵ʸ-4 |
| A-90 | R²-1 | R⁵ʸ-5 |
| A-91 | R²-1 | R⁵ʸ-6 |
| A-92 | R²-1 | R⁵ʸ-7 |
| A-93 | R²-1 | R⁵ʸ-8 |
| A-94 | R²-1 | R⁵ʸ-9 |
| A-95 | R²-1 | R⁵ʸ-10 |
| A-96 | R²-1 | R⁵ʸ-11 |
| A-97 | R²-1 | R⁵ʸ-12 |
| A-98 | R²-1 | R⁵ʸ-13 |
| A-99 | R²-1 | R⁵ʸ-14 |
| A-100 | R²-1 | R⁵ʸ-15 |
| A-101 | R²-1 | R⁵ʸ-16 |
| A-102 | R²-1 | R⁵ʸ-17 |
| A-103 | R²-4 | R⁵ʸ-1 |
| A-104 | R²-4 | R⁵ʸ-2 |
| A-105 | R²-4 | R⁵ʸ-3 |
| A-106 | R²-4 | R⁵ʸ-4 |
| A-107 | R²-4 | R⁵ʸ-5 |
| A-108 | R²-4 | R⁵ʸ-6 |
| A-109 | R²-4 | R⁵ʸ-7 |
| A-110 | R²-4 | R⁵ʸ-8 |
| A-111 | R²-4 | R⁵ʸ-9 |
| A-112 | R²-4 | R⁵ʸ-10 |
| A-113 | R²-4 | R⁵ʸ-11 |
| A-114 | R²-4 | R⁵ʸ-12 |
| A-115 | R²-4 | R⁵ʸ-13 |
| A-116 | R²-4 | R⁵ʸ-14 |
| A-117 | R²-4 | R⁵ʸ-15 |
| A-118 | R²-4 | R⁵ʸ-16 |
| A-119 | R²-4 | R⁵ʸ-17 |
| A-120 | R²-9 | R⁵ʸ-1 |
| A-121 | R²-9 | R⁵ʸ-2 |
| A-122 | R²-9 | R⁵ʸ-3 |
| A-123 | R²-9 | R⁵ʸ-4 |
| A-124 | R²-9 | R⁵ʸ-5 |
| A-125 | R²-9 | R⁵ʸ-6 |
| A-126 | R²-9 | R⁵ʸ-7 |
| A-127 | R²-9 | R⁵ʸ-8 |
| A-128 | R²-9 | R⁵ʸ-9 |
| A-129 | R²-9 | R⁵ʸ-10 |
| A-130 | R²-9 | R⁵ʸ-11 |
| A-131 | R²-9 | R⁵ʸ-12 |
| A-132 | R²-9 | R⁵ʸ-13 |
| A-133 | R²-9 | R⁵ʸ-14 |
| A-134 | R²-9 | R⁵ʸ-15 |
| A-135 | R²-9 | R⁵ʸ-16 |
| A-136 | R²-9 | R⁵ʸ-17 |
| A-137 | R²-10 | R⁵ʸ-1 |
| A-138 | R²-10 | R⁵ʸ-2 |
| A-139 | R²-10 | R⁵ʸ-3 |
| A-140 | R²-10 | R⁵ʸ-4 |
| A-141 | R²-10 | R⁵ʸ-5 |
| A-142 | R²-10 | R⁵ʸ-6 |
| A-143 | R²-10 | R⁵ʸ-7 |
| A-144 | R²-10 | R⁵ʸ-8 |
| A-145 | R²-10 | R⁵ʸ-9 |
| A-146 | R²-10 | R⁵ʸ-10 |
| A-147 | R²-10 | R⁵ʸ-11 |
| A-148 | R²-10 | R⁵ʸ-12 |
| A-149 | R²-10 | R⁵ʸ-13 |
| A-150 | R²-10 | R⁵ʸ-14 |
| A-151 | R²-10 | R⁵ʸ-15 |
| A-152 | R²-10 | R⁵ʸ-16 |
| A-153 | R²-10 | R⁵ʸ-17 |
| A-154 | R²-11 | R⁵ʸ-1 |
| A-155 | R²-11 | R⁵ʸ-2 |
| A-156 | R²-11 | R⁵ʸ-3 |
| A-157 | R²-11 | R⁵ʸ-4 |
| A-158 | R²-11 | R⁵ʸ-5 |
| A-159 | R²-11 | R⁵ʸ-6 |
| A-160 | R²-11 | R⁵ʸ-7 |
| A-161 | R²-11 | R⁵ʸ-8 |
| A-162 | R²-11 | R⁵ʸ-9 |
| A-163 | R²-11 | R⁵ʸ-10 |
| A-164 | R²-11 | R⁵ʸ-11 |
| A-165 | R²-11 | R⁵ʸ-12 |
| A-166 | R²-11 | R⁵ʸ-13 |
| A-167 | R²-11 | R⁵ʸ-14 |
| A-168 | R²-11 | R⁵ʸ-15 |
| A-169 | R²-11 | R⁵ʸ-16 |
| A-170 | R²-11 | R⁵ʸ-17 |
| A-171 | R²-12 | R⁵ʸ-1 |
| A-172 | R²-12 | R⁵ʸ-2 |
| A-173 | R²-12 | R⁵ʸ-3 |
| A-174 | R²-12 | R⁵ʸ-4 |
| A-175 | R²-12 | R⁵ʸ-5 |
| A-176 | R²-12 | R⁵ʸ-6 |
| A-177 | R²-12 | R⁵ʸ-7 |
| A-178 | R²-12 | R⁵ʸ-8 |
| A-179 | R²-12 | R⁵ʸ-9 |
| A-180 | R²-12 | R⁵ʸ-10 |
| A-181 | R²-12 | R⁵ʸ-11 |
| A-182 | R²-12 | R⁵ʸ-12 |
| A-183 | R²-12 | R⁵ʸ-13 |
| A-184 | R²-12 | R⁵ʸ-14 |
| A-185 | R²-12 | R⁵ʸ-15 |
| A-186 | R²-12 | R⁵ʸ-16 |
| A-187 | R²-12 | R⁵ʸ-17 |

It has been found that the compounds as defined in the above tables are particularly advantageous as STING agonists, and may therefore particularly advantageously be used in the pharmaceutical compositions of the present invention as well as the medical uses as defined herein. Therefore, the compound of formula (I) of the invention is preferably a compound according to any one of tables 1-18, and the present invention preferably relates to pharmaceutical compositions comprising the same and to medical uses thereof.

In certain particularly preferred embodiments, the compound according to formula (I) is selected from the group consisting of 3-({[(2-methoxypyridin-4-yl)methyl][(3S)-1-(pyridin-3-yl)piperidin-3-yl]amino}methyl)-1-methyl-1,4-dihydroquinolin-4-one, 1-methyl-3-({[(2-methylpyridin-4-yl)methyl][1-(pyridin-3-yl)piperidin-3-yl]amino}methyl)-1,4-dihydroquinolin-4-one, 3-({[(2-methoxypyridin-4-yl)methyl][1-(pyridazin-3-yl)piperidin-3-yl]amino}methyl)-1-methyl-1,4-dihydroquinolin-4-one, 3-({[(2-methoxypyridin-4-yl)methyl][1-(pyrazin-2-yl)piperidin-3-yl]amino}methyl)-1-methyl-1,4-dihydroquinolin-4-one, 1-methyl-3-({[(2-methylpyridin-4-yl)methyl][(3S)-1-(pyridin-3-yl)piperidin-3-yl]amino}methyl)-1,4-dihydroquinolin-4-one, 3-({[(2-methoxypyridin-4-yl)methyl][(3S)-1-(pyridin-3-yl)piperidin-3-yl]amino}methyl)-1,4-dihydroquinolin-4-one, 1-methyl-3-({[(3S)-1-(6-methylpyridin-3-yl)piperidin-3-yl][(2-methylpyridin-4-yl)methyl]amino}methyl)-1,4-dihydroquinolin-4-one, 3-({[(3S)-1-(2-methoxypyrimidin-5-yl)piperidin-3-yl][(2-methylpyridin-4-yl)methyl]amino}methyl)-1-methyl-1,4-dihydroquinolin-4-one, 1-cyclopropyl-6-fluoro-3-({[(2-methoxypyridin-4-yl)methyl][(3S)-1-(pyridin-3-yl)piperidin-3-yl]amino}methyl)-7-(4-methylpiperazin-1-yl)-

1,4-dihydroquinolin-4-one, 1-cyclopropyl-6-fluoro-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-methoxypyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-methylpyridin-4-yl)methyl][(3S)-1-(pyridin-3-yl)piperidin-3-yl]amino}methyl)-1,4-dihydroquinolin-4-one, 1-methyl-3-({[(2-methylpyridin-4-yl)methyl][(3S)-1-(pyridin-2-yl)piperidin-3-yl]amino}methyl)-1,4-dihydroquinolin-4-one, 1-methyl-3-({[(2-methylpyridin-4-yl)methyl][(3S)-1-(6-nitropyridin-3-yl)piperidin-3-yl]amino}methyl)-1,4-dihydroquinolin-4-one, 3-({[(3S)-1-(3-bromopyridin-4-yl)piperidin-3-yl][(2-methylpyridin-4-yl)methyl]amino}methyl)-1-methyl-1,4-dihydroquinolin-4-one, 3-({[(3S)-1-(6-fluoropyridin-3-yl)piperidin-3-yl][(2-methylpyridin-4-yl)methyl]amino}methyl)-1-methyl-1,4-dihydroquinolin-4-one, 3-({[(3S)-1-(6-chloropyrimidin-4-yl)piperidin-3-yl][(2-methylpyridin-4-yl)methyl]amino}methyl)-1-methyl-1,4-dihydroquinolin-4-one, 1-methyl-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one, 3-({[(3S)-1-(2-chloropyrimidin-4-yl)piperidin-3-yl][(2-methylpyridin-4-yl)methyl]amino}methyl)-1-methyl-1,4-dihydroquinolin-4-one, 3-({[(3S)-1-(2-methoxypyridin-4-yl)piperidin-3-yl][(2-methylpyridin-4-yl)methyl]amino}methyl)-1-methyl-1,4-dihydroquinolin-4-one, 3-({[(2-ethylpyridin-4-yl)methyl][1-(pyridin-3-yl)piperidin-3-yl]amino}methyl)-1-methyl-1,4-dihydroquinolin-4-one, 1-methyl-3-({[(2-methylpyridin-4-yl)methyl][(3S)-1-(6-oxo-1,6-dihydropyrimidin-4-yl)piperidin-3-yl]amino}methyl)-1,4-dihydroquinolin-4-one, 7-bromo-1-methyl-3-({[(2-methylpyridin-4-yl)methyl][(3S)-1-(pyridin-3-yl)piperidin-3-yl]amino}methyl)-1,4-dihydroquinolin-4-one, 3-({[(3R,4R)-4-hydroxy-1-(pyridin-3-yl)piperidin-3-yl][(2-methylpyridin-4-yl)methyl]amino}methyl)-1-methyl-1,4-dihydroquinolin-4-one, 7-chloro-6-fluoro-1-methyl-3-({[(2-methylpyridin-4-yl)methyl][(3S)-1-(pyridin-3-yl)piperidin-3-yl]amino}methyl)-1,4-dihydroquinolin-4-one, 3-({[(3S,5S)-5-fluoro-1-(pyridin-3-yl)piperidin-3-yl][(2-methylpyridin-4-yl)methyl]amino}methyl)-1-methyl-1,4-dihydroquinolin-4-one, 1-methyl-3-({[(3S,5R)-5-methyl-1-(pyridin-3-yl)piperidin-3-yl][(2-methylpyridin-4-yl)methyl]amino}methyl)-1,4-dihydroquinolin-4-one, 7-chloro-1-cyclopropyl-6-fluoro-3-({[(2-methoxypyridin-4-yl)methyl][(3S)-1-(pyridin-3-yl)piperidin-3-yl]amino}methyl)-1,4-dihydroquinolin-4-one, methyl 1-[1-methyl-3-({[(2-methylpyridin-4-yl)methyl][(3S)-1-(pyridin-3-yl)piperidin-3-yl]amino}methyl)-4-oxo-1,4-dihydroquinolin-7-yl]piperidine-4-carboxylate, 1-methyl-3-({[(2-methylpyridin-4-yl)methyl][(3S)-1-(2-oxo-1,2-dihydropyridin-4-yl)piperidin-3-yl]amino}methyl)-1,4-dihydroquinolin-4-one, 1-cyclopropyl-6,7-difluoro-3-({[(2-methoxypyridin-4-yl)methyl][(3S)-1-(6-methylpyridin-3-yl)piperidin-3-yl]amino}methyl)-1,4-dihydroquinolin-4-one, 7-chloro-1-cyclopropyl-6-fluoro-3-({[(2-methylpyridin-4-yl)methyl][(3S)-1-(pyridin-3-yl)piperidin-3-yl]amino}methyl)-1,4-dihydroquinolin-4-one, 3-({[(2-methoxypyridin-4-yl)methyl][(3S)-1-(pyridin-3-yl)piperidin-3-yl]amino}methyl)-1,4-dihydroquinolin-4-one, 3-({[(2-methylpyridin-4-yl)methyl][(3S)-1-(pyridin-3-yl)piperidin-3-yl]amino}methyl)-1,4-dihydroquinolin-4-one, 7-bromo-1-methyl-3-({[(3S)-1-(6-methylpyridin-3-yl)piperidin-3-yl][(2-methylpyridin-4-yl)methyl]amino}methyl)-1,4-dihydroquinolin-4-one, 7-chloro-1-cyclopropyl-3-({[(3S)-1-(6-methylpyridin-3-yl)piperidin-3-yl][(2-methylpyridin-4-yl)methyl]amino}methyl)-1,4-dihydroquinolin-4-one, 1-cyclopropyl-6-fluoro-7-methoxy-3-({[(3S)-1-(6-methylpyridin-3-yl)piperidin-3-yl][(2-methylpyridin-4-yl)methyl]amino}methyl)-1,4-dihydro-1,8-naphthyridin-4-one, 3-({[(3S)-1-(5-bromopyrimidin-2-yl)piperidin-3-yl][(2-methylpyridin-4-yl)methyl]amino}methyl)-1-methyl-1,4-dihydroquinolin-4-one 3-({[5,5-difluoro-1-(pyridin-3-yl)piperidin-3-yl][(2-methylpyridin-4-yl)methyl]amino}methyl)-1-methyl-1,4-dihydroquinolin-4-one, 1-methyl-3-({[(2-methylpyridin-4-yl)methyl][(3S)-1-(2-nitropyridin-3-yl)piperidin-3-yl]amino}methyl)-1,4-dihydroquinolin-4-one, 3-({[(2,6-dimethylpyridin-4-yl)methyl][(3S)-1-(pyridine-3-yl)piperidin-3-yl]amino}methyl)-1-methyl-1,4-dihydroquinolin-4-one, 1-methyl-3-({[(3S)-1-(pyridin-3-yl)piperidin-3-yl][(pyridin-4-yl)methyl]amino}methyl)-1,4-dihydroquinolin-4-one, 1-methyl-3-({[(3S)-1-(1-methyl-2-oxo-1,2-dihydropyridin-4-yl)piperidin-3-yl][(2-methylpyridin-4-yl)methyl]amino}methyl)-1,4-dihydroquinolin-4-one, 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydro-1,8-naphthyridin-4-one, 1-cyclopropyl-6-fluoro-7-hydroxy-3-({[(3S)-1-(6-methylpyridin-3-yl)piperidin-3-yl][(2-methylpyridin-4-yl)methyl]amino}methyl)-1,4-dihydro-1,8-naphthyridin-4-one, 1-cyclopropyl-6-fluoro-7-methoxy-3-({[(3S)-1-(6-methylpyridin-3-yl)piperidin-3-yl][(2-methylpyridin-4-yl)methyl]amino}methyl)-1,4-dihydroquinolin-4-one, 1-cyclopropyl-6-fluoro-7-[(3R)-3-methylpiperazin-1-yl]-3-({[(3S)-1-(6-methylpyridin-3-yl)piperidin-3-yl][(2-methylpyridin-4-yl)methyl]amino}methyl)-1,4-dihydroquinolin-4-one, 1-cyclopropyl-6-fluoro-3-({[(3S)-1-(6-methylpyridin-3-yl)piperidin-3-yl][(2-methylpyridin-4-yl)methyl]amino}methyl)-7-(piperazin-1-yl)-1,4-dihydroquinolin-4-one, 1-cyclopropyl-7-[4-(2,2-difluoroethyl)piperazin-1-yl]-6-fluoro-3-({[(3S)-1-(6-methylpyridin-3-yl)piperidin-3-yl][(2-methylpyridin-4-yl)methyl]amino}methyl)-1,4-dihydroquinolin-4-one, 1-methyl-3-({[(3S)-1-(6-methylpyridin-3-yl)piperidin-3-yl][(2-methylpyridin-4-yl)methyl]amino}methyl)-7-(2-oxopiperazin-1-yl)-1,4-dihydroquinolin-4-one, 3-({[(3S)-1-(6-methylpyridin-3-yl)piperidin-3-yl][(2-methylpyridin-4-yl)methyl]amino}methyl)-1-(oxetan-3-yl)-1,4-dihydroquinolin-4-one, 2-[3-({[(3S)-1-(6-Methylpyridin-3-yl)piperidin-3-yl][(2-methylpyridin-4-yl)methyl]amino}methyl)-4-oxo-1,4-dihydroquinolin-1-yl]acetic acid, 1-cyclopropyl-7-{4,7-diazaspiro[2.5]octan-7-yl}-6-fluoro-3-({[(3S)-1-(6-methylpyridin-3-yl)piperidin-3-yl][(2-methylpyridin-4-yl)methyl]amino}methyl)-1,4-dihydroquinolin-4-one, 1-methyl-3-({[(3S)-1-(5-methyl-1,3,4-oxadiazol-2-yl)piperidin-3-yl][(2-methylpyridin-4-yl)methyl]amino}methyl)-1,4-dihydroquinolin-4-one, 3-({[(3S)-1-(2-chloropyrimidin-4-yl)piperidin-3-yl][(2-methylpyridin-4-yl)methyl]amino}methyl)-1-methyl-1,4-dihydroquinolin-4-one, 1-methyl-3-({[(3S)-1-(pyridin-3-yl)piperidin-3-yl][(1,2-thiazol-5-yl)methyl]amino}methyl)-1,4-dihydroquinolin-4-one, 7-chloro-1-cyclopropyl-3-({[(3S)-1-(6-methylpyridin-3-yl)piperidin-3-yl][(2-methylpyridin-4-yl)methyl]amino}methyl)-1,4-dihydro-1,6-naphthyridin-4-one, 7-(cyclohex-1-en-1-yl)-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one, 3-({[(3S)-1-(6-methylpyridin-3-yl)piperidin-3-yl][(2-methylpyridin-4-yl)methyl]amino}methyl)-1,4-dihydroquinolin-4-one, 1-cyclopropyl-6-fluoro-7-hydroxy-3-({[(3S)-1-(6-methylpyridin-3-yl)piperidin-3-yl][(2- methylpyridin-4-yl)methyl]amino}methyl)-1,4-dihydroquinolin-4-one, 8-bromo-1-methyl-3-({[(3S)-1-(6-methylpyridin-3-yl)piperidin-3-yl][(2-methylpyridin-4-yl)methyl]amino}methyl)-1,4-dihydroquinolin-4-one, 7-chloro-6-fluoro-3-({[(3S)-1-(6-methylpyridin-3-yl)piperidin-3-yl][(2-methylpyridin-4-yl)methyl]amino}methyl)-1-(propan-2-yl)-1,4-dihydro-1,8-naphthyridin-4-one, 6-fluoro-7-methoxy-3-({[(3S)-1-(6-methylpyridin-3-yl)piperidin-3-yl][(2-methylpyridin-4-yl)methyl]amino}methyl)-1-(propan-2-yl)-1,4-dihydro-1,8-naphthyridin-4-one, 3-({[(1,3-dimethyl-1H-pyrazol-5-yl)methyl][(3S)-1-(pyridin-3-yl)piperidin-3-yl]amino}methyl)-1-methyl-1,4-dihydroquinolin-4-one, and 1-cyclopropyl-3-({[(3S)-1-(6-methylpyridin-3-yl)piperidin-3-yl][(2-methylpyridin-4-yl)methyl]amino}methyl)-7-(morpholin-3-yl)-1,4-dihydroquinolin-4-one.

In other particularly preferred embodiments, the compound according to formula (I) is a compound selected from the group consisting of 3-({[(2-methoxypyridin-4-yl)methyl][(3S)-1-(pyridin-3-yl)piperidin-3-yl]amino}methyl)-1-methyl-1,4-dihydroquinolin-4-one, 1-methyl-3-({[(2-methylpyridin-4-yl)methyl][1-(pyridin-3-yl)piperidin-3-yl]amino}methyl)-1,4-dihydroquinolin-4-one, 3-({[(2-methoxypyridin-4-yl)methyl][1-(pyridazin-3-yl)piperidin-3-yl]amino}methyl)-1-methyl-1,4-dihydroquinolin-4-one, 3-({[(2-methoxypyridin-4-yl)methyl][1-(pyrazin-2-yl)piperidin-3-yl]amino}methyl)-1-methyl-1,4-dihydroquinolin-4-one, 1-methyl-3-({[(2-methylpyridin-4-yl)methyl][(3S)-1-(pyridin-3-yl)piperidin-3-yl]amino}methyl)-1,4-dihydroquinolin-4-one, 3-({[(2-methoxypyridin-4-yl)methyl][(3S)-1-(pyridin-3-yl)piperidin-3-yl]amino}methyl)-1,4-dihydroquinolin-4-one, 1-methyl-3-({[(3S)-1-(6-methylpyridin-3-yl)piperidin-3-yl][(2-methylpyridin-4-yl)methyl]amino}methyl)-1,4-dihydroquinolin-4-one, 3-({[(3S)-1-(2-methoxypyrimidin-5-yl)piperidin-3-yl][(2-methylpyridin-4-yl)methyl]amino}methyl)-1-methyl-1,4-dihydroquinolin-4-one, 1-cyclopropyl-6-fluoro-3-({[(2-methoxypyridin-4-yl)methyl][(3S)-1-(pyridin-3-yl)piperidin-3-yl]amino}methyl)-7-(4-methylpiperazin-1-yl)-1,4-dihydroquinolin-4-one, 1-cyclopropyl-6-fluoro-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-methoxypyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-methylpyridin-4-yl)methyl][(3S)-1-(pyridin-3-yl)piperidin-3-yl]amino}methyl)-1,4-dihydroquinolin-4-one, 1-methyl-3-({[(2-methylpyridin-4-yl)methyl][(3S)-1-(pyridin-2-yl)piperidin-3-yl]amino}methyl)-1,4-dihydroquinolin-4-one, 1-methyl-3-({[(2-methylpyridin-4-yl)methyl][(3S)-1-(6-nitropyridin-3-yl)piperidin-3-yl]amino}methyl)-1,4-dihydroquinolin-4-one, 3-({[(3S)-1-(3-bromopyridin-4-yl)piperidin-3-yl][(2-methylpyridin-4-yl)methyl]amino}methyl)-1-methyl-1,4-dihydroquinolin-4-one, 3-({[(3S)-1-(6-fluoropyridin-3-yl)piperidin-3-yl][(2-methylpyridin-4-yl)methyl]amino}methyl)-1-methyl-1,4-dihydroquinolin-4-one, 3-({[(3S)-1-(6-chloropyrimidin-4-yl)piperidin-3-yl][(2-methylpyridin-4-yl)methyl]amino}methyl)-1-methyl-1,4-dihydroquinolin-4-one, 1-methyl-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one, 3-({[(3S)-1-(2-chloropyrimidin-4-yl)piperidin-3-yl][(2-methylpyridin-4-yl)methyl]amino}methyl)-1-methyl-1,4-dihydroquinolin-4-one, 3-({[(3S)-1-(2-methoxypyridin-4-yl)piperidin-3-yl][(2-methylpyridin-4-yl)methyl]amino}methyl)-1-methyl-1,4-dihydroquinolin-4-one, 3-({[(2-ethylpyridin-4-yl)methyl][1-(pyridin-3-yl)piperidin-3-yl]amino}methyl)-1-methyl-1,4-dihydroquinolin-4-one, 1-methyl-3-({[(2-methylpyridin-4-yl)methyl][(3S)-1-(6-oxo-1,6-dihydropyrimidin-4-yl)piperidin-3-yl]amino}methyl)-1,4-dihydroquinolin-4-one, 7-bromo-1-methyl-3-({[(2-methylpyridin-4-yl)methyl][(3S)-1-(pyridin-3-yl)piperidin-3-yl]amino}methyl)-1,4-dihydroquinolin-4-one, 3-({[(3R,4-4-hydroxy-1-(pyridin-3-yl)piperidin-3-yl][(2-methylpyridin-4-yl)methyl]amino}methyl)-1-methyl-1,4-dihydroquinolin-4-one, 7-chloro-6-fluoro-1-methyl-3-({[(2-methylpyridin-4-yl)methyl][(3S)-1-(pyridin-3-yl)piperidin-3-yl]amino}methyl)-1,4-dihydroquinolin-4-one, 3-({[(3S,5S)-5-fluoro-1-(pyridin-3-yl)piperidin-3-yl][(2-methylpyridin-4-yl)methyl]amino}methyl)-1-methyl-1,4-dihydroquinolin-4-one, 1-methyl-3-({[(3S,5S)-5-methyl-1-(pyridin-3-yl)piperidin-3-yl][(2-methylpyridin-4-yl)methyl]amino}methyl)-1,4-dihydroquinolin-4-one, 7-chloro-1-cyclopropyl-6-fluoro-3-({[(2-methoxypyridin-4-yl)methyl][(3S)-1-(pyridin-3-yl)piperidin-3-yl]amino}methyl)-1,4-dihydroquinolin-4-one, methyl 1-[1-methyl-3-({[(2-methylpyridin-4-yl)methyl][(3S)-1-(pyridin-3-yl)piperidin-3-yl]amino}methyl)-4-oxo-1,4-dihydroquinolin-7-yl]piperidine-4-carboxylate, 1-methyl-3-({[(2-methylpyridin-4-yl)methyl][(36)-1-(2-oxo-1,2-dihydropyridin-4-yl)piperidin-3-yl]amino}methyl)-1,4-dihydroquinolin-4-one, 1-cyclopropyl-6,7-difluoro-3-({[(2-methoxypyridin-4-yl)methyl][(3S)-1-(6-methylpyridin-3-yl)piperidin-3-yl]amino}methyl)-1,4-dihydroquinolin-4-one, 7-chloro-1-cyclopropyl-6-fluoro-3-({[(2-methylpyridin-4-yl)methyl][(36)-1-(pyridin-3-yl)piperidin-3-yl]amino}methyl)-1,4-dihydroquinolin-4-one, 3-({[(2-methoxypyridin-4-yl)methyl][(3S)-1-(pyridin-3-yl)piperidin-3-yl]amino}methyl)-1,4-dihydroquinolin-4-one, 3-({[(2-methylpyridin-4-yl)methyl][(36)-1-(pyridin-3-yl)piperidin-3-yl]amino}methyl)-1,4-dihydroquinolin-4-one, 7-bromo-1-methyl-3-({[(3S)-1-(6-methylpyridin-3-yl)piperidin-3-yl][(2-methylpyridin-4-yl)methyl]amino}methyl)-1,4-dihydroquinolin-4-one, 7-chloro-1-cyclopropyl-6-fluoro-3-({[(36)-1-(6-methylpyridin-3-yl)piperidin-3-yl][(2-methylpyridin-4-yl)methyl]amino}methyl)-1,4-dihydroquinolin-4-one, and 1-cyclopropyl-6-fluoro-7-methoxy-3-({[(3S)-1-(6-methylpyridin-3-yl)piperidin-3-yl][(2-methylpyridin-4-yl)methyl]amino}methyl)-1,4-dihydro-1,8-naphthyridin-4-one.

In other particularly preferred embodiments, the compound of formula (I) is a compound selected from the group consisting of 3-({[(2-methoxypyridin-4-yl)methyl][(3S)-1-(pyridin-3-yl)piperidin-3-yl]amino}methyl)-1-methyl-1,4-dihydroquinolin-4-one, 1-methyl-3-({[(2-methylpyridin-4-yl)methyl][1-(pyridin-3-yl)piperidin-3-yl]amino}methyl)-1,4-dihydroquinolin-4-one, 3-({[(2-methoxypyridin-4-yl)methyl][1-(pyridazin-3-yl)piperidin-3-yl]amino}methyl)-1-methyl-1,4-dihydroquinolin-4-one, 3-({[(2-methoxypyridin-4-yl)methyl][1-(pyrazin-2-yl)piperidin-3-yl]amino}methyl)-1-methyl-1,4-dihydroquinolin-4-one, 1-methyl-3-({[(2-methylpyridin-4-yl)methyl][(3S)-1-(pyridin-3-yl)piperidin-3-yl]amino}methyl)-1,4-dihydroquinolin-4-one, 3-({[(2-methoxypyridin-4-yl)methyl][(3S)-1-(pyridin-3-yl)piperidin-3-yl]amino}methyl)-1,4-dihydroquinolin-4-one, 1-methyl-3-({[(3S)-1-(6-methylpyridin-3-yl)piperidin-3-yl][(2-methylpyridin-4-yl)methyl]amino}methyl)-1,4-dihydroquinolin-4-one, 3-({[(3S)-1-(2-methoxypyrimidin-5-yl)piperidin-3-yl][(2-methylpyridin-4-yl)methyl]amino}methyl)-1-methyl-1,4-dihydroquinolin-4-one, 1-cyclopropyl-6-fluoro-3-({[(2-methoxypyridin-4-yl)methyl][(3S)-1-(pyridin-3-yl)

piperidin-3-yl]amino}methyl)-7-(4-methylpiperazin-1-yl)-1,4-dihydroquinolin-4-one, 1-cyclopropyl-6-fluoro-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-methoxypyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-methylpyridin-4-yl)methyl][(3S)-1-(pyridin-3-yl)piperidin-3-yl]amino}methyl)-1,4-dihydroquinolin-4-one, 1-methyl-3-({[(2-methylpyridin-4-yl)methyl][(3S)-1-(pyridin-2-yl)piperidin-3-yl]amino}methyl)-1,4-dihydroquinolin-4-one, 1-methyl-3-({[(2-methylpyridin-4-yl)methyl][(3S)-1-(6-nitropyridin-3-yl)piperidin-3-yl]amino}methyl)-1,4-dihydroquinolin-4-one, 3-({[(3S)-1-(3-bromopyridin-4-yl)piperidin-3-yl][(2-methylpyridin-4-yl)methyl]amino}methyl)-1-methyl-1,4-dihydroquinolin-4-one, 3-({[(3S)-1-(6-fluoropyridin-3-yl)piperidin-3-yl][(2-methylpyridin-4-yl)methyl]amino}methyl)-1-methyl-1,4-dihydroquinolin-4-one, 3-({[(3S)-1-(6-chloropyrimidin-4-yl)piperidin-3-yl][(2-methylpyridin-4-yl)methyl]amino}methyl)-1-methyl-1,4-dihydroquinolin-4-one, 1-methyl-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one, 3-({[(3S)-1-(2-chloropyrimidin-4-yl)piperidin-3-yl][(2-methylpyridin-4-yl)methyl]amino}methyl)-1-methyl-1,4-dihydroquinolin-4-one, 3-({[(3S)-1-(2-methoxypyridin-4-yl)piperidin-3-yl][(2-methylpyridin-4-yl)methyl]amino}methyl)-1-methyl-1,4-dihydroquinolin-4-one, 3-({[(2-ethylpyridin-4-yl)methyl][1-(pyridin-3-yl)piperidin-3-yl]amino}methyl)-1-methyl-1,4-dihydroquinolin-4-one, 1-methyl-3-({[(2-methylpyridin-4-yl)methyl][(3S)-1-(6-oxo-1,6-dihydropyrimidin-4-yl)piperidin-3-yl]amino}methyl)-1,4-dihydroquinolin-4-one, 7-bromo-1-methyl-3-({[(2-methylpyridin-4-yl)methyl][(3S)-1-(pyridin-3-yl)piperidin-3-yl]amino}methyl)-1,4-dihydroquinolin-4-one, 3-({[(3R,4R)-4-hydroxy-1-(pyridin-3-yl)piperidin-3-yl][(2-methylpyridin-4-yl)methyl]amino}methyl)-1-methyl-1,4-dihydroquinolin-4-one, 7-chloro-6-fluoro-1-methyl-3-({[(2-methylpyridin-4-yl)methyl][(3S)-1-(pyridin-3-yl)piperidin-3-yl]amino}methyl)-1,4-dihydroquinolin-4-one, 3-({[(3S,5S)-5-fluoro-1-(pyridin-3-yl)piperidin-3-yl][(2-methylpyridin-4-yl)methyl]amino}methyl)-1-methyl-1,4-dihydroquinolin-4-one, 1-methyl-3-({[(3S,5R)-5-methyl-1-(pyridin-3-yl)piperidin-3-yl][(2-methylpyridin-4-yl)methyl]amino}methyl)-1,4-dihydroquinolin-4-one, 7-chloro-1-cyclopropyl-6-fluoro-3-({[(2-methoxypyridin-4-yl)methyl][(3S)-1-(pyridin-3-yl)piperidin-3-yl]amino}methyl)-1,4-dihydroquinolin-4-one, methyl 1-[1-methyl-3-({[(2-methylpyridin-4-yl)methyl][(3S)-1-(pyridin-3-yl)piperidin-3-yl]amino}methyl)-4-oxo-1,4-dihydroquinolin-7-yl]piperidine-4-carboxylate, 1-methyl-3-({[(2-methylpyridin-4-yl)methyl][(3S)-1-(2-oxo-1,2-dihydropyridin-4-yl)piperidin-3-yl]amino}methyl)-1,4-dihydroquinolin-4-one and 1-cyclopropyl-6,7-difluoro-3-({[(2-methoxypyridin-4-yl)methyl][(3S)-1-(6-methylpyridin-3-yl)piperidin-3-yl]amino}methyl)-1,4-dihydroquinolin-4-one.

In certain even more particularly preferred embodiments, the compound according to formula (I) is selected from the group consisting of 3-({[(2-methoxypyridin-4-yl)methyl][(3S)-1-(pyridin-3-yl)piperidin-3-yl]amino}methyl)-1-methyl-1,4-dihydroquinolin-4-one, 1-methyl-3-({[(2-methylpyridin-4-yl)methyl][(3S)-1-(pyridin-3-yl)piperidin-3-yl]amino}methyl)-1,4-dihydroquinolin-4-one, 1-methyl-3-({[(3S)-1-(6-methylpyridin-3-yl)piperidin-3-yl][(2-methylpyridin-4-yl)methyl]amino}methyl)-1,4-dihydroquinolin-4-one, 1-cyclopropyl-6-fluoro-3-({[(2-methoxypyridin-4-yl)methyl][(3S)-1-(pyridin-3-yl)piperidin-3-yl]amino}methyl)-7-(4-methylpiperazin-1-yl)-1,4-dihydroquinolin-4-one, 1-cyclopropyl-6-fluoro-7-(4-methylpiperazin-1-yl)-3-({[(2-methylpyridin-4-yl)methyl][(3,5)-1-(pyridin-3-yl)piperidin-3-yl]amino}methyl)-1,4-dihydroquinolin-4-one, 1-cyclopropyl-6,7-difluoro-3-({[(2-methoxypyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-methylpyridin-4-yl)methyl][(3S)-1-(pyridin-3-yl)piperidin-3-yl]amino}methyl)-1,4-dihydroquinolin-4-one, 1-methyl-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one, 7-bromo-1-methyl-3-({[(2-methylpyridin-4-yl)methyl][(3S)-1-(pyridin-3-yl)piperidin-3-yl]amino}methyl)-1,4-dihydroquinolin-4-one, 7-chloro-6-fluoro-1-methyl-3-({[(2-methylpyridin-4-yl)methyl][(3S)-1-(pyridin-3-yl)piperidin-3-yl]amino}methyl)-1,4-dihydroquinolin-4-one, 3-({[(3S,5S)-5-fluoro-1-(pyridin-3-yl)piperidin-3-yl][(2-methylpyridin-4-yl)methyl]amino}methyl)-1-methyl-1,4-dihydroquinolin-4-one, 7-chloro-1-cyclopropyl-6-fluoro-3-({[(2-methoxypyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-methoxypyridin-4-yl)methyl][(3S)-1-(6-methylpyridin-3-yl)piperidin-3-yl]amino}methyl)-1,4-dihydroquinolin-4-one, 7-chloro-1-cyclopropyl-6-fluoro-3-({[(2-methylpyridin-4-yl)methyl][(3S)-1-(pyridin-3-yl)piperidin-3-yl]amino}methyl)-1,4-dihydroquinolin-4-one, 3-({[(2-methoxypyridin-4-yl)methyl][(3S)-1-(pyridin-3-yl)piperidin-3-yl]amino}methyl)-1,4-dihydroquinolin-4-one, 3-({[(2-methylpyridin-4-yl)methyl][(3S)-1-(pyridin-3-yl)piperidin-3-yl]amino}methyl)-1,4-dihydroquinolin-4-one, 7-bromo-1-methyl-3-({[(3S)-1-(6-methylpyridin-3-yl)piperidin-3-yl][(2-methylpyridin-4-yl)methyl]amino}methyl)-1,4-dihydroquinolin-4-one, 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one, 1-cyclopropyl-6-fluoro-7-methoxy-3-({[(3S)-1-(6-methylpyridin-3-yl)piperidin-3-yl][(2-methylpyridin-4-yl)methyl]amino}methyl)-1,4-dihydro-1,8-naphthyridin-4-one, 1-cyclopropyl-6-fluoro-7-methoxy-3-({[(3S)-1-(6-methylpyridin-3-yl)piperidin-3-yl][(2-methylpyridin-4-yl)methyl]amino}methyl)-1,4-dihydroquinolin-4-one 1-cyclopropyl-6-fluoro-7-[(3R)-3-methylpiperazin-1-yl]-3-({[(3S)-1-(6-methylpyridin-3-yl)piperidin-3-yl][(2-methylpyridin-4-yl)methyl]amino}methyl)-1,4-dihydroquinolin-4-one, 1-cyclopropyl-6-fluoro-3-({[(3S)-1-(6-methylpyridin-3-yl)piperidin-3-yl][(2-methylpyridin-4-yl)methyl]amino}methyl)-7-(piperazin-1-yl)-1,4-dihydroquinolin-4-one, 1-cyclopropyl-7-{4,7-diazaspiro[2.5]octan-7-yl}-6-fluoro-3-({[(3S)-1-(6-methylpyridin-3-yl)piperidin-3-yl][(2-methylpyridin-4-yl)methyl]amino}methyl)-1,4-dihydroquinolin-4-one, 3-({[(3S)-1-(6-methylpyridin-3-yl)piperidin-3-yl][(2-methylpyridin-4-yl)methyl]amino}methyl)-1,4-dihydroquinolin-4-one, 1-cyclopropyl-6-fluoro-7-hydroxy-3-({[(3S)-1-(6-methylpyridin-3-yl)piperidin-3-yl][(2-methylpyridin-4-yl)methyl]amino}methyl)-1,4-dihydroquinolin-4-one, 6-fluoro-7-methoxy-3-({[(3S)-1-(6-methylpyridin-3-yl)piperidin-3-yl][(2-methylpyridin-4-yl)methyl]amino}methyl)-1-(propan-2-yl)-1,4-dihydro-1,8-naphthyridin-4-one, and 1-cyclopropyl-3-({[(3S)-1-(6-methylpyridin-3-yl)piperidin-3-yl][(2-methylpyridin-4-yl)methyl]amino}methyl)-7-(morpholin-3-yl)-1,4-dihydroquinolin-4-one.

Further, the compound of formula (I) is in certain even more particularly preferred embodiments a compound selected from the group consisting of 3-({[(2-methoxypyridin-4-yl)methyl][(3S)-1-(pyridin-3-yl)piperidin-3-yl]amino}methyl)-1-methyl-1,4-dihydroquinolin-4-one, 1-methyl-3-({[(2-methylpyridin-4-yl)methyl][(3S)-1-(pyridin-3-yl)piperidin-3-yl]amino}methyl)-1,4-dihydroquinolin-4-one, 1-methyl-3-({[(3S)-1-(6-methylpyridin-3-yl)piperidin-3-yl][(2-methylpyridin-4-yl)methyl]amino}methyl)-1,4-dihydroquinolin-4-one, 1-cyclopropyl-6-fluoro-3-({[(2-methoxypyridin-4-yl)methyl][(3S)-1-(pyridin-3-yl)piperidin-3-yl]amino}methyl)-7-(4-methylpiperazin-1-yl)-1,4-dihydroquinolin-4-one, 1-cyclopropyl-6-fluoro-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-methoxypyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-methylpyridin-4-yl)methyl][(3S)-1-(pyridin-3-yl)piperidin-3-yl]amino}methyl)-1,4-dihydroquinolin-4-one, 1-methyl-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one, 7-bromo-1-methyl-3-({[(2-methylpyridin-4-yl)methyl][(3S)-1-(pyridin-3-yl)piperidin-3-yl]amino}methyl)-1,4-dihydroquinolin-4-one, 7-chloro-6-fluoro-1-methyl-3-({[(2-methylpyridin-4-yl)methyl][(3S)-1-(pyridin-3-yl)piperidin-3-yl]amino}methyl)-1,4-dihydroquinolin-4-one, 3-({[(3S,5S)-5-fluoro-1-(pyridin-3-yl)piperidin-3-yl][(2-methylpyridin-4-yl)methyl]amino}methyl)-1-methyl-1,4-dihydroquinolin-4-one, 7-chloro-1-cyclopropyl-6-fluoro-3-({[(2-methoxypyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-methoxypyridin-4-yl)methyl][(3S)-1-(6-methylpyridin-3-yl)piperidin-3-yl]amino}methyl)-1,4-dihydroquinolin-4-one, 7-chloro-1-cyclopropyl-6-fluoro-3-({[(2-methylpyridin-4-yl)methyl][(3S)-1-(pyridin-3-yl)piperidin-3-yl]amino}methyl)-1,4-dihydroquinolin-4-one, 3-({[(2-methoxypyridin-4-yl)methyl][(3S)-1-(pyridin-3-yl)piperidin-3-yl]amino}methyl)-1,4-dihydroquinolin-4-one, 3-({[(2-methylpyridin-4-yl)methyl][(3S)-1-(pyridin-3-yl)piperidin-3-yl]amino}methyl)-1,4-dihydroquinolin-4-one, 7-bromo-1-methyl-3-({[(3S)-1-(6-methylpyridin-3-yl)piperidin-3-yl][(2-methylpyridin-4-yl)methyl]amino}methyl)-1,4-dihydroquinolin-4-one, 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one, 1-cyclopropyl-6-fluoro-7-methoxy-3-({[(3S)-1-(6-methylpyridin-3-yl)piperidin-3-yl][(2-methylpyridin-4-yl)methyl]amino}methyl)-1,4-dihydro-1,8-naphthyridin-4-one.

Further, the compound of formula (I) is in certain even more particularly preferred embodiments a compound selected from the group consisting of 3-({[(2-methoxypyridin-4-yl)methyl][(3S)-1-(pyridin-3-yl)piperidin-3-yl]amino}methyl)-1-methyl-1,4-dihydroquinolin-4-one, 1-methyl-3-({[(2-methylpyridin-4-yl)methyl][(3S)-1-(pyridin-3-yl)piperidin-3-yl]amino}methyl)-1,4-dihydroquinolin-4-one, 1-methyl-3-({[(3S)-1-(6-methylpyridin-3-yl)piperidin-3-yl][(2-methylpyridin-4-yl)methyl]amino}methyl)-1,4-dihydroquinolin-4-one, 1-cyclopropyl-6-fluoro-3-({[(2-methoxypyridin-4-yl)methyl][(3S)-1-(pyridin-3-yl)piperidin-3-yl]amino}methyl)-7-(4-methylpiperazin-1-yl)-1,4-dihydroquinolin-4-one, 1-cyclopropyl-6-fluoro-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-methoxypyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-methylpyridin-4-yl)methyl][(3S)-1-(pyridin-3-yl)piperidin-3-yl]amino}methyl)-1,4-dihydroquinolin-4-one, 1-methyl-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one, 7-bromo-1-methyl-3-({[(2-methylpyridin-4-yl)methyl][(3S)-1-(pyridin-3-yl)piperidin-3-yl]amino}methyl)-1,4-dihydroquinolin-4-one, 7-chloro-6-fluoro-1-methyl-3-({[(2-methylpyridin-4-yl)methyl][(3S)-1-(pyridin-3-yl)piperidin-3-yl]amino}methyl)-1,4-dihydroquinolin-4-one, 3-({[(3S,5S)-5-fluoro-1-(pyridin-3-yl)piperidin-3-yl][(2-methylpyridin-4-yl)methyl]amino}methyl)-1-methyl-1,4-dihydroquinolin-4-one, 7-chloro-1-cyclopropyl-6-fluoro-3-({[(2-methoxypyridin-4-yl)methyl][(3S)-1-(pyridin-3-yl)piperidin-3-yl]amino}methyl)-1,4-dihydroquinolin-4-one and 1-cyclopropyl-6,7-difluoro-3-({[(2-methoxypyridin-4-yl)methyl][(3S)-1-(6-methylpyridin-3-yl)piperidin-3-yl]amino}methyl)-1,4-dihydroquinolin-4-one.

Further, the compound of formula (I) is in certain even more particularly preferred embodiments a compound selected from the group consisting of 7-chloro-1-cyclopropyl-6-fluoro-3-({[(2-methylpyridin-4-yl)methyl][(3S)-1-(pyridin-3-yl)piperidin-3-yl]amino}methyl)-1,4-dihydroquinolin-4-one, 3-({[(2-methoxypyridin-4-yl)methyl][(3S)-1-(pyridin-3-yl)piperidin-3-yl]amino}methyl)-1,4-dihydroquinolin-4-one, 3-({[(2-methylpyridin-4-yl)methyl][(3S)-1-(pyridin-3-yl)piperidin-3-yl]amino}methyl)-1,4-dihydroquinolin-4-one, 7-bromo-1-methyl-3-({[(3S)-1-(6-methylpyridin-3-yl)piperidin-3-yl][(2-methylpyridin-4-yl)methyl]amino}methyl)-1,4-dihydroquinolin-4-one, 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one, 1-cyclopropyl-6-fluoro-7-methoxy-3-({[(3S)-1-(6-methylpyridin-3-yl)piperidin-3-yl][(2-methylpyridin-4-yl)methyl]amino}methyl)-1,4-dihydro-1,8-naphthyridin-4-one, 1-cyclopropyl-6-fluoro-7-methoxy-3-({[(3S)-1-(6-methylpyridin-3-yl)piperidin-3-yl][(2-methylpyridin-4-yl)methyl]amino}methyl)-1,4-dihydroquinolin-4-one 1-cyclopropyl-6-fluoro-7-[(3R)-3-methylpiperazin-1-yl]-3-({[(3S)-1-(6-methylpyridin-3-yl)piperidin-3-yl][(2-methylpyridin-4-yl)methyl]amino}methyl)-1,4-dihydroquinolin-4-one, 1-cyclopropyl-6-fluoro-3-({[(3S)-1-(6-methylpyridin-3-yl)piperidin-3-yl][(2-methylpyridin-4-yl)methyl]amino}methyl)-7-(piperazin-1-yl)-1,4-dihydroquinolin-4-one, and 1-cyclopropyl-7-{4,7-diazaspiro[2.5]octan-7-yl}-6-fluoro-3-({[(3S)-1-(6-methylpyridin-3-yl)piperidin-3-yl][(2-methylpyridin-4-yl)methyl]amino}methyl)-1,4-dihydroquinolin-4-one.

Further, the compound of formula (I) is in certain even more particularly preferred embodiments a compound selected from the group consisting of 3-({[(3S)-1-(6-methylpyridin-3-yl)piperidin-3-yl][(2-methylpyridin-4-yl)methyl]amino}methyl)-1,4-dihydroquinolin-4-one, 1-cyclopropyl-6-fluoro-7-hydroxy-3-({[(3S)-1-(6-methylpyridin-3-yl)piperidin-3-yl][(2-methylpyridin-4-yl)methyl]amino}methyl)-1,4-dihydroquinolin-4-one, 6-fluoro-7-methoxy-3-({[(3S)-1-(6-methylpyridin-3-yl)piperidin-3-yl][(2-methylpyridin-4-yl)methyl]amino}methyl)-1-(propan-2-yl)-1,4-dihydro-1,8-naphthyridin-4-one, and 1-cyclopropyl-3-({[(3S)-1-(6-methylpyridin-3-yl)piperidin-3-yl][(2-methylpyridin-4-yl)methyl]amino}methyl)-7-(morpholin-3-yl)-1,4-dihydroquinolin-4-one.

Definitions

The term "compound(s) of the present invention" is to be understood as equivalent to the term "compound(s) according to the invention", and also covers a salt, stereoisomer, tautomer or N-oxide thereof.

The compounds according to the invention may be amorphous or may exist in one or more different crystalline states (polymorphs), which may have different macroscopic properties such as stability or show different biological properties such as activities. The present invention relates to amorphous and crystalline forms of compounds of formula (I), mixtures of different crystalline states of the compounds of formula (I), as well as amorphous or crystalline salts thereof.

Salts of the compounds according to the invention are preferably pharmaceutically acceptable salts, such as those containing counterions present in drug products listed in the US FDA Orange Book database. They can be formed in a customary manner, e.g., by reacting the compound with an acid of the anion in question, if the compounds according to the invention have a basic functionality, or by reacting acidic compounds according to the invention with a suitable base.

Suitable cationic counterions are in particular the ions of the alkali metals, preferably lithium, sodium and potassium, of the alkaline earth metals, preferably calcium, magnesium and barium, and of the transition metals, preferably manganese, copper, silver, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethyl-ammonium, bis(2-hydroxyethyl)ammonium, benzyltrimethylammonium and benzyltriethylammonium, furthermore the cations of 1,4-piperazine, meglumine, benzathine and lysine.

Suitable anionic counterions are in particular chloride, bromide, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate, furthermore lactate, gluconate, and the anions of poly acids such as succinate, oxalate, maleate, fumarate, malate, tartrate and citrate, furthermore sulfonate anions such as besylate (benzenesulfonate), tosylate (p-toluenesulfonate), napsylate (naphthalene-2-sulfonate), mesylate (methanesulfonate), esylate (ethanesulfonate), and ethanedisulfonate. They can be formed by reacting compounds according to the invention that have a basic functionality with an acid of the corresponding anion.

Depending on the substitution pattern, the compounds according to the invention may have one or more centres of chirality, including axial chirality. The invention provides both, pure enantiomers or pure diastereomers, of the compounds according to the invention, and their mixtures, including racemic mixtures. Suitable compounds according to the invention also include all possible geometrical stereoisomers (cis/trans isomers or E/Z isomers) and mixtures thereof. E/Z-isomers may be present with respect to, e.g., an alkene, carbon-nitrogen double-bond or amide group.

Tautomers may be formed, if a substituent is present at the compound of formula (I), which allows for the formation of tautomers such as keto-enol tautomers, imine-enamine tautomers, amide-imidic acid tautomers or the like. Furthermore, the core structure comprising the 6-membered ring that contains the =O substituent principally allows for keto-enol-tautomerization.

The term "N-oxide" includes any compound of the present invention which has at least one tertiary nitrogen atom that is oxidized to a N-oxide moiety.

The term "substituted", as used herein, means that a hydrogen atom bonded to a designated atom is replaced with a specified substituent, provided that the substitution results in a stable or chemically feasible compound. Unless otherwise indicated, a substituted atom may have one or more substituents and each substituent is independently selected.

The term "substitutable", when used in reference to a designated atom, means that attached to the atom is a hydrogen, which can be replaced with a suitable substituent.

When it is referred to certain atoms or moieties being substituted with "one or more" substituents, the term "one or more" is intended to cover at least one substituent, e.g. 1 to 10 substituents, preferably 1, 2, 3, 4, or 5 substituents, more preferably 1, 2, or 3 substituents, most preferably 1, or 2 substituents. When neither the term "unsubstituted" nor "substituted" is explicitly mentioned concerning a moiety, said moiety is to be considered as unsubstituted.

The organic moieties mentioned in the above definitions of the variables are—like the term halogen—collective terms for individual listings of the individual group members. The prefix $C_n$-$C_m$ indicates in each case the possible number of carbon atoms in the group.

The term "halogen" denotes in each case fluorine, bromine, chlorine or iodine, in particular fluorine, chlorine, or bromine.

The term "alkyl" as used herein denotes in each case a straight-chain or branched alkyl group having usually from 1 to 6 carbon atoms, preferably 1 to 5 or 1 to 4 carbon atoms, more preferably 1 to 3 or 1 or 2 carbon atoms. Examples of an alkyl group are methyl, ethyl, n-propyl, iso-propyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl.

The term "haloalkyl" as used herein denotes in each case a straight-chain or branched alkyl group having usually from 1 to 6 carbon atoms, frequently 1 to 5 or 1 to 4 carbon atoms, preferably 1 to 3 or 1 or 2 carbon atoms, wherein the hydrogen atoms of this group are partially or totally replaced with halogen atoms. Preferred haloalkyl moieties are selected from $C_1$-$C_4$-haloalkyl, more preferably from $C_1$-$C_3$-haloalkyl or $C_1$-$C_2$-haloalkyl, in particular from $C_1$-$C_2$-fluoroalkyl such as fluoromethyl, difluoromethyl, trifluoromethyl, 1-fluoroethyl, 2-fluoroethyl, 2,2-difluoroethyl, 2,2,2-trifluoroethyl, pentafluoroethyl, and the like.

The term "alkenyl" as used herein denotes in each case an unsaturated hydrocarbon group having usually 2 to 6, preferably 2 to 4 carbon atoms comprising at least one carbon-carbon double bond in any position, e.g. vinyl (ethenyl), allyl (2-propen-1-yl), 1-propen-1-yl, 2-propen-2-yl, methallyl (2-methylprop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl and the like. If geometric isomers are possible with regard to the double bond, the present invention relates to both, the E- and Z-isomers. Preferred alkenyl groups according to the invention are terminal alkenyl groups. The bonding of vinyl is exemplified below:

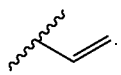

The term "haloalkenyl" as used herein refers to an alkenyl group as defined above, wherein the hydrogen atoms are partially or totally replaced with halogen atoms.

The term "alkynyl" as used herein denotes in each case an unsaturated hydrocarbon group having usually 2 to 6, preferably 2 to 5 or 2 to 4 carbon atoms, more preferably 2 to 3 carbon atoms, comprising at least one carbon-carbon triple bond in any position, e.g. ethynyl, propargyl (2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term "haloalkynyl" as used herein refers to an alkynyl group as defined above, wherein the hydrogen atoms are partially or totally replaced with halogen atoms.

The term "alkoxy" as used herein denotes in each case a straight-chain or branched alkyl group which is bonded via an oxygen atom and has usually from 1 to 6 carbon atoms, preferably 1 to 2 carbon atoms, more preferably 1 carbon atom. Examples of an alkoxy group are methoxy, ethoxy, n-propoxy, iso-propoxy, n-butyloxy, 2-butyloxy, iso-butyloxy, tert.-butyloxy, and the like.

The term "haloalkoxy" as used herein denotes in each case a straight-chain or branched alkoxy group having from 1 to 6 carbon atoms, preferably 1 to 2 carbon atoms, more preferably 1 carbon atom, wherein the hydrogen atoms of this group are partially or totally replaced with halogen atoms, in particular fluorine atoms. Preferred haloalkoxy moieties include $C_1$-haloalkoxy, in particular $C_1$-fluoroalkoxy, such as trifluoromethoxy and the like.

The term "HO(C=O)—$C_1$-$C_4$-alkyl" as used herein refers to a carboxylalkyl group, i.e. to a carboxyl group C(=O)OH which is bonded to the remainder of the molecule via an alkyl group, preferably a $C_1$-$C_4$-alkyl group, more preferably a $C_1$-$C_2$-alkyl group. Preferred examples include carboxylmethyl and carboxylethyl.

The term "cycloalkyl" as used herein denotes in each case a monocyclic cycloaliphatic radical having usually from 3 to 10 or from 3 to 6 carbon atoms, such as cyclopropyl, cyclobutyl, cyclopentyl, cyclohexyl, cycloheptyl, cyclooctyl, cyclononyl and cyclodecyl or cyclopropyl, cyclobutyl, cyclopentyl and cyclohexyl.

The term "carbocyclic" or "carbocyclyl" includes, unless otherwise indicated, in general a 3- to 9-membered, preferably a 4- to 8-membered or a 3- to 6-membered or a 5- to 7-membered, more preferably a 5- or 6-membered monocyclic ring comprising 3 to 9, preferably 4 to 8 or 3 to 6 or 5 to 7, more preferably 5 or 6 carbon atoms. The carbocycle may be saturated, partially or fully unsaturated, or aromatic, wherein saturated means that only single bonds are present, and partially or fully unsaturated means that one or more double bonds may be present in suitable positions, while the Hückel rule for aromaticity is not fulfilled, whereas aromatic means that the Hückel (4n+2) rule is fulfilled. The term "carbocycle" or "carbocyclyl", unless otherwise indicated, may therefore cover inter alia cycloalkyl, cycloalkenyl, as well as phenyl. Preferably, the term "carbocycle" covers cycloalkyl and cycloalkenyl groups, for example cyclopropane, cyclobutane, cyclopentane and cyclohexane rings.

The term "carbobicyclic" or "carbobicyclyl" includes in general 6 to 14-membered, preferably 7- to 12-membered or 8- to 10-membered, more preferably 9- or 10-membered bicyclic rings comprising 6 to 14, preferably 7 to 12 or 8 to 10, more preferably 9 or 10 carbon atoms. The carbobicycle may be saturated, partially or fully unsaturated, or aromatic, wherein saturated means that only single bonds are present, and partially or fully unsaturated means that one or more double bonds may be present in suitable positions, while the Hückel rule for aromaticity is not fulfilled, whereas aromatic means that the Hückel (4n+2) rule is fulfilled. Preferably, the term "aromatic" in connection with the carbobicyclic ring means that both rings of the bicyclic moiety are aromatic, so that, e.g., 8π electrons are present in case of a 10-membered aromatic carbobicyclic ring. The term "carbobicyclic" or "carbobicyclyl", unless otherwise indicated, may therefore cover inter alia bicycloalkyl, bicycloalkenyl, as well as bicyclic aromatic groups, for example bicyclohexane (decalin), bicycloheptane (such as norbornane), bicyclooctane (such as bicyclo[2.2.2]octane, bicyclo[3.2.1]octane or bicyclo[4.2.0]octane), bicyclononane (such as bicyclo[3.3.1]nonane or bicyclo[4.3.0]nonane), bicyclodecane (such as bicyclo[4.4.0]decane), bicycloundecane (such as bicyclo[3.3.3]undecane), norbornene, naphthalene and the like. Preferably, the carbobicycle is a fused carbobicycle, which is preferably aromatic, for example naphthalene.

The term "carbocyclyloxy" includes a carbocyclic ring or carbocyclyl which is bonded to the remainder of the molecule via an oxygen atom.

The term "heterocyclic" or "heterocyclyl" includes, unless otherwise indicated, in general a 3- to 9-membered, preferably a 4- to 8-membered or 5- to 7-membered, more preferably 5- or 6-membered, in particular 6-membered monocyclic ring. The heterocycle may be saturated, partially or fully unsaturated, or aromatic, wherein saturated means that only single bonds are present, and partially or fully unsaturated means that one or more double bonds may be present in suitable positions, while the Hückel rule for aromaticity is not fulfilled, whereas aromatic means that the Hückel (4n+2) rule is fulfilled. The heterocycle typically comprises one or more, e.g. 1, 2, 3, or 4, preferably 1, 2, or 3 heteroatoms selected from N, O and S as ring members, where S-atoms as ring members may be present as S, SO or $SO_2$. The remaining ring members are carbon atoms. In a preferred embodiment, the heterocycle is an aromatic heterocycle, preferably a 5- or 6-membered aromatic heterocycle comprising one or more, e.g. 1, 2, 3, or 4, preferably 1, 2, or 3 heteroatoms selected from N, O and S as ring members, where S-atoms as ring members may be present as S, SO or $SO_2$. Examples of aromatic heterocycles are provided below in connection with the definition of "hetaryl". "Hetaryls" or "heteroaryls" are covered by the term "heterocycles". The saturated or partially or fully unsaturated heterocycles usually comprise 1, 2, 3, 4 or 5, preferably 1, 2 or 3 heteroatoms selected from N, O and S as ring members, where S-atoms as ring members may be present as S, SO or $SO_2$. The skilled person is aware that S, SO or $SO_2$ is to be understood as follows:

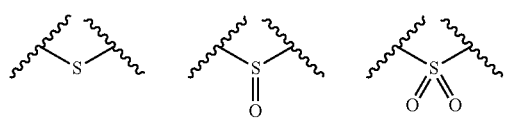

Further, a skilled person is aware that resonance structures of the oxidized forms may be possible. Saturated heterocycles include, unless otherwise indicated, in general 3- to 9-membered, preferably 4- to 8-membered or 5- to 7-membered, more preferably 5- or 6-membered monocyclic rings comprising 3 to 9, preferably 4 to 8 or 5 to 7, more preferably 5 or 6 atoms comprising at least one heteroatom, such as pyrrolidine, tetrahydrothiophene, tetrahydrofuran, piperidine, tetrahydropyran, dioxane, morpholine or piperazine.

The term "heterocyclyloxy" includes a heterocyclic ring or heterocyclyl which is bonded to the remainder of the molecule via an oxygen atom.

The term "heterobicyclic" or "heterobicyclyl" includes, unless otherwise indicated, in general 6 to 14-membered, preferably 7- to 12-membered or 8- to 10-membered, more preferably 9- or 10-membered bicyclic rings. The heterobicycle may be saturated, partially or fully unsaturated, or aromatic, wherein saturated means that only single bonds are present, and partially or fully unsaturated means that one or more double bonds may be present in suitable positions, while the Hückel rule for aromaticity is not fulfilled, whereas aromatic means that the Hückel (4n+2) rule is fulfilled. In principal, for being "aromatic", it is sufficient if one of the two rings of the bicyclic moieties is aromatic, while the other is non-aromatic. However, it is preferred in connection with the term "aromatic" that both rings of the bicyclic moiety are aromatic, so that, e.g., 8π electrons are present in case of a 9- or 10-membered aromatic heterobicyclic ring. The heterobicycle typically comprises one or more, e.g. 1, 2, 3, or 4, preferably 1, 2, or 3 heteroatoms selected from N, O and S as ring members, where S-atoms as ring members may be present as S, SO or $SO_2$. The remaining ring members are carbon atoms. Examples of heterobicycles include benzofuranyl, benzothienyl, indolyl, indazolyl, benzimidazolyl, benzoxathiazolyl, benzoxadiazolyl, benzothiadiazolyl, benzoxazinyl, quinolinyl, isoquinolinyl, purinyl, 1,8-naphthyridyl, pteridyl, pyrido[3,2-d]pyrimidyl, pyridoimidazolyl, triethylenediamine or quinuclidine and the like. Preferred heterobicycles according to the invention are aromatic heterobicycles such as benzodiazole, benzothiazole, quinoline, and iso-quinoline.

The term "hetaryl" or "heteroaryl" or "aromatic heterocycle" or "aromatic heterocyclic ring" includes monocyclic 5- or 6-membered aromatic heterocycles comprising as ring members 1, 2, 3 or 4 heteroatoms selected from N, O and S, where S-atoms as ring members may be present as S, SO or $SO_2$. Examples of 5- or 6-membered aromatic heterocycles include pyridyl (also referred to as pyridinyl), i.e. 2-, 3-, or 4-pyridyl, pyrimidinyl, i.e. 2-, 4- or 5-pyrimidinyl, pyrazinyl, pyridazinyl, i.e. 3- or 4-pyridazinyl, thienyl, i.e. 2- or 3-thienyl, furyl, i.e. 2- or 3-furyl, pyrrolyl, i.e. 2- or 3-pyrrolyl, oxazolyl, i.e. 2-, 3- or 5-oxazolyl, isoxazolyl, i.e. 3-, 4- or 5-isoxazolyl, thiazolyl, i.e. 2-, 3- or 5-thiazolyl, isothiazolyl, i.e. 3-, 4- or 5-isothiazolyl, pyrazolyl, i.e. 1-, 3-, 4- or 5-pyrazolyl, i.e. 1-, 2-, 4- or 5-imidazolyl, oxadiazolyl, e.g. 2- or 5-[1,3,4]oxadiazolyl, 4- or 5-(1,2,3-oxadiazol)yl, 3- or 5-(1,2,4-oxadiazol)yl, 2- or 5-(1,3,4-thiadiazol)yl, thiadiazolyl, e.g. 2- or 5-(1,3,4-thiadiazol)yl, 4- or 5-(1,2,3-thiadiazol)yl, 3- or 5-(1,2,4-thiadiazol)yl, triazolyl, e.g. 1H-, 2H- or 3H-1,2,3-triazol-4-yl, 2H-triazol-3-yl, 1H-, 2H-, or 4H-1,2,4-triazolyl and tetrazolyl, i.e. 1H- or 2H-tetrazolyl. Unless otherwise indicated, the term "hetaryl" further covers "aromatic heterobicycles" as defined above.

The term "aryl" or "aromatic carbocycle" preferably includes 6-membered aromatic carbocyclic rings based on carbon atoms as ring members. A preferred example is phenyl. Unless otherwise indicated, the term "aryl" further covers "aromatic carbobicycles" as defined above.

As used herein, the terms "carbocyclylalkyl" and "heterocyclylalkyl" as well as the terms "arylalkyl", "cycloalkylalkyl", "hetarylalkyl", and the like refer to the corresponding groups, which are bonded to the remainder of the molecule via an alkyl, preferably via a $C_1$-$C_2$-alkyl group. Preferred examples include benzyl (i.e. phenylmethyl), cyclohexylmethyl, pyridinylmethyl, and piperidinomethyl.

As used herein, the terms "aryloxy" and "benzyloxy" refer to the corresponding groups, which are bonded to the remainder of the molecule via an oxygen atom. Preferred examples include phenyloxy and phenylmethyloxy (i.e. benzyloxy).

As used herein, the term "alkylene" refers to a linking straight-chain or branched alkylene group having usually from 1 to 4 carbon atoms, e.g. 1, 2, 3, or 4 carbon atoms. The alkylene group bridges a certain group to the remainder of the molecule. Preferred alkylene groups include methylene ($CH_2$), ethylene ($CH_2CH_2$), propylene ($CH_2CH_2CH_2$) and the like. A skilled person understands that, if it is referred, e.g., to $CH_2$ that the carbon atom being tetravalent has two valences left for forming a bridge (—$CH_2$—). Similarly, when it is referred, e.g., to $CH_2CH_2$, each carbon atom has one valence left for forming a bridge (—$CH_2CH_2$—). Furthermore, when it is referred, e.g., to $CH_2CH_2CH_2$, each terminal carbon atom has one valence left for forming a bridge (—$CH_2CH_2CH_2$—).

If the term "alkylene" is used in connection with, e.g. $NR^F$—($C_1$-$C_4$-alkylene)-C(=O)$R^E$, it is to be understood that the alkylene chain bridges the C(=O)$R^E$ group to the $NR^F$ group, which is bonded to the remainder of the molecule.

The term "cyclic" moiety can refer to any cyclic groups, which are present in the compounds of formula (I), and which are defined above, e.g., cycloalkyl, cycloalkenyl, carbocycle.

As used in the specification and the claims, the singular forms of "a" and "an" also include the corresponding plurals unless the context clearly dictates otherwise. The same applies for plural forms used herein, which also include the singular forms unless the context clearly dictates otherwise.

The terms "about" and "approximately" in the context of the present invention denotes an interval of accuracy that a person skilled in the art will understand to still ensure the technical effect of the feature in question. The term typically indicates a deviation from the indicated numerical value of ±10% and preferably ±5%.

It needs to be understood that the term "comprising" is not limiting. For the purposes of the present invention, the term "consisting of" is considered to be a preferred embodiment of the term "comprising of". If hereinafter a group is defined to comprise at least a certain number of embodiments, this is also meant to encompass a group, which preferably consists of these embodiments only.

The term "pharmaceutically acceptable excipient" as used herein refers to compounds commonly comprised in pharmaceutical compositions, which are known to the skilled person. Examples of suitable excipients are exemplary listed below. Typically, a pharmaceutically acceptable excipient can be defined as being pharmaceutically inactive.

The term "treatment" is to be understood as also including the option of "prophylaxis". Thus, whenever reference is made herein to a "treatment" or "treating", this is to be understood as "treatment and/or prophylaxis" or "treating and/or preventing".

Description of Pharmaceutical Compositions According to the Present Invention

A pharmaceutical composition according to the present invention may be formulated for oral, buccal, nasal, rectal, topical, transdermal or parenteral application. Preferred non-parenteral routes include mucosal (e.g., oral, vaginal, nasal, cervical, etc.) routes, of which the oral application may be preferred. Preferred parenteral routes include but, are not limited to, one or more of subcutaneous, intravenous, intramuscular, intraarterial, intradermal, intrathecal and epidural administrations. Preferably administration is by subcutaneous, intra-tumoral or peritumoral routes. Particularly preferred is intratumoral administration. The compound according to formula (I) should be applied in pharmaceutically effective amounts, for example in the amounts as set out herein below.

A pharmaceutical composition of the present invention may also be designated as formulation or dosage form. A compound of formula (I) may also be designated in the following as (pharmaceutically) active agent or active compound.

Pharmaceutical compositions may be solid or liquid dosage forms or may have an intermediate, e.g. gel-like character depending inter alia on the route of administration.

In general, the inventive dosage forms can comprise various pharmaceutically acceptable excipients which will be selected depending on which functionality is to be achieved for the dosage form. A "pharmaceutically acceptable excipient" in the meaning of the present invention can be any substance used for the preparation of pharmaceutical dosage forms, including coating materials, film-forming materials, fillers, disintegrating agents, release-modifying materials, carrier materials, diluents, binding agents and other adjuvants. Typical pharmaceutically acceptable excipients include substances like sucrose, mannitol, sorbitol, starch and starch derivatives, lactose, and lubricating agents such as magnesium stearate, disintegrants and buffering agents.

The term "carrier" denotes pharmaceutically acceptable organic or inorganic carrier substances with which the active ingredient is combined to facilitate the application. Suitable pharmaceutically acceptable carriers include, for instance, water, aqueous salt solutions, alcohols, oils, preferably vegetable oils, propylene glycol, polyoxyethelene sorbitans, polyethylene-polypropylene block co-polymers such as poloxamer 188 or poloxamer 407, polyethylene glycols such as polyethylene glycol 200, 300, 400, 600, etc., gelatin, lactose, amylose, magnesium stearate, surfactants, perfume oil, fatty acid monoglycerides, diglycerides and triglycerides, polyoxyethylated medium or long chain fatty acids such as ricinoleic acid, and polyoxyethylated fatty acid mono-, di, and triglycerides such as capric or caprilic acids, petroethral fatty acid esters, hydroxymethyl celluloses such as hydroxymethyl, hydroxyethyl, hydroxypropyl, hydroxypropyl acetate succinate, polyvinylpyrrolidone, crosspovidone and the like. Preferably, the compounds of the present invention are administered in a pharmaceutical composition comprising of lipids, interbilayer crosslinked multilamellar vesicles, biodegradeable poly(D,L-lactic-co-glycolic acid) [PLGA]-based or poly anhydride-based nanoparticles or microparticles, nanoporous particle-supported lipid bilayers and as a conjugate with an antibody.

The pharmaceutical compositions can be sterile and, if desired, mixed with auxiliary agents, like lubricants, preservatives, stabilizers, wetting agents, emulsifiers, salts for influencing osmotic pressure, buffers, colorings, flavoring and/or aromatic substances and the like which do not deleteriously react with the active compound. It is to be understood that the term "carrier" also covers an antibody that delivers the compound of formula (I).

If liquid dosage forms are considered for the present invention, these can include pharmaceutically acceptable emulsions, solutions, suspensions and syrups containing inert diluents commonly used in the art such as water. These dosage forms may contain e.g. microcrystalline cellulose for imparting bulk, alginic acid or sodium alginate as a suspending agent, methylcellulose as a viscosity enhancer and sweeteners/flavoring agents.

For parenteral application, particularly suitable vehicles consist of solutions, preferably oily or aqueous solutions, as well as suspensions, emulsions, or implants. Pharmaceutical formulations for parenteral administration are particularly preferred and include aqueous solutions of the compounds of formula (I) in water-soluble form. Additionally, suspensions of the compounds of formula (I) may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran.

Particularly preferred dosage forms are injectable preparations of a compound of formula (I). Thus, sterile injectable aqueous or oleaginous suspensions can for example be formulated according to the known art using suitable dispersing agents, wetting agents and/or suspending agents. A sterile injectable preparation can also be a sterile injectable solution or suspension in a non-toxic parenterally acceptable diluent or solvent. Among the acceptable vehicles and solvents that can be used are water and isotonic sodium chloride solution. Sterile oils are also conventionally used as solvent or suspending medium. Preferred applications for injectable preparations comprising the compounds of the present invention are intravenous, intratumoral and peritumoral administration.

Suppositories for rectal administration of a compound of formula (I) can be prepared by e.g. mixing the compound with a suitable non-irritating excipient such as cocoa butter, synthetic triglycerides and polyethylene glycols which are solid at room temperature but liquid at rectal temperature such that they will melt in the rectum and release the compound according to formula (I) from said suppositories.

For administration by inhalation, the compounds according to the present invention may be conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Oral dosage forms may be liquid or solid and include e.g. tablets, troches, pills, capsules, powders, effervescent formulations, dragees and granules. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. The oral dosage forms may be formulated to ensure an immediate release of the compound of formula (I) or a sustained release of the compound of formula (I).

A solid dosage form may comprise a film coating. For example, the inventive dosage form may be in the form of a so-called film tablet. A capsule of the invention may be a two-piece hard gelatin capsule, a two-piece hydroxypropylmethylcellulose capsule, a two-piece capsule made of vegetable or plant-based cellulose or a two-piece capsule made of polysaccharide.

The dosage form according to the invention may be formulated for topical application. Suitable pharmaceutical application forms for such an application may be a topical nasal spray, sublingual administration forms and controlled and/or sustained release skin patches. For buccal administration, the compositions may take the form of tablets or lozenges formulated in conventional manner.

The compositions may conveniently be presented in unit dosage forms and may be prepared by any of the methods well known in the art of pharmacy. The methods can include the step of bringing the compounds into association with a carrier, which constitutes one or more accessory ingredients. In general, the compositions are prepared by uniformly and intimately bringing the compounds into association with a liquid carrier, a finely divided solid carrier, or both, and then, if necessary, shaping the product. Liquid dose units are vials or ampoules. Solid dose units are tablets, capsules and suppositories.

As regards human patients, the compound of formula (I) may be administered to a patient in an amount of about 0.001 mg to about 5000 mg per day, preferably of about 0.01 mg to about 1000 mg per day, more preferably of about 0.05 mg to about 250 mg per day, which is the effective amount. The phrase "effective amount" means an amount of compound that, when administered to a mammal in need of such treatment, is sufficient to treat or prevent a particular disease or condition.

Furthermore, the pharmaceutical composition may also contain the compound of formula (I) as a prodrug such as an ester or amide thereof. A prodrug is any compound, which is converted under physiological conditions or by solvolysis to any of the compounds of the invention. A prodrug may be inactive prior to administration but may be converted to an active compound of the invention in vivo.

Indications, for which the Compounds of the Present Invention may be Used

The compounds according to the present invention are suitable for use in medicine. In particular, the compounds according to the present invention are suitable for use in the treatment of a disease selected from the group consisting of inflammatory diseases, allergic diseases, autoimmune diseases, infectious diseases, cancer, and pre-cancerous syndromes. Further, the compounds of formula (I) are suitable for use in immunogenic compositions and as vaccine adjuvants.

In one embodiment, the compound of the present invention or a pharmaceutical composition comprising the same is for use in the treatment of a disease selected from the group consisting of cancer, pre-cancerous syndromes, and infectious diseases; or for use in an immunogenic composition or as vaccine adjuvant.

In another embodiment, the compound of the present invention or a pharmaceutical composition comprising the same is for use in the treatment of a disease selected from the group consisting of inflammatory diseases, allergic diseases, and autoimmune diseases.

In one preferred embodiment, the compound of the present invention or a pharmaceutical composition comprising the same is for use in the treatment of a disease selected from the group consisting of cancer or pre-cancerous syndromes.

In another preferred embodiment, the compound of the present invention or a pharmaceutical composition comprising the same is for use in the treatment of a disease selected from the group consisting of infectious diseases or for use in an immunogenic composition or as vaccine adjuvant.

In another preferred embodiment, the compound of the present invention or a pharmaceutical composition comprising the same is for use in the treatment of inflammatory diseases, allergic diseases, infectious diseases.

Of particular relevance in connection with the present invention is the treatment of cancer. Preferably, said cancer is selected from the group consisting of breast cancer, inflammatory breast cancer, ductal carcinoma, lobular carcinoma, colon cancer, pancreatic cancer, insulinomas, adenocarcinoma, ductal adenocarcinoma, adenosquamous carcinoma, acinar cell carcinoma, glucagonoma, skin cancer, melanoma, metastatic melanoma, lung cancer, small cell lung cancer, non-small cell lung cancer, squamous cell carcinoma, adenocarcinoma, large cell carcinoma, brain (gliomas), glioblastomas, astrocytomas, glioblastoma multiforme, Bannayan-Zonana syndrome, Cowden disease, Lhermitte-Duclos disease, Wilm's tumor, Ewing's sarcoma, Rhabdomyosarcoma, ependymoma, medulloblastoma, head and neck, kidney, liver, melanoma, ovarian, pancreatic, adenocarcinoma, ductal adenocarcinoma, adenosquamous carcinoma, acinar cell carcinoma, glucagonoma, insulinoma, prostate, sarcoma, osteosarcoma, giant cell tumor of bone, thyroid, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, Immunoblastic large cell leukemia, mantle cell leukemia, multiple myeloma, megakaryoblastic leukemia, multiple myeloma, acute megakaryocyte leukemia, promyelocytic leukemia, erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), neuroendocrine cancers and testicular cancer.

More preferably, said cancer is selected from prostate cancer, renal carcinoma, melanoma, pancreatic cancer, cervical cancer, ovarian cancer, colon cancer, head and neck cancer, lung cancer, fibrosarcoma and breast cancer.

In a particularly preferred embodiment, the compounds of the present invention or pharmaceutical compositions comprising the same are for use in the treatment of colon cancer.

Preferably, said autoimmune disease is selected from the group consisting of systemic lupus erythematosis, Addison's disease, autoimmune polyglandular disease (also known as autoimmune polyglandular syndrome), glomerulonephritis, rheumatoid arthritis scleroderma, chronic thyroiditis, Graves' disease, autoimmune gastritis, diabetes, autoimmune hemolytic anemia, glomerulonephritis, rheumatoid arthritis autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, asthma, bronchitis, acute pancreatitis, chronic pancreatitis and allergies of various types.

It is to be understood that in connection with the medical uses of the invention it can be preferred that the compounds according to the present invention are administered in combination with antibodies, radiotherapy, surgical therapy, immunotherapy, chemotherapy, toxin therapy, gene therapy, or any other therapy known to those of ordinary skill in the art for treatment of a particular disease. This is particularly relevant in connection with the treatment of cancer. Preferably, the compounds of the present invention are administered in combination with antibodies. Preferred antibodies include anti-PD-1, anti-PD-L1, anti-CTLA-4, anti-IDO, anti-KIR, anti-TIM-3, anti-Vista, anti-TIGIT, anti-BTLA and anti-LAG3 antibody. Non-limiting examples are BMS-936559, MPDL3280A and MEDI4736 or avelumab (anti-PD-L1 antibodies), MK-3475, pembrolizumab or pidilizumab (anti-PD-1 antibodies) as well as ipilimumab (anti-CTLA-4 antibodies). Preferably, the compounds of the present invention are administered in a pharmaceutical composition comprising one or more of adjuvants, inactivated or attenuated bacteria (e.g., inactivated or attenuated Listeria monocytogenes), modulators of innate immune activation, preferably agonists of Toll-like Receptors (TLRs, preferably TLR7 or TLR9 agonists, e.g. SM360320, AZD8848), (NOD)-like receptors (NLRs, preferably NOD2 agonist), retinoic acid inducible gene-based (RIG)-1-like receptors (RLRs), C-type lectin receptors (CLRs), or pathogen-associated molecular patterns ("PAMPs"), cytokines (not limiting examples e.g. IL-2, IL-12, IL-6), interferons (including, but not limited to IFN alpha, IFN beta, IFN gamma, IFN lambda) or chemotherapeutic agents. The medical use may further compromise administering at least one HBV vaccine, a nucleoside HBV inhibitor or any combination thereof (e.g. RECOMBIVAX HB, ENGERIX-B, GENEVAC-B).

Combination therapy may be achieved by use of a single pharmaceutical composition that includes both agents, or by administering two distinct compositions at the same time, wherein one composition includes a compound of the present invention, and the other includes the second agent(s).

The two therapies may be given in either order and may precede or follow the other treatment by intervals ranging from minutes to weeks. In embodiments where the other agents are applied separately, one would generally ensure that a significant period of time did not expire between the time of each delivery, such that the agents would still be able to exert an advantageously combined effect on the patient. In such instances, it is contemplated that one may administer both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. In some embodiments, the compound of the present invention is administered prior to administration of the distinct cancer treatment. In other embodiments, the distinct cancer treatment is administered prior to administration of the compound of the present invention.

The present invention is further illustrated by the following examples.

EXAMPLES

The following abbreviations are used herein:

| Abbreviation | Meaning |
|---|---|
| AcCl | Acetyl chloride |
| $Ac_2O$ | Acetic anhydride |
| $ACN/CH_3CN$ | Acetonitrile |
| AcOH | Acetic acid |
| AcOEt | Ethyl acetate (also referred to as EtOAc) |
| AcONa | Sodium acetate |
| $AlCl_3$ | Aluminum chloride |
| $Al_2O_3$ | Aluminium oxide |
| Anh. | Anhydrous |
| aq | Aqueous solution |
| BINAP | 2,2'-Bis(diphenylphosphino)-1,1-binaphthalene |
| $Boc_2O$ | Di-tert-butyl-dicarbonate |
| Brettphos | 2-(Dicyclohexylphosphino)-3,6-dimethoxy-2',4',6'-triisopropyl-1,1'-biphenyl |
| tBuONa/t-BuONa | Sodium tert-butoxide |
| $CH_3I$ | Iodomethane |
| $CHCl_3$ | Chloroform |
| $CH(OEt)_3$ | Triethyl orthoformate |
| Conc. | Concentrated |
| $Cs_2CO_3$ | Cesium carbonate |
| $CuCl_2$ | Copper(II) chloride |
| CuI | Copper(I) iodide |
| d | Deuterated |
| DBU | 1,8-Diazabicyclo(5.4.0)undec-7-en |
| DCC | N,N'-dicyclohexylcarbodiimide |
| DCE | 1,2-Dichloroethane |
| DCM | Dichloromethane |
| DIAD | Diisopropyl azodicarboxylate |
| DIBAL-H | Diisobutylaluminium hydride |
| DIPA | Diisopropylamine |
| DIPEA/DIEA | N,N-diisopropylethylamine, Hunig's base |
| DMAc | N,N-Dimethylacetamide |
| DMAP | 4-(Dimethylamino)pyridine |
| DMF | N,N-Dimethylformamide |
| DMSO | Dimethylsulfoxide |
| $DMSO-d_6$ | Deuterated dimethylsulfoxide |
| EDC | N-(3-Dimethylaminopropyl)-N-ethylcarbodiimide |
| eq | Equivalent |
| ESI-MS | Electrospray Ionisation - Mass spectrometry |
| Et | Ethyl |
| $Et_2O$ | Diethyl ether |
| EtOH | Ethanol |
| $Et_3N$ | Triethylamine |
| FCC | Flash column chromatography |
| $H_2$ | Molecular hydrogen |
| HATU | 1-[Bis(dimethylamino)methylene]-1H-1,2,3-triazolo[4,5-b]pyridinium 3-oxid hexafluorophosphate |
| HBTU | N,N,N',N'-Tetramethyl-O-(1H-benzotriazol-1-yl) uronium hexafluorophosphate |
| HCl | Hydrochloric acid |
| HCOOH | Formic acid |
| Hex | Hexane |
| $H_2O$ | Water |
| HMT | 1,3,5,7-tetraazatricyclo[3.3.1.13,7]decane |
| HPLC | High-performance liquid chromatography |
| $H_2SO_4$ | Sulfuric acid |
| i-PrOH/iPrOH | Isopropanol |
| K | Potassium |
| $K_2CO_3$ | Potassium carbonate |
| KHMDS | Potassium bis(trimethylsilyl)amide |
| KI | Potassium iodide |
| KOH | Potassium hydroxide |
| LAH | Lithium aluminium hydride |
| LAD | Lithium aluminium deuteride |
| LC-MS | Liquid chromatography - mass spectrometry |
| MeOH | Methanol |
| MeONa | Sodium methoxide |
| $MgSO_4$ | Magnesium sulfate |
| $MnO_2$ | Manganese(IV) oxide |
| MOMCl/Cl-MOM | Chloromethyl methyl ether |

| Abbreviation | Meaning |
| --- | --- |
| MPA scavenger | QuadraPure ® Mercaptophenylaminobut-2-enoate ester |
| MsCl | Methanesulfonyl chloride |
| 3Å MS | 3Å molecular sieves |
| 4Å MS | 4Å molecular sieves |
| MW | Microwave |
| N/M | Molar concentration [mol/dm$^3$] |
| Na | Sodium |
| NaBH$_4$ | Sodium borohydride |
| NaBH$_3$CN | Sodium cyanoborohydride |
| NaBH(OAc)$_3$ | Sodium triacetoxyborohydride |
| NaH | Sodium hydride |
| NaHCO$_3$ | Sodium bicarbonate |
| NaHMDS | Sodium bis(trimethylsilyl)amide |
| NaNO$_2$ | Sodium nitrite |
| NaOAc | Sodium acetate |
| NaOH | Sodium hydroxide |
| Na$_2$SO$_4$ | Sodium sulfate |
| nBuOH | n-Butanol |
| NH$_3$ | Ammonia |
| NH$_2$-NH$_2$ | Hydrazine |
| NH$_2$-NH$_2$•H$_2$O | Hydrazine monohydrate |
| NH$_4$Cl | Ammonium chloride |
| NH$_4$HCO$_3$ | Ammonium bicarbonate |
| NMM | N-methylmorpholine |
| NMP | N-methyl-2-pyrrolidone |
| NMR | Nuclear magnetic resonance |
| on/o.n. | Overnight |
| PBr$_3$ | Phosphorus tribromide |
| Pd/C | Palladium(0) on carbon |
| PdCl$_2$(PPh$_3$)$_2$ | Bis(triphenylphosphine)palladium(II) dichloride |
| Pd$_2$(dba)$_3$ | Tris(dibenzylideneacetone)dipalladium(0) |
| Pd(dppf) | [1,1'-Bis(diphenylphosphino)ferrocene] |
| Cl$_2$•DCM | dichloropalladium(II), complex with dichloromethane |
| Pd(OH)$_2$/C | Palladium(II) hydroxide on carbon |
| Pd(PPh$_3$)$_4$ | Tetrakis(triphenylphosphine)palladium(0) |
| PhOPh | Diphenyl ether |
| POCl$_3$ | Phosphorus (V) oxychloride |
| PPA | Polyphosphoric acid |
| prep-HPLC | Preparative high-performance liquid chromatography |
| prep-TLC | Preparative thin layer chromatography |
| Pt/C | Platinum (0) on carbon |
| PtO$_2$ | Platinum dioxide |
| PTSA | p-Toluenesulfonic acid |
| rac | Racemate/racemic |
| RP-FCC/RP FCC/RPFCC | Reversed phase flash column chromatography |
| RT/r.t./rt | Room temperature, i.e. 20-25° C. |
| SiHP | Silica PuriFlash Columns High Performance, 60A-500 m$^2$/g |
| SiC18/Si-C18 | Silica PuriFlash Columns High Performance C18 |
| Si-Diol | Silica PuriFlash Columns Diol, 60A-500 m$^2$/g |
| Si-NH$_2$/SiNH$_2$ | Amino silica PuriFlash Columns |
| SOCl$_2$ | Thionyl chloride |
| Sphos | 2-Dicyclohexylphosphino-2',6'-dimethoxybiphenyl |
| SPhos Pd G3 | (2-Dicyclohexylphosphino-2',6'-dimethoxybiphenyl) [2-(2'-Amino-1,1'-biphenyl)]palladium(II) methanesulfonate |
| T3P | 1-Propanephosphonic anhydride |
| TBAB | Tetrabutylammonium bromide |
| TBSCl | tert-Butyldimethylsilyl chloride |
| tBuOK | Potassium tert-butoxide |
| tBuXPhos | 2-Di-tert-butylphosphino-2',4',6'-triisopropylbiphenyl |
| TEA | Triethylamine |
| TESCl | Chlorotriethylsilane |
| TFA | Trifluoroacetic acid |
| TIPSCl | Triisopropylsilyl chloride |
| THF | Tetrahydrofurane |
| TLC | Thin layer chromatography |
| TMP | Trimethyl phosphate |
| TPP/PPh$_3$ | Triphenylphosphine |
| UPLC | Ultra performance liquid chromatography |
| UPLC-MS | Ultra performance liquid chromatography tandem mass spectrometry |
| Xantphos | (9,9-dimethyl-9H-xanthene-4,5-diyl)bis(diphenylphosphine) |
| ZnCl$_2$ | Zinc chloride |
| APCI-MS | Atmospheric pressure chemical ionization mass spectrometry |
| tBuBrettPhos | [3,6-Dimethoxy-2',4',6'-tris(1-methylethyl) [1,1'-biphenyl]-2-yl]bis(1,1-dimethylethyl)phosphine |
| Na$_2$CO$_3$ | Sodium carbonate |
| Pd(OAc)2 | Palladium(II) acetate |
| RuPhos Pd G3 | (2-Dicyclohexylphosphino-2',6'-diisopropoxy-1,1'-biphenyl)[2-(2'-amino-1,1'-biphenyl)]palladium(II) methanesulfonate |

The compounds of the present invention were prepared according to the procedures of the following Schemes and Examples, using appropriate materials and are further exemplified by the following specific examples.

Unless otherwise specified, all starting materials are obtained from commercial suppliers and used without further purifications. Unless otherwise specified, all temperatures are expressed in ° C. and all reactions are conducted at rt.

Methods and Analytical Data:
General:

Microwave heating was done using a Biotage Emrys Initiator microwave, Column chromatography was carried out using an Isco Rf200d or an Interchim Puriflash 450. Solvent removal was carried out using either a Büchi rotary evaporator or a Genevac centrifugal evaporator. Preparative LC/MS was conducted using a Waters mass directed autopurification system and a Waters 19×100 mm XBridge 5 micron C18 column under basic mobile phase conditions or an equivalent Waters CSH C18 column under acidic conditions. NMR spectra were recorded using a Bruker 300 MHz or 400 MHz spectrometer. Chemical shifts (δ) are reported in ppm relative to the residual solvent signal (measurement range −6.4 kHz). 1H NMR data are reported as follows: chemical shift (multiplicity, coupling constants and number of hydrogens). Multiplicity is abbreviated as follows: s (singlet), d (doublet), t (triplet), q (quartet), m (multiplet), dd (doublet of doublets), dt (doublet of triplets). ESI-MS: Desolvatation Gas Flow 993 l/h; Desolvatation temperature 500° C.; cone gas: 50 l/min; 500-1000 m/z; polarity: positive and/or negative.

Photochemical reactions were carried out using Penn PhDM2 photoreactor (100% LED). Integrated photoreactor—Royal Blue (450 nm) LED lights, with fan rate: 5200 rpm, stir rate: 600 rpm, LED light intensity: 100%.

Preparative HPLC Conditions for the Purification of Target Compounds:
Chromatography Conditions 1:
Prep HPLC Instrument: Shimadzu
  Column: Gemini-NX 5 µm C18 110 Ç, 21.2*250 mm
  Detector: SPD −20A/20AV UV-VIS
  Flow Rate: 20 mL/min
Representative Mobile Phase:
(1)
  Mobile Phase: A: 0.01% formic acid in water or TFA
  Mobile Phase: B: 0.01% formic acid in ACN or TFA
(2)
  Mobile Phase: A: 0.01% NH4OH in water
  Mobile Phase: B: 0.01% NH4OH in ACN
Chromatography Conditions 2:
Prep HPLC Instrument: Shimadzu
  Column: Chiralpak AD-H, 5 µm, 20*250 mm
  Detector: SPD −20A/20AV UV-VIS
  Flow Rate: 20 mL/min Representative Mobile Phase:
Mobile Phase: A: EtOH
Mobile Phase: B: hexane
UPLC, HPLC and MS data provided in the examples described below were registered on:
LC-MS analyses on Shimadzu:
Method name: lc-ms1-2-ba
Equipment:
Shimadzu LC-MS 2020
HPLC with UV-Vis or DAD detector
column: Waters Acquity UPLC HSS C18, 50 mm×2.1 mm×1.8 μm
Eluents:
(A) 0.1% formic acid in ACN
(B) 0.1% formic acid in water
Analytical Method:
Autosampler: injection volume: 1 μL
Pump:

| Time [min] | Flow [ml/min] | % B |
|---|---|---|
| 0.00 | 0.5 | 95 |
| 0.00 | 0.5 | 95 |
| 4.00 | 0.5 | 5 |
| 5.00 | 0.5 | 5 |
| 5.20 | 0.5 | 95 |
| 6.00 | 0.5 | 95 |

Column compartment: column temperature: 25° C.; time of analysis: 6 min
Detector: wave length: 254, 230, 270, 280 nm
LC-MS Analyses on Bruker Amazon SL
Method name: lc-ms1-2-ba
Equipment:
MS Bruker Amazon SL
LC Dionex Ultimate 3000
HPLC with UV-Vis or DAD detector
column: Waters Acquity UPLC HSS C18, 50 mm×2.1 mm×1.8 μm
Eluents:
(A) 0.1% formic acid in ACN
(B) 0.1% formic acid in water
Analytical Method:
Auto sampler: injection volume: 1 μL
Pump:

| Time [min] | Flow [ml/min] | % B |
|---|---|---|
| 0.00 | 0.5 | 95 |
| 0.00 | 0.5 | 95 |
| 4.00 | 0.5 | 5 |
| 5.00 | 0.5 | 5 |
| 5.20 | 0.5 | 95 |
| 6.00 | 0.5 | 95 |

Column compartment: column temperature: 25° C.; time of analysis: 6 min
Detector: wave length: 254, 230, 270, 280 nm
LC-MS Analyses on Bruker Amazon SL
Method name: BCM-30
Equipment:
MS Bruker Amazon SL
LC Dionex Ultimate 3000
HPLC with UV-Vis or DAD detector
column: Waters Symmetry C18 3.9×150 mm 5 μm
Eluents:
(A) 0.1% formic acid-water solution
(B) 0.1% formic acid-ACN solution
Analytical Method:
Autosampler: injection volume: 3 μL
Pump:
flow: 1.2 ml/min

| Time [min] | [%] B |
|---|---|
| 0.0 | 20 |
| 20.0 | 80 |
| 22.0 | 80 |
| 22.5 | 95 |
| 25.0 | 95 |
| 25.3 | 20 |
| 30.0 | 20 |

Column compartment: column temperature: 25° C.; time of analysis: 30 min
Detector: wave length: 254 nm
LC-MS Analyses on Corona Ultra:
Method name: BCM-30
Equipment:
Corona ultra
LC Dionex Ultimate 3000
column: Waters Symmetry C18 3.9×150 mm 5 μm
Eluents:
(A) 0.1% formic acid-water solution
(B) 0.1% formic acid-ACN solution
Analytical Method:
Autosampler: injection volume: 3 μL
Pump:
flow: 1.2 ml/min

| Time [min] | [%] B |
|---|---|
| 0.0 | 20 |
| 20.0 | 80 |
| 22.0 | 80 |
| 22.5 | 95 |
| 25.0 | 95 |
| 25.3 | 20 |
| 30.0 | 20 |

Synthetic Procedures

The following compounds are commercially available and/or can be prepared in a number of ways well known to one skilled in the art of organic synthesis. More specifically, disclosed compounds can be prepared using the reactions and techniques described herein. In the description of the synthetic methods described below, it is to be understood that all proposed reaction conditions, including choice of solvent, reaction atmosphere, reaction temperature, duration of the experiment, and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

Procedure 1. Preparation of (3S)-1-(pyridin-3-yl)piperidin-3-amine

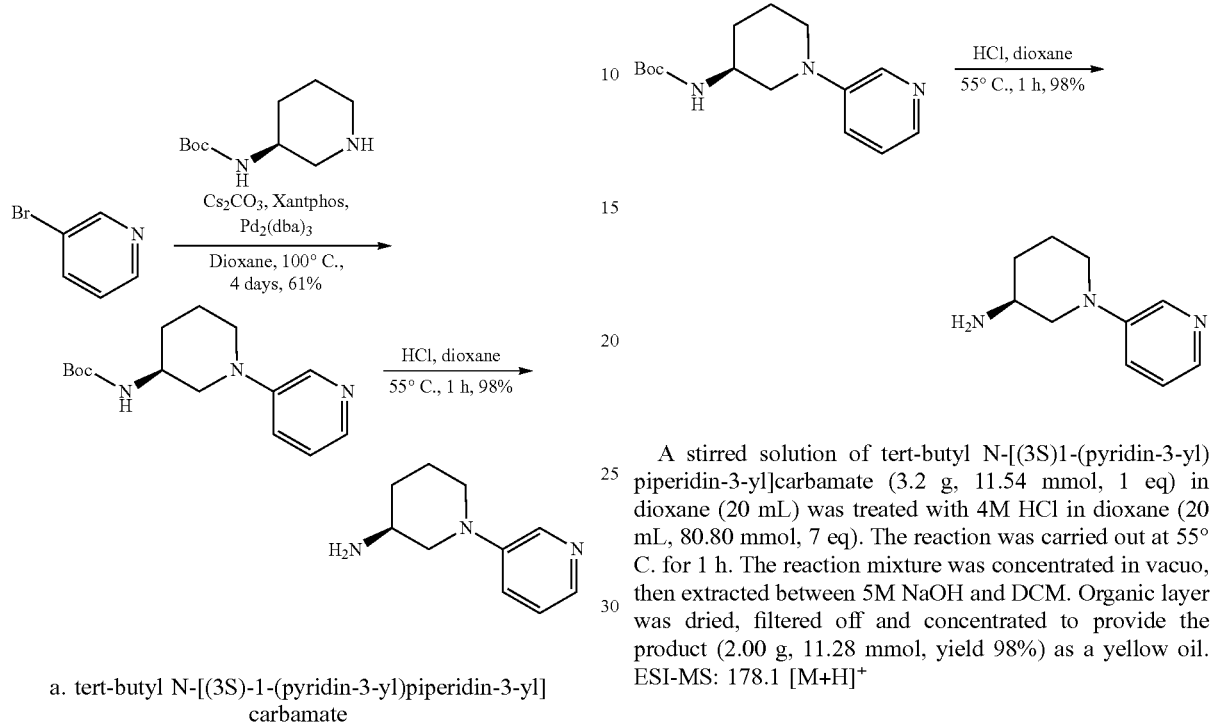

a. tert-butyl N-[(3S)-1-(pyridin-3-yl)piperidin-3-yl]carbamate

To a stirred solution of 3-bromopyridine (3.00 g, 18.99 mmol, 1 eq) in anhydrous dioxane (80 mL) tert-butyl N-[(3S)-piperidin-3-yl]carbamate (4.94 g, 24.68 mmol, 1.3 eq), tris(dibenzylideneacetone)dipalladium(0) (Pd₂(dba)₃, 869 mg, 0.949 mmol, 0.05 eq), Cs₂CO₃ (8.35 g, 25.63 mmol, 1.35 eq), and 4,5-Bis(diphenylphosphino)-9,9-dimethylxanthene (Xantphos, 659 mg, 1.14 mmol, 0.06 eq) were added. The resulting mixture was stirred while heating at 100° C. under inert atmosphere for 4 days. Subsequently, the mixture was cooled to ambient temperature, filtered through Celite® pad and concentrated under reduced pressure. The residue was purified by FCC (SiHP; AcOEt 100%) to give the product (3.2 g, 11.54 mmol, yield 61%) as a pale yellow oil. ESI-MS: 278.4 [M+H]⁺ b. (3S)-1-(pyridin-3-yl)piperidin-3-amine

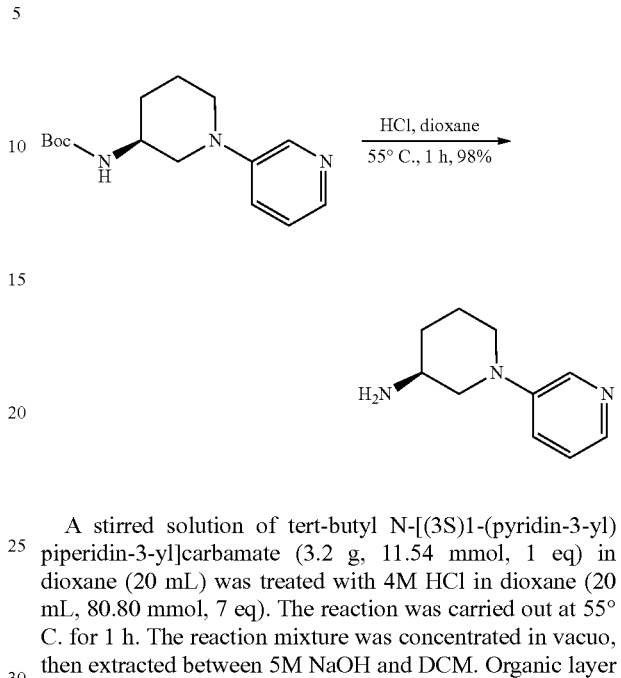

A stirred solution of tert-butyl N-[(3S)1-(pyridin-3-yl)piperidin-3-yl]carbamate (3.2 g, 11.54 mmol, 1 eq) in dioxane (20 mL) was treated with 4M HCl in dioxane (20 mL, 80.80 mmol, 7 eq). The reaction was carried out at 55° C. for 1 h. The reaction mixture was concentrated in vacuo, then extracted between 5M NaOH and DCM. Organic layer was dried, filtered off and concentrated to provide the product (2.00 g, 11.28 mmol, yield 98%) as a yellow oil. ESI-MS: 178.1 [M+H]⁺

Procedure 2. Preparation of 1-(pyridin-3-yl)piperidin-3-amine

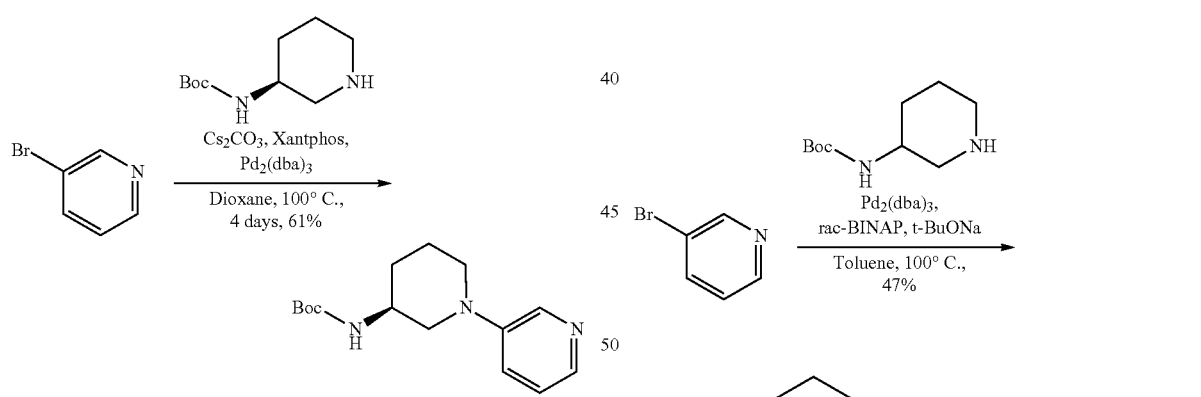

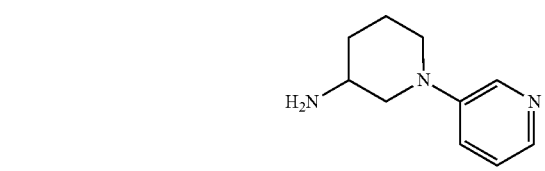

a. tert-butyl N-[1-(pyridin-3-yl)piperidin-3-yl]carbamate

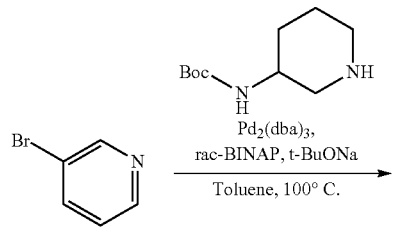

To a stirred solution of 3-bromopyridine (394 mg, 2.497 mmol, 1 eq) in anhydrous toluene (15 mL) tert-butyl N-(piperidin-3-yl)carbamate (500 mg, 2.497 mmol, 1 eq), tris(dibenzylideneacetone)dipalladium(0) (Pd$_2$(dba)$_3$, 114 mg, 0.125 mmol, 0.05 eq), sodium tert-butoxide (288 mg, 2.966 mmol, 1.2 eq), and (±)-2,2'-Bis(diphenylphosphino)-1,1'-binaphthalene (rac-BINAP, 155 mg, 0.250 mmol, 0.1 eq) were added. The resulting mixture was stirred while heating at 100° C. under inert atmosphere for 24 h. Subsequently, the mixture was cooled to ambient temperature, filtered through Celite® pad and partitioned between water and AcOEt. Combined organic phases were washed with brine, dried over sodium sulfate and concentrated under reduced pressure. The residue was purified by FCC (SiHP; DCM:MeOH 95:5) to give the product (359 mg, 1.2 mmol, yield 47%) as a yellow oil. ESI-MS: 278.5 [M+H]$^+$ b. 1-(pyridin-3-yl)piperidin-3-amine

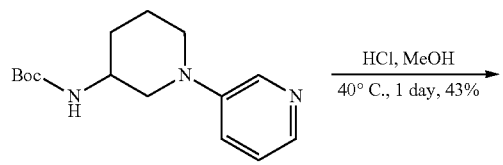

A stirred solution of tert-butyl N-[1-(pyridin-3-yl)piperidin-3-yl]carbamate (315 mg. 1.136 mmol, 1 eq) in MeOH (5 mL) was treated with 3M HCl in MeOH (1.5 mL, 4.543 mmol, 4 eq). The mixture was allowed to stir at 40° C. overnight. The reaction mixture was concentrated in vacuo, then dissolved in water and freeze-dried to provide the product as a hydrochloride (111 mg, 0.500 mmol, yield 43%) as a yellow powder. ESI-MS: 178.15 [M+H]$^+$ Procedure 3. Preparation of 1-methyl-3-({[(2-methylpyridin-4-yl)methyl][(3S)-1-(pyridin-3-yl)piperidin-3-yl]amino}methyl)-1,4-dihydroquinolin-4-one To a stirred solution of 3-bromopyridine (190 mg, 1.206 mmol, 1.2 eq) in anhydrous dioxane (5 mL) 1-methyl-3-({[(2-methylpyridin-4-yl)methyl][(3S)-piperidin-3-yl]amino}methyl)-1,4-dihydroquinolin-4-one (378 mg, 1.005 mmol, 1 eq), tris(dibenzylideneacetone)dipalladium(0) (Pd$_2$(dba)$_3$, 46 mg, 0.050 mmol, 0.05 eq), cesium carbonate (442 mg, 1.356 mmol, 1.35 eq), and 4,5-Bis(diphenylphosphino)-9,9-dimethylxanthene (Xantphos, 35 mg, 0.060 mmol, 0.06 eq) were added. The reaction was carried out at 95° C. under inert atmosphere for 24 h. Subsequently, the mixture was cooled to ambient temperature, filtered through Celite® pad and concentrated under reduced pressure. The residue was purified by RP-FCC (SiC18; H$_2$O:MeCN 100%) to give the product (48 mg, 0.106 mmol, yield 10%) as a yellow oil. The product was converted into hydrochloric acid salt. ESI-MS: 454.3 [M+H]$^+$ $^1$H NMR (300 MHz, DMSO-d$_6$) δ 8.61 (d, J=5.9 Hz, 1H), 8.58 (d, J=2.7 Hz, 1H), 8.31 (s, 1H), 8.22-8.11 (m, 3H), 8.06-7.93 (m, 2H), 7.89-7.73 (m, 2H), 7.68 (d, J=8.6 Hz, 1H), 7.44 (ddd, J=8.0, 6.8, 1.0 Hz, 1H), 4.49 (d, J=12.6 Hz, 1H), 4.40 (s, 2H), 4.04 (s, 2H), 3.94 (d, J=13.1 Hz, 1H), 3.85 (s, 3H), 3.37-3.25 (m, 1H), 3.23-3.08 (m, 1H), 3.03-2.85 (m, 1H), 2.57 (s, 3H), 2.25-2.18 (m, 1H), 1.96-1.82 (m, 2H), 1.65-1.43 (m, 1H).

Procedure 4. Preparation of 1-methyl-3-({[(2-methylpyridin-4-yl)methyl][(3S)-1-(pyridin-3-yl)piperidin-3-yl]amino}methyl)-1,4-dihydroquinolin-4-one

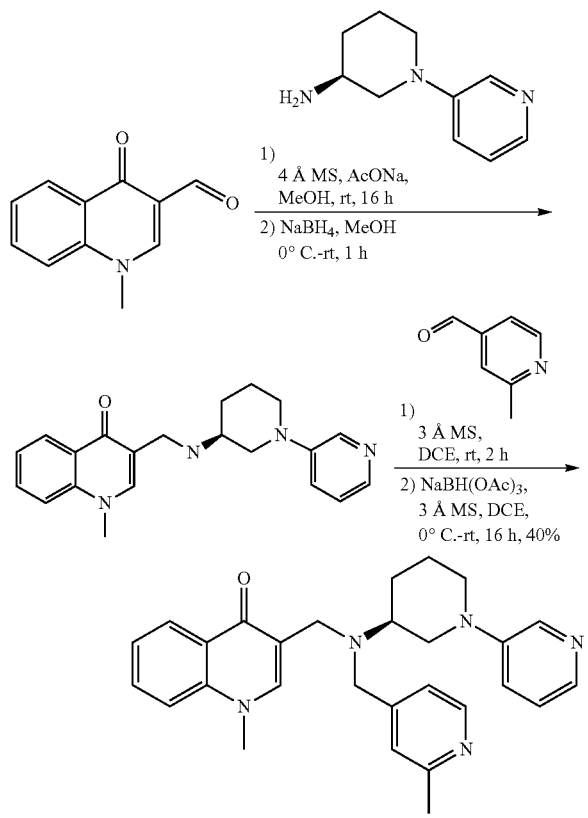

a. 1-methyl-3-({[(3S)-1-(pyridin-3-yl)piperidin-3-yl]amino}methyl)-1,4-dihydroquinolin-4-one

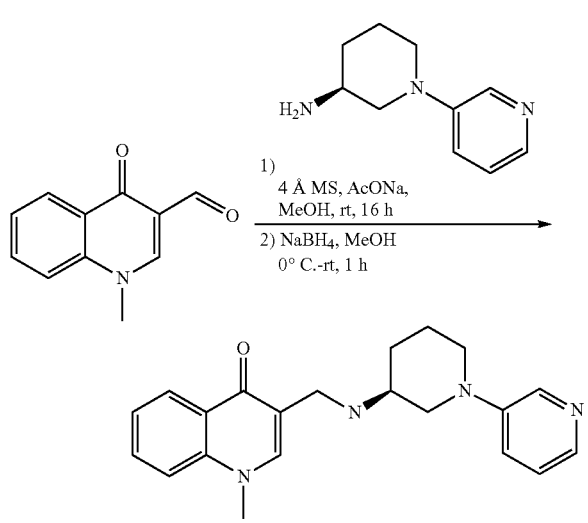

A mixture of 1-methyl-4-oxo-1,4-dihydroquinoline-3-carbaldehyde (2.90 g, 15.50 mmol, 1 eq.), (3S)-1-(pyridin-3-yl)piperidin-3-amine (3.02 g, 17.00 mmol, 1.1 eq), sodium acetate (1.27 g, 15.55 mmol, 1 eq.) in MeOH (100 mL) was stirred at rt for 16 h over activated 4 Å molecular sieves. Then, the mixture was cooled to 0° C. and sodium borohydride (0.64 g, 17.00 mmol, 1.1 eq.) was added portionwise over 30 min. The reaction was allowed to reach rt over 1 h. When the reaction was complete, the mixture was filtered through Celite® pad, washed with MeOH and the solvent was removed in vacuo. The residue was partitioned between DCM and NaOH aqueous solution (10%, 2N or 5N). The layers were separated. Organic layer was dried, filtered off and concentrated in vacuo. Crude product was used for the next step without further purification. Product as a yellow oil. ESI-MS: 349 [M+H]+ b. 1-methyl-3-({[(2-methylpyridin-4-yl)methyl][(3S)-1-(pyridin-3-yl)piperidin-3-yl]amino}methyl)-1,4-dihydroquinolin-4-one

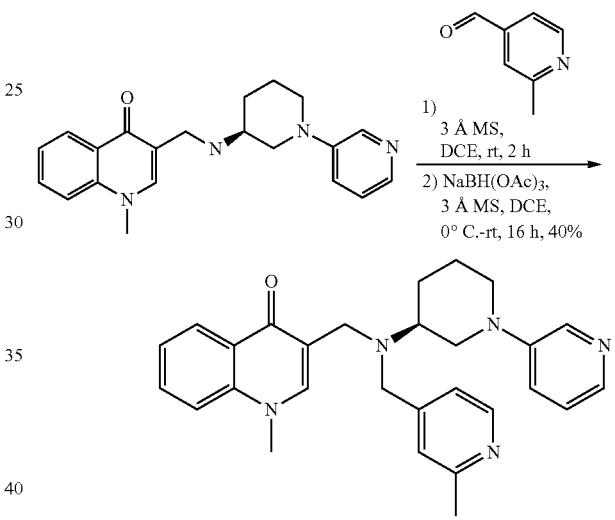

A mixture of 1-methyl-3-({[(3S)-1-(pyridin-3-yl)piperidin-3-yl]amino}methyl)-1,4-dihydroquinolin-4-one (0.95 g, 2.70 mmol, 1 eq) and 2-methylpyridine-4-carbaldehyde (0.33 g, 2.70 mmol, 1 eq) in DCE (20 mL) was stirred at rt for 2 h over activated 4 Å molecular sieves. Then, the mixture was cooled to 0° C. and sodium triacetoxyborohydride (0.87 g, 4.1 mmol, 1.5 eq) was added portionwise. The reaction was allowed to reach rt over 16 h. The reaction mixture was filtered through Celite® pad and washed with DCM. The filtrate was extracted with water. Organic layer was dried, filtered off and concentrated in vacuo. The residue was purified by FCC (SiHP, DCM:MeOH 9:1) to afford the title compound (500 mg, 1.1 mmol, yield 40%) as a white solid. ESI-MS: 454 [M+H]+

$^1$H NMR (400 MHz, DMSO-d$_6$) δ 8.32-8.27 (m, 2H), 8.20 (dd, J=8.0, 1.6 Hz, 1H), 8.04 (s, 1H), 7.92 (dd, J=4.5, 1.3 Hz, 1H), 7.72 (ddd, J=8.6, 6.9, 1.7 Hz, 1H), 7.63 (d, J=8.2 Hz, 1H), 7.38 (ddd, J=8.0, 6.9, 1.0 Hz, 1H), 7.32-7.23 (m, 3H), 7.15 (dd, J=8.5, 4.5 Hz, 1H), 4.00-3.92 (m, 1H), 3.79-3.56 (m, 5H), 2.90-2.82 (m, 1H), 2.79-2.60 (m, 3H), 2.38 (s, 3H), 2.04-1.97 (m, 1H), 1.80-1.73 (m, 1H), 1.61-1.43 (m, 2H). Some aliphatic H overlapped with solvent peak.

Procedure 5. Preparation of 3-({[(2-methoxypyridin-4-yl)methyl][1-(pyridazin-3-yl)piperidin-3-yl]amino}methyl)-1-methyl-1,4-dihydroquinolin-4-one Procedure 6. Preparation of 3-({[(2-methoxypyridin-4-yl)methyl][1-(pyrazin-2-yl)piperidin-3-yl]amino}methyl)-1-methyl-1,4-dihydroquinolin-4-one

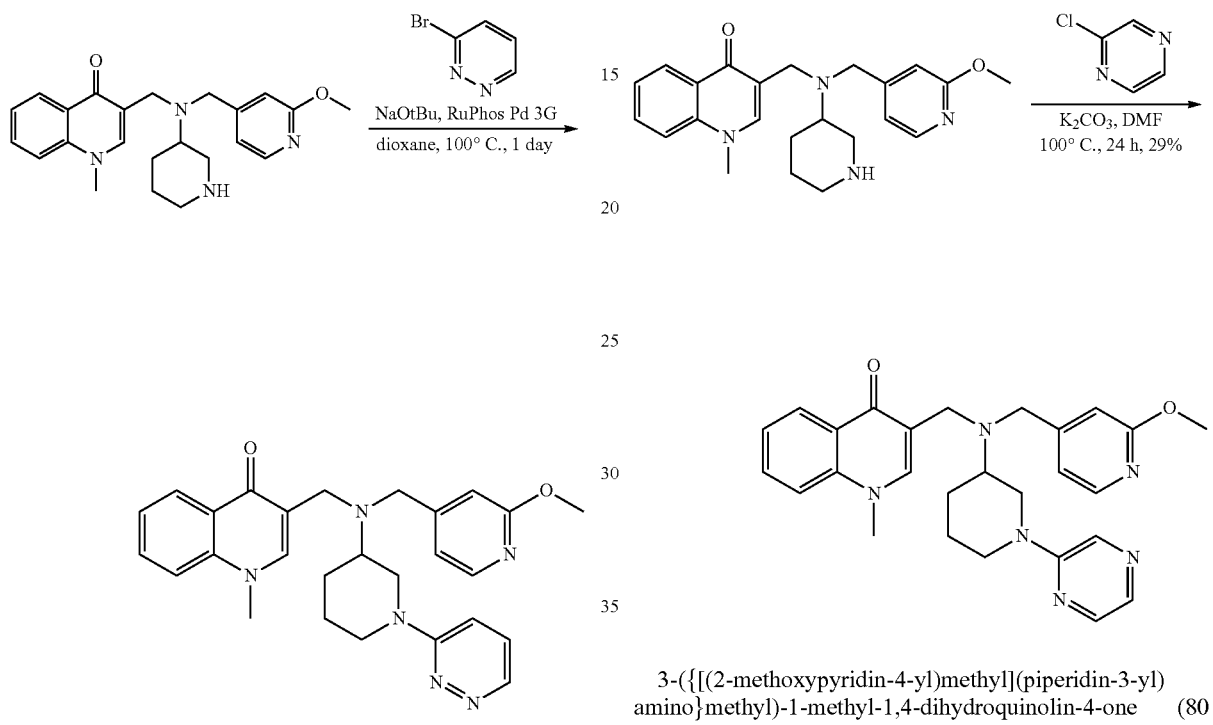

To a degassed solution of 3-bromopyridazine (29 mg, 0.18 mmol, 0.9 eq) in anhydrous dioxane (2 mL), 3-({[(2-methoxypyridin-4-yl)methyl](piperidin-3-yl)amino}methyl)-1-methyl-1,4-dihydroquinolin-4-one (80 mg, 0.20 mmol, 1 eq), sodium tert-butoxide (39 mg, 0.41 mmol, 2 eq) and (2-Dicyclohexylphosphino-2',6'-diisopropoxy-1,1-biphenyl)[2-(2'-amino-1,1-biphenyl)]palladium(II) methanesulfonate (RuPhos Pd 3G, 18 mg, 0.020 mmol, 0.1 eq) were added. The reaction was carried out at 100° C. under inert atmosphere for 1 day. Subsequently, the mixture was cooled to ambient temperature, filtered through Celite® pad and concentrated under reduced pressure. The residue was purified by FCC (SiHP; DCM:MeOH 9:1) to give the product (31 mg, 0.06 mmol, yield 30%) as a yellow solid. ESI-MS: 471 [M+H]$^+$ $^1$H NMR (300 MHz, DMSO-d$_6$) δ 8.49-8.46 (m, 1H), 8.21-8.16 (m, 1H), 8.06 (s, 1H), 8.03-7.99 (m, 1H), 7.76-7.69 (m, 1H), 7.66-7.60 (m, 1H), 7.41-7.23 (m, 3H), 7.06-7.01 (m, 1H), 6.85 (s, 1H), 4.66-4.56 (m, 1H), 4.34-4.23 (m, 1H), 3.87 (s, 3H), 3.77 (s, 3H), 3.74-3.54 (m, 2H), 3.06-2.95 (m, 1H), 2.87-2.75 (m, 1H), 2.05-1.92 (m, 1H), 1.80-1.61 (m, 2H), 1.43-1.29 (m, 1H). Some aliphatic H overlapped with solvent peak.

3-({[(2-methoxypyridin-4-yl)methyl](piperidin-3-yl)amino}methyl)-1-methyl-1,4-dihydroquinolin-4-one (80 mg, 0.20 mmol, 1 eq.), 3-chloropyrazine (20 μL, 0.22 mmol, 1.10 eq.) and potassium carbonate (56 mg, 0.41 mmol, 2 eq.) were dissolved in DMF (2 mL). The reaction was carried out at 100° C. for 24 h. The resulting mixture was cooled to rt and partitioned between saturated NaHCO$_3$ and AcOEt. Organic layer was washed with water and brine (30 mL). Organic layer was dried, filtered off and concentrated in vacuo. The residue was purified by prep-HPLC to afford the title compound as a yellow solid (28 mg, 0.059 mmol yield 29%). ESI-MS: 471 [M+H]$^+$ $^1$H NMR (300 MHz, DMSO-d$_6$) δ 8.33 (s, 1H), 8.21-8.15 (m, 1H), 8.07-7.98 (m, 3H), 7.78-7.68 (m, 2H), 7.66-7.60 (m, 1H), 7.43-7.33 (m, 1H), 7.07-7.00 (m, 1H), 6.85 (s, 1H), 4.59-4.48 (m, 1H), 4.34-4.22 (m, 1H), 3.86 (s, 3H), 3.81-3.74 (m, 4H), 3.73-3.52 (m, 2H), 3.05-2.93 (m, 1H), 2.84-2.71 (m, 1H), 2.07-1.95 (m, 1H), 1.83-1.58 (m, 2H), 1.45-1.30 (m, 1H). Some aliphatic H overlapped with solvent peak.

The product was converted into hydrochloric acid salt. Product as a yellow solid. ESI-MS: 471 [M+H]$^+$ $^1$H NMR (400 MHz, Deuterium Oxide) δ 8.07 (s, 1H), 7.99-7.93 (m, 1H), 7.93-7.87 (m, 1H), 7.85-7.79 (m, 1H), 7.79-7.72 (m, 1H), 7.71-7.59 (m, 2H), 7.56-7.49 (m, 1H), 7.49-7.42 (m, 1H), 6.81 (s, 1H), 6.58 (s, 1H), 4.41-4.17 (m, 4H), 3.79-3.74 (m, 1H), 3.73-3.70 (m, 3H), 3.67-3.57 (m, 2H), 3.41 (s, 3H), 3.31-3.18 (m, 1H), 2.31-2.22 (m, 1H), 2.22-2.08 (m, 1H), 2.05-1.94 (m, 1H), 1.75-1.62 (m, 1H). Aliphatic H overlapped with solvent peak.

Procedure 7. Preparation of 1-cyclopropyl-6-fluoro-3-({[(2-methoxypyridin-4-yl)methyl][(3S)-1-(pyridin-3-yl)piperidin-3-yl]amino}methyl)-7-(4-methylpiperazin-1-yl)-1,4-dihydroquinolin-4-one

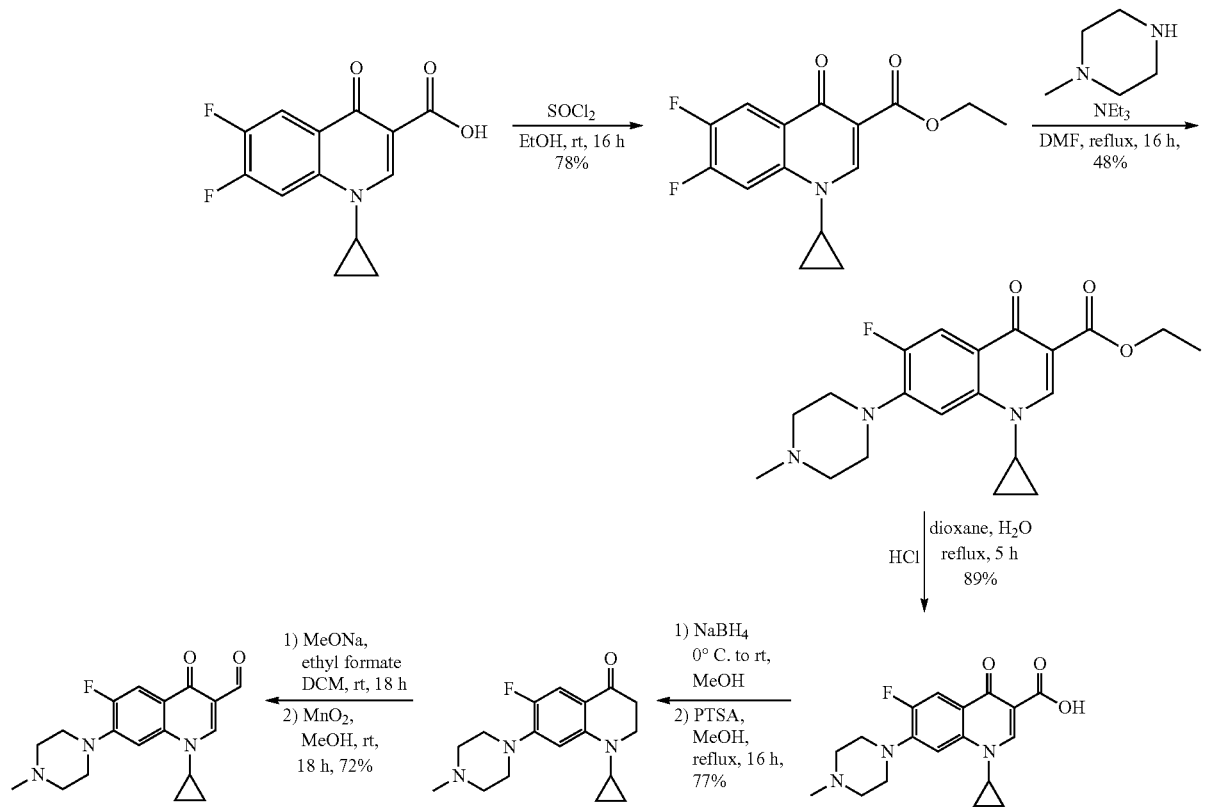

a. ethyl 1-cyclopropyl-6,7-difluoro-4-oxo-1,4-dihydroquinoline-3-carboxylate

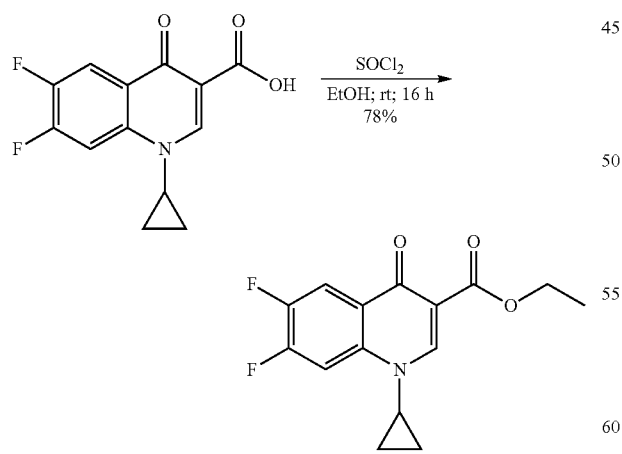

Thionyl chloride (2.47 mL, 33.93 mmol, 30 eq) was added dropwise to a stirred solution of ethanol (16.5 mL) at 22° C. After 30 minutes, the mixture turned into a yellowish solution; then 1-cyclopropyl-6,7-difluoro-4-oxo-1,4-dihydroquinoline-3-carboxylic acid (0.30 g, 1.13 mmol, 1 eq) was added and it was stirred for 16 h. After completion of the reaction solvents were removed in vacuo and the residue partitioned between DCM and water. Extraction with DCM was done. Organic layers were connected, dried over magnesium sulfate and concentrated under reduced pressure. Product was purified by FCC (SiHP; Hex:AcOEt 4:1) to afford the product as a white solid (0.33 g, 0.88 mmol, yield 78%). ESI-MS: 294 [M+H]⁺ b. ethyl 1-cyclopropyl-6-fluoro-7-(4-methylpiperazin-1-yl)-4-oxo-1,4-dihydroquinoline-3-carboxylate

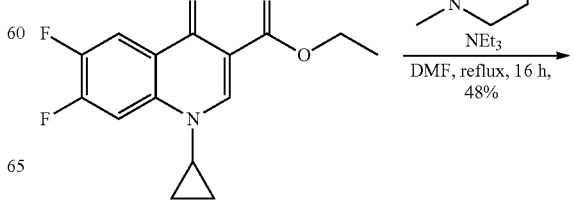

-continued

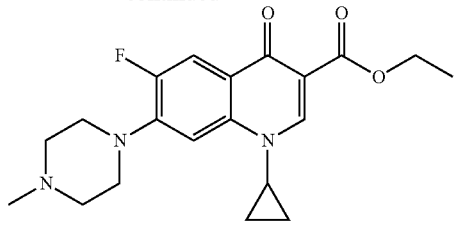

A solution of ethyl 1-cyclopropyl-6,7-difluoro-4-oxo-1,4-dihydroquinoline-3-carboxylate (0.26 g, 0.88 mmol, 1 eq), 1-methylpiperazine (0.293 mL, 2.64 mmol, 3 eq) and triethylamine (0.368 mL, 2.64 mmol, 3 eq) in MeCN (5 mL) was refluxed for 16 h under inert atmosphere. After cooling to room temperature, the mixture was diluted with water and extracted with DCM. Organic layers were dried, filtered off and evaporated. The residue was purified by FCC (SiHP; DCM:MeOH 9:1) to afford the product as a yellow solid (0.14 g, 0.27 mmol, yield 48%). ESI-MS: 374 [M+H]+ c. 1-cyclopropyl-6-fluoro-7-(4-methylpiperazin-1-yl)-4-oxo-1,4-dihydroquinoline-3-carboxylic acid

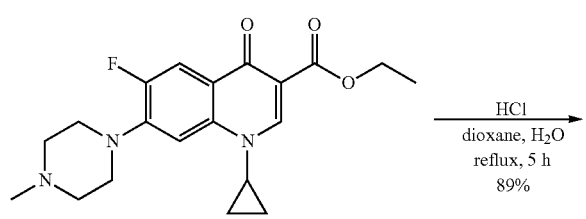

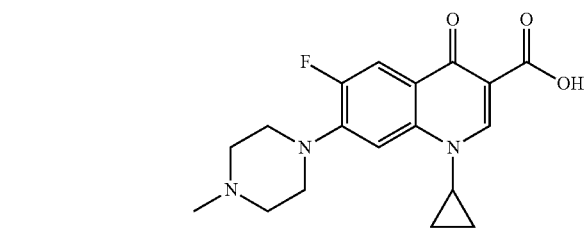

A solution of ethyl 1-cyclopropyl-6-fluoro-7-(4-methylpiperazin-1-yl)-4-oxo-1,4-dihydroquinoline-3-carboxylate (0.14 g, 0.39 mmol, 1 eq) in conc. HCl (1 mL), H2O (3 mL), and dioxane (9 mL) was stirred at reflux for 5 h. Solvents were evaporated, then crude was partitioned between water and DCM. Organic layers were combined, dried, and concentrated in vacuo. Product as a white solid (0.12 g, 0.34 mmol, yield 89%). ESI-MS: 346 [M+H]+

$^1$H NMR (400 MHz, DMSO-d6) δ 8.67 (s, 1H), 7.91 (d, J=13.4 Hz, 1H), 7.56 (d, J=7.5 Hz, 1H), 3.83 (s, 1H), 3.74-3.64 (m, 1H), 3.53-3.44 (m, 1H), 2.26 (s, 3H), 1.37-1.14 (m, 4H). Some aliphatic H overlapped with solvent peak.

d. 1-cyclopropyl-6-fluoro-7-(4-methylpiperazin-1-yl)-1,2,3,4-tetrahydroquinolin-4-one

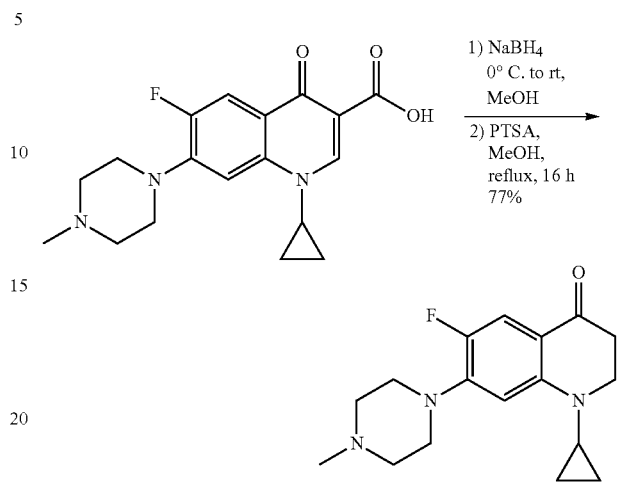

To a cooled solution of 1-cyclopropyl-6-fluoro-7-(4-methylpiperazin-1-yl)-4-oxo-1,4-dihydroquinoline-3-carboxylic acid (0.19 g, 0.34 mmol, 1 eq) in anhydrous MeOH (5 mL) sodium borohydride (0.059 g, 1.55 mmol, 4.5 eq) was added slowly over 30 minutes. The mixture was allowed to warm up to rt, p-toluenesulfonic acid (0.007 g, 0.034 mmol, 0.10 eq) was added and the reaction mixture was heated at reflux for 16 h. Subsequently, the mixture was allowed to cool to rt, solvent was removed in vacuo. The residue partitioned between chloroform and water. Organic layer was dried, filtered and concentrated under reduced pressure. FCC (SiHP; Hex:AcOEt 4:1) afforded the product (0.081 g, 0.27 mmol, yield 77%) as a yellow solid. ESI-MS: 304 [M+H]+

$^1$H NMR (400 MHz, DMSO-d6) δ 7.29 (d, J=13.8 Hz, 1H), 6.74 (d, J=7.6 Hz, 1H), 3.44 (dd, J=7.5, 6.2 Hz, 2H), 3.19-3.16 (m, 4H), 2.42-2.35 (m, 1H), 2.24 (s, 3H), 0.91-0.86 (m, 2H), 0.70-0.64 (m, 2H). Aliphatic H overlapped with solvent peak.

e. 1-cyclopropyl-6-fluoro-7-(4-methylpiperazin-1-yl)-4-oxo-1,4-dihydroquinoline-3-carbaldehyde

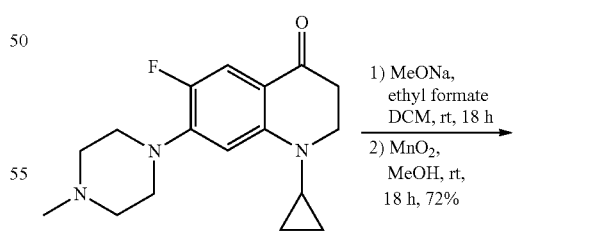

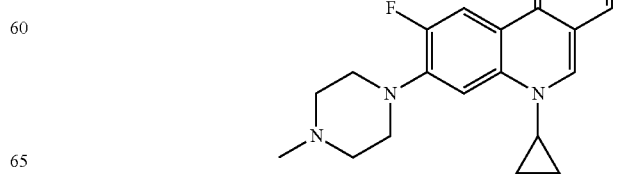

To a mixture of sodium methoxide (0.056 g, 1.04 mmol, 3.9 eq) and ethyl formate (0.085 mL, 1.05 mmol, 3.94 eq) in anhydrous DCM (5 mL) a solution of 1-cyclopropyl-6-fluoro-7-(4-methylpiperazin-1-yl)-1,2,3,4-tetrahydroquinolin-4-one (0.081 g, 0.27 mmol, 1 eq) was added and the mixture was stirred at rt for 18 h. Subsequently, the reaction mixture was poured into ice-cold water. Phases were separated. Organic layer was washed with 3 M sodium hydroxide. Combined aqueous phases were acidified to pH 6 and extracted with DCM. Organic layers were combined, dried, filtered and concentrated under reduced pressure. The residue was redissolved in anhydrous MeOH (5 mL) and manganese dioxide (0.088 g, 1.01 mmol, 5 eq) was added. After stirring at room temperature for 18 h, the mixture was filtered through Celite® and washed with MeOH and DCM. The filtrate was concentrated in vacuo. The residue was purified by FCC (SiHP, Hexane: AcOEt 1:1) to afford the product as a white solid (0.048 g, 0.15 mmol, yield 72%). ESI-MS: 330 [M+H]$^+$ $^1$H NMR (400 MHz, DMSO-d6) δ 10.11 (s, 1H), 8.32 (s, 1H), 7.81 (d, J=13.5 Hz, 1H), 7.49 (d, J=7.4 Hz, 1H), 3.75-3.68 (m, 1H), 3.27 (dd, J=6.1, 3.8 Hz, 4H), 2.26 (s, 3H), 1.28-1.22 (m, 2H), 1.16-1.10 (m, 2H). Some aliphatic H overlapped with solvent peak.

Procedure 8. Preparation of 1-methyl-3-({[(2-methylpyridin-4-yl)methyl][(3S)-1-(pyridin-2-yl)piperidin-3-yl]amino}methyl)-1,4-dihydroquinolin-4-one

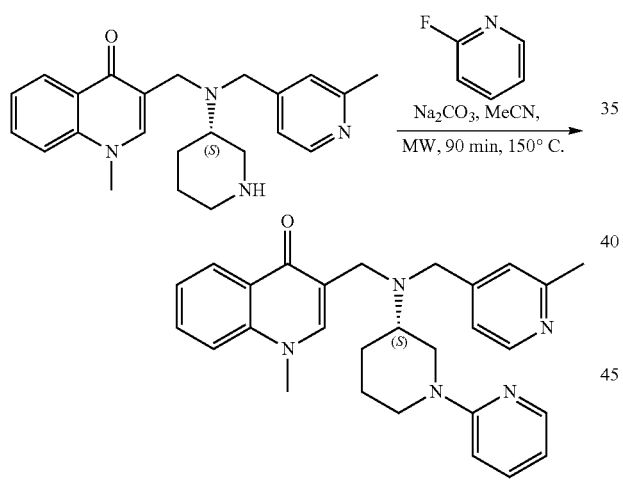

To a solution of 1-methyl-3-({[(2-methylpyridin-4-yl)methyl][(3S)-piperidin-3-yl]amino}methyl)-1,4-dihydroquinolin-4-one (116 mg, 0.31 mmol, 1.2 eq) in anhydrous MeCN (2 mL), 2-fluoropyridine (22 μL, 0.26 mmol, 1 eq) and Na$_2$CO$_3$ (55 mg, 0.51 mmol, 2 eq) were added. The reaction was carried out for 90 min at 150° C. under microwave radiation. The reaction was cooled to rt and partitioned between DCM and water. Organic layer was washed with brine, dried, filtered off and the solvent was removed in vacuo. The residue was purified by prep-HPLC to afford the title compound as a yellow solid (10 mg, 0.02 mmol yield 9%). ESI-MS: 454 [M+H]$^+$ $^1$H NMR (300 MHz, DMSO-d6) δ 8.31-8.25 (m, 1H), 8.22-8.16 (m, 1H), 8.09-8.04 (m, 1H), 8.01 (s, 1H), 7.76-7.68 (m, 1H), 7.66-7.59 (m, 1H), 7.50-7.41 (m, 1H), 7.41-7.33 (m, 1H), 7.25 (s, 1H), 7.24-7.20 (m, 1H), 6.84-6.77 (m, 1H), 6.57-6.50 (m, 1H), 4.55-4.42 (m, 1H), 4.28-4.17 (m, 1H), 3.85 (s, 3H), 3.79-3.73 (m, 2H), 3.71-3.54 (m, 2H), 2.96-2.84 (m, 1H), 2.76-2.68 (m, 1H), 2.67-2.58 (m, 1H), 2.37 (s, 3H), 2.05-1.94 (m, 1H), 1.79-1.68 (m, 1H), 1.68-1.54 (m, 1H), 1.42-1.21 (m, 1H).

Procedure 9. Preparation of 1-methyl-7-(4-methylpiperazin-1-yl)-4-oxo-1,4-dihydroquinoline-3-carbaldehyde

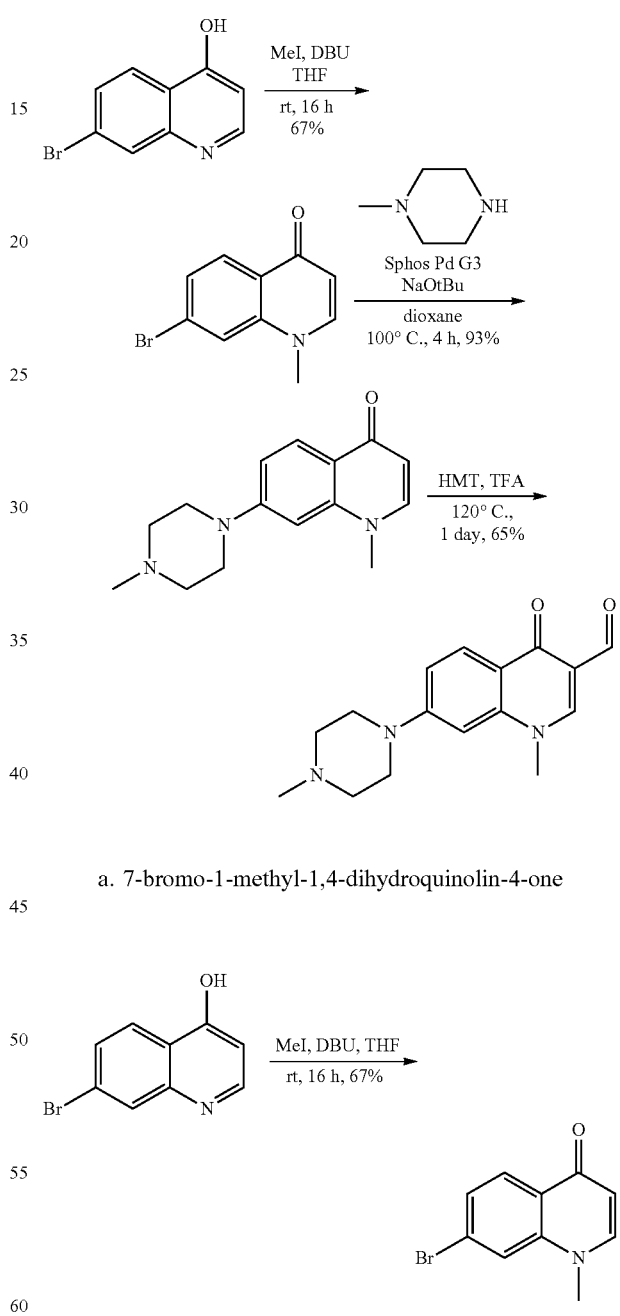

a. 7-bromo-1-methyl-1,4-dihydroquinolin-4-one 7-bromoquinolin-4-ol (3.00 g, 13.39 mmol, 1 eq) was suspended in anhydrous THF (10 mL). Then, 1,8-diazabicyclo(5.4.0)undec-7-en (DBU) (0.99 mL, 7.00 mmol, 1.5 eq) was added dropwise, followed methyl iodide (0.55 mL, 8.00 mmol, 2 eq) and the resulting mixture was stirred at rt overnight. The reaction was quenched with water and extracted with DCM. Organic layers were combined, washed with brine, dried over anhydrous sodium sulfate and concentrated. The residue was purified by FCC (SiHP, DCM:MeOH, 95:5) to give the product (0.72 g, 4.40 mmol, yield 67%) as a yellow solid. ESI-MS: 239 [M+H]+ b. 1-methyl-7-(4-methylpiperazin-1-1)-1,4-dihydro-quinolin-4-one

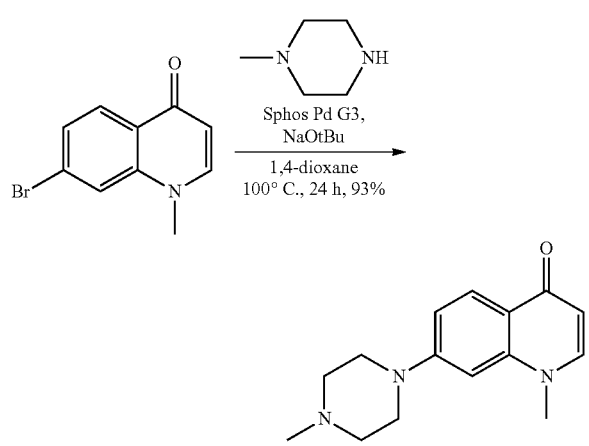

To a solution of 7-bromo-1-methyl-1,4-dihydroquinolin-4-one (700 mg, 2.94 mmol, 1 eq) in anhydrous dioxane (15 mL), 1-methylpiperazine (330 μL, 2.94 mmol, 1 eq), sodium tert-butoxide (339 mg, 3.53 mmol, 1.2 eq), and 2-dicyclohexylphosphino-2',6'-dimethoxybiphenyl) [2-(2'-amino-1,1'-biphenyl)]palladium(11) methanesulfonate (Sphos Pd 3G, (229 mg, 0.29 mmol, 0.1 eq) were added. The reaction was carried out at 100° C. under inert atmosphere for 24 h. Subsequently, the mixture was cooled to ambient temperature, filtered through Celite® pad and concentrated under reduced pressure. The residue was purified by FCC (SiHP, DCM:MeOH, 8:2) to obtain the product (722 mg, 2.81 mmol, yield 93%) as a yellow solid ESI-MS: 258 [M+H]+ c. 1-methyl-7-(4-methylpiperazin-1-yl)-4-oxo-1,4-dihydroquinoline-3-carbaldehyde 1-methyl-7-(4-methylpiperazin-1-yl)-1,4-dihydroquinolin-4-one (300 mg, 1.17 mmol, 1 eq), 1,3,5,7-tetraazatricyclo[3.3.1.1.3,7]decane (HMT) (327 mg, 2.33 mmol, 2 eq) and TFA (2 mL) were irradiated with microwave at 120° C. for 15 min. The reaction mixture was diluted with water (5 mL) and stirred for 10 min. Then, the mixture was neutralized using saturated Na2CO3 solution and extracted with DCM. Organic layers were combined, dried and concentrated in vacuo. The residue was triturated with ethyl acetate give the product (270 mg, 0.95 mmol, yield 65%) as a yellow solid.

Procedure 10. Preparation of (2-ethylpyridin-4-yl)methanamine

2-Ethylisonicotinitrile (400 mg, 3.03 mmol, 1 eq) was dissolved in THF and cooled to −78° C. Then, a solution of LiAlH4 (1M in THF, 3.63 mL, 3.63 mmol, 1.2 eq) was added dropwise. The reaction was carried out at −78° C. for 30 min, quenched with saturated Na2SO4 solution and extracted with DCM. Organic layers were combined, washed with brine, dried, filtered off and concentrated in vacuo. Crude product was used in the next reaction without further purification. Product as a yellow oil (360 mg, 2.64 mmol, yield 87%). ESI-MS: 137 [M+H]+

1H NMR (400 MHz, DMSO-d6) δ 8.37-8.34 (m, 1H), 7.22 (s, 1H), 7.16-7.13 (m, 1H), 3.71 (s, 2H), 2.75-2.68 (m, 2H), 1.25-1.18 (m, 3H).

Procedure 11. Preparation of 1-methyl-3-({[(2-methylpyridin-4-yl)methyl][(3S)-1-(6-oxo-1,6-dihydropyrimidin-4-yl)piperidin-3-yl]amino}methyl)-1,4-dihydroquinolin-4-one 3-({[(3S)-1-(6-chloropyrimidin-4-yl)piperidin-3-yl][(2-methylpyridin-4-yl)methyl]amino}methyl)-1-methyl-1,4-dihydroquinolin-4-one was dissolved in a mixture of dioxane and 2N NaOH (v/v 1:10) and heated at 100° C. for 2 days. The mixture was diluted with 15% aqueous NaOH and extracted with CHCl$_3$:iPrOH (v/v 3:1). Organic layer was dried, filtered off and concentrated in vacuo. The residue was purified by prep-HPLC to afford the title compound as a beige solid (3 mg, 0.006 mmol, yield 6%). ESI-MS: 471 [M+H]$^+$ $^1$H NMR (400 MHz, DMSO-d$_6$) δ 11.51 (s, 1H), 8.29-8.25 (m, 1H), 8.19 (dd, J=8.1, 1.6 Hz, 1H), 8.02 (s, 1H), 7.85 (s, 1H), 7.72 (ddd, J=8.6, 6.9, 1.6 Hz, 1H), 7.62 (d, J=8.5 Hz, 1H), 7.37 (ddd, J=8.1, 6.9, 1.0 Hz, 1H), 7.24 (s, 1H), 7.23-7.19 (m, 1H), 5.30 (s, 1H), 4.42-4.30 (m, 1H), 4.22-4.12 (m, 1H), 3.85 (s, 3H), 3.80-3.70 (m, 2H), 3.70-3.51 (m, 2H), 3.01-2.92 (m, 1H), 2.77-2.70 (m, 1H), 2.60-2.54 (m, 1H), 2.37 (s, 3H), 2.04-1.96 (m, 1H), 1.76-1.68 (m, 1H), 1.68-1.57 (m, 1H), 1.35-1.25 (m, 1H).

Procedure 12. Preparation of ethyl 7-chloro-6-fluoro-1-methyl-4-oxo-1,4-dihydroquinoline-3-carboxylate a. 1,3-diethyl 2-{[(3-chloro-4-fluorophenyl)amino]methylidene}propanedioate

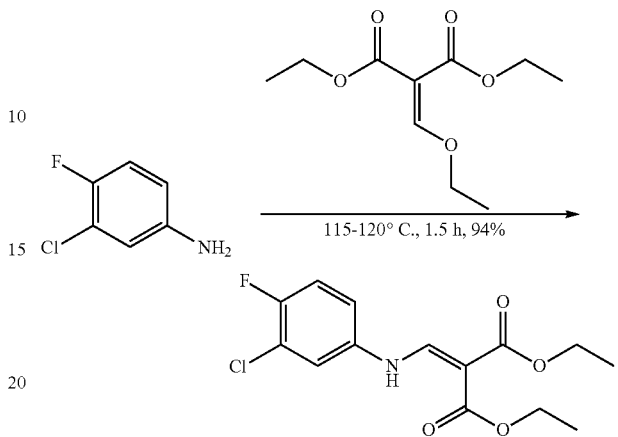

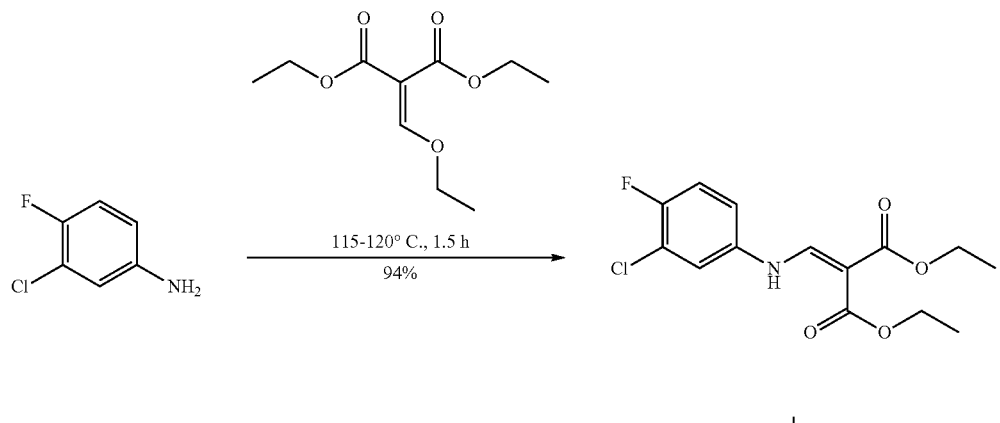

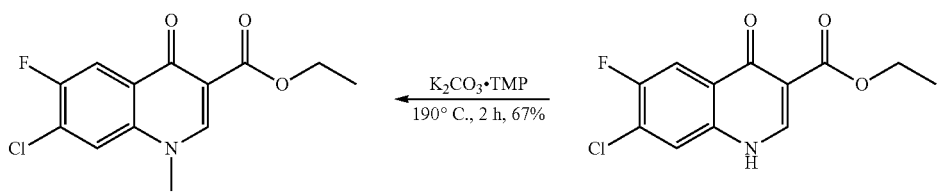

3-chloro-4-fluoroaniline (2.5 g, 17.17 mmol, 1 eq) and diethyl ethoxymethylenemalonate (3.47 mL, 17.17 mmol, 1 eq) were heated at 115-120° C. for 90 min. The reaction mixture was cooled to room temperature and diluted with 70% aqueous methanol. Precipitated crystals were collected, washed with 70% aqueous methanol and dried. Product (5.10 g, 16.17 mmol, yield 94%) as a white solid. ESI-MS: 316 [M+H]$^+$ b. ethyl 7-chloro-6-fluoro-4-oxo-1,4-dihydroquinoline-3-carboxylate

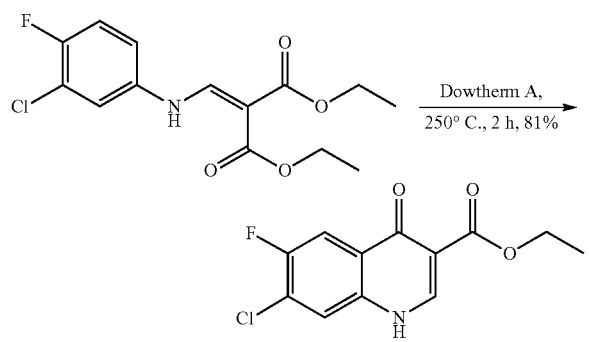

Dowtherm A (100 mL) was pre-heated at 250° C. and 1,3-diethyl 2-{[(3-chloro-4-fluorophenyl)amino]methylidene}propanedioate (5.10 g, 16.17 mmol, 1 eq) was added. The mixture was stirred at 250° C. for 3 h under reflux. The reaction mixture was cooled to room temperature. Precipitated crystals were collected, washed with diethyl ether and dried. Product was suspended in EtOH. The mixture was stirred under reflux conditions for 30 min, cooled to room temperature with the crystals being collected and dried. The product (3.50 g, 13.13 mmol, yield 81%) was used in the next step without further purification. ESI-MS: 268 [M+H]$^+$ c. ethyl 7-chloro-6-fluoro-1-methyl-4-oxo-1,4-dihydroquinoline-3-carboxylate

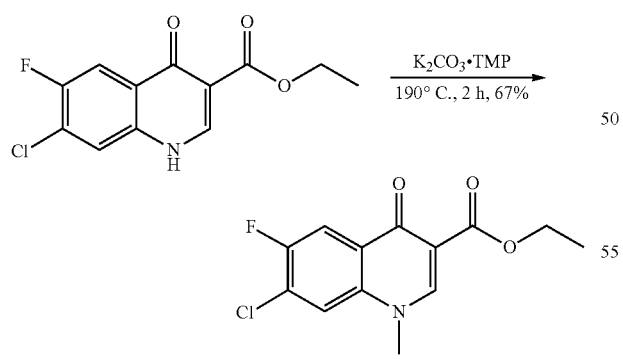

To ethyl 7-chloro-6-fluoro-4-oxo-1,4-dihydroquinoline-3-carboxylate (1.00 g, 3.71 mmol, 1 eq), trimethyl phosphate (1.736 mL, 14.83 mmol, 4 eq) and anhydrous potassium carbonate (0.54 g, 3.89 mmol, 1.05 eq) were added. The mixture was stirred at 190° C. for 2 h, then cooled to 100° C. and poured into ice-cold water. The precipitated crystals were collected, washed with water and ethanol, and dried. The residue was purified by FCC (Si-Diol; Hex: AcOEt 1:1). Product (0.70 g, 2.48 mmol, yield 67%) as a white solid. ESI-MS: 284 [M+H]$^+$ $^1$H NMR (400 MHz, DMSO-d$_6$) δ 8.66 (s, 1H), 8.06 (d, J=6.1 Hz, 1H), 7.98 (d, J=9.4 Hz, 1H), 4.22 (q, J=7.1 Hz, 2H), 3.91 (s, 3H), 1.28 (t, J=7.1 Hz, 3H).

Procedure 13. Preparation of 1-cyclopropyl-6,7-difluoro-4-oxo-1,4-dihydroquinoline-3-carbaldehyde

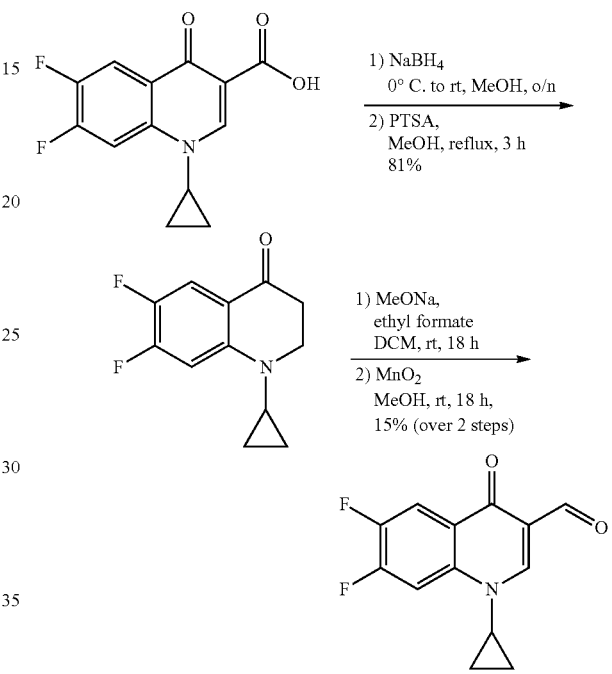

a. 1-cyclopropyl-6,7-difluoro-1,2,3,4-tetrahydroquinolin-4-one

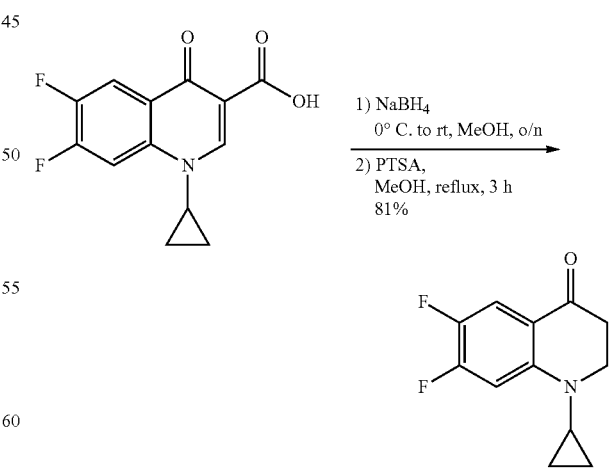

The title compound was synthesized following the approach outlined in Procedure 7d substituting 1-cyclopropyl-6-fluoro-7-(4-methylpiperazin-1-yl)-4-oxo-1,4-dihydroquinoline-3-carboxylic acid with 1-cyclopropyl-6,7-difluoro-4-oxo-1,4-dihydroquinoline-3-carboxylic acid. The mixture was stirred at room temperature overnight. After addition of p-toluenesulfonic acid, reaction mixture was heated at reflux for 3 hours. Product was obtained as a yellow solid (6.82 g, 30.55 mmol, yield 81%). ESI-MS: 224 [M+H]⁺

¹H NMR (400 MHz, Chloroform-d) δ 7.69 (dd, J=10.6, 9.2 Hz, 1H), 7.07 (dd, J=13.0, 6.5 Hz, 1H), 3.56-3.50 (m, 2H), 2.67-2.62 (m, 2H), 2.36-2.30 (m, 1H), 0.96-0.91 (m, 2H), 0.75-0.70 (m, 2H).

b. 1-cyclopropyl-6,7-difluoro-4-oxo-1,4-dihydroquinoline-3-carbaldehyde

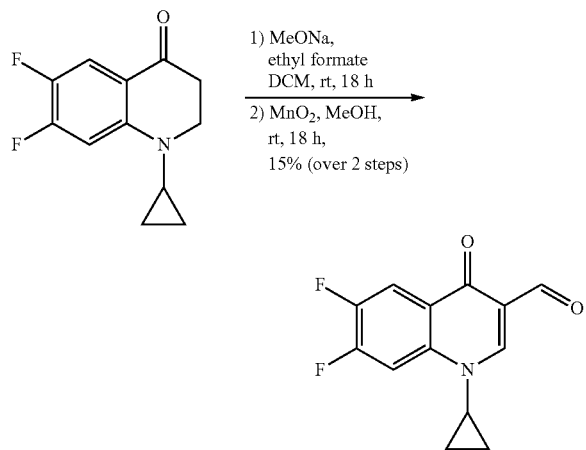

The title compound was synthesized following the approach outlined in Procedure 7e substituting 1-cyclopropyl-6-fluoro-7-(4-methylpiperazin-1-yl)-1,2,3,4-tetrahydroquinolin-4-one with 1-cyclopropyl-6,7-difluoro-1,2,3,4-tetrahydroquinolin-4-one. Product after FCC was triturated with Et₂O and hexane to give the title compound as a beige solid (1.17 g, 4.69 mmol, yield 15%). ESI-MS: 250 [M+H]⁺

¹H NMR (400 MHz, DMSO-d₆) δ 10.12 (s, 1H), 8.41 (s, 1H), 8.23 (dd, J=12.1, 6.7 Hz, 1H), 8.15 (dd, J=10.5, 8.8 Hz, 1H), 3.69 (tt, J=7.3, 4.0 Hz, 1H), 1.32-1.23 (m, 2H), 1.18-1.11 (m, 2H).

Procedure 14. Preparation of 1-methyl-4-oxo-1,4-dihydroquinoline-3-carbaldehyde

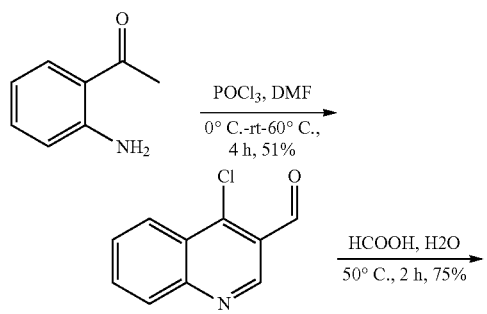

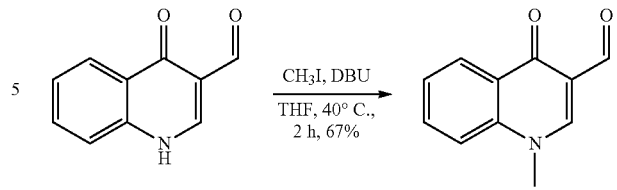

a. 4-chloroquinoline-3-carbaldehyde

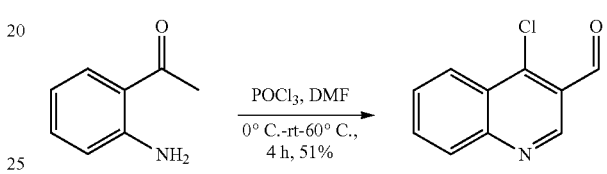

To an anh. DMF (20 mL), POCl₃ (8.27 mL, 88.8 mmol, 6 eq) was added dropwise at 0° C. Then 1-(2-aminophenyl)ethan-1-one (2.00 g, 14.8 mmol, 1 eq) in anh. DMF (5 mL) was added dropwise, and the reaction was heated for 4 h at 60° C. Afterwards, the reactions was cooled down to 0° C., quenched with water. Then solution was neutralized with saturated NaHCO₃ aqueous solution, diluted in water and extracted with DCM. The layers were separated. Organic layer was dried over MgSO₄, filtered off and concentrated in vacuo to afford the title compound (1.43 g, 7.49 mmol, yield 51%) as an orange solid that was taken to the next step without additional purification. ESI-MS: 192 [M+H]⁺ b. 4-oxo-1,4-dihydroquinoline-3-carbaldehyde

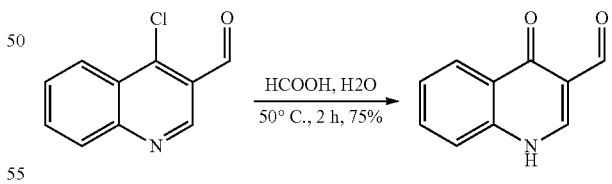

4-chloroquinoline-3-carbaldehyde (1.10 g, 5.74 mmol, 1 eq) was suspended in 54% aqueous solution HCOOH (13.41 mL). The reaction was carried out at 50° C. for 2 h. The resulting mixture was being frozen in a fridge for 16 h. Precipitate was filtered off and washed with water to give product (0.75 g, 4.33 mmol, yield 75%) as an orange solid. ESI-MS: 174 [M+H]⁺

¹H NMR (400 MHz, DMSO-d₆) δ 12.69 (s, 1H), 10.20 (s, 1H), 8.49 (s, 1H), 8.22 (dd, J=8.0, 1.5 Hz, 1H), 7.77 (m, 1H), 7.67 (dd, J=8.3, 1.1 Hz, 1H), 7.48 (m, 1H).

c.
1-methyl-4-oxo-1,4-dihydroquinoline-3-carbaldehyde

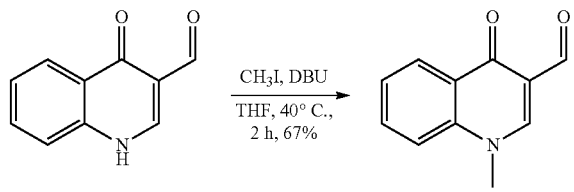

4-oxo-1,4-dihydroquinoline-3-carbaldehyde (0.50 g, 2.89 mmol, 1 eq) was suspended in THF (13 mL). DBU (1.01 g, 7.22, 2.5 eq) was added, followed by methyl iodide (4.10 g, 28.8 mmol, 10 eq). The reaction was carried out at 40° C. for 2 h. Afterwards, reactions was quenched with water and extracted with DCM. The layers were separated. Organic layer was dried over MgSO4, filtered off and concentrated in vacuo. The residue was purified by crystallization from hot EtOH to afford the title compound (0.36 g, 1.94 mmol, yield 67%) as a beige solid. ESI-MS: 188 [M+H]+

$^1$H NMR (400 MHz, DMSO-$d_6$) δ 10.19 (s, 1H), 8.63 (s, 1H), 8.31 (dd, J=8.0, 1.6 Hz, 1H), 7.87 (m, 1H), 7.80 (dd, J=8.6, 1.1 Hz, 1H), 7.57 (m, 1H), 3.98 (s, 3H).

Procedure 15. Preparation of 7-chloro-1-cyclopropyl-6-fluoro-3-({[(2-methylpyridin-4-yl)methyl][(3S)-1-(pyridin-3-yl)piperidin-3-yl]amino}methyl)-1,4-dihydroquinolin-4-one

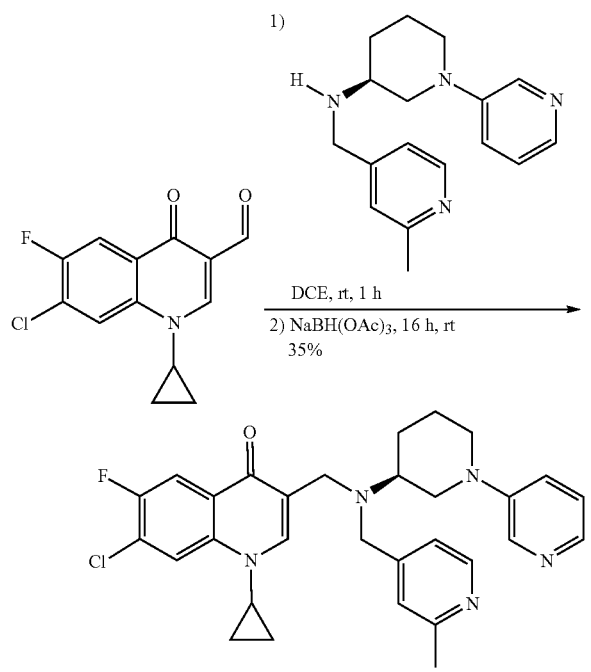

To the (3S)—N-[(2-methylpyridin-4-yl)methyl]-1-(pyridin-3-yl)piperidin-3-amine (0.12 g, 0.425 mmol, 1 eq.) in DCE (10 mL), 7-chloro-1-cyclopropyl-6-fluoro-4-oxo-1,4-dihydroquinoline-3-carbaldehyde (0.124 g, 0.467 mmol, 1.1 eq.) was added under argon atmosphere and it was stirred for 1 h. Next, NaBH(OAc)$_3$ (0.126 g, 0.595 mmol, 1.4 eq.) was added portionwise. The reaction was left stirring at rt for 16 h. Subsequently, the reaction mixture was diluted with DCM, filtered through Celite® and concentrated. The residue was purified by FCC (SiHP, DCM:MeOH 9:1) and re-purified by prep-HPLC to give the product (0.080 g, 0.043 mmol, yield 35%) as a yellow solid. ESI-MS: 533.3 [M-FH]+

$^1$H NMR (400 MHz, DMSO-$d_6$) δ 8.36-8.22 (m, 2H), 8.16 (d, J=6.1 Hz, 1H), 7.97 (d, J=9.4 Hz, 1H), 7.92 (s, 2H), 7.38-7.24 (m, 1H), 7.21 (s, 1H), 7.18-7.07 (m, 2H), 3.90 (d, J=11.8 Hz, 1H), 3.83-3.61 (m, 5H), 3.57-3.48 (m, 1H), 2.84 (t, J=11.3 Hz, 1H), 2.78-2.61 (m, 2H), 2.36 (s, 3H), 2.06-1.89 (m, 1H), 1.86-1.69 (m, 1H), 1.68-1.39 (m, 2H), 1.36-1.09 (m, 2H), 1.03-0.77 (m, 2H).

Procedure 16. Preparation of 3-({[5,5-difluoro-1-(pyridin-3-yl)piperidin-3-yl][(2-methylpyridin-4-yl)methyl]amino}methyl)-1-methyl-1,4-dihydroquinolin-4-one

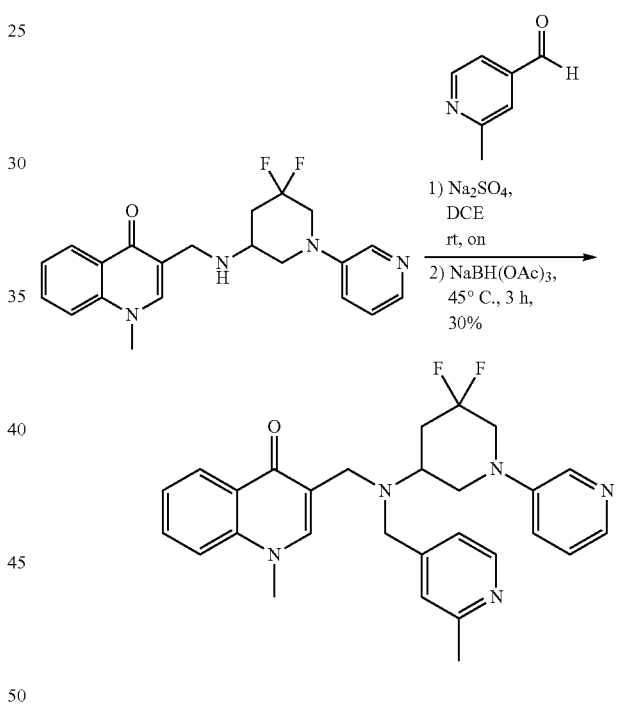

A mixture of 3-({[5,5-difluoro-1-(pyridin-3-yl)piperidin-3-yl]amino}methyl)-1-methyl-1,4-dihydroquinolin-4-one (0.130 g, 0.338 mmol, 1 eq.), 2-methylpyridine-4-carbaldehyde (0.053 g, 0.440 mmol, 1.3 eq.), Na$_2$SO$_4$ (0.2 g) and DCE (5 mL) was stirred overnight at rt. Then, the mixture was cooled to 0° C. and NaBH(OAc)$_3$ (0.108 g, 0.508 mmol, 1.5 eq.) portionwise over 5 min. Then, the reaction was carried out for 3 h at 45° C. Subsequently, the crude mixture was filtered through Celite® pad, the pad was washed with DCM and the filtrate was partitioned between DCM and NaOH aqueous solution (10%). Organic layers were combined, dried over anhydrous Na$_2$SO$_4$, filtered and evaporated. The residue was purified by FCC (SiHP; DCM:MeOH 9:1) and re-purified by RP-FCC (SiC18; H$_2$O:MeCN) to give the product (0.050 g, 0.102 mmol, yield 30%) as a yellow solid. ESI-MS: 490.4 [M+H]+

Procedure 17. Preparation of 1-methyl-3-({[(2-methylpyridin-4-yl)methyl][(3S)-1-(2-nitropyridin-3-yl)piperidin-3-yl]amino}methyl)-1,4-dihydroquinolin-4-one

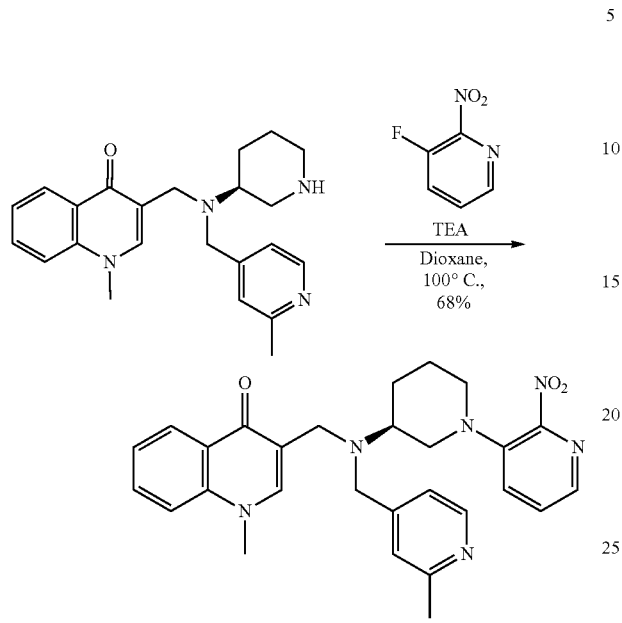

To a solution of 1-methyl-3-({[(2-methylpyridin-4-yl)methyl][(3S)-piperidin-3-yl]amino}methyl)-1,4-dihydroquinolin-4-one (0.080 g, 0.212 mmol, 1 eq.) in 1,4-dioxane (1.5 mL) 3-fluoro-2-nitropyridine (0.030 g, 0.212 mmol, 1 eq.) and triethylamine (0.022 g, 0.212 mmol, 1 eq.) were added and the resulting mixture was heated overnight at 100° C. Subsequently, the mixture was evaporated, the residue was combined with the residue from a similar reaction (0.133 mmol of the starting material) and purified by RP-FCC (SiC18; H$_2$O:MeCN) to afford the product (0.117 g, 0.345 mmol, yield 68%) as an orange solid. ESI-MS: 499.3 [M+H]$^+$ $^1$H NMR (300 MHz, DMSO-d$_6$) δ 8.27 (d, J=5.0 Hz, 1H), 8.19 (dd, J=8.1, 1.6 Hz, 1H), 8.09 (dd, J=4.4, 1.3 Hz, 1H), 7.98-7.89 (m, 2H), 7.77-7.59 (m, 3H), 7.38 (ddd, J=8.0, 6.9, 1.1 Hz, 1H), 7.21-7.13 (m, 2H), 3.83 (s, 3H), 3.72 (s, 2H), 3.68-3.51 (m, 2H), 3.44-3.35 (m, 1H), 3.11-3.02 (m, 1H), 2.95 (t, J=11.1 Hz, 1H), 2.82-2.70 (m, 2H), 2.36 (s, 3H), 2.05-1.95 (m, 1H), 1.83-1.73 (m, 1H), 1.61-1.38 (m, 2H).

Procedure 18. Preparation of 3-({[(2,6-dimethylpyridin-4-yl)methyl][(3S)-1-(pyridine-3-yl)piperidin-3-yl]amino}methyl)-1-methyl-1,4-dihydroquinolin-4-one

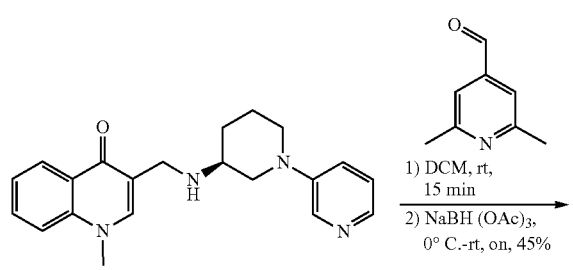

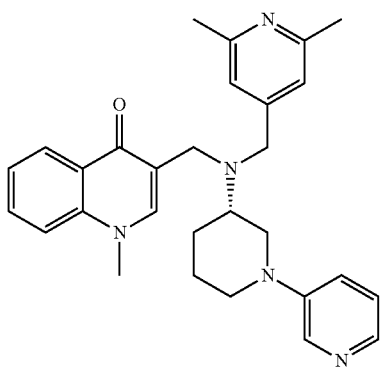

A mixture of 1-methyl-3-({[(3S)-1-(pyridin-3-yl)piperidin-3-yl]amino}methyl)-1,4-dihydroquinolin-4-one (0.05 g, 0.143 mmol, 1 eq.), 2,6-dimethylpyridine-4-carbaldehyde (0.024 g, 0.179 mmol, 1.3 eq.) and DCM (3 mL) was stirred for 15 min at rt. Then, the reaction mixture was cooled to 0° C. and NaBH(OAc)$_3$ (0.076 g, 0.359 mmol, 2.5 eq.) was added portionwise. Afterwards, the reaction was carried out overnight at rt. Subsequently, the mixture was partitioned between DCM and water. Organic layers were passed through silica pad and the filtrate was concentrated under reduced pressure. The residue was purified by prep-HPLC to give the product (0.031 g, 0.065 mmol, yield 45%) as a beige solid. ESI-MS: 468.3 [M+H]$^+$ $^1$H NMR (300 MHz, Methanol-d$_4$) δ 8.34 (dd, J=8.3, 1.5 Hz, 1H), 8.24 (d, J=2.9 Hz, 1H), 7.95 (s, 1H), 7.90 (dd, J=4.7, 1.3 Hz, 1H), 7.76 (ddd, J=8.6, 6.9, 1.6 Hz, 1H), 7.64 (d, J=8.5 Hz, 1H), 7.49-7.38 (m, 2H), 7.24 (dd, J=8.6, 4.8 Hz, 1H), 7.01 (s, 2H), 4.05-3.94 (m, 1H), 3.84 (s, 3H), 3.81 (d, J=9.0 Hz, 4H), 3.77-3.65 (m, 1H), 3.03-2.84 (m, 2H), 2.82-2.61 (m, 1H), 2.28 (s, 6H), 2.21-2.10 (m, 1H), 1.97-1.83 (m, 1H), 1.77-1.56 (m, 2H).

Procedure 19. Preparation of 1-methyl-3-({[(3S)-1-(1-methyl-2-oxo-1,2-dihydropyridin-4-yl)piperidin-3-yl][(2-methylpyridin-4-yl)methyl]amino}methyl)-1,4-dihydroquinolin-4-one

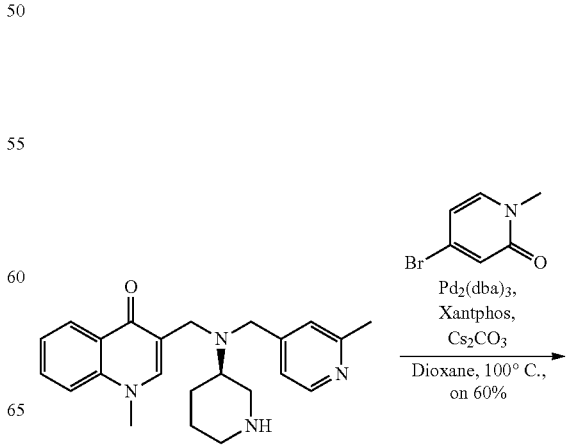

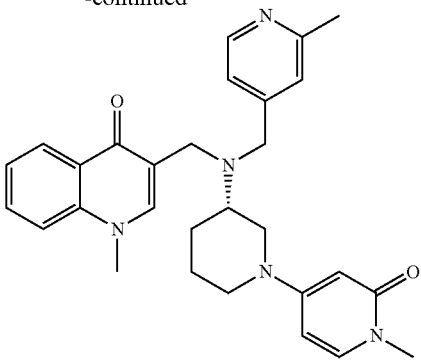

To a degassed mixture of 1-methyl-3-({[(2-methylpyridin-4-yl)methyl][(3S)-piperidin-3-yl]amino}methyl)-1,4-dihydroquinolin-4-one (0.100 g, 0.266 mmol, 1 eq.), 4-bromo-1-methyl-1,2-dihydropyridin-2-one (0.060 g, 0.319 mmol, 1.2 eq.), $Cs_2CO_3$ (0.173 g, 0.531 mmol, 2 eq.) and 1,4-dioxane (3 mL) $Pd_2(dba)_3$ (0.012 g, 0.013 mmol, 0.1 eq.) and Xantphos (0.014 g, 0.024 mmol, 0.1 eq.) were added. The reaction was carried out overnight at 100° C. Then, the mixture was filtered through Celite® pad, stirred with MPA scavenger for 30 min, filtered and concentrated. The residue was partitioned between DCM and water. The aqueous layer was additionally basified with NaOH solution (15%) and extracted with $CHCl_3$/iPrOH (3:1). Organic layers were dried over anh. $Na_2SO_4$, filtered and evaporated under reduced pressure. The residue was purified by FCC (SiHP; DCM:MeOH) and re-purified by FCC (SiHP; DCM:MeOH) to give the product (0.077 g, 0.159 mmol, yield 60%) as a yellow solid. ESI-MS: 484.7 [M+H]+

$^1$H NMR (300 MHz, DMSO-$d_6$) δ 8.28 (d, J=5.0 Hz, 1H), 8.18 (d, J=8.0 Hz, 1H), 8.05 (s, 1H), 7.83-7.57 (m, 2H), 7.45-7.30 (m, 2H), 7.30-7.19 (m, 2H), 6.06 (dd, J=7.6, 2.6 Hz, 1H), 5.50 (d, J=2.7 Hz, 1H), 4.05-3.92 (m, 1H), 3.88 (s, 3H), 3.85-3.46 (m, 5H), 3.23 (s, 4H), 2.98 (t, J=12.1 Hz, 1H), 2.81-2.67 (m, 1H), 2.38 (s, 4H), 2.10-1.88 (m, 2H), 1.79-1.51 (m, 3H), 1.43-1.25 (m, 2H).

Procedure 20. 1-cyclopropyl-6-fluoro-7-hydroxy-3-({[(3S)-1-(6-methylpyridin-3-yl)piperidin-3-yl][(2-methylpyridin-4-yl)methyl]amino}methyl)-1,4-dihydro-1,8-naphthyridin-4-one

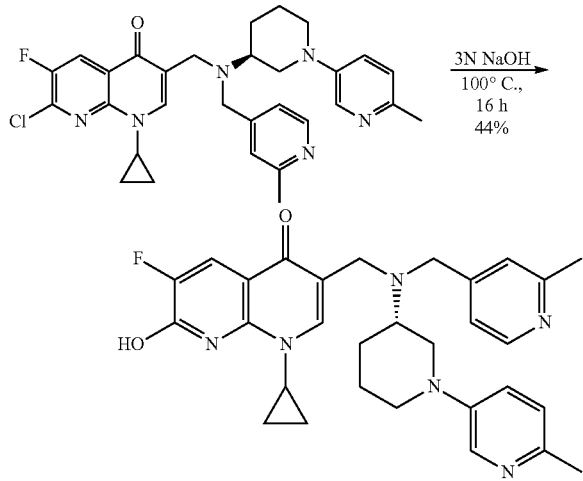

A mixture of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydro-1,8-naphthyridin-4-one (0.061 g, 0.112 mmol, 1 eq.) and 2N NaOH (4 mL) was heated for 16 h at 100° C. Afterwards, the reactions was cooled down and acidified to pH 5 with glacial acid. Then, sodium bicarbonate was added and the resulting mixture was evaporated. The residue was dissolved in DCM, filtered through Celite® and purified by RP-FCC (SiC18; $H_2O$:MeCN) to give the product (0.026 g, 0.049 mmol, yield 44%) as a white powder. ESI-MS: 529.7 [M+H]+

$^1$H NMR (400 MHz, Methanol-$d_4$) δ 8.21 (d, J=5.2 Hz, 1H), 8.07 (d, J=2.9 Hz, 1H), 7.75-7.71 (m, 2H), 7.33 (dd, J=8.6, 3.0 Hz, 1H), 7.28 (s, 1H), 7.26-7.22 (m, 1H), 7.11 (d, J=8.6 Hz, 1H), 3.91-3.80 (m, 3H), 3.75 (s, 2H), 3.64-3.56 (m, 1H), 3.56-3.47 (m, 1H), 2.99-2.88 (m, 1H), 2.87-2.78 (m, 1H), 2.73-2.62 (m, 1H), 2.41 (s, 3H), 2.40 (s, 3H), 2.18-2.05 (m, 1H), 1.96-1.83 (m, 1H), 1.73-1.57 (m, 2H), 1.17-1.10 (m, 2H), 0.81-0.75 (m, 2H).

Procedure 21. Preparation of 1-cyclopropyl-6-fluoro-7-methoxy-3-({[(3S)-1-(6-methylpyridin-3-yl)piperidin-3-yl][(2-methylpyridin-4-yl)methyl]amino}methyl)-1,4-dihydro-1,8-naphthyridin-4-one

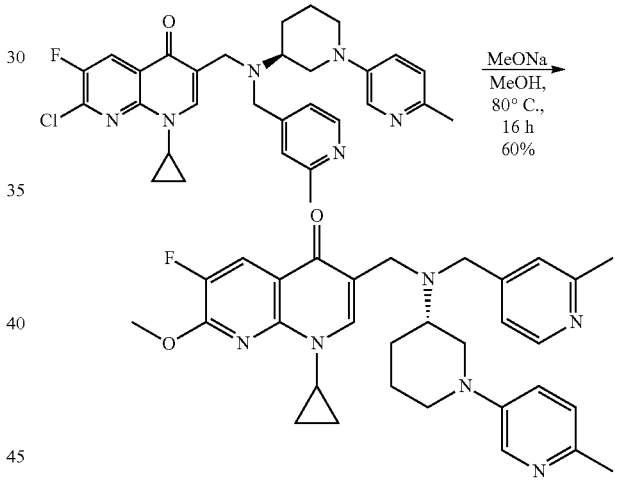

To a solution of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydro-1,8-naphthyridin-4-one (0.061 g, 0.112 mmol, 1 eq.) in MeOH (4 mL) MeONa (0.03 g, 0.558 mmol, 5 eq.) was added. The suspension was stirred for 16 h at 80° C. Afterwards, the reactions was cooled down and acidified to pH 5 with glacial acid. Then, sodium bicarbonate was added and the resulting mixture was evaporated. The residue was dissolved in DCM, filtered through Celite® and purified by RP-FCC (SiC18; $H_2O$:MeCN) to give the product (0.037 g, 0.066 mmol, yield 60%) as a white powder. ESI-MS: 543.2 [M+H]+

$^1$H NMR (400 MHz, Methanol-$d_4$) δ 8.17 (d, J=5.2 Hz, 1H), 8.10 (d, J=9.9 Hz, 1H), 8.08 (d, J=2.9 Hz, 1H), 7.96 (s, 1H), 7.35 (dd, J=8.6, 3.0 Hz, 1H), 7.26 (s, 1H), 7.24-7.20 (m, 1H), 7.12 (d, J=8.6 Hz, 1H), 4.17 (s, 3H), 3.91-3.81 (m, 3H), 3.79 (s, 2H), 3.63-3.52 (m, 2H), 3.01-2.92 (m, 1H), 2.90-2.82 (m, 1H), 2.74-2.66 (m, 1H), 2.40 (s, 3H), 2.38 (s, 3H), 2.17-2.09 (m, 1H), 1.96-1.89 (m, 1H), 1.75-1.60 (m, 2H), 1.27-1.21 (m, 2H), 0.94-0.88 (m, 2H).

Procedure 22. Preparation of 1-cyclopropyl-6-fluoro-7-methoxy-3-({[(3S)-1-(6-methylpyridin-3-yl)piperidin-3-yl][(2-methylpyridin-4-yl)methyl]amino}methyl)-1,4-dihydroquinolin-4-one

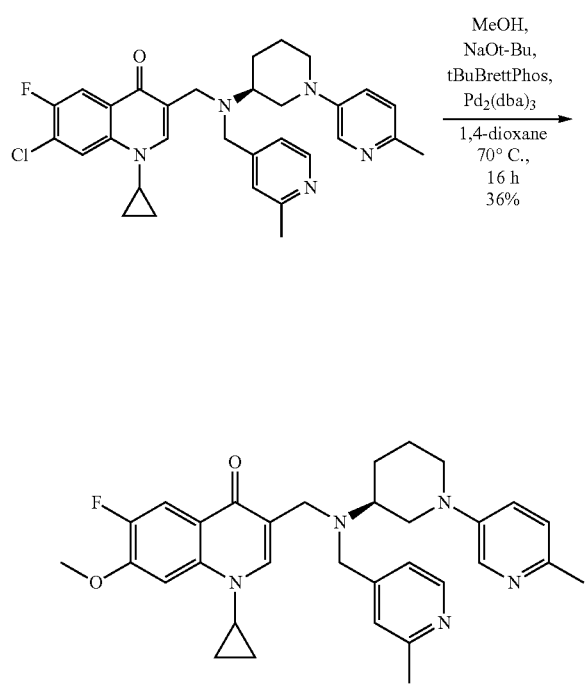

To a solution of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (0.1 g, 0.183 mmol, 1 eq.), MeOH (0.074 mL, 1.831 mmol, 10 eq.) and tBuONa (0.025 g, 0.256 mmol, 1.4 eq.) in 1,4-dioxane (1 mL) a mixture of tBuBrettPhos (0.007 g, 0.015 mmol, 0.08 eq.) and $Pd_2(dba)_3$ (0.003 g, 0.004 mmol, 0.02 eq.) was added under inert atmosphere. The reaction was carried out at 70° C. for 16 h. Subsequently, the mixture was diluted with AcOEt, filtered through Celite® pad and concentrated under reduced pressure. The residue was purified by FCC (SiHP; DCM:MeOH 9:1), re-purified by RP-FCC (SiC18, $H_2O:CH_3CN$) and prep-HPLC. The title compound was isolated as a free base (0.036 g, 0.066 mmol, yield 36%). The product as a white powder. ESI-MS: 542.4 $[M+H]^+$ $^1H$ NMR (400 MHz, Methanol-$d_4$) δ 8.16 (d, J=5.3 Hz, 1H), 8.09 (d, J=2.9 Hz, 1H), 7.95 (s, 1H), 7.89 (d, J=11.6 Hz, 1H), 7.51 (d, J=7.2 Hz, 1H), 7.35 (dd, J=8.6, 3.0 Hz, 1H), 7.25 (s, 1H), 7.24-7.20 (m, 1H), 7.12 (d, J=8.6 Hz, 1H), 4.05 (s, 3H), 3.92-3.83 (m, 3H), 3.79 (s, 2H), 3.64-3.58 (m, 1H), 3.54-3.47 (m, 1H), 3.01-2.91 (m, 1H), 2.89-2.82 (m, 1H), 2.75-2.65 (m, 1H), 2.41 (s, 3H), 2.35 (s, 3H), 2.19-2.11 (m, 1H), 1.97-1.89 (m, 1H), 1.75-1.59 (m, 2H), 1.37-1.29 (m, 2H), 0.98-0.92 (m, 2H).

Procedure 23. Preparation of tert-butyl(2R)-4-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]-2-methylpiperazine-1-carboxylate

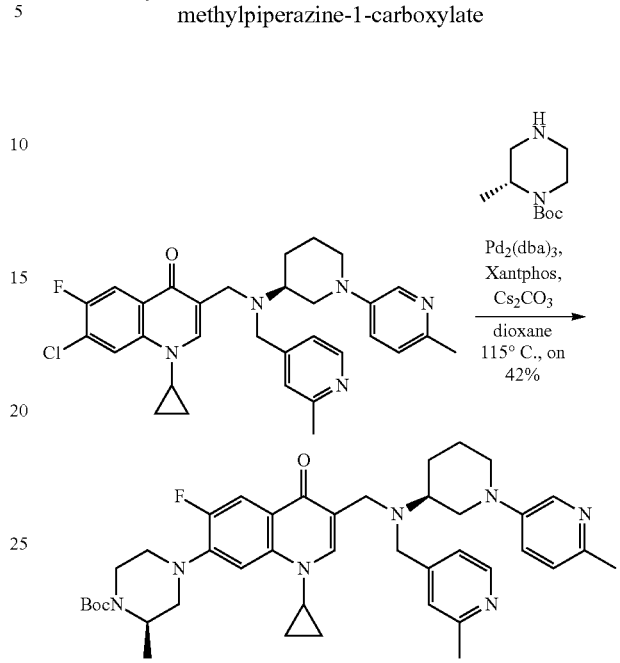

To a degassed solution of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (0.1 g, 0.183 mmol, 1 eq.), tert-butyl (2R)-2-methylpiperazine-1-carboxylate (0.055 g, 0.275 mmol, 1.5 eq.), $Cs_2CO_3$ (0.119 g, 0.366 mmol, 2 eq.) in 1,4-dioxane (2.6 mL) $Pd_2(dba)_3$ (0.034 g, 0.037 mmol, 0.2 eq.) and Xantphos (0.032 g, 0.055 mmol, 0.3 eq.) were added. The resulting mixture was degassed and the reaction was heated overnight at 115° C. under inert atmosphere. Subsequently, the reaction mixture was filtered through Celite®, washed with DCM and purified by FCC (SiHP deactivated with $NH_3$:DCM, DCM:MeOH 9:1) to give the product (0.055 g, 0.077 mmol, yield 42%) as a yellow solid. ESI-MS: 710.9 $[M+H]^+$

Procedure 24. Preparation of 1-cyclopropyl-6-fluoro-3-({[(3S)-1-(6-methylpyridin-3-yl)piperidin-3-yl][(2-methylpyridin-4-yl)methyl]amino}methyl)-7-(piperazin-1-yl)-1,4-dihydroquinolin-4-one

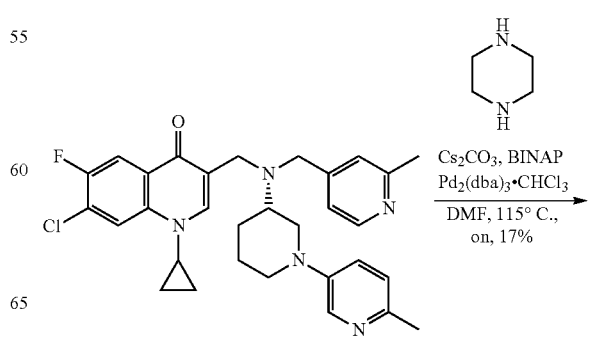

-continued

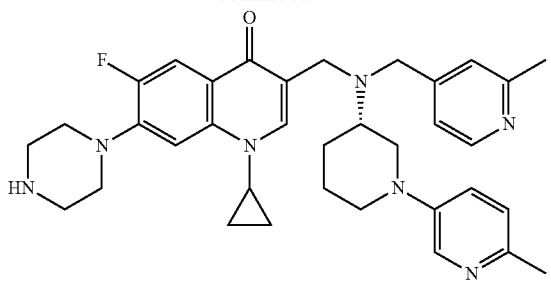

To a degassed solution of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (0.100 g, 0.183 mmol, 1 eq.), piperazine (0.032 g, 0.366 mmol, 2 eq.), Cs$_2$CO$_3$ (0.125 g, 0.385 mmol, 2.1 eq.) in DMF (3 mL) BINAP (0.034 g, 0.055 mmol, 0.3 eq.) and Pd$_2$(dba)$_3$*CHCl$_3$ (0.038 g, 0.037 mmol, 0.2 eq.). The reaction mixture was stirred overnight at 115° C. Subsequently, the mixture was cooled to ambient temperature, filtered through Celite® pad and the pad was washed with DCM. The filtrate was stirred with MPA scavenger for 15 min, filtered and evaporated. The residue was purified by FCC (SiHP, DCM:MeOH 9:1) and re-purified by prep-HPLC. The product was obtained as a free base after extraction using DCM/aq. NaHCO$_3$, drying the organic layer over anhydrous Na$_2$SO$_4$ and evaporation. The titled compound was isolated as a light yellow solid (0.019 g, 0.032 mmol, yield 17%). ESI-MS: 596.8 [M+H]$^+$ Procedure 25. Preparation of 1-methyl-3-({[(3S)-1-(6-methylpyridin-3-yl)piperidin-3-yl][(2-methylpyridin-4-yl)methyl]amino}methyl)-7-(2-oxopiperazin-1-yl)-1,4-dihydroquinolin-4-one

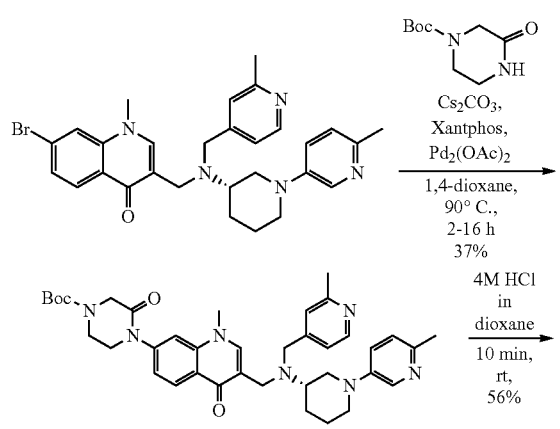

a. tert-butyl 4-[1-methyl-3-({[(3S)-1-(6-methylpyridin-3-yl)piperidin-3-yl][(2-methylpyridin-4-yl)methyl]amino}methyl)-4-oxo-1,4-dihydroquinolin-7-yl]-3-oxopiperazine-1-carboxylate

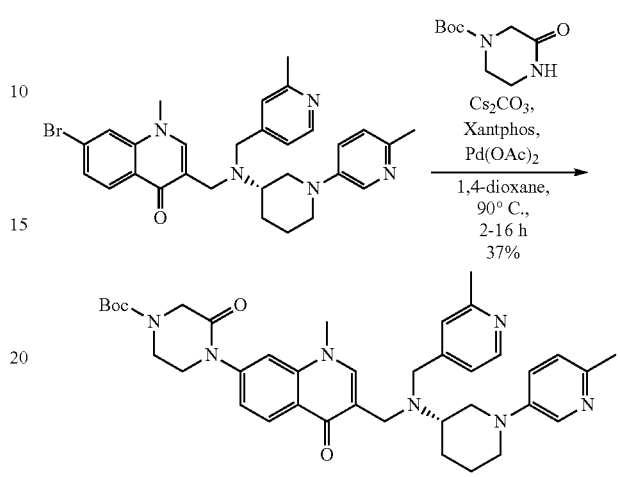

To a degassed and dried mixture of 7-bromo-1-methyl-3-({[(3S)-1-(6-methylpyridin-3-yl)piperidin-3-yl][(2-methylpyridin-4-yl)methyl]amino}methyl)-1,4-dihydroquinolin-4-one (0.050 g, 0.091 mmol, 1 eq.), tert-butyl 3-oxopiperazine-1-carboxylate (0.018 g, 0.091 mmol, 1 eq.), Xantphos (0.003 g, 0.005 mmol, 0.06 eq.), Cs$_2$CO$_3$ (0.045 g, 0.137 mmol, 1.5 eq.), Pd(OAc)$_2$ (0.001 g, 0.005 mmol, 0.05 eq.) placed in a reaction vessel 1,4-dioxane (3 mL) was added and the resulting mixture was stirred for 16 h at 90° C. under inert atmosphere. Subsequently, the mixture was combined with another from similar reaction (same amounts, 2 h of heating), diluted with AcOEt and washed with Na$_2$CO$_3$ aqueous solution. Combined organic fractions were dried over anh. Na$_2$SO$_4$, filtered and evaporated. The residue was purified by FCC (SiHP; DCM:MeOH 9:1). The obtained sample was dissolved in DCM and stirred with MPA scavenger for 10 min. The scavenger was filtered off and the filtrate was evaporated under reduced pressure to give the product (0.047 g, 0.068 mmol, yield 37%) as a beige powder. ESI-MS: 666.8 [M+H]$^+$ $^1$H NMR (400 MHz, DMSO-d$_6$) δ 8.31-8.28 (m, 1H), 8.18 (d, J=8.7 Hz, 1H), 8.15 (d, J=3.0 Hz, 1H), 8.02 (s, 1H), 7.62 (d, J=2.0 Hz, 1H), 7.38 (dd, J=8.7, 1.8 Hz, 1H), 7.27-7.19 (m, 3H), 7.02 (d, J=8.5 Hz, 1H), 4.17-4.10 (m, 2H), 3.88-3.79 (m, 6H), 3.78-3.69 (m, 4H), 3.68-3.56 (m, 2H), 3.44-3.35 (m, 1H), 3.34-3.25 (m, 1H), 2.83-2.70 (m, 2H), 2.64-2.54 (m, 1H), 2.39 (s, 3H), 2.33 (s, 3H), 2.03-1.96 (m, 1H), 1.79-1.72 (m, 1H), 1.56-1.48 (m, 1H), 1.46 (s, 9H).

b. 1-methyl-3-({[(3S)-1-(6-methylpyridin-3-yl)piperidin-3-yl][(2-methylpyridin-4-yl)methyl]amino}methyl)-7-(2-oxopiperazin-1-yl)-1,4-dihydroquinolin-4-one

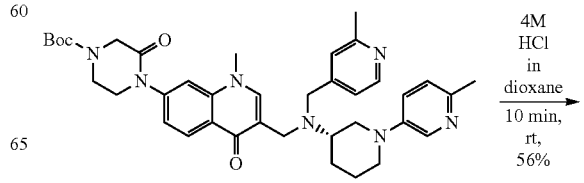

101

-continued

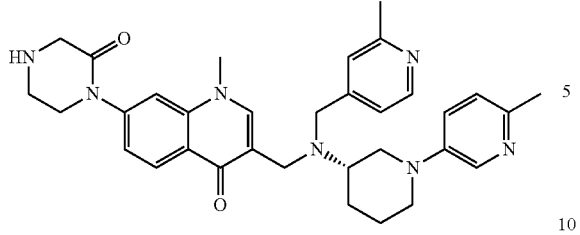

To a stirred solution of tert-butyl 4-[1-methyl-3-({[(3S)-1-(6-methylpyridin-3-yl)piperidin-3-yl][(2-methylpyridin-4-yl)methyl]amino}methyl)-4-oxo-1,4-dihydroquinolin-7-yl]-3-oxopiperazine-1-carboxylate (0.045 g, 0.068 mmol, 1 eq.) in 1,4-dioxane (3 mL) 4M HCl in dioxane (0.169 mL, 0.676 mmol, 10 eq.) was added and the resulting mixture was stirred for 10 min at rt. Subsequently, the reaction mixture was concentrated under reduced pressure and the residue was purified by FCC (SiHP; DCM:MeOH 95:5) to give the product (0.023 g, 0.038 mmol, yield 56%) as an off-white powder. ESI-MS: 566.3 [M+H]+

$^1$H NMR (400 MHz, DMSO-d$_6$) δ 8.31-8.27 (m, 1H), 8.16 (d, J=8.7 Hz, 1H), 8.14 (d, J=3.1 Hz, 1H), 8.01 (s, 1H), 7.56 (d, J=1.9 Hz, 1H), 7.36 (dd, J=8.7, 1.8 Hz, 1H), 7.26-7.19 (m, 3H), 7.01 (d, J=8.5 Hz, 1H), 3.88-3.80 (m, 4H), 3.79-3.68 (m, 4H), 3.67-3.54 (m, 3H), 3.43 (s, 2H), 3.09-3.01 (m, 2H), 2.85-2.69 (m, 3H), 2.62-2.54 (m, 1H), 2.38 (s, 3H), 2.32 (s, 3H), 2.03-1.93 (m, 1H), 1.79-1.70 (m, 1H), 1.60-1.38 (m, 2H).

Procedure 26. Preparation of 3-({[(3S)-1-(6-methylpyridin-3-yl)piperidin-3-yl][(2-methylpyridin-4-yl)methyl]amino}methyl)-1-(oxetan-3-yl)-1,4-dihydroquinolin-4-one

102 f. 1-(oxetan-3-yl)-4-oxo-1,4-dihydroquinoline-3-carbaldehyde

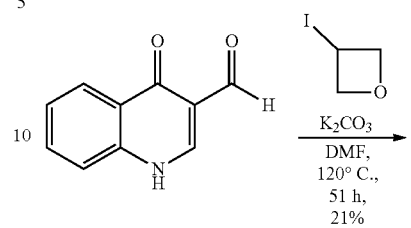

To a solution of 3-iodooxetane (0.728 g, 3.955 mmol, 1.37 eq.) in DMF (13.3 mL) 4-oxo-1,4-dihydroquinoline-3-carbaldehyde (0.500 g, 2.887 mmol, 1 eq.) and K$_2$CO$_3$ (1.596 g, 11.549 mmol, 4 eq.) were added and the resulting mixture was stirred for 1 day at 120° C. Then, 3-iodoxetan (0.500 g, 2.717 mmol, 0.94 eq.) was added and the reaction mixture was heated for additional 27 h at 120° C. Subsequently, the mixture was filtered through Celite® pad and concentrated under reduced pressure. The residue was purified by FCC (SiHP; DCM:MeOH 9:1) and re-purified by RP-FCC (SiC18; H$_2$O:MeCN) to give the product (0.037 g, 0.139 mmol, yield 21%) as a beige solid. ESI-MS: 230.1 [M+H]+

$^1$H NMR (400 MHz, DMSO-d$_6$) δ 10.20 (s, 1H), 8.47 (s, 1H), 8.34 (dd, J=8.0, 1.6 Hz, 1H), 7.83 (ddd, J=8.7, 7.1, 1.7 Hz, 1H), 7.60-7.55 (m, 1H), 7.51 (d, J=8.5 Hz, 1H), 5.82 (p, J=6.9 Hz, 1H), 5.13-5.06 (m, 2H), 5.00-4.94 (m, 2H).

g. 3-({[(3S)-1-(6-methylpyridin-3-yl)piperidin-3-yl][(2-methylpyridin-4-yl)methyl]amino}methyl)-1-(oxetan-3-yl)-1,4-dihydroquinolin-4-one

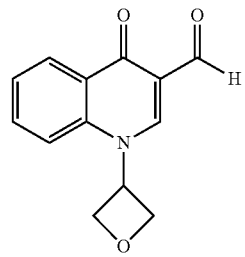

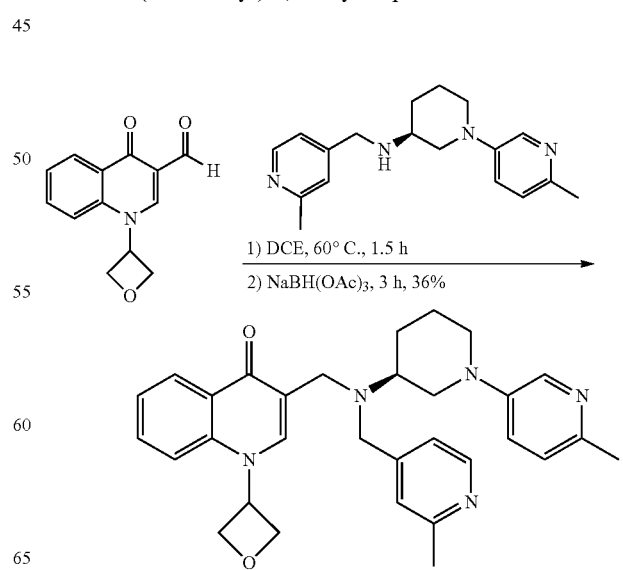

A mixture of (3S)-1-(6-methylpyridin-3-yl)-N-[(2-methylpyridin-4-yl)methyl]piperidin-3-amine (0.060 g, 0.202 mmol, 1 eq.), 1-(oxetan-3-yl)-4-oxo-1,4-dihydroquinoline-3-carbaldehyde (0.051 g, 0.223 mmol, 1.1 eq.) and DCE (3 mL) was stirred for 1.5 h at 60° C. Then, NaBH(OAc)$_3$ (0.107 g, 0.506 mmol, 2.5 eq.) was added and the reaction mixture was stirred for additional 3 h at 60° C. Afterwards, the mixture was partitioned between DCM and NaOH solution. Organic layers were combined, dried over anhydrous Na$_2$SO$_4$, filtered and evaporated. The residue was purified by prep-HPLC to give the product (0.037 g, 0.073 mmol, yield 36%) as a white solid. ESI-MS: 510.3 [M+H]$^+$ $^1$H NMR (400 MHz, Methanol-d$_4$) δ 8.38 (dd, J=8.2, 1.5 Hz, 1H), 8.21 (s, 1H), 8.20-8.18 (m, 1H), 8.10 (d, J=3.0 Hz, 1H), 7.77-7.71 (m, 1H), 7.47 (ddd, J=8.0, 7.0, 1.0 Hz, 1H), 7.39 (d, J=8.9 Hz, 1H), 7.36 (dd, J=8.6, 3.0 Hz, 1H), 7.32-7.29 (m, 1H), 7.29-7.25 (m, 1H), 7.12 (d, J=8.6 Hz, 1H), 5.80-5.72 (m, 1H), 5.20 (td, J=7.2, 2.5 Hz, 2H), 4.86 (t, J=6.7 Hz, 2H), 3.96-3.87 (m, 5H), 3.66-3.56 (m, 1H), 3.08-2.95 (m, 1H), 2.89 (t, J=11.1 Hz, 1H), 2.77-2.66 (m, 1H), 2.41 (s, 3H), 2.34 (s, 3H), 2.23-2.13 (m, 1H), 2.03-1.89 (m, 1H), 1.78-1.63 (m, 2H).

Procedure 27. Preparation of 2-[3-({[(3S)-1-(6-Methylpyridin-3-yl)piperidin-3-yl][(2-methylpyridin-4-yl)methyl]amino}methyl)-4-oxo-1,4-dihydroquinolin-1-yl]acetic acid

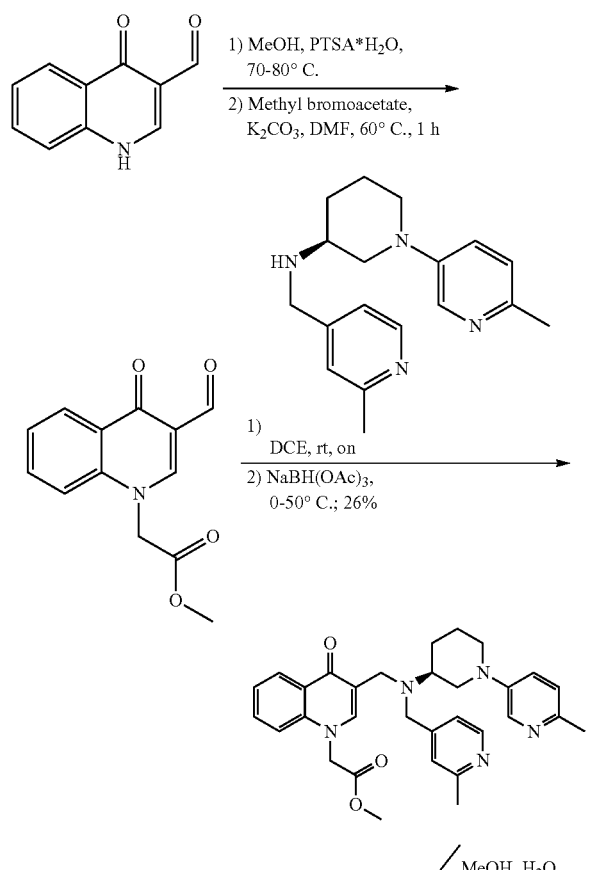

a. methyl 2-(3-formyl-4-oxo-1,4-dihydroquinolin-1-yl)acetate

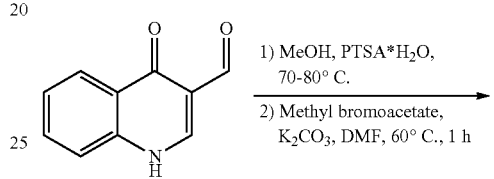

A mixture of 4-oxo-1,4-dihydroquinoline-3-carbaldehyde (0.200 g, 1.155 mmol, 1.0 eq.) and methanol (10 mL) was heated at 70° C. overnight. PTSA monohydrate (0.044 g, 0.231 mmol, 0.2 eq.) was added and the resulting mixture was heated at 80° C. overnight and evaporated under reduced pressure. Part of the crude material (0.100 g,) was dissolved in DMF (1 mL) and potassium carbonate (0.113 g, 0.821 mmol) was added. The resulting mixture was stirred for 5 min at RT then methyl bromoacetate (0.075 mL, 0.794 mmol) was added and the mixture was stirred for 1 h at 60° C. After that, the mixture was partitioned between water and DCM and the aqueous layer was additionally extracted with DCM. The combined organic layers were washed with brine, dried over anh. Na$_2$SO$_4$, filtered and evaporated in vacuo. The residue was purified by FCC (SiHP; hexane:DCM:EtOAc) to afford the product (0.073 g, 0.294 mmol) as a white solid. ESI-MS: 246.3 [M+H]$^+$ $^1$H NMR (300 MHz, DMSO-d$_6$) δ 10.21 (s, 1H), 8.66 (s, 1H), 8.31 (dd, J=8.0, 1.6 Hz, 1H), 7.81 (ddd, J=8.6, 7.1, 1.7 Hz, 1H), 7.63 (d, J=8.5 Hz, 1H), 7.55 (ddd, J=8.0, 7.1, 0.9 Hz, 1H), 5.43 (s, 2H), 3.72 (s, 3H).

b. methyl 2-[3-({[(3S)-1-(6-methylpyridin-3-yl)pip-eridin-3-yl][(2-methylpyridin-4-yl)methyl]amino}methyl)-4-oxo-1,4-dihydroquinolin-1-yl]acetate

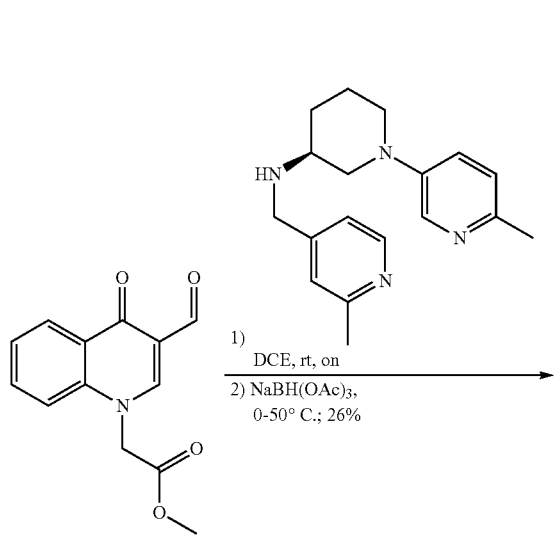

A mixture of methyl 2-(3-formyl-4-oxo-1,4-dihydroquinolin-1-yl)acetate (0.073 g, 73 mg, 0.298 mmol, 1.0 eq.), (3S)-1-(6-methylpyridin-3-yl)-N-[(2-methylpyridin-4-yl)methyl]piperidin-3-amine (0.106 g, 0.357 mmol, 1.2 eq.) and anh. DCE (5 mL) was stirred overnight at RT. Subsequently the reaction was cooled to 0° C., NaBH(OAc)$_3$ (0.076 g, 0.357 mmol, 1.2 eq.) was added and the mixture was stirred at RT for 100 min. Then NaBH(OAc)$_3$ (0.076 g, 0.357 mmol, 1.2 eq.) was added and the reaction mixture was heated at 40-50° C. for approx. 220 min with addition of another portion of NaBH(OAc)$_3$ (0.038 g, 0.179 mmol, 0.6 eq.) during that time. Then the reaction mixture was left stirring over weekend at RT. DCE was removed under reduced pressure and the residue was partitioned between water and ethyl acetate. The organic layer was washed with brine, dried over anh. Na$_2$SO$_4$, filtered and evaporated in vacuo. The residue was purified by FCC (SiHP; DCM: MeOH) to afford the product (0.043 g, 43 mg, 0.076 mmol, yield 26%) as a light yellow glass. ESI-MS: 526.7 [M+H]$^+$.

c. 2-[3-({[(3S)-1-(6-methylpyridin-3-yl)piperidin-3-yl][(2-methylpyridin-4-yl)methyl]amino}methyl)-4-oxo-1,4-dihydroquinolin-1-yl]acetic acid

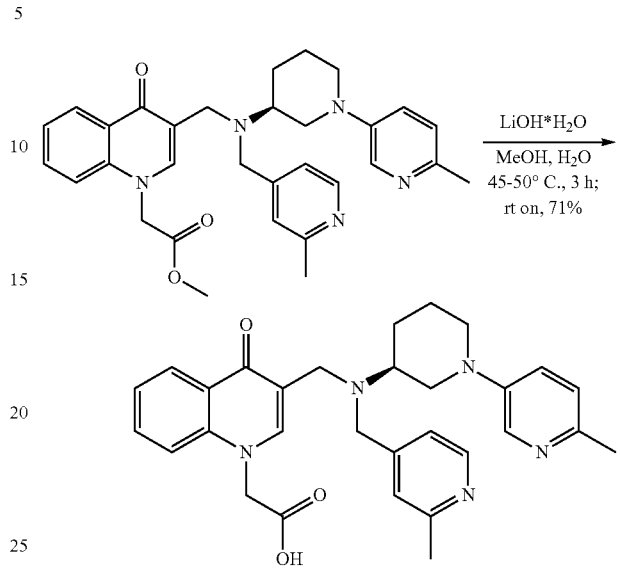

A mixture of methyl 2-[3-({[(3S)-1-(6-methylpyridin-3-yl)piperidin-3-yl][(2-methylpyridin-4-yl)methyl]amino}methyl)-4-oxo-1,4-dihydroquinolin-1-yl]acetate (0.043 g, 0.082 mmol, 1.0 eq.), lithium hydroxide monohydrate (0.020 g, 0.466 mmol, 5.7 eq.), methanol (5 mL) and water (1 mL) was heated at 45-50° C. for 3 h and then left stirring overnight at RT. 2M aq. solution of HCl was added (0.147 mL, 3.6 eq.) and the mixture was evaporated in vacuo. The residue was purified by FCC (C18HP; H$_2$O: MeCN) to afford the product (0.030 g, 0.058 mmol, yield 71%) as an off-white solid. ESI-MS: 512.3 [M+H]$^+$ $^1$H NMR (400 MHz, Methanol-d$_4$) δ 8.33 (dd, J=8.2, 1.6 Hz, 1H), 8.21 (dd, J=5.1, 0.9 Hz, 1H), 8.10-8.01 (m, 2H), 7.70 (ddd, J=8.6, 6.9, 1.6 Hz, 1H), 7.53 (d, J=8.7 Hz, 1H), 7.44-7.33 (m, 2H), 7.33-7.27 (m, 2H), 7.11 (d, J=8.6 Hz, 1H), 4.78 (s, 2H), 3.94-3.76 (m, 5H), 3.65-3.55 (m, 1H), 2.99-2.80 (m, 2H), 2.75-2.62 (m, 1H), 2.40 (s, 6H), 2.20-2.09 (m, 1H), 1.94-1.83 (m, 1H), 1.71-1.55 (m, 2H).

Procedure 28. Preparation of 1-cyclopropyl-7-{4,7-diazaspiro[2.5]octan-7-yl}-6-fluoro-3-({[(3S)-1-(6-methylpyridin-3-yl)piperidin-3-yl][(2-methylpyridin-4-yl)methyl]amino}methyl)-1,4-dihydroquinolin-4-one

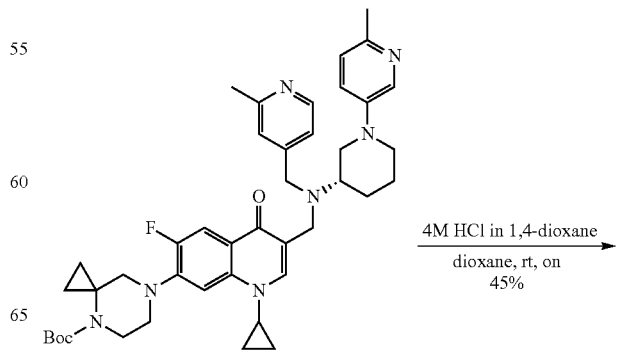

-continued

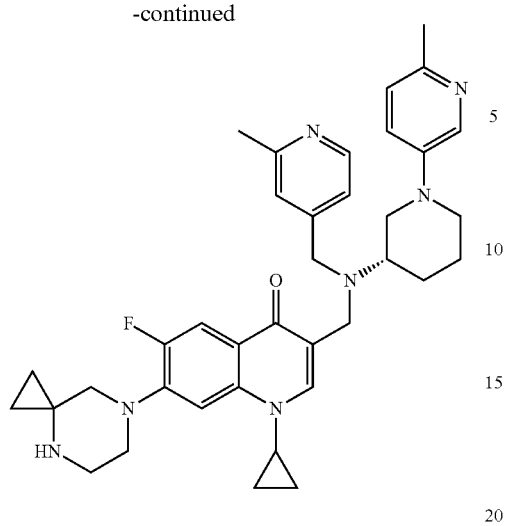

To a solution of tert-butyl 7-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]-4,7-diazaspiro[2.5]octane-4-carboxylate (0.087 g, 0.121 mmol, 1 eq.) in 1,4-dioxane (5 mL) 4M HCl in dioxane (0.9 mL, 3.615 mmol, 30 eq.) was added and the resulting mixture was left stirring overnight at rt. Subsequently, the reaction mixture was poured into water, basified with NaOH aqueous solution (2M) and extracted to DCM. The organic layer was dried over anhydrous Na$_2$SO$_4$, filtered and evaporated. The residue was purified by FCC (SiHP, DCM:MeOH 9:1) to give the product (0.034 g, 0.055 mmol, yield 45%) as a white solid. ESI-MS: 622.7 [M+H]$^+$ $^1$H NMR (400 MHz, DMSO-d$_6$) δ 8.31-8.27 (m, 1H), 8.13 (d, J=3.0 Hz, 1H), 7.81 (s, 1H), 7.69 (d, J=13.7 Hz, 1H), 7.28 (d, J=7.5 Hz, 1H), 7.24-7.20 (m, 2H), 7.20-7.15 (m, 1H), 7.04-7.00 (m, 1H), 3.83-3.56 (m, 6H), 3.54-3.45 (m, 1H), 3.16-3.11 (m, 2H), 2.98 (d, J=24.0 Hz, 4H), 2.75 (d, J=7.8 Hz, 2H), 2.63-2.54 (m, 1H), 2.38 (s, 3H), 2.33 (s, 3H), 2.01-1.93 (m, 1H), 1.81-1.72 (m, 1H), 1.59-1.44 (m, 2H), 1.27-1.16 (m, 3H), 0.94-0.82 (m, 2H), 0.54-0.50 (m, 4H).

Procedure 29. Preparation of 1-methyl-3-({[(2-methylpyridin-4-yl)methyl][(3S)-piperidin-3-yl]amino}methyl)-1,4-dihydroquinolin-4-one

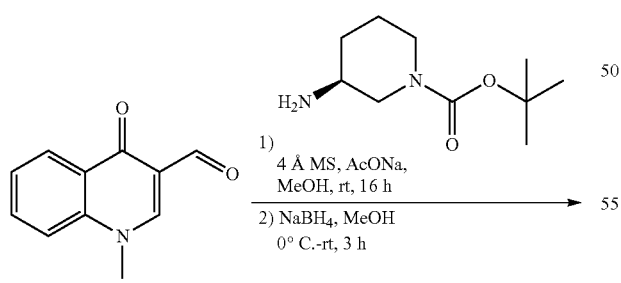

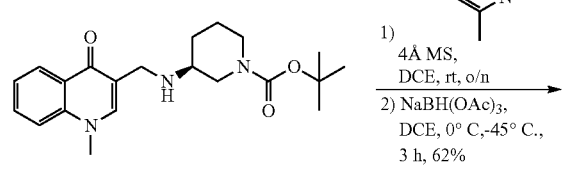

a) tert-butyl (3S)-3-{[(1-methyl-4-oxo-1,4-dihydroquinolin-3-yl)methyl]amino}piperidine-1-carboxylate

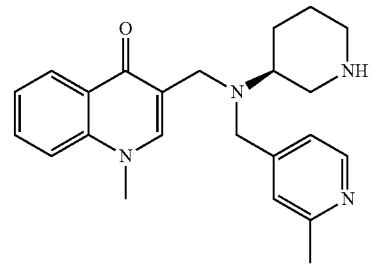

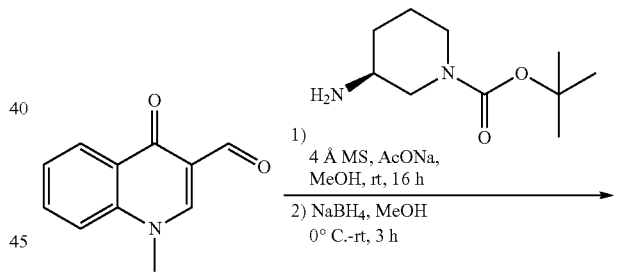

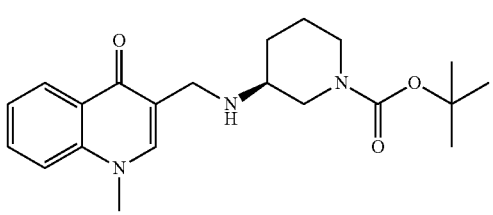

The title compound was synthesized following the approach outlined in Procedure 4a substituting (3S)-1-(pyridin-3-yl)piperidin-3-amine with tert-butyl (3S)-3-aminopiperidine-1-carboxylate (1.5 eq.). After the addition of NaBH$_4$ the mixture was stirred for 3 h. The residue was purified by FCC (Al$_2$O$_3$; DCM:MeOH=9:1) to give the product (5.6 g, 15.1 mmol, yield 94%) as a yellow solid. AP-MS: 372.4 [M+H]$^+$ b) 1-methyl-3-({[(2-methylpyridin-4-yl)methyl][(3S)-piperidin-3-yl]amino}methyl)-1,4-dihydroquinolin-4-one

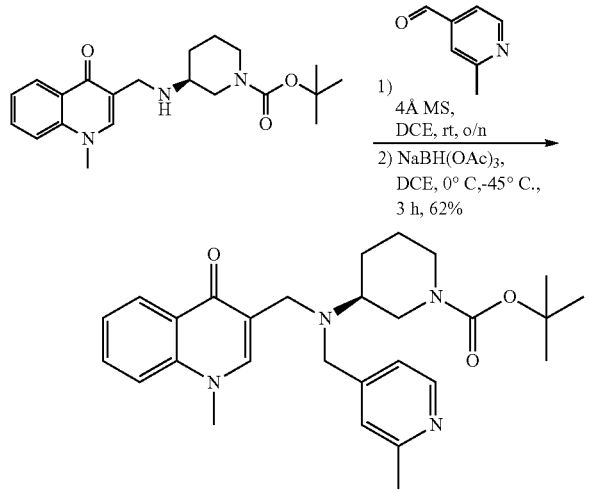

A mixture of 4 Å MS, tert-butyl (3S)-3-{[(1-methyl-4-oxo-1,4-dihydroquinolin-3-yl)methyl]amino}piperidine-1-carboxylate (3.0 g, 8.1 mmol, 1 eq.), 2-methylpyridine-4-carbaldehyde (0.9 g, 8.1 mmol, 1 eq.) and DCE (30 mL) was stirred overnight at rt. Then the reaction mixture was cooled to 0° C. and NaBH(OAc)$_3$ (2.6 g, 12.1 mmol, 1.5 eq.) was added. Afterwards the reaction was carried out for 3 h at 45° C. Subsequently the mixture was filtered through a celite pad, washed with DCM and the filtrate was concentrated in vacuo. The residue was partitioned between DCM and 10% NaOH aqueous solution. The aqueous layer was additionally washed with DCM. The combined organic layers were washed with brine, dried over anhydrous MgSO$_4$, filtered and concentrated in vacuo. The residue was purified by FCC (SiHP, DCM/MeOH) to give the product (2.4 g, 5.0 mmol, yield 62%) as a yellow oil. ESI-MS: 477.6 [M+H]$^+$ c) 1-methyl-3-({[(2-methylpyridin-4-yl)methyl][(3S)-piperidin-3-yl]amino}methyl)-1,4-dihydroquinolin-4-one

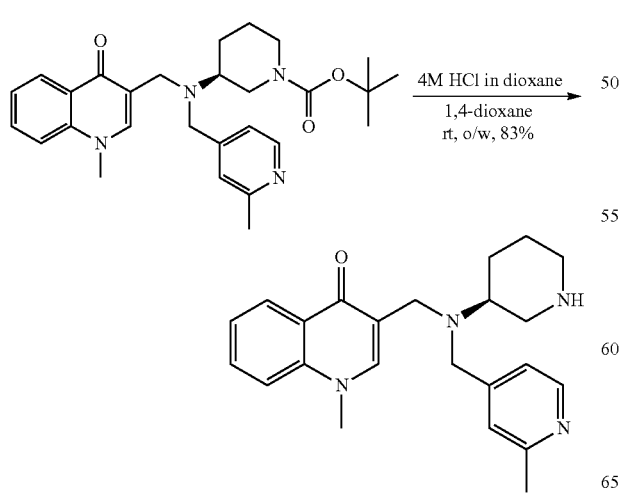

A solution of tert-butyl (3S)-3-{[(1-methyl-4-oxo-1,4-dihydroquinolin-3-yl)methyl][(2-methylpyridin-4-yl)methyl]amino}piperidine-1-carboxylate (2.4 g, 5.0 mmol, 1 eq.) in 1,4-dioxane (20 mL) was treated with 4 M HCl in dioxane (6.5 mL, 25.2 mmol, 5 eq.). The resulting slurry was stirred over the weekend. Subsequently the volatiles in the reaction mixture were evaporated and the residue was partitioned between DCM and 15% NaOH aqueous solution. The organic layer was washed with brine, dried over Na$_2$SO$_4$, filtered and concentrated to give the product (1.6 g, 4.2 mmol, yield 83%) as a yellow oil.

ESI-MS: 377.5 [M+H]$^+$ $^1$H NMR (400 MHz, DMSO-d6) δ 8.29-8.23 (m, 1H), 8.18 (dd, J=8.1, 1.6 Hz, 1H), 7.93 (s, 1H), 7.71 (ddd, J=8.6, 6.9, 1.7 Hz, 1H), 7.63-7.59 (m, 1H), 7.36 (ddd, J=8.0, 6.9, 1.0 Hz, 1H), 7.24-7.15 (m, 2H), 3.82 (s, 3H), 3.66 (s, 2H), 3.63-3.49 (m, 5H), 3.11-3.00 (m, 1H), 2.80-2.72 (m, 1H), 2.35 (s, 3H), 2.34-2.24 (m, 1H), 2.01-1.88 (m, 1H), 1.63 (d, J=12.3 Hz, 1H), 1.51-1.36 (m, 1H), 1.33-1.18 (m, 1H).

Procedure 30. Preparation of 3-({[(3S)-1-(2-chloro-pyrimidin-4-yl)piperidin-3-yl][(2-methylpyridin-4-yl)methyl]amino}methyl)-1-methyl-1,4-dihydroquinolin-4-one

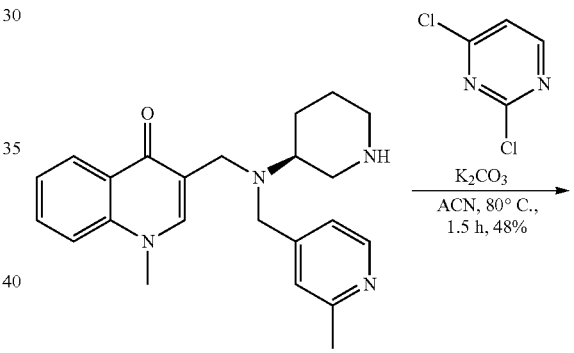

A mixture of 1-methyl-3-({[(2-methylpyridin-4-yl)methyl][(3S)-piperidin-3-yl]amino}methyl)-1,4-dihydroquinolin-4-one (0.12 g, 0.3 mmol, 1 eq.), 2,4-dichloropyrimidine (0.052 g, 0.4 mmol, 1.1 eq.), K$_2$CO$_3$ (0.066 g, 0.5 mmol, 1.5 eq.) and acetonitrile (2.5 mL) was heated at 80° C. for 1.5 h. Then 2 M NaOH aqueous solution was added and the reaction mixture was washed with DCM. Organics were washed with brine, dried over Na$_2$SO$_4$, filtered and concentrated under reduced pressure. The residue was purified by FCC (SiHP: DCM/MeOH) to give the product (0.076 g, 0.2 mmol, yield 49%) as a yellowish solid. 0.026 g of the sample was re-purified by prep-HPLC affording formic salt of the compound (0.013 g, 0.03 mmol, yield 8%) as a yellowish solid. ESI-MS: 489.2 [M+H]+

$^1$H NMR (400 MHz, DMSO-d6) δ 8.28 (d, J=5.0 Hz, 1H), 8.19 (dd, J=8.1, 1.6 Hz, 1H), 8.15 (s, 1H), 8.03-7.97 (m, 2H), 7.71 (ddd, J=8.6, 6.9, 1.7 Hz, 1H), 7.64-7.60 (m, 1H), 7.37 (ddd, J=8.0, 6.9, 1.0 Hz, 1H), 7.25-7.19 (m, 2H), 6.89-6.83 (m, 1H), 4.63-4.11 (m, 2H), 3.84 (s, 3H), 3.82-3.71 (m, 2H), 3.69-3.57 (m, 2H), 3.14-3.03 (m, 1H), 2.91-2.80 (m, 1H), 2.61-2.54 (m, 1H), 2.36 (s, 3H), 2.02-1.95 (m, 1H), 1.80-1.65 (m, 2H), 1.37-1.22 (m, 1H).

Procedure 31. Preparation of 7-chloro-1-cyclopropyl-4-oxo-1,4-dihydro-1,6-naphthyridine-3-carbaldehyde

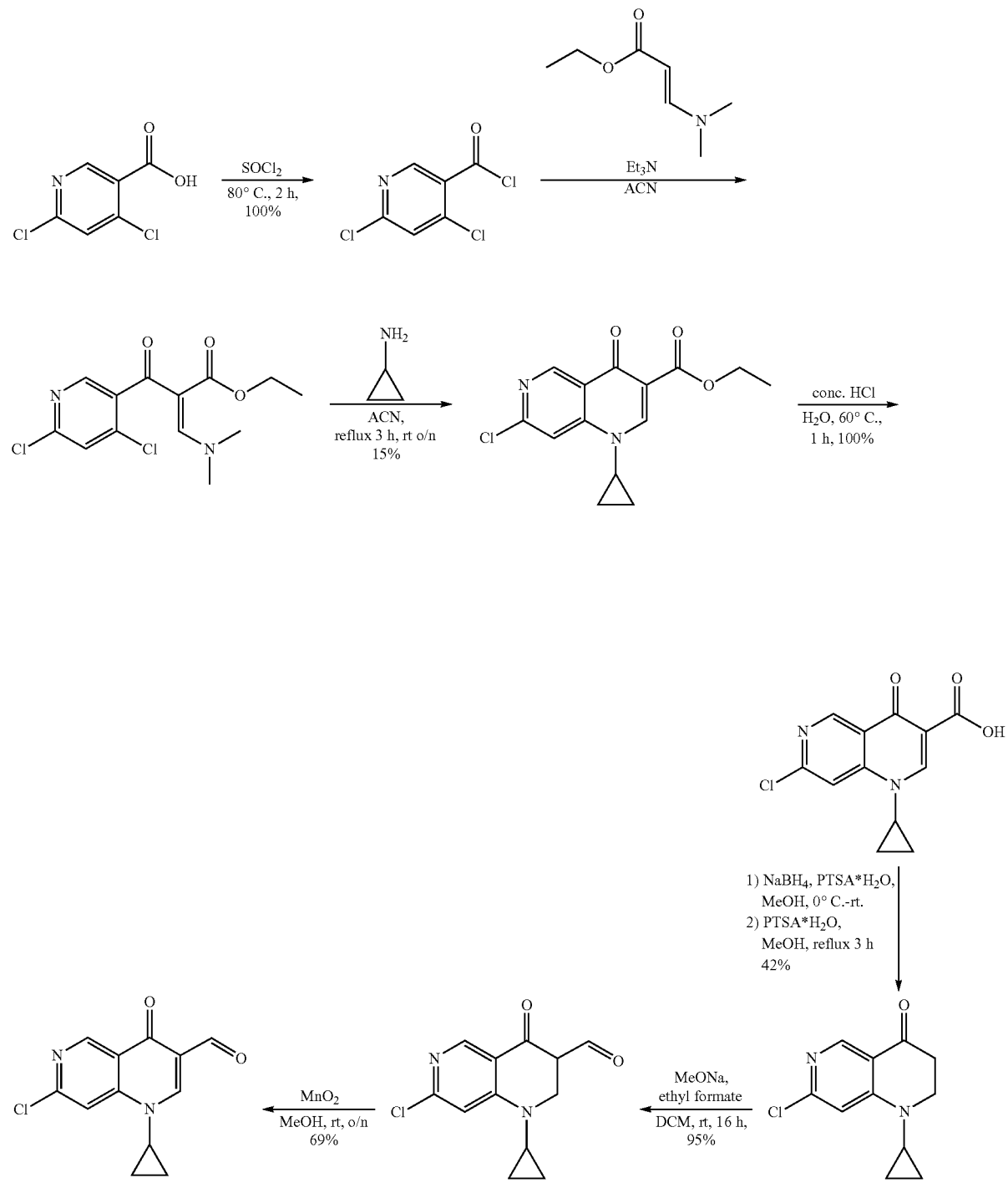

a) 4,6-dichloropyridine-3-carbonyl chloride

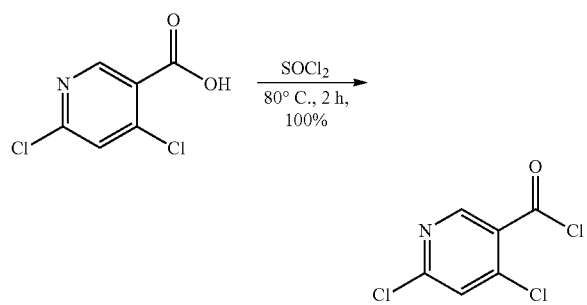

4,6-dichloropyridine-3-carboxylic acid (1.0 g, 5.2 mmol, 1 eq.) and SOCl$_2$ (4.0 mL, 54.7 mmol, 10.5 eq.) was heated for 2 h at 80° C. Then, the mixture was cooled to rt and co-evaporated with DCM to give the product (1.1 g, 5.2 mmol, yield 99%) as a yellow oil which was used in the next step without further purification.

b) ethyl 7-chloro-1-cyclopropyl-4-oxo-1,4-dihydro-1,6-naphthyridine-3-carboxylate

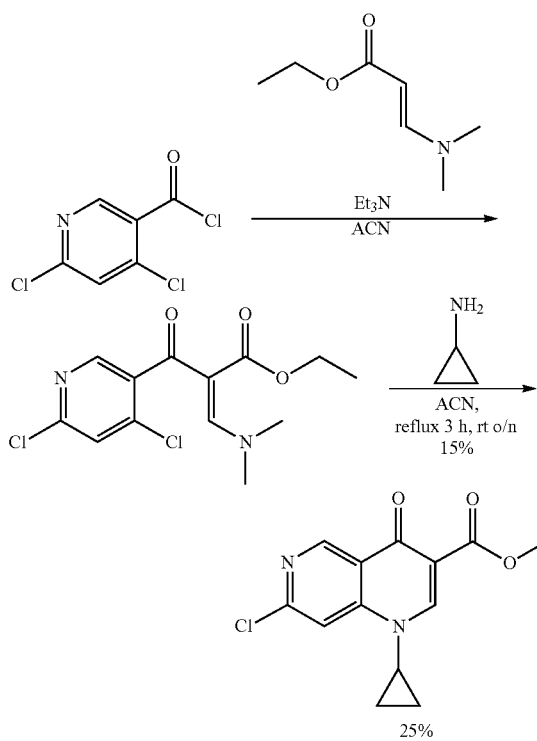

TEA (2.9 mL, 20.8 mmol, 4 eq.) was added to acetonitrile (5 mL) followed by ethyl 3-(dimethylamino)prop-2-enoate (1.1 g, 7.8 mmol, 1.5 eq.) and 4,6-dichloropyridine-3-carbonyl chloride (1.1 g, 5.2 mmol, 1 eq.). The reaction mixture was stirred at 65° C. overnight, then was cooled to rt and cyclopropanamine (0.4 g, 7.9 mmol, 1 eq.) was added. The resulting mixture was heated at reflux for 3 h and heating was continued overnight. Subsequently, the reaction mixture was concentrated, diluted with EtOAc, washed sequentially with NaHCO$_3$ aqueous solution, water, brine, dried over anh. Na$_2$SO$_4$, filtered and evaporated. The residue was purified by FCC (SiHP; Hex/AcOEt 0-100%) to give the product (0.4 g, 1.3 mmol, yield 25%) as a yellow solid.
ESI-MS: 293.8 [M+H]$^+$
$^1$H NMR (300 MHz, DMSO-d6) δ 9.07 (s, 1H), 8.50 (s, 1H), 8.01 (s, 1H), 4.24 (q, J=7.1 Hz, 2H), 3.62 (tt, J=7.2, 3.9 Hz, 1H), 1.32 1.21 (m, 5H), 1.15 1.08 (m, 2H).

c) 7-chloro-1-cyclopropyl-4-oxo-1,4-dihydro-1,6-naphthyridine-3-carboxylic acid

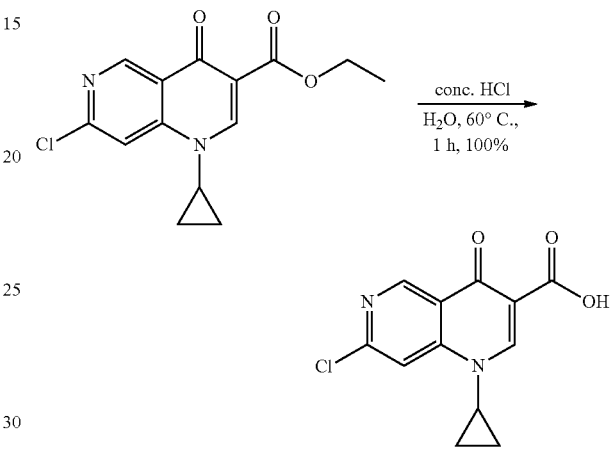

Ethyl 7-chloro-1-cyclopropyl-4-oxo-1,4-dihydro-1,6-naphthyridine-3-carboxylate (0.15 g, 0.5 mmol, 1 eq.) was suspended in water (2 mL) and conc. HCl (2 mL). The reaction mixture was stirred for 1 h at 60° C. and then concentrated to give the product (0.14 g, 0.5 mmol, yield 99%) as a white solid.
ESI-MS: 265.8 [M+H]$^+$ d) 7-chloro-1-cyclopropyl-1,2,3,4-tetrahydro-1,6-naphthyridin-4-one

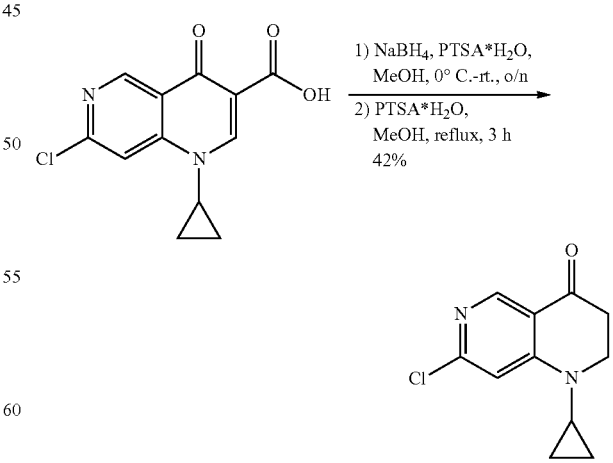

The title compound was synthesized following the approach outlined in Procedure 7d substituting 1-cyclopropyl-6-fluoro-7-(4-methylpiperazin-1-yl)-4-oxo-1,4-dihydroquinoline-3-carboxylic acid with 7-chloro-1-cyclopropyl- 4-oxo-1,4-dihydro-1,6-naphthyridine-3-carboxylic acid. The first stage of the reaction was prolonged to overnight stirring with NaBH₄ while the second stage with PTSA was shortened to 3 h. Additionally DCM and aq. solution of NaHCO₃ were used for washing during work-up. The residue after evaporation of the volatiles was purified by FCC (SiHP; Hex:AcOEt 4:1) to give the product (0.05 g, 0.2 mmol, yield 42%) as a white solid.

ESI-MS: 223.0 [M+H]⁺ e) 7-chloro-1-cyclopropyl-4-oxo-1,2,3,4-tetrahydro-1,6-naphthyridine-3-carbaldehyde

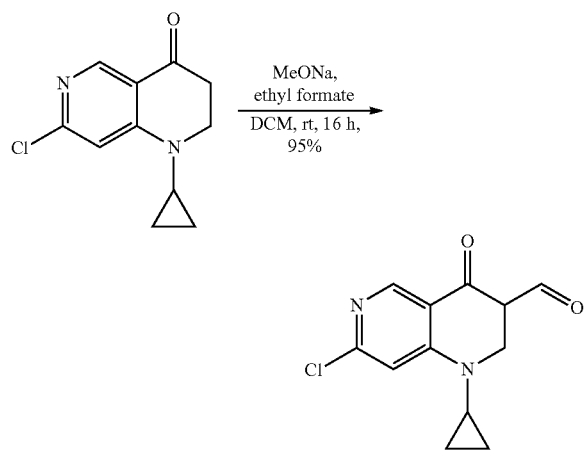

A mixture of MeONa (0.05 g, 0.8 mmol, 3.9 eq.) and ethyl formate (0.07 mL 0.9 mmol, 3.9 eq.) was treated with a solution of 7-chloro-1-cyclopropyl-1,2,3,4-tetrahydro-1,6-naphthyridin-4-one (0.05 g, 0.2 mmol, 1 eq.) in anh. DCM (5 mL) at rt under inert atmosphere. The reaction mixture was stirred for 16 h at rt and ice-water was added. The organic layer was washed with 2 M NaOH aqueous solution, the aqueous phases were acidified to pH 6 with conc. HCl and then washed with DCM. The combined organic extracts were dried over MgSO₄, filtered and concentrated to give the crude product (0.053 g, 0.2 mmol, yield 94%) as a yellow solid which was used directly in the next step.

ESI-MS: 250.9 [M+H]⁺ f) 7-chloro-1-cyclopropyl-4-oxo-1,4-dihydro-1,6-naphthyridine-3-carbaldehyde

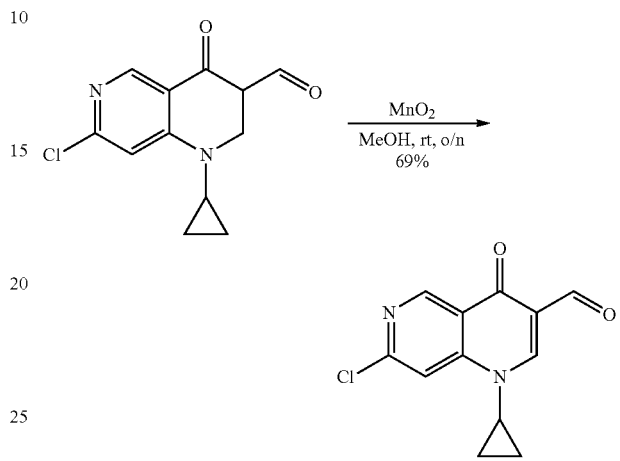

7-chloro-1-cyclopropyl-4-oxo-1,2,3,4-tetrahydro-1,6-naphthyridine-3-carbaldehyde (0.053 g, 0.2 mmol, 1 eq.) was dissolved in anh. MeOH (5 mL) and MnO₂ (0.09 g, 1.1 mmol, 5 eq.) was added. The reaction mixture was stirred overnight at rt. Then the volatiles in the mixture were evaporated and the residue was diluted with DCM and passed through a pad of Celite. The filtrate was concentrated and the residue was purified by FCC (SiHP; DCM:MeOH 95:5) to give the product (0.036 g, 0.1 mmol, yield 68%) as a light yellow solid.

AP-MS: 249.0 [M+H]⁺

Procedure 32. Preparation of 7-(cyclohex-1-en-1-yl)-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one

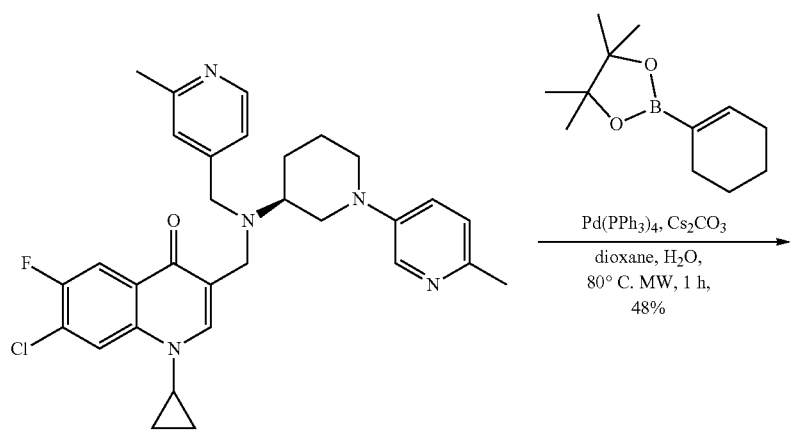

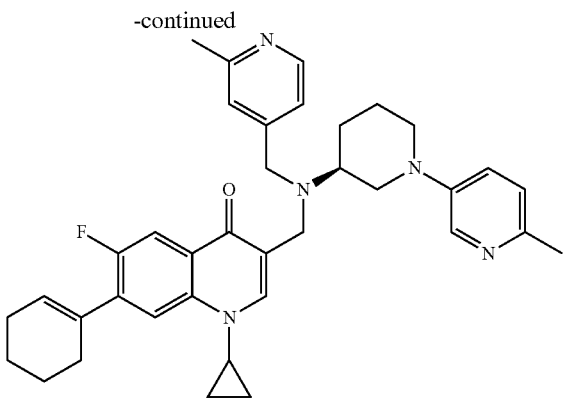

A mixture of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (0.06 g, 0.1 mmol, 1 eq.), 2-(cyclohex-1-en-1-yl)-4,4,5,5-tetramethyl-1,3,2-dioxaborolane (0.046 g, 0.2 mmol, 2 eq.), Na$_2$CO$_3$ (0.072 g, 0.2 mmol, 2 eq.), dioxane (3 mL) and water (0.3 mL) was purged with argon for 10 min. Then Pd(PPh$_3$)$_4$ (0.006 g, 0.005 mmol, 0.05 eq.) was added and the mixture was irradiated with microwaves at 140° C. for 1 h. Subsequently the reaction mixture was filtered through a Celite pad. The residue adsorbed on silica and purified by FCC (SiHP deactivated with NH$_3$:DCM; DCM:MeOH 8:2) and re-purified by prep-HPLC to give the product (0.031 g, 0.05 mmol, yield 47%) as a white solid.

ESI-MS: 592.7 [M+H]$^+$

Procedure 33. Preparation of 3-({[(3S)-1-(6-methylpyridin-3-yl)piperidin-3-yl][(2-methylpyridin-4-yl)methyl]amino}methyl)-1,4-dihydroquinolin-4-one

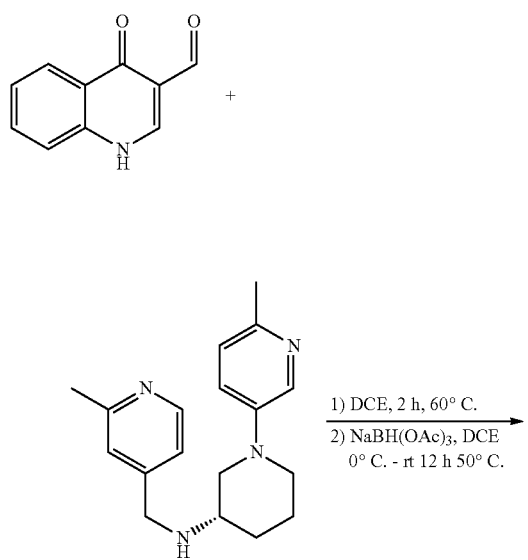

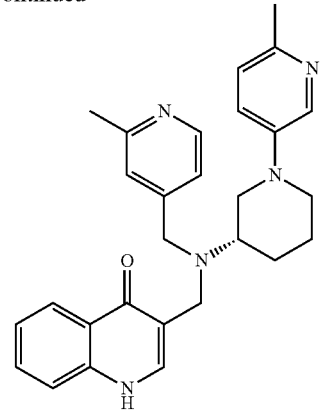

A dry reactor vessel was charged with (3S)-1-(6-methylpyridin-3-yl)-N-[(2-methylpyridin-4-yl)methyl]piperidin-3-amine (0.342 g, 1.2 mmol, 1 eq.), 4-oxo-1,4-dihydroquinoline-3-carbaldehyde (0.2 g, 1.2 mmol, 1 eq.) and anh. DCE (10 mL). The reaction was carried out at 60° C. for 2 h and then cooled to 0° C. NaBH(OAc)$_3$ (0.34 g, 1.6 mmol, 1.4 eq.) was added and the reaction mixture stirring was continued overnight at rt. Then additional NaBH(OAc)$_3$ (0.122 g, 0.6 mmol, 0.5 eq.) was added and the reaction was heated while stirring for another 12 h at 50° C. Subsequently H$_2$O was added followed by NaHCO$_3$ and the resulting mixture was washed with DCM. The organic layer was washed with brine, dried over Na$_2$SO$_4$ and concentrated in vacuo. The residue was purified by FCC (SiHP; DCM:MeOH 9:1) and additionally by RP-FCC (SiC18; H$_2$O:MeCN) to give the product (0.29 g, 0.6 mmol, yield 51%) as a yellowish powder. 0.12 g of the sample was re-purified by prep-HPLC. The collected fractions were neutralized with 1 N NaOH aqueous solution, extracted with EtOAc, dried over anhydrous Na$_2$SO$_4$ and concentrated in vacuo. The residue was suspended in water and freeze-dried to give the product (0.08 g, 0.2 mmol, yield 14%) as a beige powder.

ESI-MS: 454.2 [M+H]$^+$ $^1$H NMR (400 MHz, DMSO-d6) δ 11.68 (s, 1H), 8.30 (d, J=5.1 Hz, 1H), 8.12 (d, J=3.1 Hz, 1H), 8.11-8.09 (m, 1H), 7.94 (s, 1H), 7.60 (ddd, J=8.5, 6.9, 1.6 Hz, 1H), 7.50 (d, J=8.3 Hz, 1H), 7.32-7.17 (m, 4H), 7.01 (d, J=8.5 Hz, 1H), 3.84-3.70 (m, 3H), 3.66-3.54 (m, 3H), 2.79-2.69 (m, 2H), 2.60-2.55 (m, 1H), 2.39 (s, 3H), 2.32 (s, 3H), 2.00-1.92 (m, 1H), 1.80-1.71 (m, 1H), 1.59-1.39 (m, 2H).

Procedure 34. 1-cyclopropyl-6-fluoro-7-hydroxy-3-({[(3S)-1-(6-methylpyridin-3-yl)piperidin-3-yl][(2-methylpyridin-4-yl)methyl]amino}methyl)-1,4-dihydroquinolin-4-one

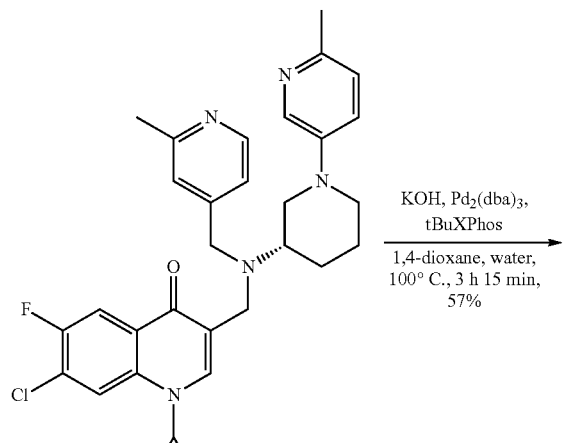

A mixture of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one (0.1 g, 0.2 mmol, 1 eq.), 1,4-dioxane (1 mL) and H₂O (1 mL) was purged with argon, subsequently KOH (0.013 g, 0.2 mmol, 1.3 eq.), tBuXPhos (0.006 g, 0.015 mmol, 0.08 eq.) and Pd₂(dba)₃ (0.003 g, 0.004 mmol, 0.02 eq.) were added. The reaction vial was capped and the reaction mixture was heated at 100° C. for 75 min. Then the mixture was purged again with argon and additional KOH (0.006 g, 0.1 mmol, 0.6 eq.), tBuXPhos (0.006 g, 0.015 mmol, 0.08 eq.) and Pd₂(dba)₃ (0.003 g, 0.004 mmol, 0.02 eq.) were added and the reaction was continued for 2 h at 100° C. H₂O was then added and the reaction mixture was partitioned between DCM and NH₄Cl aqueous solution. The aqueous layer was additionally washed with DCM (3 times). The combined organic layers were evaporated in vacuo and the residue was purified by FCC (SiHP; DCM:MeOH 9:1) the give 1-cyclopropyl-6-fluoro-7-hydroxy-3-({[(3S)-1-(6-methylpyridin-3-yl)piperidin-3-yl][(2-methylpyridin-4-yl)methyl]amino}methyl)-1,4-dihydroquinolin-4-one (0.055 g, 0.1 mmol, yield 57%) as a beige solid.

ESI-MS: 528.3 [M+H]⁺

$^1$H NMR (300 MHz, DMSO-d6) δ 10.97 (s, 1H), 8.28 (d, J=5.0 Hz, 1H), 8.13 (d, J=2.9 Hz, 1H), 7.78 (s, 1H), 7.74 (d, J=11.5 Hz, 1H), 7.44 (d, J=7.5 Hz, 1H), 7.28-7.12 (m, 3H), 7.02 (d, J=8.5 Hz, 1H), 3.89-3.50 (m, 6H), 3.47-3.37 (m, 1H), 2.83-2.65 (m, 2H), 2.64-2.54 (m, 1H), 2.37 (s, 3H), 2.32 (s, 3H), 2.04-1.90 (m, 1H), 1.83-1.67 (m, 1H), 1.60-1.38 (m, 2H), 1.23-1.08 (m, 2H), 0.95-0.81 (m, 2H).

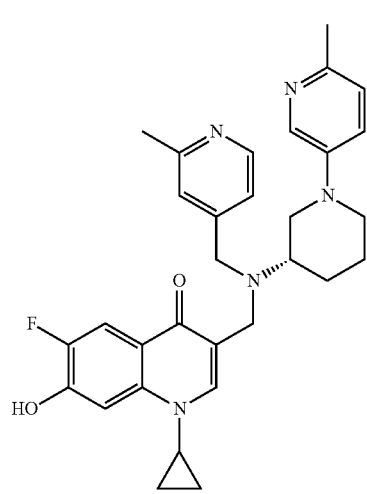

Procedure 35. Preparation of 8-bromo-1-methyl-3-({[(3S)-1-(6-methylpyridin-3-yl)piperidin-3-yl][(2-methylpyridin-4-yl)methyl]amino}methyl)-1,4-dihydroquinolin-4-one

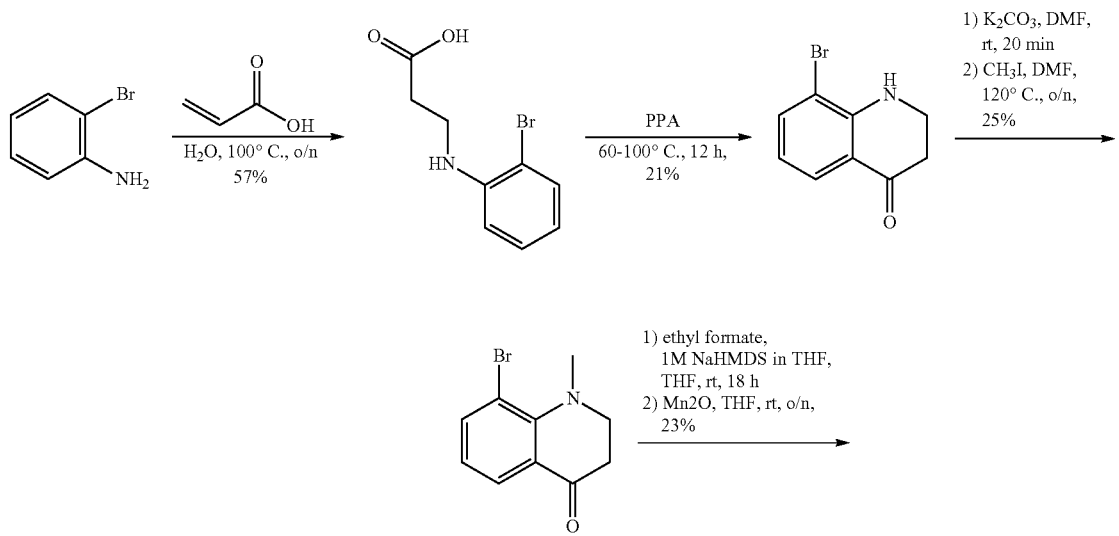

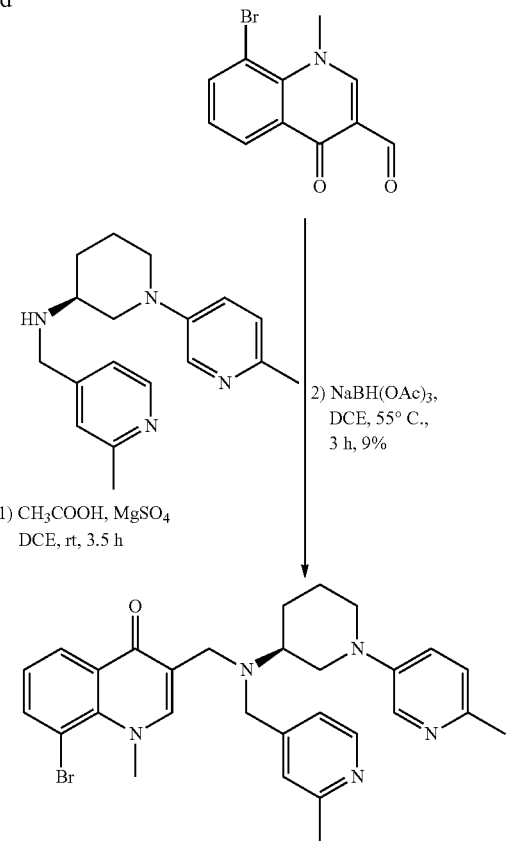

a) 3-[(2-bromophenyl)amino]propanoic acid b) 8-bromo-1,2,3,4-tetrahydroquinolin-4-one

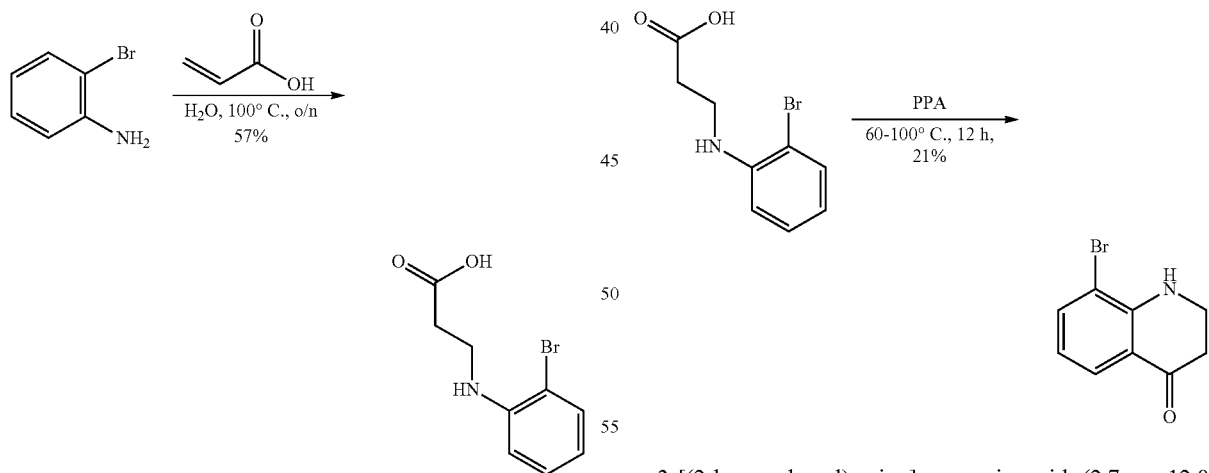

2-Bromoaniline (2 g, 11.6 mmol, 1 eq.) and prop-2-enoic acid (1.5 mL, 37.2 mmol, 3.2 eq.) were added to H₂O (40 mL). The resulting mixture was heated overnight at 100° C. Then the mixture was cooled to rt. The precipitate was filtered off and washed with cold water. The solid was mixed with 20 mL of toluene and the solvent was evaporated to give crude product (2.7 g, 11.1 mmol, yield 95%) as a yellow solid which was used in the next step without further purification.

3-[(2-bromophenyl)amino]propanoic acid (2.7 g, 12.0 mmol, 1 eq.) was added in one portion to polyphosphoric acid (14.46 mL, 78.4 mmol, 7.1 eq.) at 60° C. The resulting mixture was heated at 110° C. with stirring for 12 h. The reaction mixture was poured slowly into ice-water. The solution was washed with EtOAc (4×100 mL). The organic layer was washed in sequence with sat. NaHCO₃ solution, water & brine, dried over anh. Na₂SO₄, filtered and concentrated in vacuo. The residue was purified by FCC (SiHP; Hex:AcOEt 8:2) to give the product (0.518 g, 2.3 mmol, yield 21%) as a yellow sticky solid.

ESI-MS: 225.9 [M+H]⁺

¹H NMR (300 MHz, Chloroform-d) δ 7.82 (dd, J=7.9, 1.5 Hz, 1H), 7.56 (dd, J=7.9, 1.5 Hz, 1H), 6.62 (t, J=7.9 Hz, 1H), 4.99 (s, 1H), 3.66 (td, J=7.1, 2.2 Hz, 2H), 2.79-2.64 (m, 2H).

c) 8-bromo-1-methyl-1,2,3,4-tetrahydroquinolin-4-one

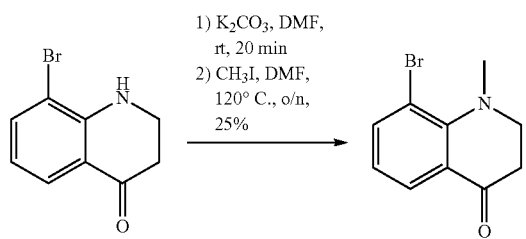

K₂CO₃ (0.7 g, 5.2 mmol, 3 eq.) was added to a solution of 8-bromo-1,2,3,4-tetrahydroquinolin-4-one (0.46 g, 1.7 mmol, 1 eq.) in anh. DMF (10 mL) and the resulting mixture was stirred for 20 min at rt. Subsequently, iodomethane (0.22 mL, 3.5 mmol, 2 eq.) was added and the mixture was heated overnight at 120° C. Then the reaction mixture was cooled to rt and additional K₂CO₃ (0.7 g, 5.2 mmol, 3 eq.) and iodomethane (0.22 mL, 3.5 mmol, 2 eq.) were added. The mixture was heated overnight at 120° C. Then the reaction mixture was cooled again to rt and additional amounts of K₂CO₃ (0.7 g, 5.2 mmol, 3 eq.) and iodomethane (0.215 mL, 3.5 mmol, 2 eq.) were added. The mixture was heated over the weekend at 120° C. DMF was then evaporated under reduced pressure and the residue was purified by FCC (SiHP; Hex:AcOEt 50-80%) to give the product (0.105 g, 0.4 mmol, yield 25%) as a yellow oil.

ESI-MS: 239.9 [M+H]⁺ d) 8-bromo-1-methyl-4-oxo-1,4-dihydroquinoline-3-carbaldehyde

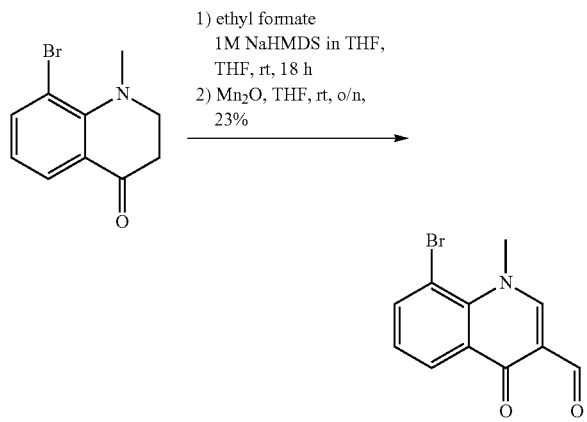

In a dry round-bottomed flask 8-bromo-1-methyl-1,2,3,4-tetrahydroquinolin-4-one (0.105 g, 0.4 mmol, 1 eq.) and ethyl formate (0.106 mL, 1.3 mmol, 3 eq.) were mixed in anh. THF (4 mL) under inert atmosphere. Then 1 M NaHMDS in THF (1.2 mL, 0.7 mmol, 1.7 eq.) was added dropwise and the resulting mixture was stirred overnight at rt. The organics were concentrated to dryness and the residue was dissolved anh. MeOH (1 mL). MnO₂ (0.013 g, 0.2 mmol, 0.5 eq.) was added to the above methanolic solution and stirred for 3 h at rt and then additionally 20 h. Subsequently, the reaction mixture was filtered through a pad of Celite and the filtrate was concentrated. The residue was purified by FCC (SiHP; DCM:MeOH 95:5) to give the product (0.03 g, 0.1 mmol, yield 23%) as a brown solid.

ESI-MS: 265.9 [M+H]⁺ e) bromo-1-methyl-3-({[(3S)-1-(6-methylpyridin-3-yl)piperidin-3-yl][(2-methylpyridin-4-yl)methyl]amino}methyl)-1,4-dihydroquinolin-4-one

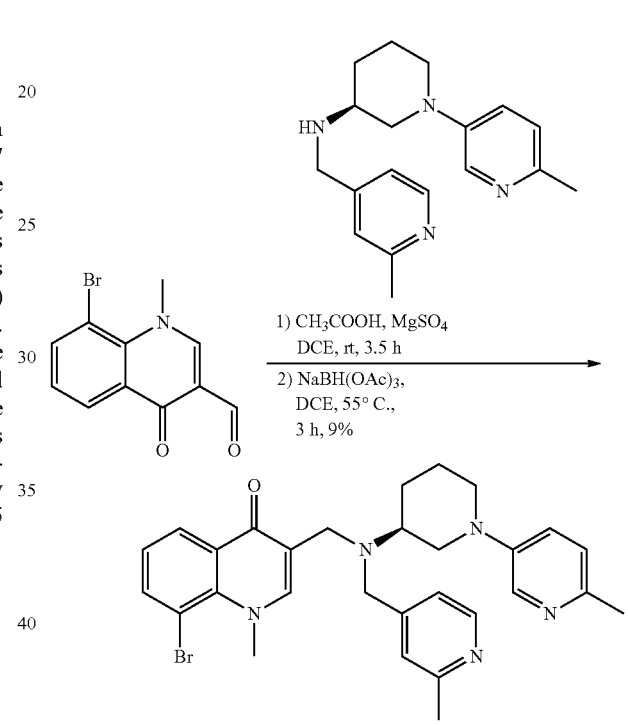

8-bromo-1-methyl-4-oxo-1,4-dihydroquinoline-3-carbaldehyde (0.063 g, 0.2 mmol, 1 eq.) dissolved in anh. DCE (1.5 mL) and (3S)-1-(6-methylpyridin-3-yl)-N-[(2-methylpyridin-4-yl)methyl]piperidin-3-amine (0.084 g, 0.3 mmol, 1.2 eq.) dissolved in anh. DCE (1.5 mL) were added to each other dropwise to a reaction vial. The solution was purged with argon for 10 min. Drops of AcOH were added dropwise via a syringe needle followed by a pinch of dried MgSO₄ and the resulting mixture was purged with argon again. The reaction vial was capped and the reaction mixture was stirred for 3.5 h at rt. Then the mixture was cooled in an ice-NaCl bath and NaBH(OAc)₃ (0.09 g, 0.4 mmol, 1.8 eq.) was added in portions. The reaction mixture was heated for 3 hours at 55° C. Next, anh. DCE (1 mL) was added and the reaction was left stirring overnight at rt. Subsequently the reaction mixture was filtered through a pad of Celite and the pad was washed with a mixture of DCM:MeOH (9:1, 100 mL). The organic layer was concentrated in vacuo and the residue was purified by FCC (SiHP; DCM:MeOH 93:7) followed by RP-FCC (Si—C18; H₂O/ACN) to give the product (0.012 g, 0.02 mmol, yield 9%) as a colorless oil.

ESI-MS: 546.3 [M+H]⁺

Procedure 36. Preparation of 7-chloro-6-fluoro-3-({[(3S)-1-(6-methylpyridin-3-yl)piperidin-3-yl][(2-methylpyridin-4-yl)methyl]amino}methyl)-1-(propan-2-yl)-1,4-dihydro-1,8-naphthyridin-4-one
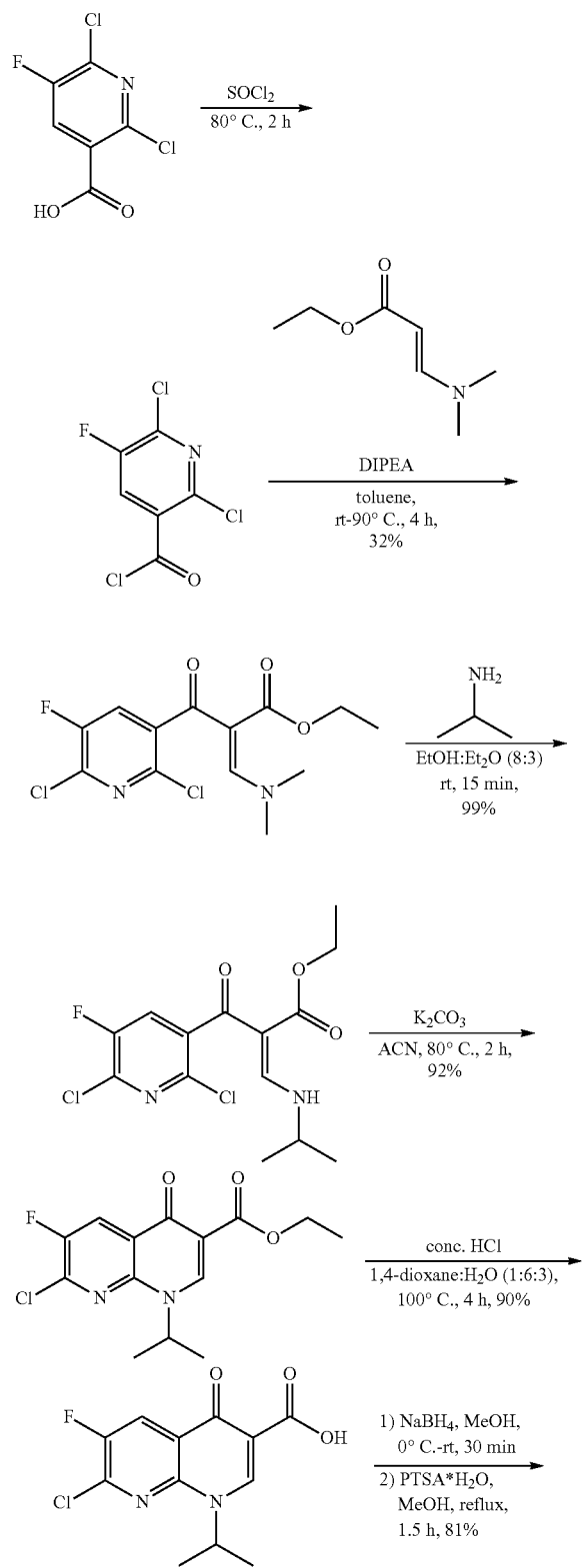
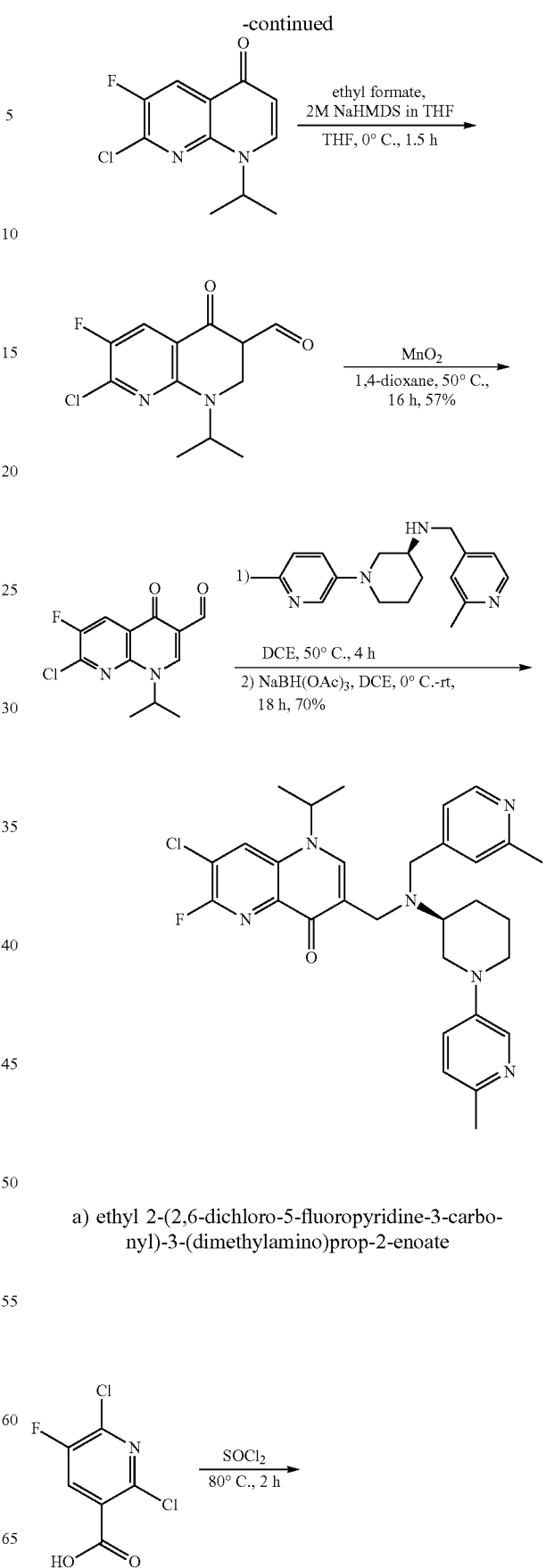
-continued
a) ethyl 2-(2,6-dichloro-5-fluoropyridine-3-carbonyl)-3-(dimethylamino)prop-2-enoate

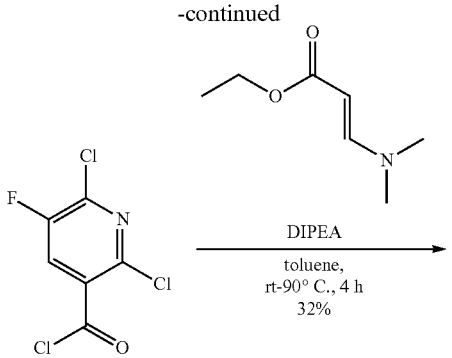

2,6-dichloro-5-fluoropyridine-3-carboxylic acid (5.4 g, 25.8 mmol, 1 eq.) was suspended in SOCl$_2$ (9.4 mL, 129.2 mmol, 5.0 eq.) and the reaction mixture was stirred for 2 h at 80° C. during which time the mixture became a clear solution. The reaction mixture was co-concentrated with DCM. The residue was added to a mixture of ethyl 3-(dimethylamino)prop-2-enoate (3.7 mL, 25.8 mmol, 1 eq.), DIPEA (9.5 mL, 54.3 mmol, 2.1 eq.) and toluene (20 mL) over 5 min at rt. The resulting solution was stirred for 15 min at rt and after that time heated for 3.5 h at 90° C. Subsequently the reaction mixture was partitioned between DCM and H$_2$O. The washed organic layer was dried over anh. Na$_2$SO$_4$, filtered and evaporated. The residue was purified by FCC (SiHP; Hex/AcOEt) to give the product (2.8 g, 8.4 mmol, yield 32%) as an orange oil.

ESI-MS: 335.0 [M+H]$^+$ $^1$H NMR (400 MHz, DMSO-d6) δ 8.04 (d, J=7.9 Hz, 1H), 7.95 (s, 1H), 3.91 (q, J=7.1 Hz, 2H), 3.39 (s, 3H), 2.93 (s, 3H), 0.94 (t, J=7.1 Hz, 3H).

b) ethyl 2-(2,6-dichloro-5-fluoropyridine-3-carbonyl)-3-[(propan-2-yl)amino]prop-2-enoate

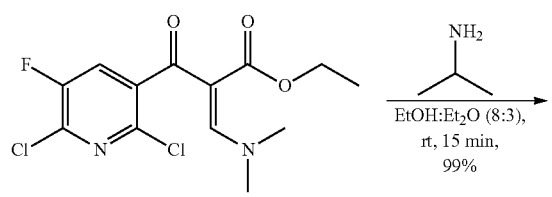

A solution of 2-(2,6-dichloro-5-fluoropyridine-3-carbonyl)-3-(dimethylamino)prop-2-enoate (1.05 g, 3.1 mmol, 1 eq.) in a mixture of EtOH (16 mL) and Et$_2$O (6 mL) was treated with propan-2-amine (0.3 mL, 3.4 mmol, 1.1 eq.). The reaction mixture was stirred for 15 min at rt. Then solvents were evaporated to give crude product (1.2 g, 3.4 mmol, yield 99%) as an orange oil which was used in next step without further purification.

ESI-MS: 349.0 [M+H]$^+$ c) 7-chloro-6-fluoro-4-oxo-1-(propan-2-yl)-1,4-dihydro-1,8-naphthyridine-3-carboxylate

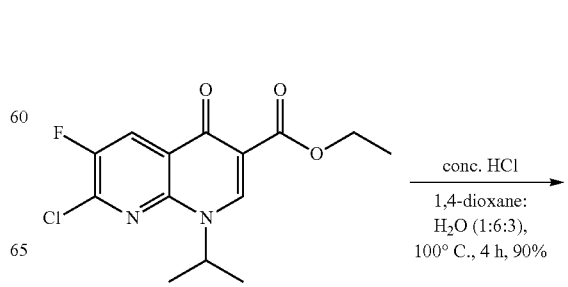

A solution of 2-(2,6-dichloro-5-fluoropyridine-3-carbonyl)-3-[(propan-2-yl)amino]prop-2-enoate (0.85 g, 2.6 mmol, 1 eq.) in ACN (8 mL) was treated with K$_2$CO$_3$ (0.5 g, 3.8 mmol, 1.6 eq.) and the reaction mixture was stirred for 2 h at 80° C. Afterwards the reaction was quenched by the addition of H$_2$O. Then, the reaction mixture was mixed with three other crude mixtures of trial reactions using different solvents (ACN, NMP and DMAc)] set up using identical conditions but starting from smaller amount of 2-(2,6-dichloro-5-fluoropyridine-3-carbonyl)-3-[(propan-2-yl)amino]prop-2-enoate (0.1 g, 0.3 mmol) and. The resulting mixture was washed with DCM. The combined organic layers were dried over anh. MgSO$_4$, filtered and concentrated. The residue was dissolved in 5 mL of DCM and heptane was added. The precipitate was filtered off and dried under vacuum affording ethyl 7-chloro-6-fluoro-4-oxo-1-(propan-2-yl)-1,4-dihydro-1,8-naphthyridine-3-carboxylate (0.81 g, 2.6 mmol, yield 85%) as an off-white solid.

ESI-MS: 313.9 [M+H]$^+$ $^1$H NMR (400 MHz, DMSO-d6) δ 8.71 (s, 1H), 8.48 (d, J=7.9 Hz, 1H), 5.53-5.43 (m, 1H), 4.26 (q, J=7.1 Hz, 2H), 1.50 (s, 3H), 1.49 (s, 3H), 1.29 (t, J=7.1 Hz, 3H).

d) 7-chloro-6-fluoro-4-oxo-1-(propan-2-yl)-1,4-dihydro-1,8-naphthyridine-3-carboxylic acid -continued

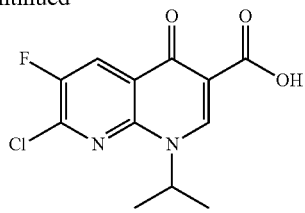

A mixture of ethyl 7-chloro-6-fluoro-4-oxo-1-(propan-2-yl)-1,4-dihydro-1,8-naphthyridine-3-carboxylate (0.81 g, 2.6 mmol, 1 eq.), conc. HCl aqueous solution (2 mL), H₂O (6 mL) and 1,4-dioxane (12 mL) was stirred for 4 h at 100° C. Subsequently, the reaction mixture was cooled to rt and the precipitate was filtered off and dried to give the product (0.67 g, 0.2 mmol, yield 90%) as an off-white solid which was used in the next step without further purification.

¹H NMR (400 MHz, DMSO-d6) δ 14.40 (s, 1H), 9.01 (s, 1H), 8.73 (d, J=7.6 Hz, 1H), 5.61 (hept, J=6.4 Hz, 1H), 1.56 (d, J=6.7 Hz, 6H).

e) 7-chloro-6-fluoro-1-(propan-2-yl)-1,2,3,4-tetrahydro-1,8-naphthyridin-4-one and 6-fluoro-7-methoxy-1-(propan-2-yl)-1,2,3,4-tetrahydro-1,8-naphthyridin-4-one

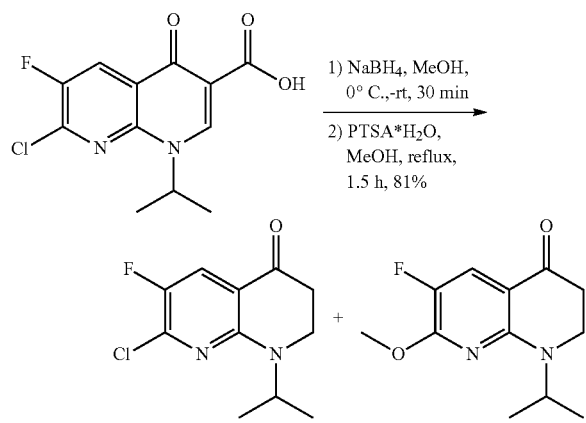

The title compounds were synthesized following the approach outlined in Procedure 7d substituting 1-cyclopropyl-6-fluoro-7-(4-methylpiperazin-1-yl)-4-oxo-1,4-dihydroquinoline-3-carboxylic acid with 7-chloro-6-fluoro-4-oxo-1-(propan-2-yl)-1,4-dihydro-1,8-naphthyridine-3-carboxylic acid and shortening the second stage to 1.5 h of heating at reflux. The residue after concentration of the reaction mixture was purified by FCC (SiHP; Hex:AcOEt 1:1) to give two compounds, 7-chloro-6-fluoro-1-(propan-2-yl)-1,2,3,4-tetrahydro-1,8-naphthyridin-4-one (0.46 g, 0.1 mmol, yield 81%) as a yellow solid

ESI-MS: 243.1 [M+H]⁺

¹H NMR (400 MHz, DMSO-d6) δ 7.88 (d, J=8.0 Hz, 1H), 4.88 (hept, J=6.7 Hz, 1H), 3.52-3.44 (m, 2H), 2.67-2.59 (m, 2H), 1.17 (d, J=6.8 Hz, 7H).

and 6-fluoro-7-methoxy-1-(propan-2-yl)-1,2,3,4-tetrahydro-1,8-naphthyridin-4-one (0.074 g, 0.02 mmol, yield 13%) as a yellow solid.

ESI-MS: 239.3 [M+H]⁺

¹H NMR (400 MHz, DMSO-d6) δ 7.66 (d, J=10.3 Hz, 1H), 4.93 (hept, J=6.8 Hz, 1H), 3.96 (s, 3H), 3.46-3.39 (m, 2H), 2.55-2.51 (m, 2H), 1.18 (d, J=6.8 Hz, 6H).

f) 7-chloro-6-fluoro-4-oxo-1-(propan-2-yl)-1,4-dihydro-1,8-naphthyridine-3-carbaldehyde

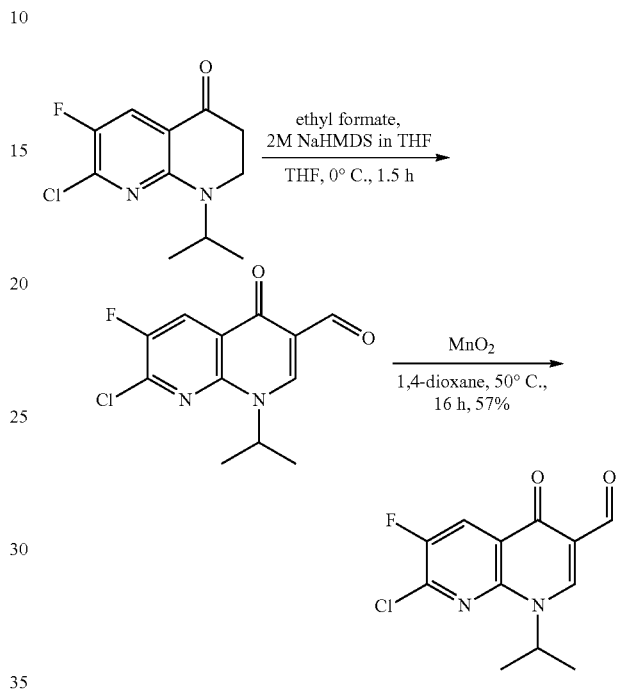

7-Chloro-6-fluoro-1-(propan-2-yl)-1,2,3,4-tetrahydro-1,8-naphthyridin-4-one (0.46 g, 1.9 mmol, 1 eq.) dissolved in anh. THF (2 mL) was added to a solution of NaHMDS (2 M in THF, 1.1 mL, 2.3 mmol, 1.2 eq.) in anh. THF (2 mL) at 0° C. The reaction mixture was stirred for 30 min at the same temperature and a solution of ethyl formate (0.2 mL, 2.5 mmol, 1.3 eq.) in THF (2 mL) was added. The reaction mixture was stirred for 1 h and then the reaction was quenched by addition of sat. NH₄Cl aqueous solution. The mixture was washed with AcOEt. The aqueous layer was washed further with AcOEt (×3). The combined organic layers were dried over anhydrous Na₂SO₄, filtered, concentrated and dried under reduced pressure. The residue was dissolved in anh. 1,4-dioxane (10 mL) and MnO₂ (0.82 g, 9.5 mmol, 4.2 eq.) was added. The resulting mixture was heated to 50° C. and stirred for 16 h. Subsequently, the reaction mixture was cooled to RT, filtered through a pad of celite and the pad was washed with a mixture of DCM:MeOH (7:3). The filtrate was concentrated and the residue was purified by FCC (SiHP; DCM:AcOEt 9:1) to give 7-chloro-6-fluoro-4-oxo-1-(propan-2-yl)-1,4-dihydro-1,8-naphthyridine-3-carbaldehyde (0.29 g, 1.1 mmol, yield 57%) as a yellow solid.

AP-MS: 269.0 [M+H]⁺

¹H NMR (400 MHz, DMSO-d6) δ 10.14 (s, 1H), 8.68 (s, 1H), 8.58 (d, J=7.7 Hz, 1H), 5.51 (hept, J=6.7 Hz, 1H), 1.52 (d, J=6.8 Hz, 6H).

g) 7-chloro-6-fluoro-3-({[(3S)-1-(6-methylpyridin-3-yl)piperidin-3-yl][(2-methylpyridin-4-yl)methyl]amino}methyl)-1-(propan-2-yl)-1,4-dihydro-1,8-naphthyridin-4-one Procedure 37. 3-({[(1,3-dimethyl-1H-pyrazol-5-yl)methyl][(3S)-1-(pyridin-3-yl)piperidin-3-yl]amino}methyl)-1-methyl-1,4-dihydroquinolin-4-one

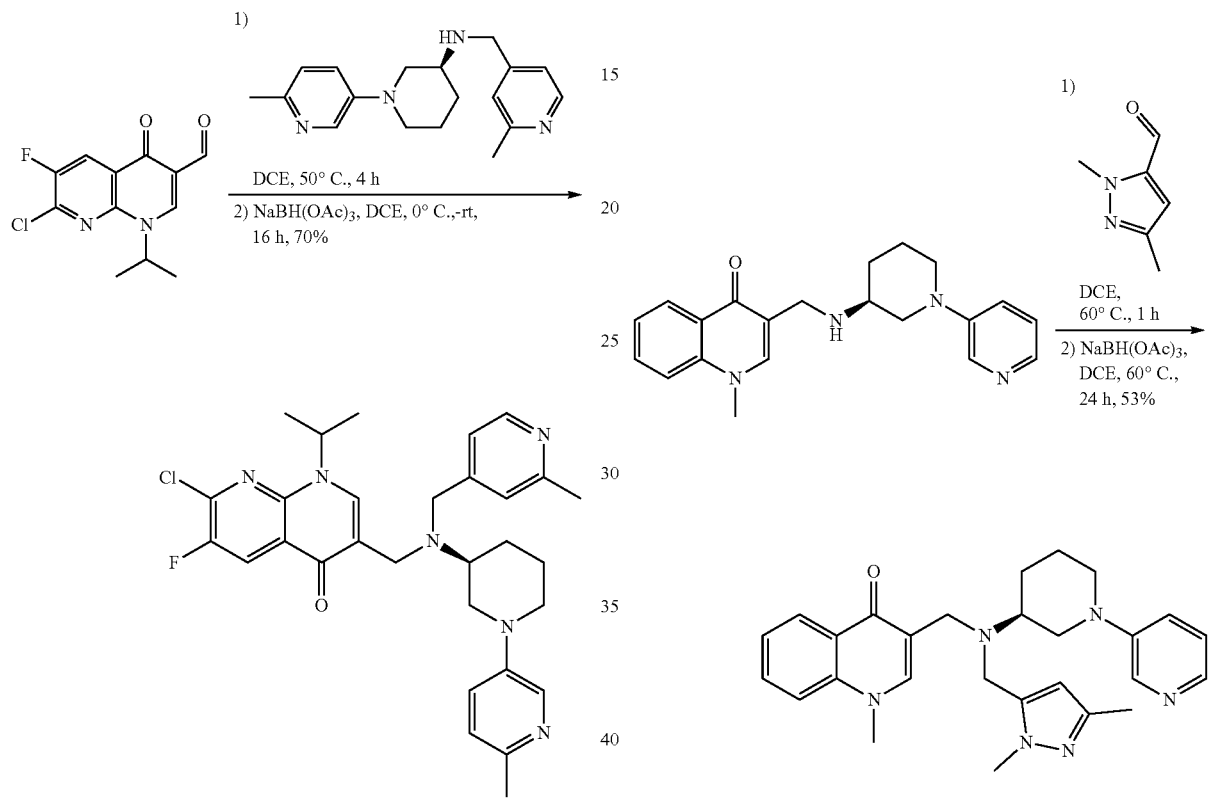

A dry reactor vessel was charged with (3S)-1-(6-methylpyridin-3-yl)-N-[(2-methylpyridin-4-yl)methyl]piperidin-3-amine (0.31 g, 1.0 mmol, 1.0 eq.) and 7-chloro-6-fluoro-4-oxo-1-(propan-2-yl)-1,4-dihydro-1,8-naphthyridine-3-carbaldehyde (0.29 g, 1.0 mmol, 1.0 eq.) taken in DCE (10 mL). The mixture was heated for 4 h at 50° C. and then cooled to 0° C. NaBH(OAc)₃ (0.43 g, 2.0 mmol, 2.0 eq.) was added and the resulting mixture was left stirring for 16 h at rt. Subsequently, the reaction mixture was quenched with H₂O and NaHCO₃ aq. solution and washed with DCM. The combined organic layers were washed with brine, dried over anh. Na₂SO₄ and concentrated in vacuo. The residue was purified by FCC (SiHP; DCM:MeOH 9:1). Product was re-purified by FCC (SiHP; DCM/MeOH/NH₃) and RP-FCC (Si—C18; H₂O/ACN) to give the product (0.40 g, 0.7 mmol, yield 70%) as a white solid.

ESI-MS: 549.4 [M+H]⁺

¹H NMR (400 MHz, Methanol-d4) δ 8.42-8.34 (m, 1H), 8.24-8.15 (m, 2H), 8.06 (d, J=3.0 Hz, 1H), 7.34 (dd, J=8.6, 3.0 Hz, 1H), 7.30 (s, 1H), 7.27-7.22 (m, 1H), 7.11 (d, J=8.6 Hz, 1H), 5.75-5.59 (m, 1H), 3.96-3.76 (m, 5H), 3.64-3.53 (m, 1H), 3.02-2.92 (m, 1H), 2.90-2.82 (m, 1H), 2.77-2.64 (m, 1H), 2.48-2.35 (m, 6H), 2.22-2.07 (m, 1H), 2.00-1.85 (m, 1H), 1.77-1.57 (m, 2H), 1.53-1.36 (m, 6H).

A solution of 1,3-dimethyl-1H-pyrazole-5-carbaldehyde (0.076 g, 0.6 mmol, 1.1 eq.) and 1-methyl-3-({[(3S)-1-(pyridin-3-yl)piperidin-3-yl]amino}methyl)-1,4-dihydroquinolin-4-one in DCE (5.0 mL) was stirred for 1 h at 60° C. Then NaBH(OAc)₃ (0.3 g, 1.4 mmol, 2.5 eq.) was added and the reaction mixture was stirred for 24 h at 60° C. Afterwards, the reaction was quenched by addition of 1M NaOH (50 mL). Then the resulting mixture was washed with DCM (3×50 mL). The combined organic layers were washed with brine, dried over anh. Na₂SO₄, filtered and evaporated. The residue was purified by FCC (SiHP; DCM:MeOH 9:1). The final compound was suspended in water and freeze-dried to give the product (0.14 g, 0.3 mmol, yield 53%) as a light yellow powder.

ESI-MS: 457.5 [M+H]⁺

¹H NMR (300 MHz, DMSO-d6) δ 8.30 (d, J=3.0 Hz, 1H), 8.20 (dd, J=8.0, 1.6 Hz, 1H), 7.92 (dd, J=4.5, 1.3 Hz, 1H), 7.87 (s, 1H), 7.72 (ddd, J=8.5, 6.8, 1.6 Hz, 1H), 7.64 (d, J=8.5 Hz, 1H), 7.38 (ddd, J=8.0, 6.8, 1.1 Hz, 1H), 7.29 (ddd, J=8.6, 3.1, 1.4 Hz, 1H), 7.21-7.10 (m, 1H), 5.97 (s, 1H), 4.03-3.49 (m, 12H), 2.93-2.80 (m, 1H), 2.80-2.68 (m, 1H), 2.68-2.56 (m, 1H), 2.07-1.91 (m, 4H), 1.83-1.69 (m, 1H), 1.68-1.35 (m, 2H).

Procedure 38. Preparation of 1-Cyclopropyl-3-({ [(3S)-1-(6-methylpyridin-3-yl)piperidin-3-yl][(2-methylpyridin-4-yl)methyl]amino}methyl)-7-(morpholin-3-yl)-1,4-dihydroquinolin-4-on
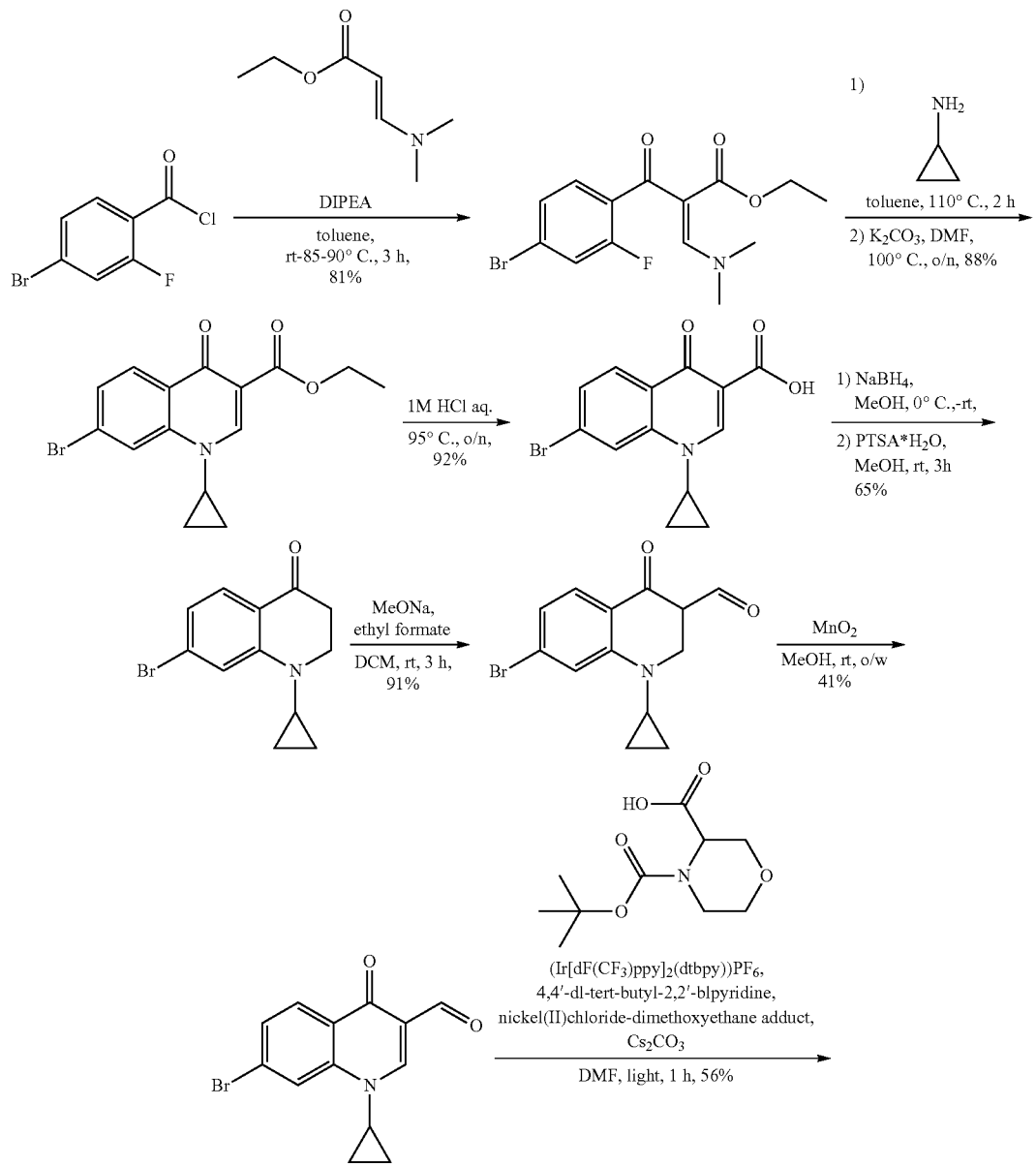

-continued

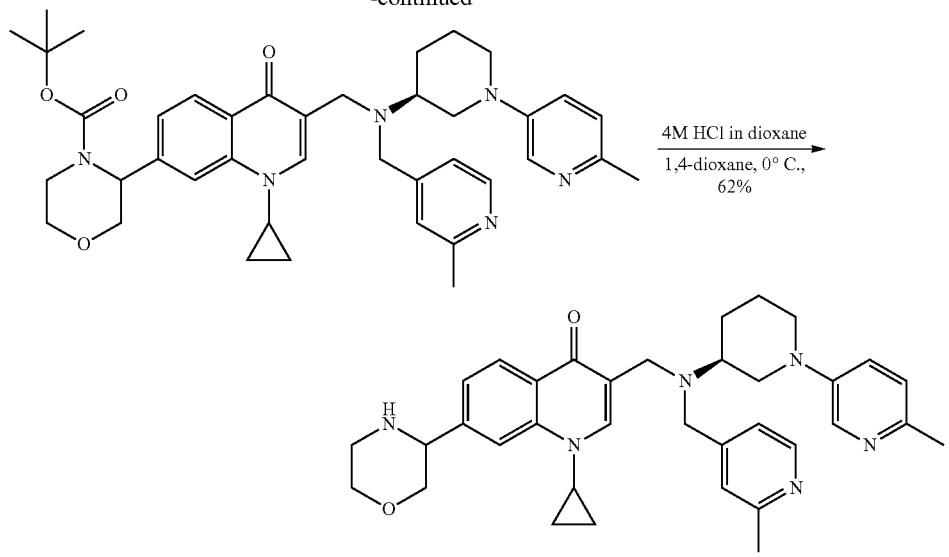

a) ethyl 2-[4-bromo-2-fluorobenzoyl]-3-(dimethyl-amino)prop-2-enoate b) ethyl 7-bromo-1-cyclopropyl-4-oxo-1,4-dihydro-quinoline-3-carboxylate

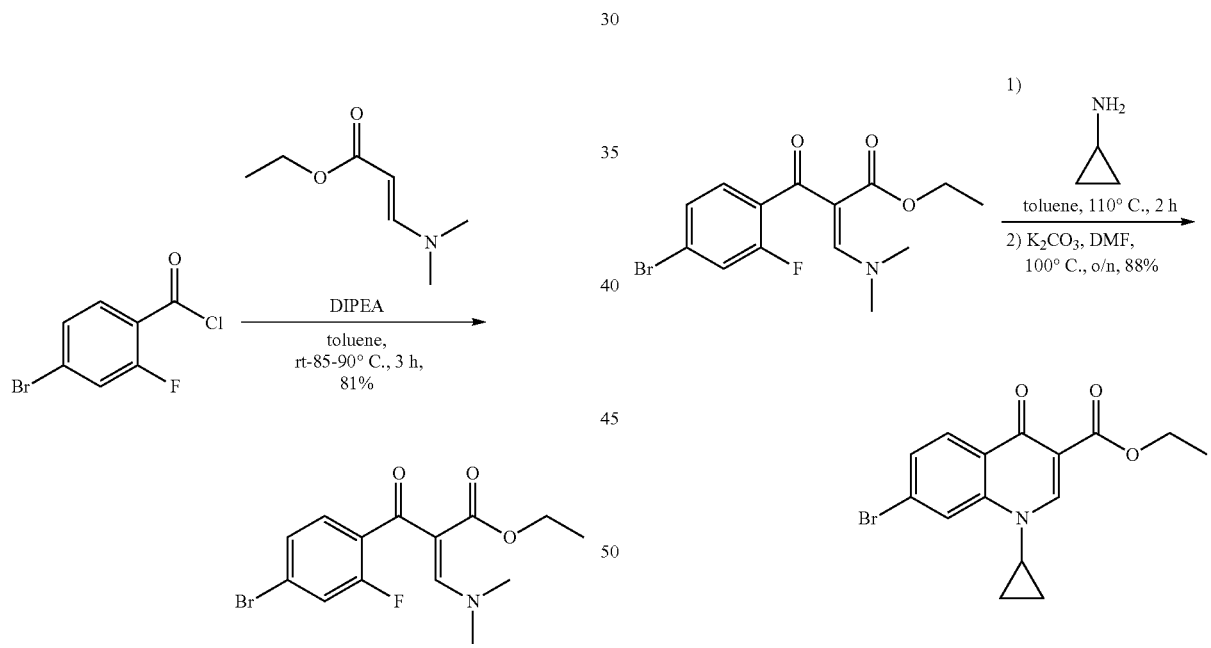

A mixture of ethyl 3-(dimethylamino)prop-2-enoate (0.6 mL, 4.2 mmol, 1 eq.) and DIPEA (1.5 mL, 8.8 mmol, 2.1 eq.) was stirred at rt and a solution of 4-bromo-2-fluorobenzoyl chloride (0.57 mL, 4.2 mmol, 1 eq.) in toluene (5 mL) was added over 5 min. The yellow solution was placed in an oil bath at 85-90° C. After 3 h of heating, the mixture was diluted with DCM and $H_2O$. Separated organic layer was dried over anhydrous $Na_2SO_4$, filtered and evaporated. The residue was purified by FCC (SiHP; Hex:AcOEt 2:3) to give the title product (1.24 g, 3.6 mmol, yield 81%) as a yellow oil.

ESI-MS: 344.0 $[M+H]^+$

Ethyl 2-[4-bromo-2-fluorobenzoyl]-3-(dimethylamino) prop-2-enoate (1.24 g, 3.6 mmol, 1 eq.) and cyclopropanamine (0.4 mL, 4.7 mmol, 1.3 eq.) were heated in toluene (10 mL) at 110° C. for 2 h. The reaction mixture was concentrated and the residue was diluted in DMF (8 mL). Then, $K_2CO_3$ (1.2 g, 9.0 mmol, 2.5 eq.) was added and the resulting mixture was heated overnight at 100° C. After cooling, the reaction mixture was diluted with DCM, washed with water, brine, dried over anhydrous $Na_2SO_4$ filtered and evaporated. The residue was purified by FCC (SiHP; Hex:AcOEt 1:4) to give the title product (0.97 g, 3.3 mmol, yield 88%) as a yellow solid.

AP-MS: 336.0 $[M+H]^+$ c) 7-bromo-1-cyclopropyl-4-oxo-1,4-dihydroquinoline-3-carboxylic acid

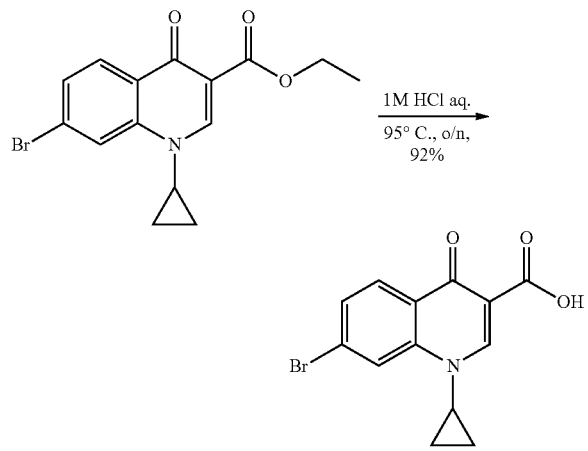

A suspension of ethyl 7-bromo-1-cyclopropyl-4-oxo-1,4-dihydroquinoline-3-carboxylate (0.95 g, 3.7 mmol, 1 eq.) in 1 M HCl aq. (8 mL) was stirred overnight at 95° C. The reaction mixture was concentrated and the residue was co-concentrated with toluene to give the title product (0.8 g, 3.5 mmol, yield 92%) as a yellow solid.
ESI-MS: 308.0 [M+H]$^+$ d) 7-bromo-1-cyclopropyl-1,2,3,4-tetrahydroquinolin-4-one

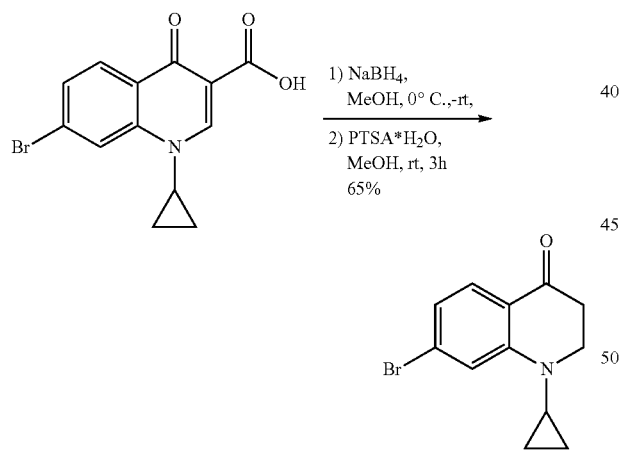

The title compound was synthesized following the approach outlined in Procedure 7d substituting 1-cyclopropyl-6-fluoro-7-(4-methylpiperazin-1-yl)-4-oxo-1,4-dihydroquinoline-3-carboxylic acid with 7-bromo-1-cyclopropyl-4-oxo-1,4-dihydroquinoline-3-carboxylic acid. First stage of the reaction was prolonged to overnight stirring with NaBH$_4$ and the second with PTSA shortened to 3 h stirring at rt. Additionally DCM was used for the washings. The crude product was purified by FCC (SiHP; Hex:AcOEt 1:1) to give the title product (0.52 g, 2.0 mmol, yield 65%) as a yellow solid.
ESI-MS: 266.0 [M+H]$^+$ e) 7-bromo-1-cyclopropyl-4-oxo-1,2,3,4-tetrahydroquinoline-3-carbaldehyde

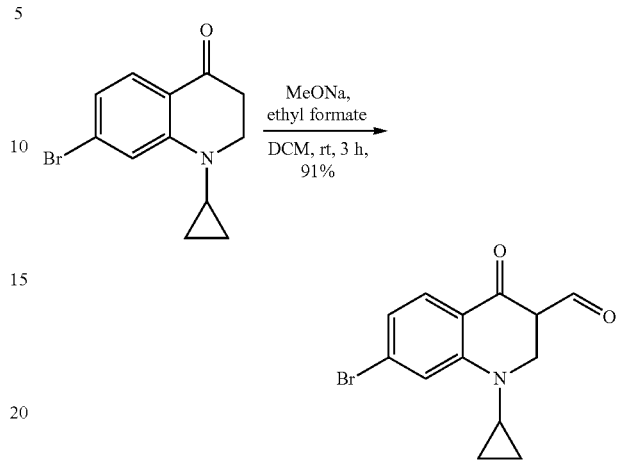

The title compound was synthesized following the approach outlined in Procedure 31e substituting 7-chloro-1-cyclopropyl-1,2,3,4-tetrahydro-1,6-naphthyridin-4-one with 7-bromo-1-cyclopropyl-1,2,3,4-tetrahydroquinolin-4-one and using 4.0 eq. of MeONa and ethyl formate. The time of the reaction was shortened to 3 h and MgSO$_4$ was used as a drying agent. The title compound (0.44 g, 1.4 mmol, yield 91%) was obtained as an orange solid.
AP-MS: 294.0 [M+H]$^+$ f) 7-bromo-1-cyclopropyl-4-oxo-1,4-dihydroquinoline-3-carbaldehyde

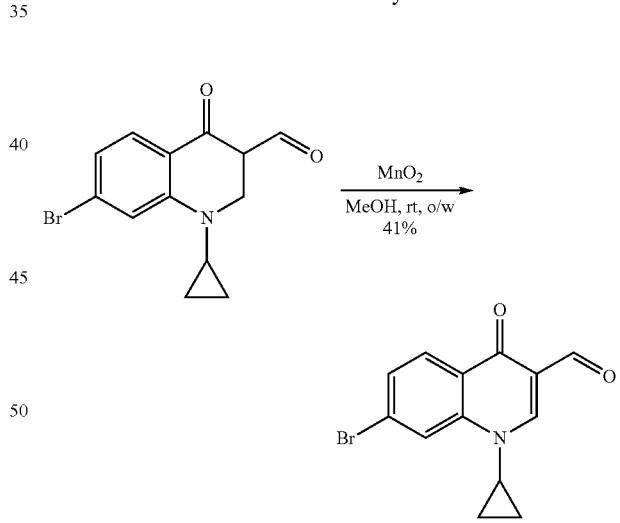

The title compound was synthesized following the approach outlined in Procedure 31f substituting 7-chloro-1-cyclopropyl-4-oxo-1,2,3,4-tetrahydro-1,6-naphthyridine-3-carbaldehyde with 7-bromo-1-cyclopropyl-4-oxo-1,2,3,4-tetrahydroquinoline-3-carbaldehyde. The time of the reaction was prolonged to over-the-weekend stirring. The reaction mixture was directly passed through a pad of Celite and the pad was thoroughly washed with DCM/MeOH mixture. FCC purification (SiHP; DCM:MeOH 95:5) afforded the title compound (0.17 g, 0.6 mmol, yield 98%) as a yellow solid.
AP-MS: 292.0 [M+H]$^+$ g) tert-butyl 3-(1-cyclopropyl-3-formyl-4-oxo-1,4-dihydroquinolin-7-yl)morpholine-4-carboxylate

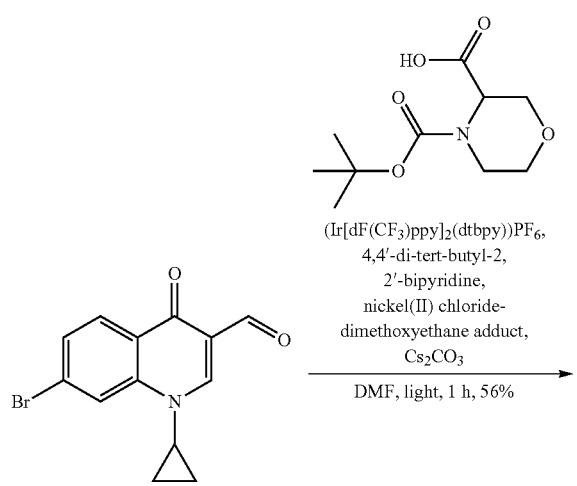

A mixture of 7-bromo-1-cyclopropyl-4-oxo-1,4-dihydroquinoline-3-carbaldehyde (0.03 g, 0.1 mmol, 1 eq.), 4-[(tert-butoxy)carbonyl]morpholine-3-carboxylic acid (0.07 g, 0.3 mmol, 3.0 eq.), [4,4'-Bis(1,1-dimethylethyl)-2,2'-bipyridine-N1,N1']bis[3,5-difluoro-2-[5-(trifluoromethyl)-2-pyridinyl-N]phenyl-C] Iridium(III) hexafluorophosphate (0.001 g, 0.001 mmol, 0.01 eq.), 4,4'-di-tert-butyl-2,-2'bipyridine (0.004 g, 0.015 mmol, 0.148 eq.) and nickel(II) chloride, dimethoxyethane adduct (0.002 g, 0.009 mmol, 0.09 eq.) was stirred under argon at rt for 1 h in Penn PhDM2 photoreactor (100% LED). The reaction mixture was evaporated in vacuo. The residue was suspended in DCM, washed with water, dried over anhydrous $Na_2SO_4$ and evaporated in vacuo. The residue was purified by FCC (SiHP; Hex:AcOEt 1:1) to give the title product (0.024 g, 0.06 mmol, yield 56%) as a white solid.

ESI-MS: 399.6 $[M+H]^+$ h) tert-butyl 3-[1-cyclopropyl-3-({[(3S)-1-(6-methylpyridin-3-yl)piperidin-3-yl][(2-methylpyridin-4-yl)methyl]amino}methyl)-4-oxo-1,4-dihydroquinolin-7-yl]morpholine-4-carboxylate

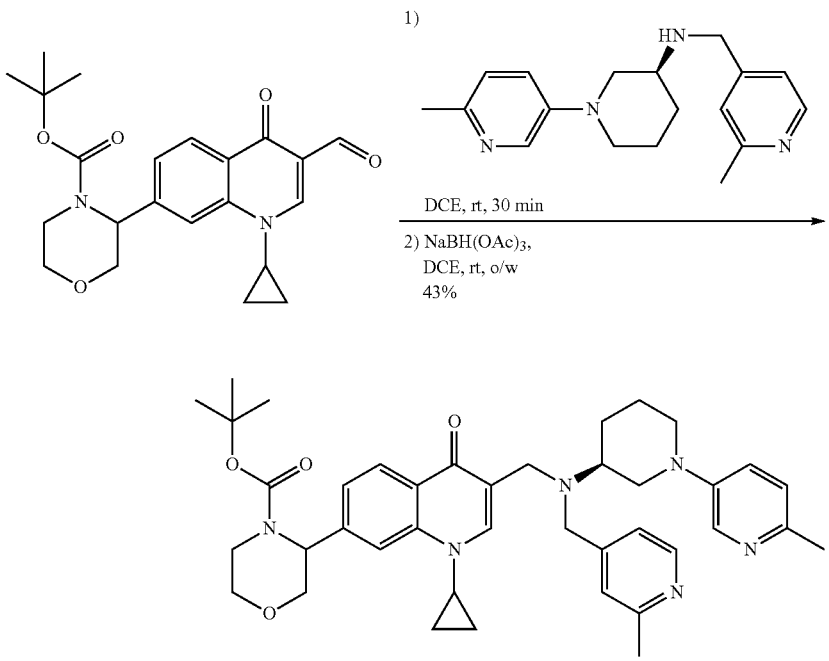

-continued

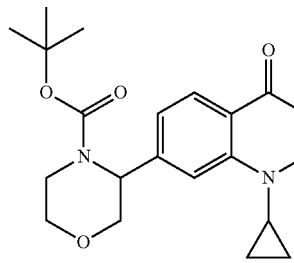

Tert-butyl 3-(1-cyclopropyl-3-formyl-4-oxo-1,4-dihydroquinolin-7-yl)morpholine-4-carboxylate (0.024 g, 0.06 mmol, 1 eq.) and (3S)-1-(6-methylpyridin-3-yl)-N-[(2-methylpyridin-4-yl)methyl]piperidin-3-amine (0.027 g, 0.08 mmol, 1.5 eq.) were suspended in DCE (5 mL). After 30 min, $NaBH(OAc)_3$ (0.034 g, 0.2 mmol, 2.8 eq.) was added and the resulting mixture was stirred overnight at rt. The residue was purified by FCC (RF-C18 column, ACN/$H_2O$) to give the title product: (0.017 g, 0.02 mmol, yield 42%) as a white solid.

ESI-MS: 679.6 $[M+H]^+$ i) 1-Cyclopropyl-3-({[(3S)-1-(6-methylpyridin-3-yl)piperidin-3-yl][(2-methylpyridin-4-yl)methyl]amino}methyl)-7-(morpholin-3-yl)-1,4-dihydroquinolin-4-one

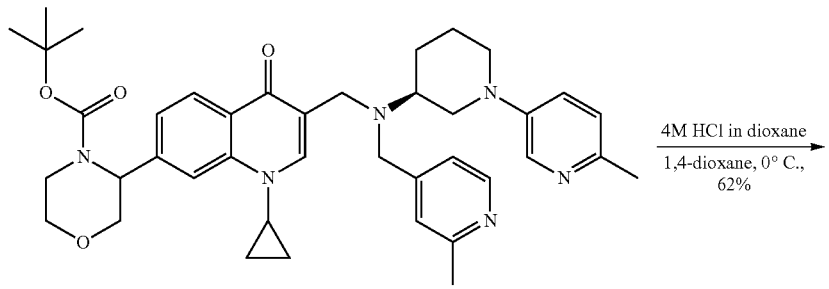

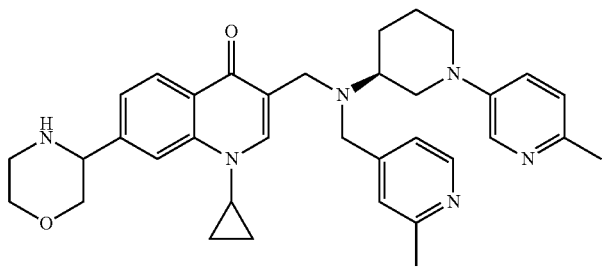

Tert-butyl 3-[1-cyclopropyl-3-({[(3S)-1-(6-methylpyridin-3-yl)piperidin-3-yl][(2-methylpyridin-4-yl)methyl]amino}methyl)-4-oxo-1,4-dihydroquinolin-7-yl]morpholine-4-carboxylate (0.017 g, 0.02 mmol, 1 eq.) was dissolved in anh. 1,4-dioxane (2 mL). The solution was cooled in an ice-bath and 4 M HCl in dioxane (1 mL) was added dropwise. The reaction mixture was concentrated. Then, the residue was diluted with DCM, washed with NaHCO₃ and the organic layer was evaporated. The residue was freeze-dried to give the title product 1-cyclopropyl-3-({[(3S)-1-(6-methylpyridin-3-yl)piperidin-3-yl][(2-methylpyridin-4-yl)methyl]amino}methyl)-7-(morpholin-3-yl)-1,4-dihydroquinolin-4-one (0.009 g, 0.02 mmol, yield 62%) as a white solid.

ESI-MS: 579.5 [M+H]⁺

¹H NMR (400 MHz, Methanol-d4) δ 8.28 (d, J=8.3 Hz, 1H), 8.16 (d, J=5.1 Hz, 1H), 8.11-8.08 (m, 2H), 8.01 (s, 1H), 7.52-7.45 (m, 1H), 7.36 (dd, J=8.6, 3.0 Hz, 1H), 7.25-7.21 (m, 2H), 7.12 (d, J=8.6 Hz, 1H), 4.11 (dd, J=10.1, 3.3 Hz, 1H), 3.98-3.84 (m, 5H), 3.83 (s, 2H), 3.72-3.64 (m, 1H), 3.64-3.58 (m, 1H), 3.53-3.43 (m, 2H), 3.17-2.92 (m, 3H), 2.90-2.83 (m, 1H), 2.75-2.64 (m, 1H), 2.41 (s, 3H), 2.32 (s, 3H), 2.18-2.12 (m, 1H), 1.95-1.90 (m, 1H), 1.74-1.61 (m, 2H), 1.39-1.28 (m, 2H), 0.97-0.89 (m, 2H).

PREPARATION EXAMPLES

Example 1. 3-({[(2-methoxypyridin-4-yl)methyl][(3S)-1-(pyridin-3-yl)piperidin-3-yl]amino}methyl)-1-methyl-1,4-dihydroquinolin-4-one

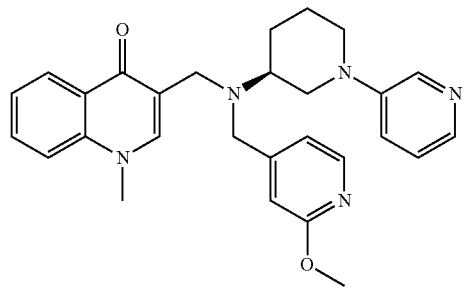 [SMILES: COc1cc(CN(Cc2cn(C)c3ccccc3c2=O)[C@H]2CCCN(c3cccnc3)C2)ccn1]

Preparation of tert-butyl N-[(3S)-1-(pyridin-3-yl)piperidin-3-yl]carbamate

The title compound was synthesized according to Procedure 1a. The residue was purified by FCC (SiHP, AcOEt 100%) to afford the product (3.2 g, 11.54 mmol, yield 61%) as a pale yellow oil.

ESI-MS: 278.4 [M+H]⁺

Preparation of
(3S)-1-(pyridin-3-yl)piperidin-3-amine

The title compound was synthesized according to Procedure 1b to afford the product (2.00 g, 11.28 mmol, yield 98%) as a yellow oil. ESI-MS: 178.1 [M+H]+

Preparation of (3S)—N-[(2-methoxypyridin-4-yl)methyl]-1-(pyridin-3-yl)piperidin-3-amine The title compound was synthesized according to Procedure 4a substituting 1-methyl-4-oxo-1,4-dihydroquinoline-3-carbaldehyde with 2-methoxypyridine-4-carboxaldehyde. The residue was purified by FCC (SiHP, DCM:MeOH 94:6) to afford the product (942 mg, 3.2 mmol, yield 62%) as a yellow oil. ESI-MS: 299.3 [M+H]+

Preparation of 3-({[(2-methoxypyridin-4-yl)methyl][(3S)-1-(pyridin-3-yl)piperidin-3-yl]amino}methyl)-1-methyl-1,4-dihydroquinolin-4-one The title compound was synthesized according to Procedure 4b substituting 1-methyl-3-({[(3S)-1-(pyridin-3-yl)piperidin-3-yl]amino}methyl)-1,4-dihydroquinolin-4-one with (3S)—N-[(2-methoxypyridin-4-yl)methyl]-1-(pyridin-3-yl)piperidin-3-amine and 3-methylpyridine-4-carboxaldehyde with 1-methyl-4-oxo-1,4-dihydroquinoline-3-carbaldehyde. The residue was purified by RP-FCC (SiC18; H$_2$O:MeCN) to afford the product (1.15 g, 2.0 mmol, yield 65%) as yellow powder. ESI-MS: 470.2 [M+H]+
$^1$H NMR (400 MHz, DMSO-d$_6$) δ 8.31-8.29 (m, 1H), 8.22-8.16 (m, 1H), 8.08 (s, 1H), 8.05-8.01 (m, 1H), 7.94-7.88 (m, 1H), 7.77-7.69 (m, 1H), 7.68-7.58 (m, 1H), 7.42-7.34 (m, 1H), 7.32-7.27 (m, 1H), 7.18-7.11 (m, 1H), 7.07-7.03 (m, 1H), 6.87 (s, 1H), 3.99-3.92 (m, 1H), 3.88 (s, 3H), 3.78 (s, 3H), 3.83-3.71 (m, 2H), 3.71-3.68 (m, 1H), 3.68-3.54 (m, 2H), 2.89-2.77 (m, 1H), 2.77-2.58 (m, 2H), 2.05-1.93 (m, 1H), 1.85-1.69 (m, 1H), 1.64-1.36 (m, 2H).

Example 2. 1-methyl-3-({[(2-methylpyridin-4-yl)methyl][1-(pyridin-3-yl)piperidin-3-yl]amino}methyl)-1,4-dihydroquinolin-4-one

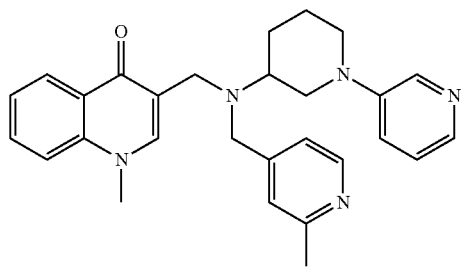 [SMILES: Cc1cc(CN(Cc2cn(C)c3ccccc3c2=O)C2CCCN(c3cccnc3)C2)ccn1]

Preparation of tert-butyl N-[1-(pyridin-3-yl)piperidin-3-yl]carbamate

The title compound was synthesized according to Procedure 1a substituting tert-butyl N-[(3S)-piperidin-3-yl]carbamate with tert-butyl N-(piperidin-3-yl)carbamate. The residue was purified by FCC (SiHP, DCM:MeOH 95:5) to give the product (359 mg, 1.2 mmol, yield 47%) as a yellow oil. ESI-MS: 278.5 [M+H]+

Preparation of 1-(pyridin-3-yl)piperidin-3-amine

The title compound was synthesized according to Procedure 1b substituting tert-butyl N-[(3S)1-(pyridin-3-yl)piperidin-3-yl]carbamate with tert-butyl N-[1-(pyridin-3-yl)piperidin-3-yl]carbamate. Product was obtained as a hydrochloride (111 mg, 0.500 mmol, yield 43%). ESI-MS: 178.15 [M+H]+

Preparation of N-[(2-methylpyridin-4-yl)methyl]-1-(pyridin-3-yl)piperidin-3-amine The title compound was synthesized following the approach outlined in Procedure 4a substituting 1-methyl-4-oxo-1,4-dihydroquinoline-3-carbaldehyde with 2-methylpyridine-4-carbaldehyde and (3S)-1-(pyridin-3-yl)piperidin-3-amine with 1-(pyridin-3-yl)piperidin-3-amine. The residue was purified by FCC (SiHP, DCM:MeOH 9:1) to afford the product (50 mg, 0.17 mmol, yield 41%) as a colorless oil. ESI-MS: 283 [M+H]+
$^1$H NMR (300 MHz, DMSO-d$_6$) δ 8.36-8.31 (m, 1H), 8.29-8.24 (m, 1H), 7.96-7.90 (m, 1H), 7.30-7.21 (m, 2H), 7.21-7.14 (m, 2H), 3.79 (s, 2H), 3.63-3.53 (m, 1H), 2.79-2.68 (m, 1H), 2.58-2.53 (m, 2H), 2.44 (s, 3H), 1.96-1.87 (m, 1H), 1.79-1.68 (m, 1H), 1.56-1.42 (m, 1H), 1.32-1.16 (m, 1H). Aliphatic H overlapped with solvent peak.

Preparation of 1-methyl-3-({[(2-methylpyridin-4-yl)methyl][1-(pyridin-3-yl)piperidin-3-yl]amino}methyl)-1,4-dihydroquinolin-4-one The title compound was synthesized following the approach outlined in Procedure 4b substituting 1-methyl-3-({[(3S)-1-(pyridin-3-yl)piperidin-3-yl]amino}methyl)-1,4-dihydroquinolin-4-one with N-[(2-methylpyridin-4-yl)methyl]-1-(pyridin-3-yl)piperidin-3-amine and 2-methylpyridine-4-carbaldehyde with 1-methyl-4-oxo-1,4-dihydroquinoline-3-carbaldehyde using DCM as a solvent. The residue was purified by FCC (SiHP, DCM:MeOH 9:1) to afford the product (28 mg, 0.06 mmol, yield 33%) as a colorless oil. ESI-MS: 454 [M+H]+
$^1$H NMR (400 MHz, DMSO-d$_6$) δ 8.32-8.28 (m, 2H), 8.22-8.18 (m, 1H), 8.05 (s, 1H), 7.93-7.90 (m, 1H), 7.75-7.69 (m, 1H), 7.66-7.61 (m, 1H), 7.41-7.35 (m, 1H), 7.32-7.23 (m, 3H), 7.18-7.13 (m, 1H), 4.00-3.93 (m, 1H), 3.87 (s, 3H), 3.81-3.69 (m, 2H), 3.68-3.56 (m, 2H), 2.90-2.82 (m, 1H), 2.75-2.61 (m, 2H), 2.38 (s, 3H), 2.04-1.97 (m, 1H), 1.80-1.72 (m, 1H), 1.62-1.41 (m, 2H). Aliphatic H overlapped with solvent peak.

Example 3. 3-({[(2-methoxypyridin-4-yl)methyl][1-(pyridazin-3-yl)piperidin-3-yl]amino}methyl)-1-methyl-1,4-dihydroquinolin-4-one

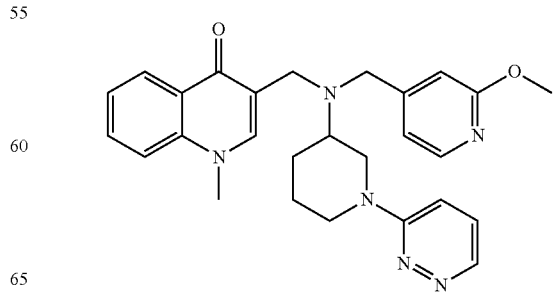

Preparation of tert-butyl 3-{[(2-methoxypyridin-4-yl)methyl]amino}piperidine-1-carboxylate The title compound was synthesized following the approach outlined in Procedure 4a substituting 1-methyl-4-oxo-1,4-dihydroquinoline-3-carbaldehyde with 2-methoxypyridine-4-carbaldehyde, and (3S)-1-(pyridin-3-yl)piperidin-3-amine with tert-butyl 3-aminopiperidine-1-carboxylate. The residue was purified by FCC (SiHP, DCM:MeOH 9:1) to afford the product (3795 g, 7.556 mmol, yield 26%) as a yellow oil. ESI-MS: 322.3[M+H]$^+$ Preparation of ted-butyl 3-{[(2-methoxypyridin-4-yl)methyl][(1-methyl-4-oxo-1,4-dihydroquinolin-3-yl)methyl]amino}piperidine-1-carboxylate The title compound was synthesized following the approach outlined in Procedure 4b substituting 1-methyl-3-({[(3S)-1-(pyridin-3-yl)piperidin-3-yl]amino}methyl)-1,4-dihydroquinolin-4-one with tert-butyl 3-{[(2-methoxypyridin-4-yl)methyl]amino}piperidine-1-carboxylate, and 2-methylpyridine-4-carbaldehyde with 1-methyl-4-oxo-1,4-dihydroquinoline-3-carbaldehyde. The residue was purified by RP-FCC (SiC18, H$_2$O:MeCN) to afford the product (363 mg, 0.722 mmol, yield 25%) as a yellowish powder. ESI-MS: 493.80 [M+H]$^+$ $^1$H NMR (400 MHz, DMSO-d$_6$) δ 8.22-8.17 (m, 1H), 8.02-7.98 (m, 1H), 7.97 (s, 1H), 7.72 (ddd, J=8.6, 6.9, 1.7 Hz, 1H), 7.65-7.60 (m, 1H), 7.38 (ddd, J=8.0, 6.9, 1.0 Hz, 1H), 6.98-6.95 (m, 1H), 6.78 (s, 1H), 4.13-3.93 (m, 1H), 3.83 (s, 3H), 3.82-3.78 (m, 1H), 3.77 (s, 3H), 3.71 (s, 2H), 3.58 (s, 2H), 2.83 (s, 1H), 2.02-1.90 (m, 1H), 1.72-1.61 (m, 1H), 1.59-1.46 (m, 1H), 1.41-1.20 (m, 12H).

Preparation of 3-({[(2-methoxypyridin-4-yl)methyl](piperidin-3-yl)amino}methyl)-1-methyl-1,4-dihydroquinolin-4-one The title compound was synthesized following the approach outlined in Procedure 2b substituting tert-butyl N-[(3S)1-(pyridin-3-yl)piperidin-3-yl]carbamate with tert-butyl 3-{[(2-methoxypyridin-4-yl)methyl][(1-methyl-4-oxo-1,4-dihydroquinolin-3yl)methyl]amino}piperidine-1-carboxylate.

Product as a free base. Product (650 mg, 1.656 mmol, yield 22%) as a yellow oil. ESI-MS: 393.3 [M+H]$^+$ Preparation of 3-({[(2-methoxypyridin-4-yl)methyl][1-(pyridazin-3-yl)piperidin-3-yl]amino}methyl)-1-methyl-1,4-dihydroquinolin-4-one The title compound was synthesized according to Procedure 5. The residue was purified by FCC (SiHP, DCM:MeOH 9:1) to give the product (30 mg, 0.06 mmol, yield 31%) as a yellow oil. ESI-MS: 471 [M+H]$^+$ $^1$H NMR (300 MHz, DMSO-d$_6$) δ 8.49-8.46 (m, 1H), 8.21-8.16 (m, 1H), 8.06 (s, 1H), 8.03-7.99 (m, 1H), 7.76-7.69 (m, 1H), 7.66-7.60 (m, 1H), 7.41-7.23 (m, 3H), 7.06-7.01 (m, 1H), 6.85 (s, 1H), 4.66-4.56 (m, 1H), 4.34-4.23 (m, 1H), 3.87 (s, 3H), 3.77 (s, 3H), 3.74-3.54 (m, 2H), 3.06-2.95 (m, 1H), 2.87-2.75 (m, 1H), 2.05-1.92 (m, 1H), 1.80-1.61 (m, 2H), 1.43-1.29 (m, 1H). Some aliphatic H overlapped with solvent peak.

The product was converted into hydrochloric acid salt. Product as a yellow solid. ESI-MS: 471 [M+H]$^+$ $^1$H NMR (400 MHz, Deuterium Oxide) δ 8.40-8.36 (m, 1H), 7.95-7.90 (m, 1H), 7.77 (s, 1H), 7.76-7.72 (m, 1H), 7.66-7.59 (m, 1H), 7.52-7.48 (m, 1H), 7.47-7.42 (m, 1H), 7.38-7.32 (m, 1H), 7.27-7.22 (m, 1H), 6.84-6.79 (m, 1H), 6.61-6.57 (m, 1H), 4.51-4.25 (m, 6H), 3.82-3.71 (m, 1H), 3.67 (s, 3H), 3.39 (s, 3H), 3.30-3.21 (m, 1H), 2.32-2.15 (m, 2H), 2.05-1.95 (m, 1H), 1.75-1.63 (m, 1H). Aliphatic H overlapped with solvent peak.

Example 4. 3-({[(2-methoxypyridin-4-yl)methyl][1-(pyrazin-2-yl)piperidin-3-yl]amino}methyl)-1-methyl-1,4-dihydroquinolin-4-one

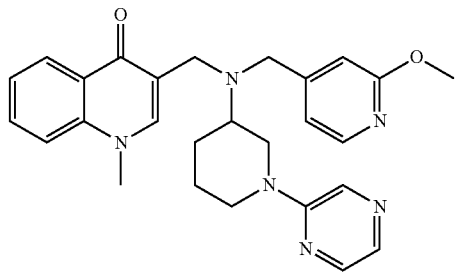 [SMILES: COc1cc(CN(Cc2cn(C)c3ccccc3c2=O)C2CCCN(c3cnccn3)C2)ccn1]

The title compound was synthesized according to Procedure 6. The residue was purified by prep-HPLC to afford the title compound as a yellow solid (28 mg, 0.059 mmol yield 29%). ESI-MS: 471 [M+H]$^+$ $^1$H NMR (300 MHz, DMSO-d$_6$) δ 8.33 (s, 1H), 8.21-8.15 (m, 1H), 8.07-7.98 (m, 3H), 7.78-7.68 (m, 2H), 7.66-7.60 (m, 1H), 7.43-7.33 (m, 1H), 7.07-7.00 (m, 1H), 6.85 (s, 1H), 4.59-4.48 (m, 1H), 4.34-4.22 (m, 1H), 3.86 (s, 3H), 3.81-3.74 (m, 4H), 3.73-3.52 (m, 2H), 3.05-2.93 (m, 1H), 2.84-2.71 (m, 1H), 2.07-1.95 (m, 1H), 1.83-1.58 (m, 2H), 1.45-1.30 (m, 1H).

Some aliphatic H overlapped with solvent peak.

The product was converted into hydrochloric acid salt. Product as a yellow solid. ESI-MS: 471 [M+H]$^+$ $^1$H NMR (400 MHz, Deuterium Oxide) δ 8.07 (s, 1H), 7.99-7.93 (m, 1H), 7.93-7.87 (m, 1H), 7.85-7.79 (m, 1H), 7.79-7.72 (m, 1H), 7.71-7.59 (m, 2H), 7.56-7.49 (m, 1H), 7.49-7.42 (m, 1H), 6.81 (s, 1H), 6.58 (s, 1H), 4.41-4.17 (m, 4H), 3.79-3.74 (m, 1H), 3.73-3.70 (m, 3H), 3.67-3.57 (m, 2H), 3.41 (s, 3H), 3.31-3.18 (m, 1H), 2.31-2.22 (m, 1H), 2.22-2.08 (m, 1H), 2.05-1.94 (m, 1H), 1.75-1.62 (m, 1H). Aliphatic H overlapped with solvent peak.

Example 5. 1-methyl-3-({[(2-methylpyridin-4-yl)methyl][(3S)-1-(pyridin-3-yl)piperidin-3-yl]amino}methyl)-1,4-dihydroquinolin-4-one

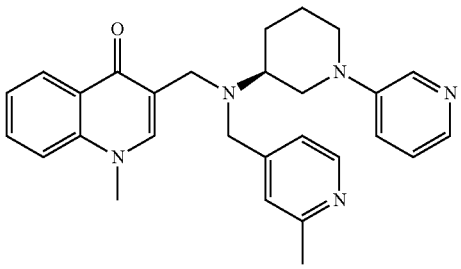

Preparation of ted-butyl(3S)-3-{[(1-methyl-4-oxo-1, 4-dihydroquinolin-3-yl)methyl]amino}piperidine-1-carboxylate The title compound was synthesized following the approach outlined in Procedure 4a substituting (3S)-1-(pyridin-3-yl)piperidine-3-amine with tert-butyl (3S)-3-aminopiperidine-1-carboxylate. The residue was purified by FCC (neutral Al₂O₃, DCM:MeOH 9:1) to afford the product (5.600 g, 15.07 mmol, yield 94%) as a yellow solid. ESI-MS: 372.2 [M+H]⁺

¹H NMR (300 MHz, DMSO-d₆) δ 8.23 (dd, J=8.1, 1.6 Hz, 1H), 8.11 (s, 1H), 7.78 (ddd, J=8.5, 6.8, 1.6 Hz, 1H), 7.73-7.64 (m, 1H), 7.43 (ddd, J=8.0, 6.8, 1.2 Hz, 1H), 3.86 (s, 3H), 3.73 (s, 2H), 3.71-3.53 (m, 1H), 2.96-2.75 (m, 2H), 2.70-2.55 (m, 2H), 2.05-1.81 (m, 2H), 1.78-1.50 (m, 1H), 1.38 (s, 9H). Some aliphatic H overlapped with solvent signals.

Preparation of tert-butyl(3S)-3-{[(1-methyl-4-oxo-1, 4-dihydroquinolin-3-yl)methyl][(2-methylpyridin-4-yl)methyl]amino}piperidine-1-carboxylate The title compound was synthesized following the approach outlined in Procedure 4b substituting 1-methyl-3-({[(3S)-1-(pyridin-3-yl)piperidin-3-yl]amino}methyl)-1,4-dihydroquinolin-4-one with tert-butyl (3S)-3-{[(1-methyl-4-oxo-1,4-dihydroquinolin-3-yl)methyl]amino}piperidine-1-carboxylate. After reducing agent was added, the reaction was continued at 45° C. for 3 h. The residue was purified by FCC (SiHP, DCM:MeOH 9:1) to afford the title compound (610 mg, 1.280 mmol, yield 86%) as a pale yellow solid. ESI-MS: 477.5 [M+H]⁺

¹H NMR (300 MHz, DMSO-d₆) δ 8.27 (d, J=5.0 Hz, 1H), 8.19 (dd, J=8.1, 1.6 Hz, 1H), 7.95 (s, 1H), 7.72 (ddd, J=8.5, 6.9, 1.6 Hz, 1H), 7.62 (d, J=8.5 Hz, 1H), 7.38 (ddd, J=7.9, 6.8, 1.1 Hz, 1H), 7.22-7.08 (m, 2H), 4.05 (br s, 1H), 3.82 (s, 3H), 3.70 (s, 2H), 3.59 (d, J=2.8 Hz, 2H), 2.36 (s, 3H), 1.97 (d, J=12.6 Hz, 1H), 1.67 (d, J=12.6 Hz, 1H), 1.53 (br s, 1H), 1.33 (brs, 11H).

Some aliphatic H overlapped with solvent signals.

Preparation of 1-methyl-3-({[(2-methylpyridin-4-yl)methyl][(3S)-piperidin-3-yl]amino}methyl)-1,4-dihydroquinolin-4-one The title compound was synthesized following the approach outlined in Procedure 1b substituting tert-butyl N-[(3S)1-(pyridin-3-yl)piperidin-3-yl]carbamate with ted-butyl (3S)-3-{[(1-methyl-4-oxo-1,4-dihydroquinolin-3-yl)methyl][(2-methylpyridin-4-yl)methyl]amino}piperidine-1-carboxylate.

The title compound was obtained as a free base. Product (375 mg, 1.000 mmol, yield 79%) as a white powder. ESI-MS: 377.5 [M+H]⁺

¹H NMR (300 MHz, DMSO-d₆) δ 8.26 (dd, J=4.9, 0.9 Hz, 1H), 8.18 (dd, J=8.1, 1.6 Hz, 1H), 7.94 (s, 1H), 7.72 (ddd, J=8.6, 6.9, 1.7 Hz, 1H), 7.62 (dd, J=8.8, 1.0 Hz, 1H), 7.37 (ddd, J=8.0, 6.8, 1.1 Hz, 1H), 7.18 (dd, J=6.9, 1.6 Hz, 2H), 3.83 (s, 3H), 3.67 (s, 2H), 3.61 (s, 1H), 3.54 (s, 1H), 3.14-2.99 (m, 1H), 2.87-2.70 (m, 1H), 2.36 (s, 3H), 2.35-2.23 (m, 2H), 2.00-1.90 (m, 1H), 1.68-1.58 (m, 1H), 1.50-1.18 (m, 2H). Some aliphatic H overlapped with solvent signals.

Preparation of 1-methyl-3-({[(2-methylpyridin-4-yl)methyl][(3S)-1-(pyridin-3-yl)piperidin-3-yl]amino}methyl)-1,4-dihydroquinolin-4-one The title compound was synthesized according to Procedure 3. The product (48 mg, 0.106 mmol, yield 10%) was converted into hydrochloric acid salt. ESI-MS: 454.3 [M+H]⁺.

¹H NMR (300 MHz, DMSO-d₆) δ 8.61 (d, J=5.9 Hz, 1H), 8.58 (d, J=2.7 Hz, 1H), 8.31 (s, 1H), 8.22-8.11 (m, 3H), 8.06-7.93 (m, 2H), 7.89-7.73 (m, 2H), 7.68 (d, J=8.6 Hz, 1H), 7.44 (ddd, J=8.0, 6.8, 1.0 Hz, 1H), 4.49 (d, J=12.6 Hz, 1H), 4.40 (s, 2H), 4.04 (s, 2H), 3.94 (d, J=13.1 Hz, 1H), 3.85 (s, 3H), 3.37-3.25 (m, 1H), 3.23-3.08 (m, 1H), 3.03-2.85 (m, 1H), 2.57 (s, 3H), 2.25-2.18 (m, 1H), 1.96-1.82 (m, 2H), 1.65-1.43 (m, 1H).

Example 6. 3-({[(2-methoxypyridin-4-yl)methyl][(3S)-1-(pyridin-3-yl)piperidin-3-yl]amino}methyl)-1,4-dihydroquinolin-4-one

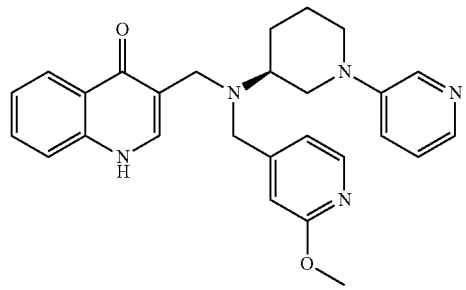 [SMILES: COc1cc(CN(Cc2c[nH]c3ccccc3c2=O)[C@H]2CCCN(c3cccnc3)C2)ccn1]

Preparation of tert-butyl N-[(3S)-1-(pyridin-3-yl)piperidin-3-yl]carbamate

The title compound was synthesized following approach outlined in Procedure 2a substituting tert-butyl N-(piperidin-3-yl)carbamate with tert-butyl N-[(3S)-piperidin-3-yl]carbamate. The residue was purified by FCC (SiHP, Hex:AcOEt 1:9) to give the product (575 mg, 1.90 mmol, yield 7%) as a yellow oil. ESI-MS: 278 [M+H]⁺

Preparation of (3S)-1-(pyridin-3-yl)piperidin-3-amine hydrochloride

The title compound was synthesized following protocol described in Procedure 1b. Product obtained as a hydrochloride (490 mg, 2.20 mmol, yield 99%). ESI-MS: 178 [M+H]⁺

Preparation of (3S)—N-[(2-methoxypyridin-4-yl)methyl]-1-(pyridin-3-yl)piperidin-3-amine The title compound was synthesized following the approach outlined in Procedure 4a substituting 1-methyl-4-oxo-1,4-dihydroquinoline-3-carbaldehyde with 2-methoxypyridine-4-carbaldehyde, and (3S)-1-(pyridin-3-yl)piperidin-3-amine with (3S)-1-(pyridin-3-yl)piperidin-3-amine hydrochloride using TEA as a base. The residue was purified by FCC (SiHP, DCM:MeOH 94:6) to afford the product (0.94 g, 3.20 mmol, yield 62%) as a yellow oil. ESI-MS: 299 [M+H]⁺

¹H NMR (400 MHz, DMSO-d₆) δ 8.30-8.22 (m, 1H), 8.12-8.05 (m, 1H), 7.95-7.92 (m, 1H), 7.31-7.22 (m, 1H), 7.22-7.13 (m, 1H), 7.02-6.96 (m, 1H), 6.85-6.78 (m, 1H), 3.83 (s, 3H), 3.79 (s, 2H), 3.78-3.73 (m, 1H), 3.63-3.52 (m, 1H), 2.78-2.69 (m, 1H), 2.56-2.52 (m, 2H), 2.38-2.28 (m, 1H), 1.98-1.84 (m, 1H), 1.79-1.67 (m, 1H), 1.58-1.42 (m, 1H), 1.30-1.16 (m, 1H). Aliphatic H overlapped with solvent peak.

Preparation of 3-({[(2-methoxypyridin-4-yl)methyl][(3S)-1-(pyridin-3-yl)piperidin-3-yl]amino}methyl)-1,4-dihydroquinolin-4-one The title compound was synthesized following the approach outlined in Procedure 4b substituting 1-methyl-3-({[(3S)-1-(pyridin-3-yl)piperidin-3-yl]amino}methyl)-1,4-dihydroquinolin-4-one with (3S)—N-[(2-methoxypyridin-4-yl)methyl]-1-(pyridin-3-yl)piperidin-3-amine, and 2-methylpyridine-4-carbaldehyde with 4-oxo-1,4-dihydroquinoline-3-carbaldehyde using a mixture of DCE:DMF (v/v 5:7) as a solvent. The residue was purified by prep-HPLC to afford the product (85 mg, 0.20 mmol, yield 48%) as a yellow solid. ESI-MS: 456 [M+H]+

$^1$H NMR (400 MHz, DMSO-$d_6$) δ 11.77-11.65 (m, 1H), 8.30-8.26 (m, 1H), 8.15 (s, 1H), 8.13-8.08 (m, 1H), 8.05-8.01 (m, 1H), 7.99-7.95 (m, 1H), 7.95-7.90 (m, 1H), 7.65-7.58 (m, 1H), 7.54-7.48 (m, 1H), 7.33-7.26 (m, 2H), 7.18-7.12 (m, 1H), 7.04-6.99 (m, 1H), 6.86 (s, 1H), 3.93-3.84 (m, 1H), 3.83-3.74 (m, 5H), 3.71-3.61 (m, 3H), 2.86-2.77 (m, 1H), 2.76-2.59 (m, 2H), 2.04-1.92 (m, 1H), 1.82-1.71 (m, 1H), 1.63-1.38 (m, 2H).

Example 7. 1-methyl-3-({[(3S)-1-(6-methylpyridin-3-yl)piperidin-3-yl][(2-methylpyridin-4-yl)methyl]amino}methyl)-1,4-dihydroquinolin-4-one

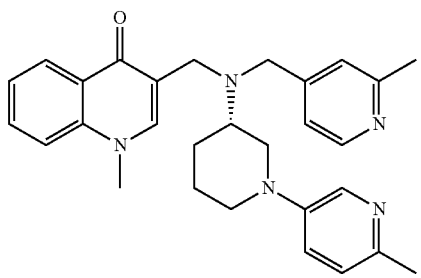 [SMILES: Cc1ccc(N2CCC[C@H](N(Cc3ccnc(C)c3)Cc3cn(C)c4ccccc4c3=O)C2)cn1]

The title compound was synthesized following the approach outlined in Procedure 9b substituting 7-bromo-1-methyl-1,4-dihydroquinolin-4-one with 5-bromo-2-methylpyridine, 1-methylpiperazine with 1-methyl-3-({[(2-methylpyridin-4-yl)methyl][(3S)-piperidin-3-yl]amino}methyl)-1,4-dihydroquinolin-4-one replacing 2-Dicyclohexylphosphino-2',6'-dimethoxybiphenyl) [2-(2'-amino-1,1'-biphenyl)]palladium(II) methanesulfonate (Sphos Pd 3G) with 2-Dicyclohexylphosphino-2',6'-dimethoxybiphenyl (Sphos) and Tris(dibenzylideneacetone)dipalladium(0) (Pd$_2$dba$_3$).

The residue was purified by FCC (SiHP, DCM:MeOH 9:1) to give the product (24 mg, 0.05 mmol, yield 48%) as a yellow solid. ESI-MS: 471 [M+H]+

$^1$H NMR (400 MHz, DMSO-$d_6$) δ 8.31-8.27 (m, 1H), 8.22-8.17 (m, 1H), 8.17-8.13 (m, 1H), 8.03 (s, 1H), 7.75-7.69 (m, 1H), 7.65-7.60 (m, 1H), 7.41-7.35 (m, 1H), 7.27-7.20 (m, 3H), 7.04-7.00 (m, 1H), 3.86 (s, 3H), 3.81-3.72 (m, 2H), 3.72-3.55 (m, 3H), 2.83-2.66 (m, 2H), 2.64-2.56 (m, 1H), 2.38 (s, 3H), 2.33 (s, 3H), 2.04-1.97 (m, 1H), 1.80-1.72 (m, 1H), 1.56-1.42 (m, 2H). Aliphatic H overlapped with solvent peak.

Example 8. 3-({[(3S)-1-(2-methoxypyrimidin-5-yl)piperidin-3-yl][(2-methylpyridin-4-yl)methyl]amino}methyl)-1-methyl-1,4-dihydroquinolin-4-one

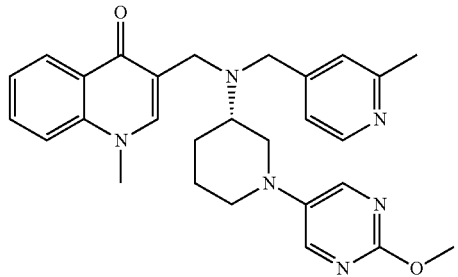 [SMILES: COc1ncc(N2CCC[C@H](N(Cc3ccnc(C)c3)Cc3cn(C)c4ccccc4c3=O)C2)cn1]

The title compound was synthesized following the approach outlined in Procedure 5 substituting 3-bromopyridazine with 5-bromo-2-methoxypyrimidine and 3-({[(2-methoxypyridin-4-yl)methyl](piperidin-3-yl)amino}methyl)-1-methyl-1,4-dihydroquinolin-4-one with 1-methyl-3-({[(2-methylpyridin-4-yl)methyl][(3S)-piperidin-3-yl]amino}methyl)-1,4-dihydroquinolin-4-one. The residue was purified by FCC (SiHP, DCM:MeOH 9:1) to give the product (31 mg, 0.06 mmol, yield 30%) as a yellow solid. ESI-MS: 485 [M+H]+

$^1$H NMR (400 MHz, DMSO-$d_6$) δ 8.34 (s, 2H), 8.30-8.28 (m, 1H), 8.21-8.18 (m, 1H), 8.02 (s, 1H), 7.75-7.70 (m, 1H), 7.65-7.61 (m, 1H), 7.40-7.35 (m, 1H), 7.27-7.22 (m, 2H), 3.86 (s, 3H), 3.83 (s, 3H), 3.81-3.73 (m, 2H), 3.71-3.63 (m, 1H), 3.61-3.55 (m, 1H), 3.55-3.48 (m, 1H), 2.79-2.74 (m, 2H), 2.61-2.53 (m, 1H), 2.38 (s, 3H), 2.02-1.97 (m, 1H), 1.81-1.75 (m, 1H), 1.53-1.46 (m, 2H). Aliphatic H overlapped with solvent peak.

Example 9. 1-cyclopropyl-6-fluoro-3-({[(2-methoxypyridin-4-yl)methyl][(3S)-1-(pyridin-3-yl)piperidin-3-yl]amino}methyl)-7-(4-methylpiperazin-1-yl)-1,4-dihydroquinolin-4-one

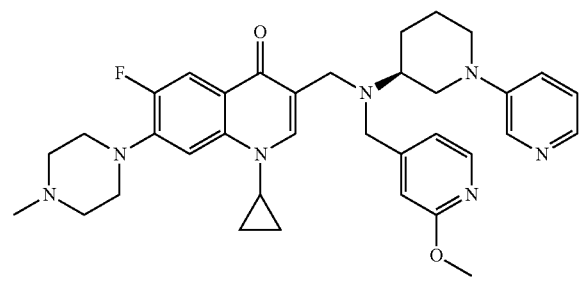 [SMILES: COc1cc(CN(Cc2cn(C3CC3)c3cc(N4CCN(C)CC4)c(F)cc3c2=O)[C@H]2CCCN(c3cccnc3)C2)ccn1]

Preparation of 1-cyclopropyl-6-fluoro-7-(4-methylpiperazin-1-yl)-3-({[(3S)-1-(pyridin-3-yl)piperidin-3-yl]amino}methyl)-1,4-dihydroquinolin-4-one The title compound was synthesized following the approach outlined in Procedure 4b substituting 1-methyl-3-

({[(3S)-1-(pyridin-3-yl)piperidin-3-yl]amino}methyl)-1,4-dihydroquinolin-4-one with (3S)-1-(pyridin-3-yl)piperidin-3-amine, and 2-methylpyridine-4-carbaldehyde with 1-cyclopropyl-6-fluoro-7-(4-methylpiperazin-1-yl)-4-oxo-1,4-dihydroquinoline-3-carbaldehyde. Product (55 mg, 0.11 mmol, yield 77%) as a yellow solid. ESI-MS: 491 [M+H]⁺

Preparation of 1-cyclopropyl-6-fluoro-3-({[(2-methoxypyridin-4-yl)methyl][(3S)-1-(pyridin-3-yl)piperidin-3-yl]amino}methyl)-7-(4-methylpiperazin-1-yl)-1,4-dihydroquinolin-4-one The title compound was synthesized following the approach outlined in Procedure 4b substituting 1-methyl-3-({[(3S)-1-(pyridin-3-yl)piperidin-3-yl]amino}methyl)-1,4-dihydroquinolin-4-one with 1-cyclopropyl-6-fluoro-7-(4-methylpiperazin-1-yl)-3-({[(3S)-1-(pyridin-3-yl)piperidin-3-yl]amino}methyl)-1,4-dihydroquinolin-4-one, and 2-methylpyridine-4-carbaldehyde with 2-methoxypyridine-4-carbaldehyde. The residue was purified by prep-HPLC to afford the product (17 mg, 0.03 mmol, yield 39%) as yellow solid. ESI-MS: 612 [M+H]⁺

¹H NMR (400 MHz, DMSO-d₆) δ 8.27 (d, J=3.0 Hz, 1H), 8.01 (d, J=5.2 Hz, 1H), 7.92 (dd, J=4.6, 1.3 Hz, 1H), 7.83 (s, 1H), 7.69 (d, J=13.6 Hz, 1H), 7.33 (d, J=7.5 Hz, 1H), 7.28 (ddd, J=8.5, 3.0, 1.3 Hz, 1H), 7.15 (dd, J=8.5, 4.5 Hz, 1H), 6.97 (dd, J=5.3, 1.3 Hz, 1H), 6.79 (s, 1H), 3.90-3.83 (m, 1H), 3.77 (s, 3H), 3.76-3.74 (m, 2H), 3.72-3.65 (m, 1H), 3.61 (s, 2H), 3.54-3.47 (m, 1H), 3.24-3.16 (m, 4H), 2.84-2.58 (m, 3H), 2.25 (s, 3H), 1.99-1.92 (m, 1H), 1.81-1.73 (m, 1H), 1.61-1.43 (m, 2H), 1.26-1.18 (m, 2H). Some aliphatic H overlapped with solvent signals.

Example 10. 1-cyclopropyl-6-fluoro-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one The title compound was synthesized following the approach outlined in Procedure 4b substituting 1-methyl-3-({[(3S)-1-(pyridin-3-yl)piperidin-3-yl]amino}methyl)-1,4-dihydroquinolin-4-one with 1-cyclopropyl-6-fluoro-7-(4-methylpiperazin-1-yl)-3-({[(3S)-1-(pyridin-3-yl)piperidin-3-yl]amino}methyl)-1,4-dihydroquinolin-4-one. The residue was purified by prep-HPLC to afford the product (13 mg, 0.02 mmol, yield 31%) as a yellow solid. ESI-MS: 596 [M+H]⁺

¹H NMR (400 MHz, DMSO-d₆) δ 8.30-8.25 (m, 2H), 7.92 (dd, J=4.5, 1.3 Hz, 1H), 7.82 (s, 1H), 7.70 (d, J=13.6 Hz, 1H), 7.33 (d, J=7.5 Hz, 1H), 7.28 (ddd, J=8.6, 3.1, 1.3 Hz, 1H), 7.22 (s, 1H), 7.19-7.12 (m, 2H), 3.92-3.86 (m, 1H), 3.77-3.72 (m, 2H), 3.72-3.65 (m, 1H), 3.61 (s, 2H), 3.54-3.46 (m, 1H), 3.23-3.17 (m, 4H), 2.86-2.60 (m, 3H), 2.37 (s, 3H), 2.25 (s, 3H), 2.00-1.93 (m, 1H), 1.80-1.74 (m, 1H), 1.62-1.43 (m, 2H), 1.25-1.16 (m, 2H), 0.94-0.83 (m, 2H). Some aliphatic H overlapped with solvent signals.

Example 11. 1-cyclopropyl-6,7-difluoro-3-({[(2-methoxypyridin-4-yl)methyl][(3S)-1-(pyridin-3-yl)piperidin-3-yl]amino}methyl)-1,4-dihydroquinolin-4-one

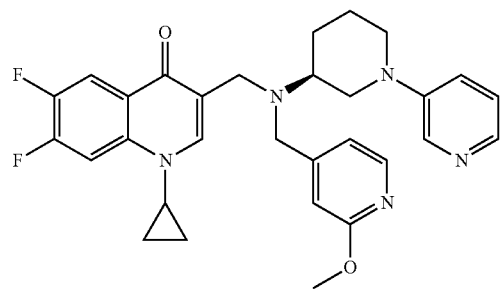 [SMILES: COc1cc(CN(Cc2cn(C3CC3)c3cc(F)c(F)cc3c2=O)[C@H]2CCCN(c3cccnc3)C2)ccn1]

The title compound was synthesized following the approach outlined in Procedure 4b substituting 1-methyl-3-({[(3S)-1-(pyridin-3-yl)piperidin-3-yl]amino}methyl)-1,4-dihydroquinolin-4-one with (3S)—N-[(2-methoxypyridin-4-yl)methyl]-1-(pyridin-3-yl)piperidin-3-amine, and 2-methylpyridine-4-carbaldehyde with 1-cyclopropyl-6,7-difluoro-4-oxo-1,4-dihydroquinoline-3-carbaldehyde. The residue was purified by prep-HPLC to afford the product (0.60 g, 1.14 mmol, yield 58%) as a white solid. The product was converted into hydrochloric acid salt. ESI-MS: 532 [M+H]⁺

¹H NMR (400 MHz, Methanol-d₄) δ 8.43 (d, J=3.1 Hz, 1H), 8.11-7.96 (m, 5H), 7.89 (d, J=5.3 Hz, 1H), 7.70 (dd, J=8.9, 5.3 Hz, 1H), 6.96 (d, J=5.3 Hz, 1H), 6.81 (s, 1H), 4.32-4.24 (m, 1H), 4.22-3.96 (m, 6H), 3.90-3.81 (m, 1H), 3.76 (s, 3H), 3.54-3.45 (m, 1H), 3.04-2.95 (m, 1H), 2.34-2.22 (m, 1H), 2.08-1.98 (m, 1H), 1.97-1.86 (m, 1H), 1.79-1.65 (m, 1H), 1.35-1.29 (m, 2H), 1.06-0.98 (m, 2H).

Example 12. 1-cyclopropyl-6,7-difluoro-3-({[(2-methylpyridin-4-yl)methyl][(3S)-1-(pyridin-3-yl)piperidin-3-yl]amino}methyl)-1,4-dihydroquinolin-4-one

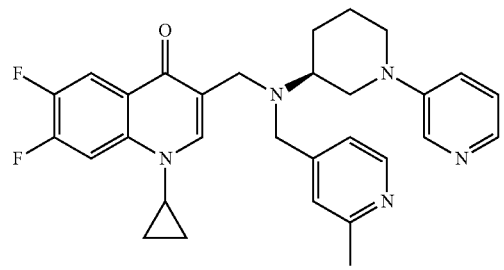 [SMILES: Cc1cc(CN(Cc2cn(C3CC3)c3cc(F)c(F)cc3c2=O)[C@H]2CCCN(c3cccnc3)C2)ccn1]

Preparation of (3S)—N-[(2-methylpyridin-4-yl)methyl]-1-(pyridin-3-yl)piperidin-3-amine The title compound was synthesized following the approach outlined in Procedure 4b substituting 1-methyl-3-({[(3S)-1-(pyridin-3-yl)piperidin-3-yl]amino}methyl)-1,4-dihydroquinolin-4-one with (3S)-1-(pyridin-3-yl)piperidin-3-amine. The reaction was carried overnight prior to the addition of sodium triacetoxyborohydride without the use of molecular sieves. The residue was purified by FCC (SiHP, DCM:MeOH 0-25%) to afford the crude product (1.7 g, 6.02 mmol, yield 66%, purity 84%) as a yellow oil. ESI-MS: 283 [M+H]$^+$ The title compound was synthesized following the approach outlined in Procedure 4b substituting 1-methyl-3-({[(3S)-1-(pyridin-3-yl)piperidin-3-yl]amino}methyl)-1,4-dihydroquinolin-4-one with (3S)—N-[(2-methylpyridin-4-yl)methyl]-1-(pyridin-3-yl)piperidin-3-amine, and 2-methylpyridine-4-carbaldehyde with 1-cyclopropyl-6,7-difluoro-4-oxo-1,4-dihydroquinoline-3-carbaldehyde. The residue was purified by prep-HPLC to afford the product (0.34 g, 0.65 mmol, yield 28%) as yellow solid. ESI-MS: 516 [M+H]$^+$ $^1$H NMR (400 MHz, Methanol-d$_4$) δ 8.29 (d, J=3.0 Hz, 1H), 8.22 (d, 1H), 8.07 (dd, J=10.8, 8.7 Hz, 1H), 8.01 (s, 1H), 7.99-7.93 (m, 2H), 7.64 (ddd, J=8.7, 3.0, 1.2 Hz, 1H), 7.46-7.37 (m, 3H), 4.09-4.01 (m, 1H), 3.97 (s, 2H), 3.91-3.73 (m, 3H), 3.52-3.44 (m, 1H), 3.06-2.96 (m, 2H), 2.88-2.79 (m, 1H), 2.20-2.13 (m, 1H), 1.99-1.91 (m, 1H), 1.78-1.61 (m, 2H), 1.34-1.26 (m, 2H), 1.00-0.93 (m, 2H). Some aliphatic H overlapped with solvent signals.

Example 13. 1-methyl-3-({[(2-methylpyridin-4-yl)methyl][(3S)-1-(pyridin-2-yl)piperidin-3-yl]amino}methyl)-1,4-dihydroquinolin-4-one

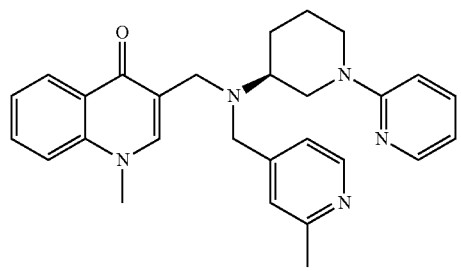 [SMILES: Cc1cc(CN(Cc2cn(C)c3ccccc3c2=O)[C@H]2CCCN(c3ccccn3)C2)ccn1]

The title compound was synthesized following the approach outlined in Procedure 8. The residue was purified by prep-HPLC to afford the title compound as a yellow solid (10 mg, 0.02 mmol yield 9%). ESI-MS: 454 [M+H]$^+$ $^1$H NMR (300 MHz, DMSO-d$_6$) δ 8.31-8.25 (m, 1H), 8.22-8.16 (m, 1H), 8.09-8.04 (m, 1H), 8.01 (s, 1H), 7.76-7.68 (m, 1H), 7.66-7.59 (m, 1H), 7.50-7.41 (m, 1H), 7.41-7.33 (m, 1H), 7.25 (s, 1H), 7.24-7.20 (m, 1H), 6.84-6.77 (m, 1H), 6.57-6.50 (m, 1H), 4.55-4.42 (m, 1H), 4.28-4.17 (m, 1H), 3.85 (s, 3H), 3.79-3.73 (m, 2H), 3.71-3.54 (m, 2H), 2.96-2.84 (m, 1H), 2.76-2.68 (m, 1H), 2.67-2.58 (m, 1H), 2.37 (s, 3H), 2.05-1.94 (m, 1H), 1.79-1.68 (m, 1H), 1.68-1.54 (m, 1H), 1.42-1.21 (m, 1H).

Example 14. 1-methyl-3-({[(2-methylpyridin-4-yl)methyl][(3S)-1-(6-nitropyridin-3-yl)piperidin-3-yl]amino}methyl)-1,4-dihydroquinolin-4-one

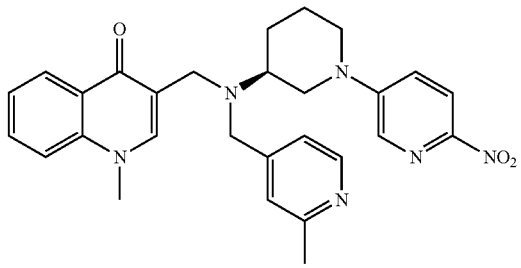 [SMILES: Cc1cc(CN(Cc2cn(C)c3ccccc3c2=O)[C@H]2CCCN(c3ccc([N+](=O)[O-])nc3)C2)ccn1]

The title compound was synthesized following the approach outlined in Procedure 5 substituting 3-bromopyridazine with 5-bromo-2-nitropyridine and 3-({[(2-methoxypyridin-4-yl)methyl](piperidin-3-yl)amino}methyl)-1-methyl-1,4-dihydroquinolin-4-one with 1-methyl-3-({[(2-methylpyridin-4-yl)methyl][(3S)-piperidin-3-yl]amino}methyl)-1,4-dihydroquinolin-4-one. The residue was purified by FCC (SiC18, H$_2$O:MeCN) to afford the title compound (0.08 g, 0.27 mmol, yield 60%) as a yellow solid. ESI-MS: 499 [M+H]$^+$ $^1$H NMR (300 MHz, DMSO-d$_6$) δ 8.30 (dd, J=4.9, 0.9 Hz, 1H), 8.26 (d, J=3.0 Hz, 1H), 8.19 (dd, J=8.0, 1.6 Hz, 1H), 8.08 (d, J=9.3 Hz, 1H), 8.03 (s, 1H), 7.72 (ddd, J=8.5, 6.8, 1.6 Hz, 1H), 7.63 (d, J=8.3 Hz, 1H), 7.45 (dd, J=9.3, 3.1 Hz, 1H), 7.37 (ddd, J=8.0, 6.8, 1.1 Hz, 1H), 7.30-7.22 (m, 2H), 4.35-4.23 (m, 1H), 4.11-3.97 (m, 1H), 3.86 (s, 3H), 3.82-3.55 (m, 4H), 3.25-3.13 (m, 1H), 3.06-2.90 (m, 1H), 2.71-2.60 (m, 1H), 2.38 (s, 3H), 2.07-1.96 (m, 1H), 1.84-1.65 (m, 2H), 1.52-1.34 (m, 1H).

Example 15. 3-({[(3S)-1-(3-bromopyridin-4-yl)piperidin-3-yl][(2-methylpyridin-4-yl)methyl]amino}methyl)-1-methyl-1,4-dihydroquinolin-4-one

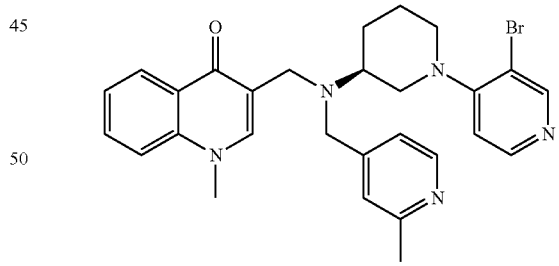

The title compound was synthesized following the approach outlined in Procedure 6 substituting 3-({[(2-methoxypyridin-4-yl)methyl](piperidin-3-yl)amino}methyl)-1-methyl-1,4-dihydroquinolin-4-one with 1-methyl-3-({[(2-methylpyridin-4-yl)methyl][(3S)-piperidin-3-yl]amino}methyl)-1,4-dihydroquinolin-4-one and 3-chloropyrazine with 3-bromo-4-fluoropyridine using sodium tert-butoxide as a base and dioxane as a solvent. The residue was purified by FCC (SiC18, H$_2$O:MeCN) to afford the title compound (21 mg, 0.03 mmol, yield 16%) as a yellow solid. Product was converted into hydrochloric salt. ESI-MS: 532 and 534 [M+H]$^+$ ¹H NMR (300 MHz, DMSO-d₆) δ 8.79 (s, 1H), 8.60 (d, J=6.0 Hz, 1H), 8.48 (d, J=6.7 Hz, 1H), 8.26 (s, 1H), 8.16 (dd, J=8.0, 1.6 Hz, 1H), 8.08-7.91 (m, 2H), 7.78 (ddd, J=8.6, 6.8, 1.6 Hz, 1H), 7.68 (d, J=8.6 Hz, 1H), 7.54-7.32 (m, 2H), 4.47-4.38 (m, 2H), 4.06-3.99 (m, 2H), 3.83 (s, 3H), 3.51-3.37 (m, 1H), 3.30-3.21 (m, 1H), 3.13-3.01 (m, 1H), 2.58 (s, 3H), 2.34-2.24 (m, 1H), 2.01-1.80 (m, 2H), 1.73-1.53 (m, 1H). Some aliphatic H overlapped with solvent signals.

Example 16. 3-({[(3S)-1-(6-fluoropyridin-3-yl)piperidin-3-yl][(2-methylpyridin-4-yl)methyl]amino}methyl)-1-methyl-1,4-dihydroquinolin-4-one

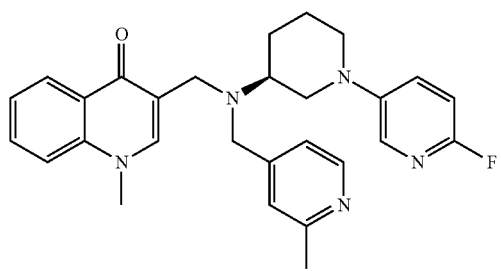 [SMILES: Cc1cc(CN(Cc2cn(C)c3ccccc3c2=O)[C@H]2CCCN(c3ccc(F)nc3)C2)ccn1]

The title compound was synthesized following the approach outlined in Procedure 5 substituting 3-bromopyridazine with 5-bromo-2-fluoropyridine and 3-({[(2-methoxypyridin-4-yl)methyl](piperidin-3-yl)amino}methyl)-1-methyl-1,4-dihydroquinolin-4-one with 1-methyl-3-({[(2-methylpyridin-4-yl)methyl][(3S)-piperidin-3-yl]amino}methyl)-1,4-dihydroquinolin-4-one. The residue was purified by FCC (SiC18, H₂O:MeCN) to afford the title compound (6 mg, 0.013 mmol, yield 55%) as a yellow solid. ESI-MS: 472 [M+H]⁺

¹H NMR (300 MHz, DMSO-d₆) δ 8.29 (d, J=5.1 Hz, 1H), 8.20 (dd, J=8.1, 1.5 Hz, 1H), 8.02 (s, 1H), 7.84-7.81 (m, 1H), 7.72 (ddd, J=8.5, 6.8, 1.6 Hz, 1H), 7.65-7.53 (m, 2H), 7.41-7.34 (m, 1H), 7.26-7.21 (m, 2H), 6.98 (dd, J=8.9, 3.5 Hz, 1H), 3.92-3.81 (m, 4H), 3.80-3.68 (m, 2H), 3.68-3.54 (m, 3H), 2.86-2.55 (m, 3H), 2.38 (s, 3H), 2.04-1.94 (m, 1H), 1.79-1.72 (m, 1H), 1.61-1.43 (m, 2H).

Example 17. 3-({[(3S)-1-(6-chloropyrimidin-4-yl)piperidin-3-yl][(2-methylpyridin-4-yl)methyl]amino}methyl)-1-methyl-1,4-dihydroquinolin-4-one

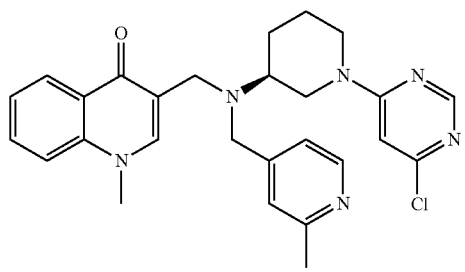

The title compound was synthesized following the approach outlined in Procedure 6 substituting 3-chloropyrazine with 4,6-dichloropyrimidine using MeCN as a solvent. The residue was purified by prep-HPLC to afford the title compound as a yellow solid (120 mg, 0.25 mmol, yield 62%).

¹H NMR (400 MHz, DMSO-d₆) δ 8.30-8.26 (m, 2H), 8.19 (dd, J=8.0, 1.6 Hz, 1H), 8.00 (s, 1H), 7.71 (ddd, J=8.6, 6.9, 1.7 Hz, 1H), 7.62 (d, J=8.6 Hz, 1H), 7.37 (ddd, J=8.0, 6.9, 1.0 Hz, 1H), 7.26-7.21 (m, 2H), 6.98 (s, 1H), 3.84 (s, 3H), 3.82-3.71 (m, 2H), 3.70-3.54 (m, 2H), 3.13-3.02 (m, 1H), 2.90-2.79 (m, 1H), 2.61-2.55 (m, 1H), 2.37 (s, 3H), 2.05-1.95 (m, 1H), 1.79-1.64 (m, 2H), 1.37-1.22 (m, 1H). Some aliphatic H overlapped with solvent signals.

Product was converted into hydrochloric salt. ESI-MS: 490 [M+H]⁺

¹H NMR (400 MHz, Deuterium Oxide) δ 8.14 (s, 1H), 8.10 (dd, J=8.2, 1.5 Hz, 1H), 8.01 (d, J=5.8 Hz, 1H), 7.91 (s, 1H), 7.85-7.79 (m, 1H), 7.61 (d, J=8.6 Hz, 1H), 7.54-7.48 (m, 1H), 7.40-7.35 (m, 1H), 7.32 (s, 1H), 6.82 (s, 1H), 4.48-4.39 (m, 1H), 4.09-3.89 (m, 5H), 3.81 (s, 3H), 3.18-3.06 (m, 2H), 2.19 (s, 3H), 2.03-1.88 (m, 3H), 1.67-1.54 (m, 2H).

Example 18. 1-methyl-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one

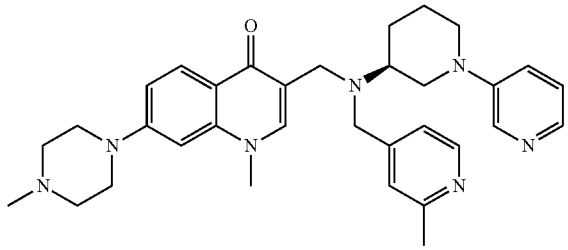 [SMILES: Cc1cc(CN(Cc2cn(C)c3cc(N4CCN(C)CC4)ccc3c2=O)[C@H]2CCCN(c3cccnc3)C2)ccn1]

Preparation of 1-methyl-7-(4-methylpiperazin-1-yl)-3-({[(3S)-1-(pyridin-3-yl)piperidin-3-yl]amino}methyl)-1,4-dihydroquinolin-4-one The title compound was synthesized following the approach outlined in Procedure 4a substituting 1-methyl-4-oxo-1,4-dihydroquinoline-3-carbaldehyde with 1-methyl-7-(4-methylpiperazin-1-yl)-4-oxo-1,4-dihydroquinoline-3-carbaldehyde. The crude was used in next step without further purification. ESI-MS: 428 [M+H]⁺

Preparation of 1-methyl-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one The title compound was synthesized following the approach outlined in Procedure 4b substituting 1-methyl-3-({[(3S)-1-(pyridin-3-yl)piperidin-3-yl]amino}methyl)-1,4-dihydroquinolin-4-one with 1-methyl-7-(4-methylpiperazin-1-yl)-3-({[(3S)-1-(pyridin-3-yl)piperidin-3-yl]amino}methyl)-1,4-dihydroquinolin-4-one. The residue was purified by prep-HPLC to afford the product (35 mg, 0.06 mmol, yield 22%) as a yellow solid. ESI-MS: 552 [M+H]⁺

¹H NMR (300 MHz, DMSO-d₆) δ 8.31-8.27 (m, 2H), 7.99-7.95 (m, 1H), 7.92-7.89 (m, 1H), 7.86 (s, 1H), 7.31-7.22 (m, 3H), 7.17-7.11 (m, 1H), 7.09-7.04 (m, 1H), 6.68 (s, 1H), 3.97-3.89 (m, 1H), 3.77 (s, 3H), 3.75-3.65 (m, 3H), 3.64-3.49 (m, 2H), 3.37-3.34 (m, 4H), 2.88-2.79 (m, 1H), 2.70-2.58 (m, 2H), 2.50-2.42 (m, 4H), 2.39 (s, 3H), 2.23 (s, 3H), 2.02-1.94 (m, 1H), 1.79-1.72 (m, 1H), 1.61-1.36 (m, 2H).

Example 19. 3-({[(3S)-1-(2-chloropyrimidin-4-yl)piperidin-3-yl][(2-methylpyridin-4-yl)methyl]amino}methyl)-1-methyl-1,4-dihydroquinolin-4-one

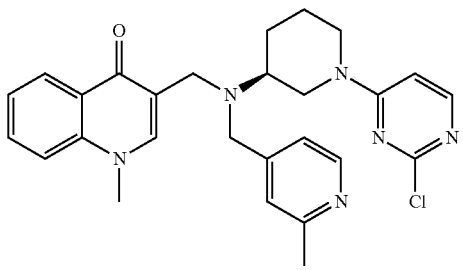 [SMILES: Cc1cc(CN(Cc2cn(C)c3ccccc3c2=O)[C@H]2CCCN(c3ccnc(Cl)n3)C2)ccn1]

The title compound was synthesized following the approach outlined in Procedure 6 substituting 3-({[(2-methoxypyridin-4-yl)methyl](piperidin-3-yl)amino}methyl)-1-methyl-1,4-dihydroquinolin-4-one with 1-methyl-3-({[(2-methylpyridin-4-yl)methyl][(3S)-piperidin-3-yl]amino}methyl)-1,4-dihydroquinolin-4-one and 3-chloropyrazine with 2,4-dichloropyrimidine. The residue was purified by FCC (SiHP, AcOEt 100%) to afford the product (89 mg, 0.17 mmol, yield 52%) as a yellow solid. ESI-MS: 489 [M+H]+

$^1$H NMR (400 MHz, DMSO-d$_6$) δ 8.28 (d, J=5.0 Hz, 1H), 8.19 (dd, J=8.1, 1.6 Hz, 1H), 8.03-7.97 (m, 2H), 7.71 (ddd, J=8.6, 6.9, 1.7 Hz, 1H), 7.64-7.60 (m, 1H), 7.37 (ddd, J=8.0, 6.9, 1.0 Hz, 1H), 7.25-7.19 (m, 2H), 6.89-6.83 (m, 1H), 4.63-4.11 (m, 2H), 3.84 (s, 3H), 3.82-3.71 (m, 2H), 3.69-3.57 (m, 2H), 3.14-3.03 (m, 1H), 2.91-2.80 (m, 1H), 2.61-2.54 (m, 1H), 2.36 (s, 3H), 2.02-1.95 (m, 1H), 1.80-1.65 (m, 2H), 1.37-1.22 (m, 1H).

Example 20. 3-({[(3S)-1-(2-methoxypyridin-4-yl)piperidin-3-yl][(2-methylpyridin-4-yl)methyl]amino}methyl)-1-methyl-1,4-dihydroquinolin-4-one

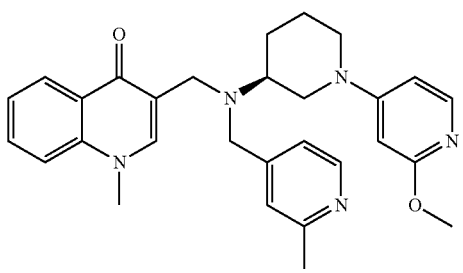 [SMILES: COc1cc(N2CCC[C@H](N(Cc3ccnc(C)c3)Cc3cn(C)c4ccccc4c3=O)C2)ccn1]

The title compound was synthesized following the approach outlined in Procedure 5 substituting 3-bromopyridazine with 4-bromo-2-methoxypyridine and 3-({[(2-methoxypyridin-4-yl)methyl](piperidin-3-yl)amino}methyl)-1-methyl-1,4-dihydroquinolin-4-one with 1-methyl-3-({[(2-methylpyridin-4-yl)methyl][(3S)-piperidin-3-yl]amino}methyl)-1,4-dihydroquinolin-4-one. The residue was purified by prep-HPLC to afford the product as a yellow oil (40 mg, 0.08 mmol, yield 62%). ESI-MS: 484 [M+H]+

$^1$H NMR (300 MHz, DMSO-d$_6$) δ 8.61-8.56 (m, 1H), 8.21-8.15 (m, 1H), 8.04 (s, 1H), 7.91-7.87 (m, 1H), 7.87 (s, 1H), 7.84-7.80 (m, 1H), 7.79-7.72 (m, 1H), 7.68-7.62 (m, 1H), 7.45-7.37 (m, 1H), 6.96-6.89 (m, 1H), 6.52-6.47 (m, 1H), 4.50-4.38 (m, 1H), 4.23-4.17 (m, 1H), 4.17-4.09 (m, 2H), 4.05 (s, 3H), 3.83 (s, 3H), 3.81-3.68 (m, 2H), 3.42-3.30 (m, 1H), 3.16-3.01 (m, 1H), 2.88-2.76 (m, 1H), 2.57 (s, 3H), 2.09-1.99 (m, 1H), 1.91-1.71 (m, 2H), 1.54-1.35 (m, 1H).

Example 21. 3-({[(2-ethylpyridin-4-yl)methyl][1-(pyridin-3-yl)piperidin-3-yl]amino}methyl)-1-methyl-1,4-dihydroquinolin-4-one

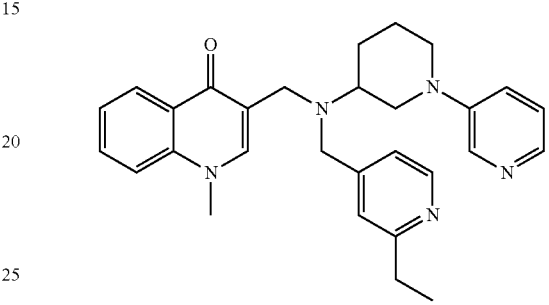

Preparation of tert-butyl 3-{[(2-ethylpyridin-4-yl)methyl]amino}piperidine-1-carboxylate The title compound was synthesized following the approach outlined in Procedure 4b substituting 1-methyl-3-({[(3S)-1-(pyridin-3-yl)piperidin-3-yl]amino}methyl)-1,4-dihydroquinolin-4-one with (2-ethylpyridin-4-yl)methanamine and 2-methylpyridine-4-carbaldehyde with tert-butyl 3-oxopiperidine-1-carboxylate using DCM as a solvent. Crude product was used in the next step without further purification. Product as a gold oil (723 mg, 2.26 mmol, yield 98%). ESI-MS: 320 [M+H]+

$^1$H NMR (300 MHz, DMSO-d$_6$) δ 8.39-8.35 (m, 1H), 7.21 (s, 1H), 7.18-7.13 (m, 1H), 3.73 (s, 2H), 3.68-3.56 (m, 1H), 2.88-2.77 (m, 1H), 2.76-2.66 (m, 2H), 2.41-2.31 (m, 2H), 1.92-1.80 (m, 1H), 1.69-1.55 (m, 1H), 1.52-1.43 (m, 1H), 1.36 (s, 9H), 1.25-1.18 (m, 3H). Some aliphatic H overlapped with solvent signals.

Preparation of tert-butyl 3-{[(2-ethylpyridin-4-yl)methyl][(1-methyl-4-oxo-1,4-dihydroquinolin-3-yl)methyl]amino}piperidine-1-carboxylate The title compound was synthesized following the approach outlined in Procedure 4b substituting 1-methyl-3-({[(3S)-1-(pyridin-3-yl)piperidin-3-yl]amino}methyl)-1,4-dihydroquinolin-4-one with tert-butyl 3-{[(2-ethylpyridin-4-yl)methyl]amino}piperidine-1-carboxylate and 2-methylpyridine-4-carbaldehyde with 1-methyl-4-oxo-1,4-dihydroquinoline-3-carbaldehyde using DCM as a solvent. The residue was purified by FCC (SiHP, DCM:MeOH 95:5) to give the product (50 mg, 0.10 mmol, yield 39%) as a gold oil. ESI-MS: 491 [M+H]+

$^1$H NMR (300 MHz, Methanol-d$_4$) δ 8.42-8.32 (m, 1H), 8.21 (d, J=5.1 Hz, 1H), 8.05 (d, J=33.4 Hz, 1H), 7.86-7.74 (m, 2H), 7.67 (d, J=8.6 Hz, 1H), 7.53-7.43 (m, 1H), 7.28-7.23 (m, 1H), 4.65 (s, 1H), 4.37-4.16 (m, 1H), 4.00 (s, 2H), 3.89 (s, 3H), 3.86-3.73 (m, 2H), 2.97-2.68 (m, 2H), 2.62 (q, J=7.7 Hz, 2H), 2.21-2.09 (m, 1H), 1.83-1.61 (m, 2H), 1.43

(s, 9H), 1.34-1.26 (m, 1H), 1.14 (t, J=7.6 Hz, 3H). Aliphatic H overlapped with solvent signal.

Preparation of 3-({[(2-ethylpyridin-4-yl)methyl](piperidin-3-yl)amino}methyl)-1-methyl-1,4-dihydroquinolin-4-one The title compound was synthesized following the approach outlined in Procedure 1b substituting tert-butyl N-[(3S)1-(pyridin-3-yl)piperidin-3-yl]carbamate with tert-butyl 3-{[(2-ethylpyridin-4-yl)methyl][(1-methyl-4-oxo-1,4-dihydroquinolin-3-yl)methyl]amino}piperidine-1-carboxylate replacing 4M HCl in dioxane with 2N HCl in Et$_2$O. Crude product was used in the next step without further purification. Product as a yellow oil (40 mg, 0.10 mmol, yield 42%). ESI-MS: 391 [M+H]$^+$ $^1$H NMR (300 MHz, DMSO-d$_6$) δ 8.32-8.28 (m, 1H), 8.19 (dd, J=8.0, 1.6 Hz, 1H), 7.94 (s, 1H), 7.76-7.67 (m, 1H), 7.62 (d, J=8.5 Hz, 1H), 7.41-7.33 (m, 1H), 7.22-7.17 (m, 2H), 3.82 (s, 3H), 3.81-3.77 (m, 1H), 3.70 (s, 2H), 3.14-3.05 (m, 1H), 2.87-2.77 (m, 1H), 2.65 (q, 2H), 2.59-2.54 (m, 1H), 2.41-2.31 (m, 2H), 2.02-1.89 (m, 2H), 1.72-1.60 (m, 1H), 1.53-1.39 (m, 2H), 1.38-1.27 (m, 2H), 1.13 (t, J=7.6 Hz, 3H).

Preparation of 3-({[(2-ethylpyridin-4-yl)methyl][1-(pyridin-3-yl)piperidin-3-yl]amino}methyl)-1-methyl-1,4-dihydroquinolin-4-one The title compound was synthesized following the approach outlined in Procedure 3 substituting 1-methyl-3-({[(2-methylpyridin-4-yl)methyl][(3S)-piperidin-3-yl]amino}methyl)-1,4-dihydroquinolin-4-one with 3-({[(2-ethylpyridin-4-yl)methyl](piperidin-3-yl)amino}methyl)-1-methyl-1,4-dihydroquinolin-4-one. The residue was purified by FCC (SiHP, DCM:MeOH, 95:5) to give the product (20 mg, 0.042 mmol, yield 42%) as a yellow solid. ESI-MS: 468 [M+H]$^+$ $^1$H NMR (300 MHz, DMSO-d$_6$) δ 8.35-8.28 (m, 2H), 8.23-8.16 (m, 1H), 8.05 (s, 1H), 7.94-7.88 (m, 1H), 7.76-7.68 (m, 1H), 7.66-7.59 (m, 1H), 7.41-7.34 (m, 1H), 7.32-7.23 (m, 3H), 7.18-7.12 (m, 1H), 4.02-3.92 (m, 1H), 3.86 (s, 3H), 3.80-3.74 (m, 2H), 3.73-3.67 (m, 1H), 3.66-3.54 (m, 2H), 2.91-2.79 (m, 1H), 2.71-2.60 (m, 4H), 2.07-1.96 (m, 1H), 1.81-1.72 (m, 1H), 1.65-1.40 (m, 2H), 1.15 (t, J=7.6 Hz, 3H).

Example 22. 1-methyl-3-({[(2-methylpyridin-4-yl)methyl][(3S)-1-(6-oxo-1,6-dihydropyrimidin-4-yl)piperidin-3-yl]amino}methyl)-1,4-dihydroquinolin-4-one

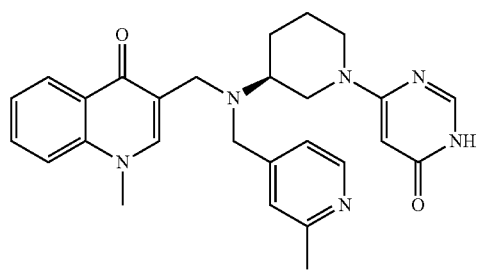 [SMILES: Cc1cc(CN(Cc2cn(C)c3ccccc3c2=O)[C@H]2CCCN(c3cc(=O)[nH]cn3)C2)ccn1]

The title compound was synthesized following the approach outlined in Procedure 11. The residue was purified by FCC (SiHP, DCM:MeOH) and re-purified by prep-HPLC to afford the product as a beige solid (3 mg, 0.006 mmol, yield 6%). ESI-MS: 471 [M+H]$^+$ $^1$H NMR (400 MHz, DMSO-d$_6$) δ 11.51 (s, 1H), 8.29-8.25 (m, 1H), 8.19 (dd, J=8.1, 1.6 Hz, 1H), 8.02 (s, 1H), 7.85 (s, 1H), 7.72 (ddd, J=8.6, 6.9, 1.6 Hz, 1H), 7.62 (d, J=8.5 Hz, 1H), 7.37 (ddd, J=8.1, 6.9, 1.0 Hz, 1H), 7.24 (s, 1H), 7.23-7.19 (m, 1H), 5.30 (s, 1H), 4.42-4.30 (m, 1H), 4.22-4.12 (m, 1H), 3.85 (s, 3H), 3.80-3.70 (m, 2H), 3.70-3.51 (m, 2H), 3.01-2.92 (m, 1H), 2.77-2.70 (m, 1H), 2.60-2.54 (m, 1H), 2.37 (s, 3H), 2.04-1.96 (m, 1H), 1.76-1.68 (m, 1H), 1.68-1.57 (m, 1H), 1.35-1.25 (m, 1H).

Example 23. 7-bromo-1-methyl-3-({[(2-methylpyridin-4-yl)methyl][(3S)-1-(pyridin-3-yl)piperidin-3-yl]amino}methyl)-1,4-dihydroquinolin-4-one

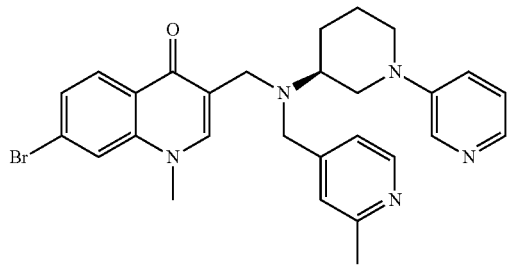

Preparation of 7-bromo-1-methyl-4-oxo-1,4-dihydroquinoline-3-carbaldehyde

The title compound was synthesized following the approach outlined in Procedure 9c substituting 1-methyl-7-(4-methylpiperazin-1-yl)-1,4-dihydroquinolin-4-one with 7-bromo-1-methyl-1,4-dihydroquinolin-4-one. The residue was triturated with ethyl acetate to give product (2.02 g, 7.59 mmol, 71%) as a yellow powder. ESI-MS: 267 [M+H]$^+$ $^1$H NMR (300 MHz, DMSO-d$_6$) δ 10.15 (s, 1H), 8.61 (s, 1H), 8.22-8.15 (m, 1H), 8.06-8.00 (m, 1H), 7.75-7.68 (m, 1H), 3.96 (s, 3H).

Preparation of 7-bromo-1-methyl-3-({[(3S)-1-(pyridin-3-yl)piperidin-3-yl]amino}methyl)-1,4-dihydroquinolin-4-one The title compound was synthesized following the approach outlined in Procedure 4a substituting 1-methyl-4-oxo-1,4-dihydroquinoline-3-carbaldehyde with 7-bromo-1-methyl-4-oxo-1,4-dihydroquinoline-3-carbaldehyde. The residue was purified by FCC (SiHP, DCM:MeOH 4:1) to give the product (474 mg, 1.11 mmol, yield 98%) as a yellow solid. ESI-MS: 428 [M+H]$^+$ $^1$H NMR (300 MHz, DMSO-d$_6$) δ 8.32-8.26 (m, 1H), 8.14-8.10 (m, 1H), 8.06 (s, 1H), 7.95-7.92 (m, 1H), 7.91-7.89 (m, 1H), 7.57-7.53 (m, 1H), 7.32-7.27 (m, 1H), 7.20-7.14 (m, 1H), 3.83 (s, 3H), 3.80-3.75 (m, 1H), 3.67 (s, 2H), 3.58-3.52 (m, 1H), 2.82-2.72 (m, 1H), 2.69-2.56 (m, 3H), 1.90 (d, J=9.7 Hz, 1H), 1.80-1.69 (m, 1H), 1.60-1.44 (m, 1H), 1.35-1.20 (m, 1H).

Preparation of 7-bromo-1-methyl-3-({[(2-methylpyridin-4-yl)methyl][(3S)-1-(pyridin-3-yl)piperidin-3-yl]amino}methyl)-1,4-dihydroquinolin-4-one The title compound was synthesized following the approach outlined in Procedure 4b substituting 1-methyl-3-

({[(3S)-1-(pyridin-3-yl)piperidin-3-yl]amino}methyl)-1,4-dihydroquinolin-4-one with 7-bromo-1-methyl-3-({[(3S)-1-(pyridin-3-yl)piperidin-3-yl]amino}methyl)-1,4-dyhydroquinolin-4-one. The residue was purified by FCC (SiHP, DCM:MeOH 9:1) to give the product (380 mg, 0.71 mmol, yield 62%) as a yellow solid. The product was converted into hydrochloric acid salt. ESI-MS: 534 [M+H]$^+$ $^1$H NMR (300 MHz, DMSO-d$_6$) δ 8.31-8.27 (m, 2H), 8.09 (d, J=8.6 Hz, 1H), 8.02 (s, 1H), 7.94-7.90 (m, 1H), 7.87-7.85 (m, 1H), 7.56-7.50 (m, 1H), 7.33-7.21 (m, 3H), 7.19-7.13 (m, 1H), 3.99-3.91 (m, 1H), 3.85 (s, 3H), 3.82-3.53 (m, 5H), 2.90-2.80 (m, 1H), 2.75-2.64 (m, 2H), 2.38 (s, 3H), 2.04-1.96 (m, 1H), 1.81-1.74 (m, 1H), 1.64-1.40 (m, 2H).

$^1$H NMR (300 MHz, Deuterium Oxide) δ 8.35-8.31 (m, 1H), 8.23-8.19 (m, 1H), 8.05 (s, 1H), 8.00-7.93 (m, 2H), 7.91-7.87 (m, 2H), 7.83-7.78 (m, 2H), 7.72-7.66 (m, 1H), 7.65-7.61 (m, 1H), 4.66-4.59 (m, 2H), 4.54-4.37 (m, 2H), 4.12-4.05 (m, 1H), 3.85-3.73 (m, 4H), 3.66-3.51 (m, 2H), 3.22-3.12 (m, 1H), 2.44 (s, 3H), 2.38-2.25 (m, 1H), 2.23-1.98 (m, 2H), 1.83-1.70 (m, 1H).

Example 24. 3-({[(3R,4R)-4-hydroxy-1-(pyridin-3-yl)piperidin-3-yl][(2-methylpyridin-4-yl)methyl]amino}methyl)-1-methyl-1,4-dihydroquinolin-4-one

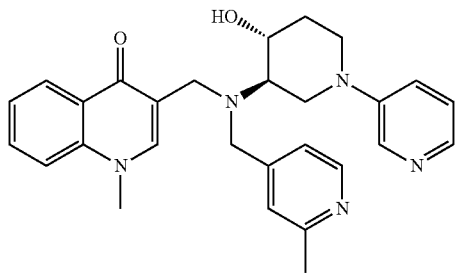 [SMILES: Cc1cc(CN(Cc2cn(C)c3ccccc3c2=O)[C@@H]2CN(c3cccnc3)CC[C@H]2O)ccn1]

Preparation of tert-butyl(3R,4R)-4-hydroxy-3-{[(1-methyl-4-oxo-1,4-dihydroquinolin-3-yl)methyl]amino}piperidine-1-carboxylate The title compound was synthesized following the approach outlined in Procedure 4a substituting (3S)-1-(pyridin-3-yl)piperidin-3-amine with tert-butyl (3R,4R)-3-amino-4-hydroxypiperidine-1-carboxylate. Crude product was purified by FCC (SiHP, DCM:MeOH) to afford the title compound as a white solid (170 mg, 0.05 mmol, yield 93%). ESI-MS: 389 [M+H]$^+$ Preparation of tert-butyl(3R,4R)-4-hydroxy-3-{[(1-methyl-4-oxo-1,4-dihydroquinolin-3-yl)methyl][(2-methylpyridin-4-yl)methyl]amino}piperidine-1-carboxylate The title compound was synthesized following the approach outlined in Procedure 4b substituting 1-methyl-3-({[(3S)-1-(pyridin-3-yl)piperidin-3-yl]amino}methyl)-1,4-dihydroquinolin-4-one with tert-butyl (3R,4R)-4-hydroxy-3-{[(1-methyl-4-oxo-1,4-dihydroquinolin-3-yl)methyl]amino}piperidine-1-carboxylate. The residue was purified by FCC (SiHP, DCM:MeOH 9:1) to afford the product (200 mg, 0.41 mmol, yield 93%) as a white solid. ESI-MS: 493 [M+H]$^+$ $^1$H NMR (400 MHz, DMSO-d$_6$) δ 8.27 (dd, J=8.1, 1.6 Hz, 1H), 8.20-8.13 (m, 1H), 8.04 (s, 1H), 7.75 (ddd, J=8.6, 6.9, 1.6 Hz, 1H), 7.64 (d, J=8.6 Hz, 1H), 7.42 (ddd, J=8.0, 6.9, 1.0 Hz, 1H), 7.06 (s, 1H), 7.02 (d, J=5.0 Hz, 1H), 6.00 (d, J=2.6 Hz, 1H), 4.16-3.82 (m, 5H), 3.79 (s, 3H), 3.71-3.63 (m, 1H), 3.20-3.14 (m, 1H), 2.81-2.64 (m, 2H), 2.24 (s, 3H), 2.19-2.11 (m, 1H), 1.92-1.84 (m, 1H), 1.34 (s, 9H), 1.24-1.09 (m, 1H). Aliphatic H overlapped with solvent signal.

Preparation of 3-({[(3R,4R)-4-hydroxypiperidin-3-yl][(2-methylpyridin-4-yl)methyl]amino}methyl)-1-methyl-1,4-dihydroquinolin-4-one The title compound was synthesized following the approach outlined in Procedure 1b substituting tert-butyl N-[(3S)1-(pyridin-3-yl)piperidin-3-yl]carbamate with tert-butyl (3R,4R)-4-hydroxy-3-{[(1-methyl-4-oxo-1,4-dihydroquinolin-3-yl)methyl][(2-methylpyridin-4-yl)methyl]amino}piperidine-1-carboxylate. The residue was used without further purification. Product as a yellow solid (157 mg, 0.39 mmol, yield 98%). ESI-MS: 393 [M+H]$^+$ $^1$H NMR (400 MHz, DMSO-d$_6$) δ 8.26 (dd, J=8.1, 1.6 Hz, 1H), 8.15 (dd, J=5.1, 0.8 Hz, 1H), 8.02 (s, 1H), 7.74 (ddd, J=8.6, 6.9, 1.6 Hz, 1H), 7.62 (d, J=8.6 Hz, 1H), 7.41 (ddd, J=8.0, 6.9, 1.0 Hz, 1H), 7.08 (s, 1H), 7.05 (d, J=5.2 Hz, 1H), 5.81 (d, J=2.4 Hz, 1H), 4.09-4.03 (m, 1H), 3.78 (s, 3H), 3.75-3.67 (m, 2H), 3.57 (s, 6H), 3.16-3.07 (m, 2H), 2.85-2.78 (m, 1H), 2.24 (s, 3H), 1.89-1.81 (m, 1H).

Preparation of 3-({[(3R,4R)-4-hydroxy-1-(pyridin-3-yl)piperidin-3-yl][(2-methylpyridin-4-yl)methyl]amino}methyl)-1-methyl-1,4-dihydroquinolin-4-one The title compound was synthesized following the approach outlined in Procedure 5 substituting 3-bromopyridazine with 3-bromopyridine, and 3-({[(2-methoxypyridin-4-yl)methyl](piperidin-3-yl)amino}methyl)-1-methyl-1,4-dihydroquinolin-4-one with 3-({[(3R,4R)-4-hydroxypiperidin-3-yl][(2-methylpyridin-4-yl)methyl]amino}methyl)-1-methyl-1,4-dihydroquinolin-4-one. The residue was purified by FCC (SiHP, DCM:MeOH 9:1) to give the product (82 mg, 0.17 mmol, yield 53%) as a yellow solid. ESI-MS: 470 [M+H]$^+$ $^1$H NMR (400 MHz, DMSO-d$_6$) δ 8.33 (d, J=3.0 Hz, 1H), 8.29 (dd, J=8.1, 1.6 Hz, 1H), 8.17 (d, J=5.1 Hz, 1H), 8.06 (s, 1H), 7.94 (dd, J=4.5, 1.3 Hz, 1H), 7.76 (ddd, J=8.6, 6.9, 1.7 Hz, 1H), 7.65 (d, J=8.6 Hz, 1H), 7.45-7.40 (m, 1H), 7.33 (ddd, J=8.5, 3.1, 1.4 Hz, 1H), 7.17 (dd, J=8.5, 4.5 Hz, 1H), 7.14 (s, 1H), 7.10-7.07 (m, 1H), 5.92 (d, J=2.7 Hz, 1H), 4.19-4.13 (m, 1H), 4.06-3.94 (m, 2H), 3.90-3.83 (m, 2H), 3.82 (s, 3H), 3.78-3.70 (m, 1H), 3.29-3.22 (m, 1H), 2.85-2.75 (m, 2H), 2.44-2.36 (m, 1H), 2.00-1.92 (m, 1H), 1.47-1.33 (m, 1H). Some aliphatic H overlapped with solvent signals.

Example 25. 7-chloro-6-fluoro-1-methyl-3-({[(2-methylpyridin-4-yl)methyl][(3S)-1-(pyridin-3-yl)piperidin-3-yl]amino}methyl)-1,4-dihydroquinolin-4-one

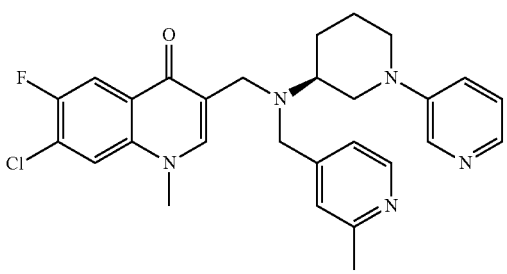 [SMILES: Cc1cc(CN(Cc2cn(C)c3cc(Cl)c(F)cc3c2=O)[C@H]2CCCN(c3cccnc3)C2)ccn1]

Preparation of 7-chloro-6-fluoro-1-methyl-4-oxo-1,4-dihydroquinoline-3-carboxylic acid The title compound was synthesized following the approach outlined in Procedure 7c substituting ethyl 1-cyclopropyl-6-fluoro-7-(4-methylpiperazin-1-yl)-4-oxo-1,4-dihydroquinoline-3-carboxylate with ethyl 7-chloro-6-fluoro-1-methyl-4-oxo-1,4-dihydroquinoline-3-carboxylate. Solvent was removed in vacuo. The mixture was acidified with precipitate being collected and dried (0.60 g, 2.34 mmol, yield 95%). ESI-MS: 256 [M+H]$^+$

Preparation of 7-chloro-6-fluoro-1-methyl-1,2,3,4-tetrahydroquinolin-4-one

The title compound was synthesized following the approach outlined in Procedure 7d substituting 1-cyclopropyl-6-fluoro-7-(4-methylpiperazin-1-yl)-4-oxo-1,4-dihydroquinoline-3-carboxylic acid with 7-chloro-6-fluoro-1-methyl-4-oxo-1,4-dihydroquinoline-3-carboxylic acid. Product (0.23 g, 1.08 mmol, yield 46%) as a yellow solid. ESI-MS: 214 [M+H]$^+$ $^1$H NMR (400 MHz, DMSO-d$_6$) δ 7.51 (d, J=9.4 Hz, 1H), 7.05 (d, J=6.0 Hz, 1H), 3.46 (dd, J=7.7, 6.5 Hz, 2H), 2.95 (s, 3H), 2.66 (dd, J=7.7, 6.4 Hz, 2H).

Preparation of 7-chloro-6-fluoro-1-methyl-4-oxo-1,4-dihydroquinoline-3-carbaldehyde The title compound was synthesized following the approach outlined in Procedure 7e substituting 1-cyclopropyl-6-fluoro-7-(4-methylpiperazin-1-yl)-1,2,3,4-tetrahydroquinolin-4-one with 7-chloro-6-fluoro-1-methyl-1,2,3,4-tetrahydroquinolin-4-one. Crude was purified by FCC (SiHP, Hex:AcOEt, 1:1) to afford the desired product (0.07 g, 0.29 mmol, yield 34%) as a yellow solid. ESI-MS: 240 [M+H]$^+$ $^1$H NMR (400 MHz, DMSO-d$_6$) δ 10.15 (s, 1H), 8.63 (s, 1H), 8.15 (d, J=6.0 Hz, 1H), 8.10 (d, J=9.1 Hz, 1H), 3.97 (s, 3H).

Preparation of 7-chloro-6-fluoro-1-methyl-3-({[(3S)-1-(pyridin-3-yl)piperidin-3-yl]amino}methyl)-1,4-dihydroquinolin-4-one The title compound was synthesized following the approach outlined in Procedure 4b substituting 1-methyl-3-({[(3S)-1-(pyridin-3-yl)piperidin-3-yl]amino}methyl)-1,4-dihydroquinolin-4-one with (3S)-1-(pyridin-3-yl)piperidin-3-amine and 2-methylpyridine-4-carbaldehyde with 7-chloro-6-fluoro-1-methyl-4-oxo-1,4-dihydroquinoline-3-carbaldehyde. Crude was used directly in the next step. ESI-MS: 401 [M+H]$^+$

Preparation of 7-chloro-6-fluoro-1-methyl-3-({[(2-methylpyridin-4-yl)methyl][(3S)-1-(pyridin-3-yl)piperidin-3-yl]amino}methyl)-1,4-dihydroquinolin-4-one The title compound was synthesized following the approach outlined in Procedure 4b substituting 1-methyl-3-({[(3S)-1-(pyridin-3-yl)piperidin-3-yl]amino}methyl)-1,4-dihydroquinolin-4-one with 7-chloro-6-fluoro-1-methyl-3-({[(3S)-1-(pyridin-3-yl)piperidin-3-yl]amino}methyl)-1,4-dihydroquinolin-4-one. The residue was purified by FCC (SiHP, DCM:MeOH 9:1) to afford the desired product (40 mg, 0.08 mmol, yield 63%) as yellow crystals. ESI-MS: 506 [M+H]$^+$ $^1$H NMR (400 MHz, DMSO-d$_6$) δ 8.32-8.25 (m, 2H), 8.06 (s, 1H), 7.99-7.95 (m, 2H), 7.91 (dd, J=4.5, 1.3 Hz, 1H), 7.32-7.26 (m, 1H), 7.25-7.21 (m, 2H), 7.15 (dd, J=8.5, 4.5 Hz, 1H), 3.98-3.91 (m, 1H), 3.86 (s, 3H), 3.81-3.66 (m, 3H), 3.64-3.53 (m, 2H), 2.91-2.81 (m, 1H), 2.75-2.61 (m, 2H), 2.37 (s, 3H), 2.04-1.95 (m, 1H), 1.81-1.72 (m, 1H), 1.64-1.39 (m, 2H).

Example 26. 3-({[(3S,5S)-5-fluoro-1-(pyridin-3-yl)piperidin-3-yl][(2-methylpyridin-4-yl)methyl]amino}methyl)-1-methyl-1,4-dihydroquinolin-4-one

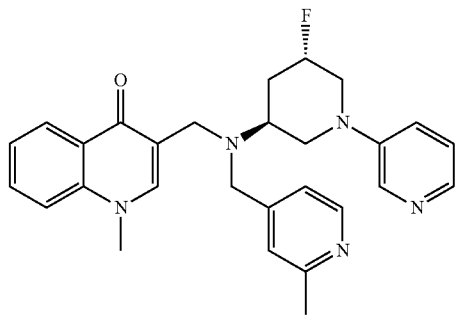 [SMILES: Cc1cc(CN(Cc2cn(C)c3ccccc3c2=O)[C@H]2C[C@H](F)CN(c3cccnc3)C2)ccn1]

Preparation of tert-butyl N-[(3S,5S)-5-fluoro-1-(pyridin-3-yl)piperidin-3-yl]carbamate The title compound was synthesized following the approach outlined in Procedure 5 substituting 3-bromopyridazine with 3-bromopyridine and 3-({[(2-methoxypyridin-4-yl)methyl](piperidin-3-yl)amino}methyl)-1-methyl-1,4-dihydroquinolin-4-one with tert-butyl N-[(3S,5S)-5-fluoropiperidin-3-yl]carbamate. The residue was purified by FCC (SiHP, DCM:MeOH, 9:1) to give the product (97 mg, 0.33 mmol, yield 72%) as a white solid. ESI-MS: 296 [M+H]$^+$ $^1$H NMR (400 MHz, DMSO-d$_6$) δ 8.32-8.28 (m, 1H), 7.98-7.93 (m, 1H), 7.34-7.29 (m, 1H), 7.22-7.16 (m, 1H), 7.07-7.01 (m, 1H), 5.08-4.92 (m, 1H), 3.97-3.87 (m, 1H), 3.79-3.68 (m, 2H), 3.12-3.06 (m, 1H), 3.03-2.97 (m, 1H), 2.71-2.62 (m, 1H), 2.15-2.04 (m, 1H), 1.80-1.56 (m, 1H), 1.42 (s, 9H).

Preparation of (3S,5S)-5-fluoro-1-(pyridin-3-yl)piperidin-3-amine

The title compound was synthesized following the approach outlined in Procedure 1 b substituting tert-butyl N-[(3S)1-(pyridin-3-yl)piperidin-3-yl]carbamate with tert-butyl N-[(3S,5S)-5-fluoro-1-(pyridin-3-yl)piperidin-3-yl]carbamate. Crude product was used in the next step without further purification. Product as a yellow oil (64 mg, 0.33 mmol, yield 99%). ESI-MS: 195 [M+H]$^+$ $^1$H NMR (300 MHz, DMSO-d$_6$) δ 8.31-8.26 (m, 1H), 7.96-7.90 (m, 1H), 7.33-7.26 (m, 1H), 7.22-7.15 (m, 1H), 5.08-4.86 (m, 1H), 3.95-3.79 (m, 1H), 3.77-3.67 (m, 1H), 3.21-3.15 (m, 1H), 3.09-2.97 (m, 2H), 2.18-2.04 (m, 1H), 1.73-1.58 (m, 2H), 1.57-1.47 (m, 1H), 1.43-1.33 (m, 1H).

Preparation of 3-({[(3S,5S)-5-fluoro-1-(pyridin-3-yl)piperidin-3-yl]amino}methyl)-1-methyl-1,4-dihydroquinolin-4-one The title compound was synthesized following the approach outlined in Procedure 4a substituting (3S)-1-(pyridin-3-yl)piperidin-3-amine with (3S,5S)-5-fluoro-1-(pyridin-3-yl)piperidin-3-amine. The residue was purified by FCC (SiHP, DCM:MeOH 9:1) to give the product (68 mg, 0.185 mmol, yield 54%) as a yellow oil. ESI-MS: 485 [M+H]$^+$ $^1$H NMR (300 MHz, DMSO-d$_6$) δ 8.32-8.28 (m, 1H), 8.25-8.21 (m, 1H), 8.08 (s, 1H), 7.96-7.90 (m, 1H), 7.79-7.71 (m, 1H), 7.70-7.64 (m, 1H), 7.44-7.37 (m, 1H), 7.35-7.29 (m, 1H), 7.20-7.13 (m, 1H), 5.10-4.88 (m, 1H), 3.85 (s, 5H), 3.69 (s, 2H), 3.18-2.88 (m, 2H), 2.68-2.58 (m, 1H), 2.14 (s, 2H), 1.71-1.47 (m, 1H). Aliphatic H overlapped with solvent signal.

Preparation of 3-({[(3S,5S)-5-fluoro-1-(pyridin-3-yl)piperidin-3-yl][(2-methylpyridin-4-yl)methyl]amino}methyl)-1-methyl-1,4-dihydroquinolin-4-one The title compound was synthesized following the approach outlined in Procedure 4b substituting 1-methyl-3-({[(3S)-1-(pyridin-3-yl)piperidin-3-yl]amino}methyl)-1,4-dihydroquinolin-4-one with 3-({[(3S,5S)-5-fluoro-1-(pyridin-3-yl)piperidin-3-yl]amino}methyl)-1-methyl-1,4-dihydroquinolin-4-one one using DCM as a solvent. The residue was purified by FCC (SiHP, DCM:MeOH 9:1) to afford the product (50 mg, 0.11 mmol, yield 57%) as a yellow solid. ESI-MS: 472 [M+H]$^+$ $^1$H NMR (400 MHz, DMSO-d$_6$) δ 8.33-8.29 (m, 2H), 8.23-8.18 (m, 1H), 8.08 (s, 1H), 7.93-7.90 (m, 1H), 7.76-7.70 (m, 1H), 7.66-7.62 (m, 1H), 7.42-7.36 (m, 1H), 7.33-7.24 (m, 3H), 7.18-7.13 (m, 1H), 5.14-4.98 (m, 1H), 4.07-3.93 (m, 2H), 3.87 (s, 3H), 3.83-3.71 (m, 2H), 3.71-3.59 (m, 2H), 3.10-2.88 (m, 3H), 2.39 (s, 3H), 2.30-2.21 (m, 1H), 2.03-1.82 (m, 1H).

Aliphatic H overlapped with solvent signal.

Example 27. 1-methyl-3-({[(3S,5R)-5-methyl-1-(pyridin-3-yl)piperidin-3-yl][(2-methylpyridin-4-yl)methyl]amino}methyl)-1,4-dihydroquinolin-4-one

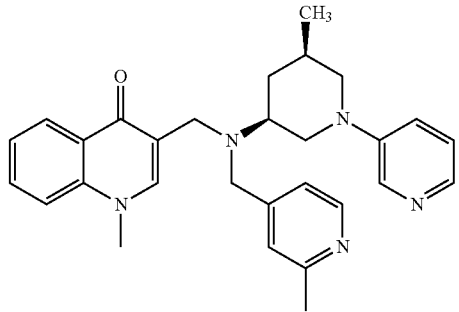 [SMILES: Cc1cc(CN(Cc2cn(C)c3ccccc3c2=O)[C@H]2C[C@@H](C)CN(c3cccnc3)C2)ccn1]

Preparation of tert-butyl N-[(3S,5R)-5-methyl-1-(pyridin-3-yl)piperidin-3-yl]carbamate The title compound was synthesized following the approach outlined in Procedure 5 substituting 3-bromopyridazine with 3-bromopyridine and 3-({[(2-methoxypyridin-4-yl)methyl](piperidin-3-yl)amino}methyl)-1-methyl-1,4-dihydroquinolin-4-one with tert-butyl N-[(3S,5R)-5-methylpiperidin-3-yl]carbamate. The residue was purified by FCC (SiHP, hexane 100% to AcOEt 100%) to give the product (142 mg, 0.49 mmol, yield 70%) as a colorless oil. ESI-MS: 292 [M+H]$^+$ $^1$H NMR (300 MHz, Chloroform-d) δ 8.32 (d, J=2.9 Hz, 1H), 8.07 (dd, J=4.6, 1.4 Hz, 1H), 7.41-7.28 (m, 1H), 7.20 (dd, J=8.4, 4.6 Hz, 1H), 4.44 (s, 1H), 4.04-3.95 (m, 1H), 3.74 (s, 1H), 3.67-3.51 (m, 1H), 2.38 (dt, J=12.4, 10.6 Hz, 2H), 2.07 (s, 2H), 1.97-1.80 (m, 1H), 1.49 (s, 9H), 1.00 (d, J=6.6 Hz, 3H).

Preparation of (3S,5R)-5-methyl-1-(pyridin-3-yl)piperidin-3-amine

The title compound was synthesized following the approach outlined in Procedure 1b substituting tert-butyl N-[(3S)1-(pyridin-3-yl)piperidin-3-yl]carbamate with tert-butyl N-[(3S,5R)-5-methyl-1-(pyridin-3-yl)piperidin-3-yl]carbamate. Product as a yellow oil (83 mg, 0.47 mmol, yield 92%). ESI-MS: 192 [M+H]$^+$ Preparation of 1-methyl-3-({[(3S,5R)-5-methyl-1-(pyridin-3-yl)piperidin-3-yl]amino}methyl)-1,4-dihydroquinolin-4-one The title compound was synthesized following the approach outlined in Procedure 4a substituting (3S)-1-(pyridin-3-yl)piperidin-3-amine with (3S,5R)-5-methyl-1-(pyridin-3-yl)piperidin-3-amine. Product (120 mg, 0.33 mmol, yield 76%) as a white solid. ESI-MS: 363 [M+H]$^+$ $^1$H NMR (300 MHz, DMSO-d$_6$) δ 8.29 (d, J=3.0 Hz, 1H), 8.22 (dd, J=8.1, 1.6 Hz, 1H), 8.08 (s, 1H), 7.91 (dd, J=4.5, 1.3 Hz, 1H), 7.80-7.71 (m, 1H), 7.67 (d, J=8.5 Hz, 1H), 7.46-7.35 (m, 1H), 7.30 (ddd, J=8.5, 3.0, 1.4 Hz, 1H), 7.16 (dd, J=8.5, 4.5 Hz, 1H), 4.06-3.93 (m, 1H), 3.85 (s, 3H), 3.75-3.71 (m, 1H), 3.68 (s, 3H), 2.37-2.10 (m, 3H), 1.95 (d, J=12.7 Hz, 1H), 0.91 (d, J=6.6 Hz, 3H). Some aliphatic H overlapped with solvent signals.

Preparation of 1-methyl-3-({[(3S,5R)-5-methyl-1-(pyridin-3-yl)piperidin-3-yl][(2-methylpyridin-4-yl)methyl]amino}methyl)-1,4-dihydroquinolin-4-one The title compound was synthesized following the approach outlined in Procedure 4b substituting 1-methyl-3-({[(3S)-1-(pyridin-3-yl)piperidin-3-yl]amino}methyl)-1,4-dihydroquinolin-4-one with 1-methyl-3-({[(3S,5R)-5-methyl-1-(pyridin-3-yl)piperidin-3-yl]amino}methyl)-1,4-dihydroquinolin-4-one. The residue was purified by FCC (SiHP, DCM:MeOH 9:1) to afford the product (55 mg, 0.12 mmol, yield 63%) as a yellow solid. ESI-MS: 468 [M+H]+

$^1$H NMR (300 MHz, DMSO-d$_6$) δ 8.34-8.27 (m, 2H), 8.19 (dd, J=8.1, 1.6 Hz, 1H), 8.05 (s, 1H), 7.90 (dd, J=4.5, 1.3 Hz, 1H), 7.77-7.68 (m, 1H), 7.66-7.56 (m, 1H), 7.38 (ddd, J=8.0, 6.8, 1.1 Hz, 1H), 7.33-7.22 (m, 3H), 7.14 (dd, J=8.5, 4.5 Hz, 1H), 4.03-3.98 (m, 1H), 3.87 (s, 3H), 3.83-3.53 (m, 5H), 2.88-2.68 (m, 2H), 2.38 (s, 3H), 2.35-2.25 (m, 1H), 2.05-1.96 (m, 1H), 1.39-1.17 (m, 2H), 1.00-0.90 (m, 3H).

Example 28. 7-chloro-1-cyclopropyl-6-fluoro-3-({[(2-methoxypyridin-4-yl)methyl][(3S)-1-(pyridin-3-yl)piperidin-3-yl]amino}methyl)-1,4-dihydroquinolin-4-one

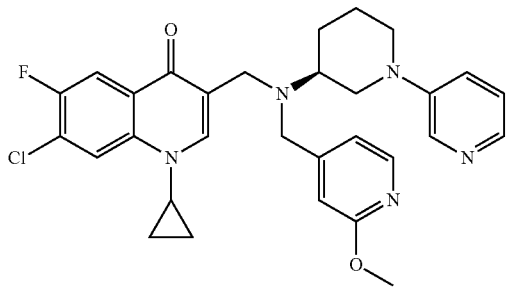 [SMILES: COc1cc(CN(Cc2cn(C3CC3)c3cc(Cl)c(F)cc3c2=O)[C@H]2CCCN(c3cccnc3)C2)ccn1]

Preparation of 7-chloro-1-cyclopropyl-6-fluoro-1,2,3,4-tetrahydroquinolin-4-one

The title compound was synthesized following the approach outlined in Procedure 7d substituting 1-cyclopropyl-6-fluoro-7-(4-methylpiperazin-1-yl)-4-oxo-1,4-dihydroquinoline-3-carboxylic acid with 7-chloro-1-cyclopropyl-6-fluoro-4-oxo-1,4-dihydroquinoline-3-carboxylic acid. The residue was purified by FCC (SiHP, Hex:AcOEt 2:1). Product a yellow solid (6.98 g, 29.14 mmol, yield 82%) as. ESI-MS: 240 [M+H]+

$^1$H NMR (400 MHz, DMSO-d$_6$) δ 7.55 (d, J=9.3 Hz, 1H), 7.39 (d, J=6.2 Hz, 1H), 3.52 (dd, J=7.5, 6.3 Hz, 2H), 2.61 (dd, J=7.5, 6.3 Hz, 2H), 2.47-2.41 (m, 1H), 0.96-0.86 (m, 2H), 0.76-0.66 (m, 2H).

Preparation of 7-chloro-1-cyclopropyl-6-fluoro-4-oxo-1,4-dihydroquinoline-3-carbaldehyde The title compound was synthesized following the approach outlined in Procedure 7e substituting 1-cyclopropyl-6-fluoro-7-(4-methylpiperazin-1-yl)-1,2,3,4-tetrahydroquinolin-4-one with 7-chloro-1-cyclopropyl-6-fluoro-1,2,3,4-tetrahydroquinolin-4-one. Crude was used directly in the next step without purification. The obtained product (3.86 g, 14.53 mmol, yield 60%) as a yellow solid. ESI-MS: 266 [M+H]+

$^1$H NMR (400 MHz, DMSO-d$_6$) δ 10.11 (s, 1H), 8.41 (s, 1H), 8.36 (d, J=6.1 Hz, 1H), 8.09 (d, J=9.1 Hz, 1H), 3.78-3.70 (m, 1H), 1.32-1.24 (m, 2H), 1.22-1.12 (m, 2H).

Preparation of 7-chloro-1-cyclopropyl-6-fluoro-3-({[(2-methoxypyridin-4-yl)methyl][(3S)-1-(pyridin-3-yl)piperidin-3-yl]amino}methyl)-1,4-dihydroquinolin-4-one The title compound was synthesized following the approach outlined in Procedure 4b substituting 1-methyl-3-({[(3S)-1-(pyridin-3-yl)piperidin-3-yl]amino}methyl)-1,4-dihydroquinolin-4-one with (3S)—N-[(2-methoxypyridin-4-yl)methyl]-1-(pyridin-3-yl)piperidin-3-amine and 2-methylpyridine-4-carbaldehyde with 7-chloro-1-cyclopropyl-6-fluoro-4-oxo-1,4-dihydroquinoline-3-carbaldehyde. The residue was purified by FCC (SiHP, DCM:MeOH 9:1) to afford the product (105 mg, 0.19 mmol, yield 57%) as a yellow solid. ESI-MS: 549 [M+H]+

$^1$H NMR (400 MHz, DMSO-d$_6$) δ 8.27 (d, J=2.9 Hz, 1H), 8.15 (d, J=6.2 Hz, 1H), 8.00-7.90 (m, 4H), 7.31-7.26 (m, 1H), 7.15 (dd, J=8.5, 4.5 Hz, 1H), 6.95 (dd, J=5.3, 1.3 Hz, 1H), 6.77 (s, 1H), 3.91-3.84 (m, 1H), 3.75 (s, 5H), 3.64 (s, 3H), 3.59-3.50 (m, 1H), 2.86-2.59 (m, 3H), 1.97 (d, J=10.8 Hz, 1H), 1.78 (d, J=11.9 Hz, 1H), 1.63-1.42 (m, 2H), 1.27-1.19 (m, 2H), 0.96-0.87 (m, 2H).

Example 29. Methyl 1-[1-methyl-3-({[(2-methylpyridin-4-yl)methyl][(3S)-1-(pyridin-3-yl)piperidin-3-yl]amino}methyl)-4-oxo-1,4-dihydroquinolin-7-yl]piperidine-4-carboxylate

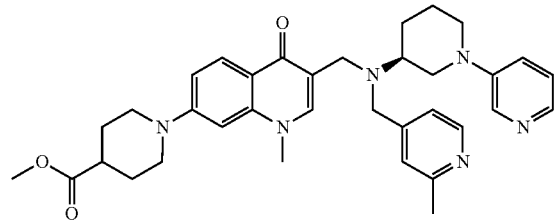 [SMILES: COC(=O)C1CCN(c2ccc3c(=O)c(CN(Cc4ccnc(C)c4)[C@H]4CCCN(c5cccnc5)C4)cn(C)c3c2)CC1]

The title compound was synthesized following the approach outlined in Procedure 3 substituting 1-methyl-3-({[(2-methylpyridin-4-yl)methyl][(3S)-piperidin-3-yl]amino}methyl)-1,4-dihydroquinolin-4-one with methyl piperidine-4-carboxylate, and 3-bromopyridine with 7-bromo-1-methyl-3-({[(2-methylpyridin-4-yl)methyl][(3S)-1-(pyridin-3-yl)piperidin-3-yl]amino}methyl)-1,4-dihydroquinolin-4-one. The residue was purified by prep-HPLC to afford the product (26 mg, 0.04 mmol, yield 23%) as a white powder. ESI-MS: 595 [M+H]+

$^1$H NMR (400 MHz, DMSO-d$_6$) δ 8.31-8.28 (m, 2H), 7.98-7.95 (m, 1H), 7.92-7.90 (m, 1H), 7.85 (s, 1H), 7.30-7.23 (m, 3H), 7.17-7.12 (m, 1H), 7.08-7.04 (m, 1H), 6.69-6.67 (m, 1H), 3.96-3.87 (m, 3H), 3.79-3.66 (m, 6H), 3.62 (s, 3H), 3.59-3.50 (m, 2H), 3.01-2.92 (m, 2H), 2.87-2.79 (m, 1H), 2.73-2.58 (m, 2H), 2.39 (s, 3H), 2.08 (s, 1H), 2.01-1.89 (m, 3H), 1.78-1.37 (m, 5H).

Example 30. 1-methyl-3-({[(2-methylpyridin-4-yl)methyl][(3S)-1-(2-oxo-1,2-dihydropyridin-4-yl)piperidin-3-yl]amino}methyl)-1,4-dihydroquinolin-4-one

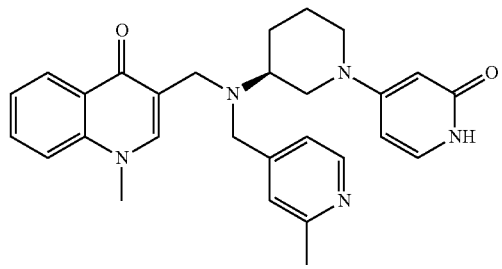 [SMILES: Cc1cc(CN(Cc2cn(C)c3ccccc3c2=O)[C@H]2CCCN(c3cc[nH]c(=O)c3)C2)ccn1]

The title compound was synthesized following the approach outlined in Procedure 5, substituting 3-bromopyridazine with 4-bromo-2-methylidene-1,2-dihydropyridine and 3-({[(2-methoxypyridin-4-yl)methyl](piperidin-3-yl)amino}methyl)-1-methyl-1,4-dihydroquinolin-4-one with 1-methyl-3-({[(2-methylpyridin-4-yl)methyl][(3S)-piperidin-3-yl]amino}methyl)-1,4-dihydroquinolin-4-one. The residue was redissolved in DCM and washed with 15% NaOH. Product was purified by FCC (SiHP; DCM/MeOH) and repurified by RP-FCC (SiC18, H₂O:CH₃CN) to afford the title compound as a yellow oil (75 mg, 0.16 mmol, yield 60%). The product was converted into hydrochloric acid salt. ESI-MS: 468 [M−H]⁻

1H NMR (400 MHz, DMSO-d6) δ 12.91 (s, 1H), 8.59 (d, J=6.0 Hz, 1H), 8.25 (s, 1H), 8.19 (dd, J=8.1, 1.6 Hz, 1H), 8.00 (s, 1H), 7.97-7.93 (m, 1H), 7.77 (ddd, J=8.6, 6.9, 1.7 Hz, 1H), 7.73 (d, J=7.5 Hz, 1H), 7.67 (d, J=8.6 Hz, 1H), 7.43 (ddd, J=8.0, 6.9, 1.0 Hz, 1H), 6.85-6.80 (m, 1H), 6.40 (s, 1H), 4.39 (d, J=12.8 Hz, 1H), 4.29 (s, 2H), 3.96 (s, 1H), 3.93 (s, 2H), 3.85 (s, 3H), 3.41 (t, J=12.0 Hz, 1H), 3.06 (t, J=12.9 Hz, 1H), 2.95 (s, 1H), 2.58 (s, 3H), 2.15 (d, J=11.1 Hz, 1H), 1.87 (d, J=11.6 Hz, 2H), 1.44 (d, J=13.3 Hz, 1H).

Example 31. 1-cyclopropyl-6,7-difluoro-3-({[(2-methoxypyridin-4-yl)methyl][(3S)-1-(6-methylpyridin-3-yl)piperidin-3-yl]amino}methyl)-1,4-dihydroquinolin-4-one

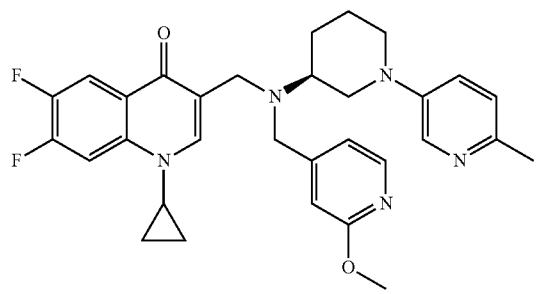 [SMILES: COc1cc(CN(Cc2cn(C3CC3)c3cc(F)c(F)cc3c2=O)[C@H]2CCCN(c3ccc(C)nc3)C2)ccn1]

Preparation of tert-butyl N-[(3S)-1-(6-methylpyridin-3-yl)piperidin-3-yl]carbamate The title product was prepared following the approach outlined in Procedure 1a. The product was additionally dissolved in DCM and stirred overnight at rt with and addition of MPA scavenger. Subsequently the reaction mixture was filtered through Celite®, washed with DCM and evaporated to provide the product (1.85 g, 6.35 mmol, yield 64%) as a yellow solid. ESI-MS: 292.3 [M+H]⁺

Preparation of (3S)-1-(6-methylpyridin-3-yl)piperidin-3-amine

The title compound was synthesized following the approach analogous to Procedure 1 b substituting tert-butyl N-[(3S)1-(pyridin-3-yl)piperidin-3-yl]carbamate with tert-butyl N-[(3S)-1-(6-methylpyridin-3-yl)piperidin-3-yl]carbamate. Reaction was carried out at 45° C. overnight. Subsequently, reaction mixture was basified with 15% NaOH, extracted with DCM, washed with brine, dried over sodium sulfate, filtered and evaporated to provide the product as an orange oil (1 g, 5.23 mmol, yield 82%) which was used for next step without further purification. ESI-MS: 192.2 [M+H]⁺

Preparation of 1-cyclopropyl-6,7-difluoro-3-({[(3S)-1-(6-methylpyridin-3-yl)piperidin-3-yl]amino}methyl)-1,4-dihydroquinolin-4-one The title compound was synthesized following the approach outlined in Procedure 4a substituting 1-methyl-4-oxo-1,4-dihydroquinoline-3-carbaldehyde with 1-cyclopropyl-6,7-difluoro-4-oxo-1,4-dihydroquinoline-3-carbaldehyde and (3S)-1-(pyridin-3-yl)piperidin-3-amine with (3S)-1-(6-methylpyridin-3-yl)piperidin-3-amine and solvent system from MeOH to a mixture of MeOH:DCM (5:1). Crude product was purified by FCC (SiHP; DCM-DCM:MeOH 9:1) to afford the title compound (0.95 g, 2.24 mmol, yield 80%) as a yellow oil. ESI-MS: 425 [MA−H]⁺

1H NMR (400 MHz, DMSO-d6) δ 8.13-8.12 (m, 1H), 8.09-8.07 (m, 1H), 8.07-8.04 (m, 1H), 8.04-8.01 (m, 1H), 7.24-7.20 (m, 1H), 7.05-7.02 (m, 1H), 3.72-3.61 (m, 3H), 3.58-3.52 (m, 1H), 3.49-3.42 (m, 1H), 2.75-2.66 (m, 1H), 2.66-2.57 (m, 1H), 2.33 (s, 3H), 1.92-1.84 (m, 1H), 1.78-1.70 (m, 1H), 1.58-1.47 (m, 1H), 1.29-1.21 (m, 3H), 1.08-1.02 (m, 2H).

Preparation of 1-cyclopropyl-6,7-difluoro-3-({[(2-methoxypyridin-4-yl)methyl][(3S)-1-(6-methylpyridin-3-yl)piperidin-3-yl]amino}methyl)-1,4-dihydroquinolin-4-one The title compound was synthesized following the approach outlined in Procedure 4b substituting 1-methyl-3-({[(3S)-1-(pyridin-3-yl)piperidin-3-yl]amino}methyl)-1,4-dihydroquinolin-4-one with 1-cyclopropyl-6,7-difluoro-3-({[(3S)-1-(6-methylpyridin-3-yl)piperidin-3-yl]amino}methyl)-1,4-dihydroquinolin-4-one and 2-methylpyridine-4-carbaldehyde with 2-methoxypyridine-4-carbaldehyde. Mixture was stirred at room temperature over weekend. After addition of sodium triacetoxyborohydride reaction was heated to 45° C. for 1 hour, 55° C. for 2 hours and finally 70° C. for 1 hour. The residue was purified by FCC (SiHP, DCM:MeOH 95:5) and repurified by RP-FCC (SiC18; H₂O:MeCN) to afford the titled compound (0.635 g, 1.16 mmol, yield 52%) as a yellow powder. The product was converted into a hydrochloric acid salt. ESI-MS: 546 [M+H]⁺

1H NMR (400 MHz, Methanol-d4) δ 8.27-8.23 (m, 1H), 8.12-8.07 (m, 1H), 8.07-7.97 (m, 3H), 7.92-7.88 (m, 1H), 7.63-7.58 (m, 1H), 6.99-6.95 (m, 1H), 6.81 (s, 1H), 4.23 4.14 (m, 1H), 4.08-3.90 (m, 3H), 3.85-3.80 (m, 1H), 3.78 (s, 3H), 3.54-3.46 (m, 1H), 3.24-3.09 (m, 1H), 3.00-2.91 (m, 1H), 2.29-2.19 (m, 1H), 2.05-1.97 (m, 1H), 1.92-1.81 (m, 1H), 1.78-1.66 (m, 1H), 1.36-1.29 (m, 2H), 1.03 (s, 2H).

Example 32. 3-({[(3S)-1-(5-bromopyrimidin-2-yl)piperidin-3-yl][(2-methylpyridin-4-yl)methyl]amino}methyl)-1-methyl-1,4-dihydroquinolin-4-one

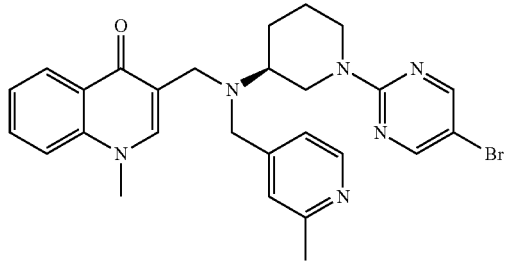 [SMILES: Cc1cc(CN(Cc2cn(C)c3ccccc3c2=O)[C@H]2CCCN(c3ncc(Br)cn3)C2)ccn1]

The title compound was synthesized following the approach outlined in Procedure 5 substituting 3-bromopyridazine with 5-bromo-2-fluoropyrimidine and 3-({[(2-methoxypyridin-4-yl)methyl](piperidin-3-yl)amino}methyl)-1-methyl-1,4-dihydroquinolin-4-one with 1-methyl-3-({[(2-methylpyridin-4-yl)methyl][(3S)-piperidin-3-yl]amino}methyl)-1,4-dihydroquinolin-4-one. The reaction was carried out overnight. Celite® pad was washed with AcOEt. Next, the filtrate was stirred with MPA scavenger for 15 min, filtered, evaporated and the residue was purified by FCC (SiHP, DCM:MeOH, 9:1) to give the product (0.076 g, 0.142 mmol, yield 67%) as a white solid.
ESI-MS: 533.4 [M+H]$^+$
$^1$H NMR (300 MHz, DMSO-d$_6$) δ 8.39 (s, 2H), 8.25 (d, J=5.0 Hz, 1H), 8.18 (dd, J=8.1, 1.6 Hz, 1H), 7.94 (s, 1H), 7.71 (ddd, J=8.6, 6.8, 1.6 Hz, 1H), 7.61 (d, J=8.5 Hz, 1H), 7.37 (ddd, J=8.0, 6.8, 1.1 Hz, 1H), 7.20-7.15 (m, 2H), 4.78-4.69 (m, 1H), 4.54-4.44 (m, 1H), 3.81 (s, 3H), 3.75 (s, 2H), 3.70-3.55 (m, 2H), 3.00 (t, J=11.8 Hz, 1H), 2.87-2.75 (m, 1H), 2.62-2.55 (m, 1H), 2.33 (s, 3H), 2.06-1.96 (m, 1H), 1.81-1.62 (m, 2H), 1.36-1.26 (m, 1H).

The product was converted into a hydrochloric acid salt. ESI-MS: 533.3 [M+H]$^+$. Product as a yellow powder.
$^1$H NMR (400 MHz, Deuterium Oxide) δ 8.39 (d, J=6.1 Hz, 1H), 8.32 (s, 2H), 8.15 (s, 1H), 8.06 (dd, J=8.2, 1.5 Hz, 1H), 7.94 (ddd, J=8.6, 7.0, 1.6 Hz, 1H), 7.88-7.82 (m, 2H), 7.75 (d, J=8.7 Hz, 1H), 7.60 (ddd, J=8.1, 7.1, 0.9 Hz, 1H), 4.72-4.51 (m, 4H), 4.10-4.03 (m, 1H), 3.93 (s, 3H), 3.93-3.88 (m, 1H), 3.85-3.77 (m, 1H), 3.46-3.38 (m, 1H), 2.49 (s, 3H), 2.46-2.22 (m, 3H), 2.09-2.01 (m, 1H), 1.82-1.72 (m, 1H).

Example 33. 7-chloro-1-cyclopropyl-6-fluoro-3-({[(2-methylpyridin-4-yl)methyl][(3S)-1-(pyridin-3-yl)piperidin-3-yl]amino}methyl)-1,4-dihydroquinolin-4-one

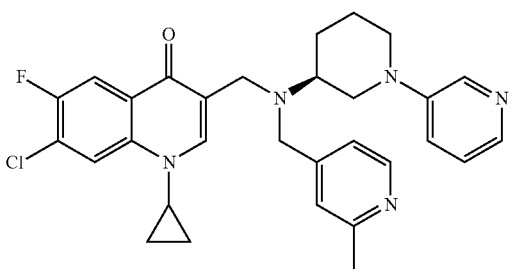 [SMILES: Cc1cc(CN(Cc2cn(C3CC3)c3cc(Cl)c(F)cc3c2=O)[C@H]2CCCN(c3cccnc3)C2)ccn1]

The title compound was synthesized according to Procedure 15. The residue was purified by FCC (SiHP, DCM:MeOH, 9:1) and re-purified by prep-HPLC to afford the product (0.080 g, 0.043 mmol, yield 35%) as yellow solid.
ESI-MS: 533.3 [M+H]$^+$.
$^1$H NMR (400 MHz, DMSO-d$_6$) δ 8.36-8.22 (m, 2H), 8.16 (d, J=6.1 Hz, 1H), 7.97 (d, J=9.4 Hz, 1H), 7.92 (s, 2H), 7.38-7.24 (m, 1H), 7.21 (s, 1H), 7.18-7.07 (m, 2H), 3.90 (d, J=11.8 Hz, 1H), 3.83-3.61 (m, 5H), 3.57-3.48 (m, 1H), 2.84 (t, J=11.3 Hz, 1H), 2.78-2.61 (m, 2H), 2.36 (s, 3H), 2.06-1.89 (m, 1H), 1.86-1.69 (m, 1H), 1.68-1.39 (m, 2H), 1.36-1.09 (m, 2H), 1.03-0.77 (m, 2H).

Example 34. 3-({[5,5-difluoro-1-(pyridin-3-yl)piperidin-3-yl][(2-methylpyridin-4-yl)methyl]amino}methyl)-1-methyl-1,4-dihydroquinolin-4-one

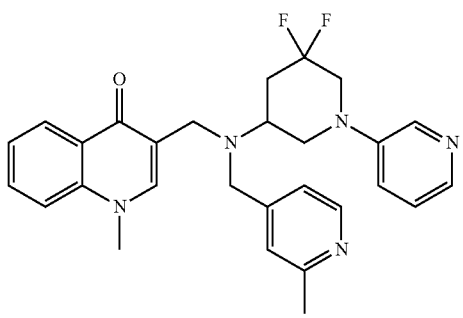 [SMILES: Cc1cc(CN(Cc2cn(C)c3ccccc3c2=O)C2CN(c3cccnc3)CC(F)(F)C2)ccn1]

Preparation of tert-butyl N-[5,5-difluoro-1-(pyridin-3-yl)piperidin-3-yl]carbamate The title compound was synthesized following the approach outlined in Procedure 1a substituting tert-butyl N-[(3S)-piperidin-3-yl]carbamate with tert-butyl N-(5,5-difluoropiperidin-3-yl)carbamate (1.1 eq.). The reaction was carried out for 1 day at 115° C. The residue was purified by FCC (SiHP; Hex:AcOEt) to give the product (0.150 g, 0.479 mmol, yield 84%) as a pale yellow oil. ESI-MS: 314.3 [M+H]$^+$ Preparation of 5,5-difluoro-1-(pyridin-3-yl)piperidin-3-amine The title compound was synthesized following the approach outlined in Procedure 1b substituting tert-butyl N-[(3S)1-(pyridin-3-yl)piperidin-3-yl]carbamate with tert-butyl N-[5,5-difluoro-1-(pyridin-3-yl)piperidin-3-yl]carbamate. The reaction was carried out for 24 h. The product (0.078 g, 0.366 mmol, yield 76%) was isolated as a yellow oil. ESI-MS: 241.1 [M+H]$^+$ Preparation of 3-({[5,5-difluoro-1-(pyridin-3-yl)piperidin-3-yl]amino}methyl)-1-methyl-1,4-dihydroquinolin-4-one The title compound was synthesized following the approach outlined in Procedure 4a substituting (3S)-1-(pyridin-3-yl)piperidin-3-amine with 5,5-difluoro-1-(pyridin-3-yl)piperidin-3-amine. The reaction was carried out without molecular sieves. The product (0.130 g, 0.338 mmol, yield 97%) was isolated as a yellow oil. ESI-MS: 385.2 [M+H]$^+$ Preparation of 3-({[5,5-difluoro-1-(pyridin-3-yl)piperidin-3-yl][(2-methylpyridin-4-yl)methyl]amino}methyl)-1-methyl-1,4-dihydroquinolin-4-one The title compound was synthesized according to Procedure 16. The residue was purified by FCC (SiHP; DCM:MeOH 9:1) and re-purified by RP-FCC (SiC18; H$_2$O:MeCN) to give the product (0.050 g, 0.102 mmol, yield 30%) as a yellow solid. ESI-MS: 490.4 [M+H]$^+$ The product was converted into hydrochloric acid salt. Product as a pale yellow solid. ESI-MS: 490.3 [M+H]$^+$ $^1$H NMR (400 MHz, DMSO-d$_6$) δ 8.74 (d, J=2.9 Hz, 1H), 8.60 (d, J=6.1 Hz, 1H), 8.28 (dd, J=9.0, 2.9 Hz, 1H), 8.24-8.17 (m, 3H), 8.03 (s, 1H), 7.93 (dd, J=6.1, 1.7 Hz, 1H), 7.85 (dd, J=9.0, 5.4 Hz, 1H), 7.76 (ddd, J=8.6, 6.9, 1.7 Hz, 1H), 7.66 (d, J=8.6 Hz, 1H), 7.49-7.34 (m, 1H), 4.51-4.39 (m, 2H), 4.31-4.13 (m, 2H), 3.88 (s, 3H), 3.86-3.74 (m, 2H), 3.49 (dd, J=33.0, 13.9 Hz, 1H), 3.38 (t, J=12.2 Hz, 1H), 3.18-3.03 (m, 1H), 2.67-2.62 (m, 3H), 2.62-2.53 (m, 1H), 2.47-2.35 (m, 1H).

Example 35. 3-({[(2-methylpyridin-4-yl)methyl][(3S)-1-(pyridin-3-yl)piperidin-3-yl]amino}methyl)-1,4-dihydroquinolin-4-one

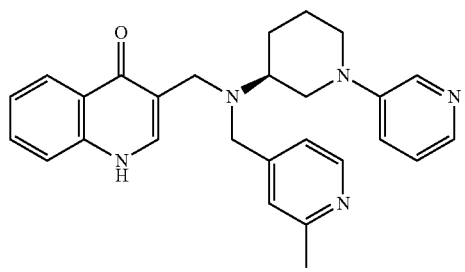 [SMILES: Cc1cc(CN(Cc2c[nH]c3ccccc3c2=O)[C@H]2CCCN(c3cccnc3)C2)ccn1]

The title compound was synthesized following the approach outlined in Procedure 15 substituting 7-chloro-1-cyclopropyl-6-fluoro-4-oxo-1,4-dihydroquinoline-3-carbaldehyde with 4-oxo-1,4-dihydroquinoline-3-carbaldehyde and extending the first stage of the reaction to overnight stirring.

The crude reaction mixture was evaporated and the residue was purified by FCC (SiHP, DCM:MeOH 15%) and re-purified twice by FCC (SiC18, H$_2$O:MeCN) to afford the title compound (0.022 g, 0.050 mmol, yield 18%) as a beige solid. ESI-MS: 440.2 [M+H]$^+$ $^1$H NMR (300 MHz, DMSO-d$_6$) δ 11.69 (s, 1H), 8.36-8.23 (m, 2H), 8.11 (dd, J=8.2, 1.5 Hz, 1H), 7.95 (s, 1H), 7.92 (dd, J=4.5, 1.3 Hz, 1H), 7.61 (ddd, J=8.4, 6.8, 1.5 Hz, 1H), 7.51 (d, J=8.1 Hz, 1H), 7.34-7.25 (m, 3H), 7.22 (d, J=5.2 Hz, 1H), 7.15 (dd, J=8.5, 4.5 Hz, 1H), 3.91 (d, J=11.7 Hz, 1H), 3.83-3.70 (m, 2H), 3.65 (s, 2H), 2.89-2.77 (m, 1H), 2.76-2.58 (m, 2H), 2.47-2.43 (m, 1H), 2.40 (s, 3H), 2.04-1.92 (m, 1H), 1.82-1.72 (m, 1H), 1.66-1.38 (m, 2H).

Example 36. 1-methyl-3-({[(2-methylpyridin-4-yl)methyl][(3S)-1-(2-nitropyridin-3-yl)piperidin-3-yl]amino}methyl)-1,4-dihydroquinolin-4-one

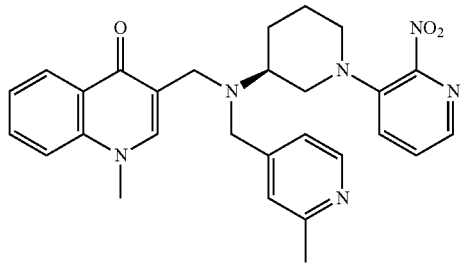 [SMILES: Cc1cc(CN(Cc2cn(C)c3ccccc3c2=O)[C@H]2CCCN(c3cccnc3[N+](=O)[O-])C2)ccn1]

The title compound was synthesized according to Procedure 17. The residue was combined with the residue from a similar reaction (0.133 mmol of the starting material) and purified by RP-FCC (SiC18; H$_2$O:MeCN) to afford the product (0.117 g, 0.345 mmol, yield 68%) as an orange solid. ESI-MS: 499.3 [M+H]$^+$ $^1$H NMR (300 MHz, DMSO-d$_6$) δ 8.27 (d, J=5.0 Hz, 1H), 8.19 (dd, J=8.1, 1.6 Hz, 1H), 8.09 (dd, J=4.4, 1.3 Hz, 1H), 7.98-7.89 (m, 2H), 7.77-7.59 (m, 3H), 7.38 (ddd, J=8.0, 6.9, 1.1 Hz, 1H), 7.21-7.13 (m, 2H), 3.83 (s, 3H), 3.72 (s, 2H), 3.68-3.51 (m, 2H), 3.44-3.35 (m, 1H), 3.11-3.02 (m, 1H), 2.95 (t, J=11.1 Hz, 1H), 2.82-2.70 (m, 2H), 2.36 (s, 3H), 2.05-1.95 (m, 1H), 1.83-1.73 (m, 1H), 1.61-1.38 (m, 2H).

Example 37. 7-bromo-1-methyl-3-({[(3S)-1-(6-methylpyridin-3-yl)piperidin-3-yl][(2-methylpyridin-4-yl)methyl]amino}methyl)-1,4-dihydroquinolin-4-one

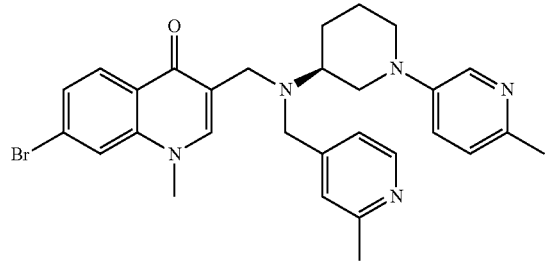 [SMILES: Cc1ccc(N2CCC[C@H](N(Cc3ccnc(C)c3)Cc3cn(C)c4cc(Br)ccc4c3=O)C2)cn1]

Preparation of 7-bromo-1-methyl-3-({[(3S)-1-(6-methylpyridin-3-yl)piperidin-3-yl]amino}methyl)-1,4-dihydroquinolin-4-one The title compound was synthesized following the approach outlined in Procedure 4b substituting 1-methyl-4-oxo-1,4-dihydroquinoline-3-carbaldehyde and (3S)-1-(pyridin-3-yl)piperidin-3-amine with 7-bromo-1-methyl-4-oxo-1,4-dihydroquinoline-3-carbaldehyde and (3S)-1-(6-methylpyridin-3-yl)piperidin-3-amine and solvent system from MeOH to a mixture of MeOH:DCM (1:1). DCM was also used for Celite® pad washing. The product (0.900 g, 2.039 mmol, yield 97%) was isolated as a yellow solid. ESI-MS: 443.1 [M+H]$^+$ Preparation of 7-bromo-1-methyl-3-({[(3S)-1-(6-methylpyridin-3-yl)piperidin-3-yl][(2-methylpyridin-4-yl)methyl]amino}methyl)-1,4-dihydroquinolin-4-one The title compound was synthesized following the approach outlined in Procedure 16 substituting 3-({[5,5-difluoro-1-(pyridin-3-yl)piperidin-3-yl]amino}methyl)-1-methyl-1,4-dihydroquinolin-4-one with 7-bromo-1-methyl-3-({[(3S)-1-(6-methylpyridin-3-yl)piperidin-3-yl]amino}methyl)-1,4-dihydroquinolin-4-one and increasing temperature of the second stage of the reaction to 50° C. The obtained filtrate was partitioned between water and DCM. Then, the organic layer was dried over anhydrous MgSO₄, filtered and evaporated. The residue was purified by two FCC (SiHP deactivated with NH₃:DCM, DCM:MeOH 9:1) and re-purified by two RP-FCC (SiC18; H₂O:MeCN) to give the product (0.450 g, 0.825 mmol, yield 40%) as a yellow solid. ESI-MS: 546.3 [M+H]⁺

The product was converted into hydrochloric acid salt. Product as an orange powder. ESI-MS: 546.3 [M+H]⁺

¹H NMR (300 MHz, DMSO-d₆) δ 8.36 (d, J=5.3 Hz, 1H), 8.21 (d, J=3.0 Hz, 1H), 8.08 (d, J=8.6 Hz, 1H), 8.04 (s, 1H), 7.87 (s, 1H), 7.67-7.55 (m, 1H), 7.53 (d, J=8.7 Hz, 1H), 7.48-7.36 (m, 2H), 7.30 (d, J=8.7 Hz, 1H), 4.21-3.53 (m, 9H), 3.03-2.81 (m, 1H), 2.82-2.59 (m, 2H), 2.43 (s, 6H), 2.12-1.91 (m, 1H), 1.87-1.71 (m, 1H), 1.67-1.33 (m, 2H).

Example 38. 3-({[(2,6-dimethylpyridin-4-yl)methyl][(3S)-1-(pyridine-3-yl)piperidin-3-yl]amino}methyl)-1-methyl-1,4-dihydroquinolin-4-one

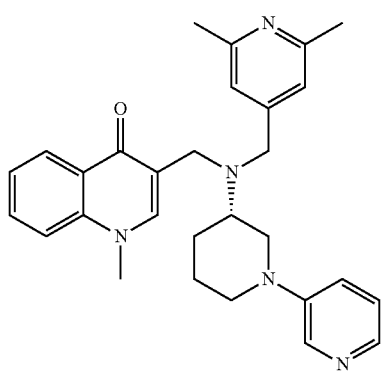 [SMILES: Cc1cc(CN(Cc2cn(C)c3ccccc3c2=O)[C@H]2CCCN(c3cccnc3)C2)cc(C)n1]

The title compound was synthesized according to Procedure 18. The residue was purified by prep-HPLC to give the product (0.031 g, 0.065 mmol, yield 45%) as a beige solid. ESI-MS: 468.3 [M+H]⁺

¹H NMR (300 MHz, Methanol-d₄) δ 8.34 (dd, J=8.3, 1.5 Hz, 1H), 8.24 (d, J=2.9 Hz, 1H), 7.95 (s, 1H), 7.90 (dd, J=4.7, 1.3 Hz, 1H), 7.76 (ddd, J=8.6, 6.9, 1.6 Hz, 1H), 7.64 (d, J=8.5 Hz, 1H), 7.49-7.38 (m, 2H), 7.24 (dd, J=8.6, 4.8 Hz, 2H), 7.01 (s, 2H), 4.05-3.94 (m, 1H), 3.84 (s, 3H), 3.81 (d, J=9.0 Hz, 4H), 3.77-3.65 (m, 1H), 3.03-2.84 (m, 2H), 2.82-2.61 (m, 1H), 2.28 (s, 6H), 2.21-2.10 (m, 1H), 1.97-1.83 (m, 1H), 1.77-1.56 (m, 2H).

Example 39. 1-methyl-3-({[(3S)-1-(pyridin-3-yl)piperidin-3-yl][(pyridin-4-yl)methyl]amino}methyl)-1,4-dihydroquinolin-4-one

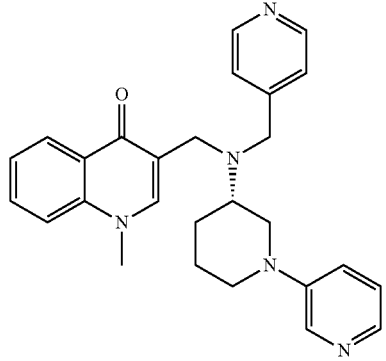 [SMILES: Cn1cc(CN(Cc2ccncc2)[C@H]2CCCN(c3cccnc3)C2)c(=O)c2ccccc21]

The title compound was synthesized following the approach outlined in Procedure proC substituting 2,6-dimethyl pyridine-4-carbaldehyde with pyridine-4-carbaldehyde. The residue was purified by prep-HPLC to give the product (0.031 g, 0.071 mmol, yield 49%) as a beige solid. ESI-MS: 440.3 [M+H]⁺

¹H NMR (300 MHz, DMSO-d₆) δ 8.54-8.37 (m, 2H), 8.29 (d, J=2.9 Hz, 1H), 8.19 (dd, J=8.2, 1.5 Hz, 1H), 8.07 (s, 1H), 7.91 (dd, J=4.5, 1.3 Hz, 1H), 7.72 (ddd, J=8.5, 6.8, 1.6 Hz, 1H), 7.63 (d, J=8.4 Hz, 1H), 7.52-7.42 (m, 2H), 7.37 (ddd, J=8.0, 6.8, 1.1 Hz, 1H), 7.33-7.24 (m, 1H), 7.14 (dd, J=8.5, 4.5 Hz, 1H), 4.02-3.91 (m, 1H), 3.87 (s, 3H), 3.84-3.52 (m, 5H), 2.85 (t, J=11.4 Hz, 1H), 2.77-2.58 (m, 2H), 2.06-1.92 (m, 1H), 1.83-1.70 (m, 1H), 1.66-1.36 (m, 2H).

Example 40. 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one

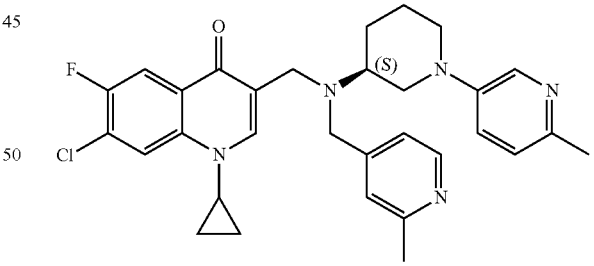

Preparation of (3S)-1-(6-methylpyridin-3-yl)-N-[(2-methylpyridin-4-yl)methyl]piperidin-3-amine The title compound was synthesized following the approach outlined in Procedure 4a substituting 1-methyl-4-oxo-1,4-dihydroquinoline-3-carbaldehyde and (3S)-1-(pyridin-3-yl)piperidin-3-amine with 2-methylpyridine-4-carbaldehyde and (3S)-1-(6-methylpyridin-3-yl)piperidin-3-amine (1 eq.), using 2 eq. of NaBH₄ and NaOAc. The solvent used was DCE. The second stage was extended up to 3 h. The residue was purified by FCC (SiHP deactivated with NH₃:

DCM; DCM:MeOH 9:1) and re-purified by RP-FCC (SiC18; H₂O:MeCN) to afford the product (3.05 g, 9.863 mmol, yield 69%) in as a yellow oil. ESI-MS: 297.3 [M+H]⁺

¹H NMR (400 MHz, DMSO-d₆) δ 8.36-8.32 (m, 1H), 8.11 (d, J=2.9 Hz, 1H), 7.25-7.22 (m, 1H), 7.20 (dd, J=8.5, 3.1 Hz, 1H), 7.17 (dd, J=5.1, 1.4 Hz, 1H), 7.04 (d, J=8.5 Hz, 1H), 3.78 (s, 2H), 3.73-3.61 (m, 1H), 3.52-3.44 (m, 1H), 2.71-2.63 (m, 1H), 2.61-2.52 (m, 2H), 2.48-2.42 (m, 4H), 2.36-2.32 (m, 3H), 1.96-1.88 (m, 1H), 1.78-1.68 (m, 1H), 1.57-1.43 (m, 1H), 1.28-1.14 (m, 1H).

Preparation of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one The title compound was synthesized following the approach outlined in Procedure 15 substituting (3S)—N-[(2-methylpyridin-4-yl)methyl]-1-(pyridin-3-yl)piperidin-3-amine with (3S)-1-(6-methylpyridin-3-yl)-N-[(2-methylpyridin-4-yl)methyl]piperidin-3-amine (1 eq.) and extending first stage of the reaction to 12 h. The crude reaction mixture was partitioned between water and NaHCO₃ solution. Combined organic layers were washed with brine, dried over anh. Na₂SO₄ and concentrated under reduced pressure. The residue was purified by FCC (SiHP; DCM:MeOH 95:5) and by RP-FCC (SiC18; H₂O:MeCN) to afford the product (3.205 g, 5.677 mmol, 76%) as a yellow powder. ESI-MS: 546.4 [M+H]⁺

¹H NMR (400 MHz, DMSO-d₆) δ 8.29-8.25 (m, 1H), 8.16 (d, J=6.2 Hz, 1H), 8.13 (d, J=2.9 Hz, 1H), 7.97 (d, J=9.5 Hz, 1H), 7.91 (s, 1H), 7.26-7.18 (m, 2H), 7.17-7.13 (m, 1H), 7.02 (d, J=8.5 Hz, 1H), 3.82-3.70 (m, 3H), 3.66-3.50 (m, 4H), 2.83-2.69 (m, 2H), 2.65-2.54 (m, 1H), 2.36 (s, 3H), 2.33 (s, 3H), 2.08-1.92 (m, 1H), 1.80-1.72 (m, 1H), 1.62-1.41 (m, 2H), 1.27-1.18 (m, 2H), 1.00-0.82 (m, 2H).

The product was converted into hydrochloric acid salt. Product as a. ESI-MS: 546.7 [M+H]⁺

¹H NMR (400 MHz, DMSO-d₆) δ 8.38 (d, J=5.4 Hz, 1H), 8.26-8.13 (m, 2H), 8.05-7.65 (m, 3H), 7.50-7.33 (m, 3H), 4.15-3.80 (m, 3H), 3.80-3.61 (m, 3H), 3.61-3.52 (m, 2H), 2.94 (br, 1H), 2.83-2.70 (m, 1H), 2.50-2.40 (m, 6H), 2.00 (br, 1H), 1.89-1.75 (m, 1H), 1.63 (br, 1H), 1.57-1.44 (m, 1H), 1.33-1.18 (m, 2H), 0.94 (s, 2H).

Example 41. 1-methyl-3-({[(3S)-1-(1-methyl-2-oxo-1,2-dihydropyridin-4-yl)piperidin-3-yl][(2-methylpyridin-4-yl)methyl]amino}methyl)-1,4-dihydroquinolin-4-one

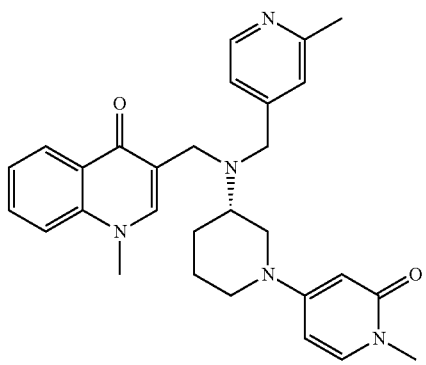 [SMILES: Cc1cc(CN(Cc2cn(C)c3ccccc3c2=O)[C@H]2CCCN(c3ccn(C)c(=O)c3)C2)ccn1]

The title compound was synthesized according to Procedure 19. The residue was purified by FCC (SiHP; DCM:MeOH) and re-purified by FCC (SiHP; DCM:MeOH) to give the product (0.077 g, 0.159 mmol, yield 60%) as a yellow solid. ESI-MS: 484.7 [M+H]⁺

¹H NMR (300 MHz, DMSO-d₆) δ 8.28 (d, J=5.0 Hz, 1H), 8.18 (d, J=8.0 Hz, 1H), 8.05 (s, 1H), 7.83-7.57 (m, 2H), 7.45-7.30 (m, 2H), 7.30-7.19 (m, 2H), 6.06 (dd, J=7.6, 2.6 Hz, 1H), 5.50 (d, J=2.7 Hz, 1H), 4.05-3.92 (m, 1H), 3.88 (s, 3H), 3.85-3.46 (m, 5H), 3.23 (s, 4H), 2.98 (t, J=12.1 Hz, 1H), 2.81-2.67 (m, 1H), 2.38 (s, 4H), 2.10-1.88 (m, 2H), 1.79-1.51 (m, 3H), 1.43-1.25 (m, 2H).

The product was converted into hydrochloric acid salt. Product as a light yellow solid. ESI-MS: 484.2 [M+H]⁺

¹H NMR (400 MHz, Methanol-d₄) a 8.34-8.28 (m, 2H), 8.06 (s, 1H), 7.83-7.76 (m, 2H), 7.74 (d, J=6.1 Hz, 1H), 7.69 (d, J=8.6 Hz, 1H), 7.48 (ddd, J=8.0, 7.0, 1.0 Hz, 1H), 7.35 (d, J=7.7 Hz, 1H), 6.26 (dd, J=7.8, 2.8 Hz, 1H), 5.74 (d, J=2.8 Hz, 1H), 4.18-4.11 (m, 3H), 3.91 (s, 3H), 3.91-3.82 (m, 3H), 3.42 (s, 3H), 3.19-3.10 (m, 1H), 2.97-2.87 (m, 2H), 2.52 (s, 3H), 2.22-2.14 (m, 1H), 1.92-1.75 (m, 2H), 1.63-1.50 (m, 1H).

Example 42. 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydro-1,8-naphthyridin-4-one

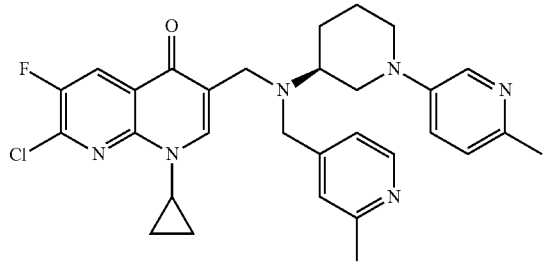 [SMILES: Cc1ccc(N2CCC[C@H](N(Cc3ccnc(C)c3)Cc3cn(C4CC4)c4nc(Cl)c(F)cc4c3=O)C2)cn1]

Preparation of 7-chloro-1-cyclopropyl-6-fluoro-1,2,3,4-tetrahydro-1,8-naphthyridin-4-one The title compound was synthesized following the approach outlined in Procedure 7d substituting 1-cyclopropyl-6-fluoro-7-(4-methylpiperazin-1-yl)-4-oxo-1,4-dihydroquinoline-3-carboxylic acid with 7-chloro-1-cyclopropyl-6-fluoro-4-oxo-1,4-dihydro-1,8-naphthyridine-3-carboxylic acid and extending time of addition of NaBH₄ to 1 h, stirring at rt prior addition of PTSA to 16 h and shortening refluxing time to 4 h. DCM was used for extracting. The residue was purified by FCC (SiHP; Hex:AcOEt 2:1) to give the product (5.974 g, 24.823 mmol, yield 70%) as a yellow solid.

ESI-MS: 241.1 [M+H]⁺

¹H NMR (400 MHz, DMSO-d₆) δ 7.90 (d, J=7.9 Hz, 1H), 3.62-3.56 (m, 2H), 2.68-2.61 (m, 3H), 0.88-0.82 (m, 2H), 0.72-0.67 (m, 2H).

Preparation of 7-chloro-1-cyclopropyl-6-fluoro-4-oxo-1,4-dihydro-1,8-naphthyridine-3-carbaldehyde The title compound was synthesized following the approach outlined in Procedure 7e substituting 1-cyclopropyl-6-fluoro-7-(4-methylpiperazin-1-yl)-1,2,3,4-tetrahydroquinolin-4-one with 7-chloro-1-cyclopropyl-6-fluoro-1,2,3, 4-tetrahydro-1,8-naphthyridin-4-one. The residue was purified by FCC (SiHP; DCM:MeOH 9:1) to give the product (0.381 g, 1.429 mmol, yield 31%) as a white solid. ESI-MS: 267.9 [M+H]+

¹H NMR (400 MHz, DMSO-d₆) δ 10.09 (s, 1H), 8.54 (d, J=7.7 Hz, 1H), 8.52 (s, 1H), 3.75-3.68 (m, 1H), 1.21-1.15 (m, 2H), 1.15-1.09 (m, 2H).

Preparation of 7-chloro-1-cyclopropyl-6-fluoro-3-({[(3S)-1-(6-methylpyridin-3-yl)piperidin-3-yl][(2-methylpyridin-4-yl)methyl]amino}methyl)-1,4-dihydro-1,8-naphthyridin-4-one The title compound was synthesized following the approach outlined in Procedure 15 substituting (3S)—N-[(2-methylpyridin-4-yl)methyl]-1-(pyridin-3-yl)piperidin-3-amine and 7-chloro-1-cyclopropyl-6-fluoro-4-oxo-1,4-dihydroquinoline-3-carbaldehyde with (3S)-1-(6-methylpyridin-3-yl)-N-[(2-methylpyridin-4-yl)methyl]piperidin-3-amine and 7-chloro-1-cyclopropyl-6-fluoro-4-oxo-1,4-dihydro-1,8-naphthyridine-3-carbaldehyde (1 eq.). The reaction was conducted without presence of Na₂SO₄ and NaBH(OAc)₃ was introduced at the beginning of the reaction. The residue was purified by FCC (SiHP, DCM:MeOH, 9:1) to give the product (0.077 g, 0.141 mmol, yield 46%) as a yellow solid. ESI-MS: 547.8 [M+H]+

The product was converted into a hydrochloric acid salt. ESI-MS: 547.2 [M+H]+

¹H NMR (400 MHz, Methanol-d₄) δ 8.34 (d, J=7.8 Hz, 1H), 8.24 (d, J=5.5 Hz, 1H), 8.17 (d, J=3.0 Hz, 1H), 8.06 (s, 1H), 7.85 (dd, J=9.0, 3.0 Hz, 1H), 7.48 (d, J=9.0 Hz, 1H), 7.46-7.44 (m, 1H), 7.42-7.39 (m, 1H), 4.09-4.01 (m, 1H), 3.95 (s, 2H), 3.90-3.82 (m, 1H), 3.80-3.70 (m, 2H), 3.62-3.54 (m, 1H), 3.06-2.90 (m, 2H), 2.89-2.80 (m, 1H), 2.54 (s, 3H), 2.45 (s, 3H), 2.20-2.10 (m, 1H), 1.98-1.90 (m, 1H), 1.78-1.61 (m, 2H), 1.27-1.20 (m, 2H), 0.95-0.89 (m, 2H), 1.20 (m, 2H), 0.95-0.89 (m, 2H).

Example 43. 1-cyclopropyl-6-fluoro-7-hydroxy-3-({[(3S)-1-(6-methylpyridin-3-yl)piperidin-3-yl][(2-methylpyridin-4-yl)methyl]amino}methyl)-1,4-dihydro-1,8-naphthyridin-4-one

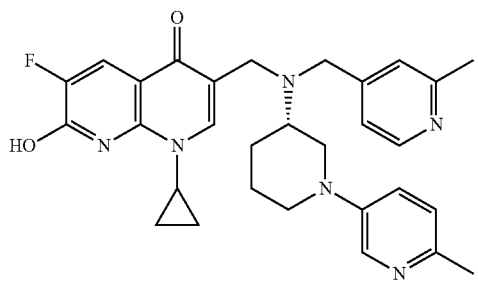 [SMILES: Cc1ccc(N2CCC[C@H](N(Cc3ccnc(C)c3)Cc3cn(C4CC4)c4nc(O)c(F)cc4c3=O)C2)cn1]

The title compound was synthesized according to Procedure 20. The residue was dissolved in DCM, filtered through Celite® and purified by RP-FCC (SiC18; H₂O:MeCN) to give the product (0.026 g, 0.049 mmol, yield 44%) as a white powder. ESI-MS: 529.7 [M+H]+

¹H NMR (400 MHz, Methanol-d₄) δ 8.21 (d, J=5.2 Hz, 1H), 8.07 (d, J=2.9 Hz, 1H), 7.75-7.71 (m, 2H), 7.33 (dd, J=8.6, 3.0 Hz, 1H), 7.28 (s, 1H), 7.26-7.22 (m, 1H), 7.11 (d, J=8.6 Hz, 1H), 3.91-3.80 (m, 3H), 3.75 (s, 2H), 3.64-3.56 (m, 1H), 3.56-3.47 (m, 1H), 2.99-2.88 (m, 1H), 2.87-2.78 (m, 1H), 2.73-2.62 (m, 1H), 2.41 (s, 3H), 2.40 (s, 3H), 2.18-2.05 (m, 1H), 1.96-1.83 (m, 1H), 1.73-1.57 (m, 2H), 1.17-1.10 (m, 2H), 0.81-0.75 (m, 2H).

Example 44. 1-cyclopropyl-6-fluoro-7-methoxy-3-({[(3S)-1-(6-methylpyridin-3-yl)piperidin-3-yl][(2-methylpyridin-4-yl)methyl]amino}methyl)-1,4-dihydro-1,8-naphthyridin-4-one

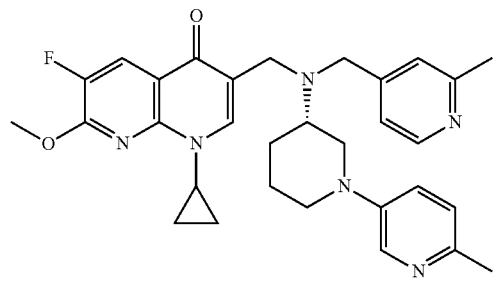

The title compound was synthesized according to Procedure 21. The residue was dissolved in DCM, filtered through Celite® and purified by RP-FCC (SiC18; H₂O:MeCN) to give the product (0.037 g, 0.066 mmol, yield 60%) as a white powder. ESI-MS: 543.2 [M+H]+

¹H NMR (400 MHz, Methanol-d₄) δ 8.17 (d, J=5.2 Hz, 1H), 8.10 (d, J=9.9 Hz, 1H), 8.08 (d, J=2.9 Hz, 1H), 7.96 (s, 1H), 7.35 (dd, J=8.6, 3.0 Hz, 1H), 7.26 (s, 1H), 7.24-7.20 (m, 1H), 7.12 (d, J=8.6 Hz, 1H), 4.17 (s, 3H), 3.91-3.81 (m, 3H), 3.79 (s, 2H), 3.63-3.52 (m, 2H), 3.01-2.92 (m, 1H), 2.90-2.82 (m, 1H), 2.74-2.66 (m, 1H), 2.40 (s, 3H), 2.38 (s, 3H), 2.17-2.09 (m, 1H), 1.96-1.89 (m, 1H), 1.75-1.60 (m, 2H), 1.27-1.21 (m, 2H), 0.94-0.88 (m, 2H).

Example 45. 1-cyclopropyl-6-fluoro-7-methoxy-3-({[(3S)-1-(6-methylpyridin-3-yl)piperidin-3-yl][(2-methylpyridin-4-yl)methyl]amino}methyl)-1,4-dihydroquinolin-4-one

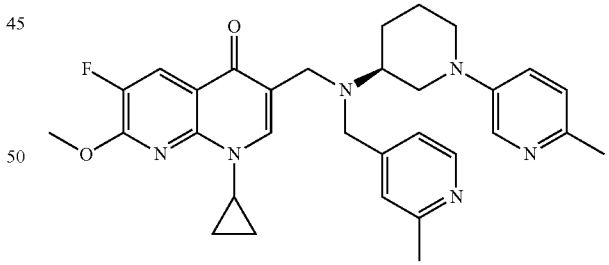

The title compound was synthesized according to Procedure 22. The residue was purified by FCC (SiHP; DCM: MeOH 9:1), re-purified by RP-FCC (SiC18, H₂O:CH₃CN) and prep-HPLC. The title compound was isolated as a free base (0.036 g, 0.066 mmol, yield 36%). The product as a white powder. ESI-MS: 542.4 [M+H]+

¹H NMR (400 MHz, Methanol-d₄) δ 8.16 (d, J=5.3 Hz, 1H), 8.09 (d, J=2.9 Hz, 1H), 7.95 (s, 1H), 7.89 (d, J=11.6 Hz, 1H), 7.51 (d, J=7.2 Hz, 1H), 7.35 (dd, J=8.6, 3.0 Hz, 1H), 7.25 (s, 1H), 7.24-7.20 (m, 1H), 7.12 (d, J=8.6 Hz, 1H), 4.05 (s, 3H), 3.92-3.83 (m, 3H), 3.79 (s, 2H), 3.64-3.58 (m, 1H), 3.54-3.47 (m, 1H), 3.01-2.91 (m, 1H), 2.89-2.82 (m, 1H), 2.75-2.65 (m, 1H), 2.41 (s, 3H), 2.35 (s, 3H), 2.19-2.11 (m, 1H), 1.97-1.89 (m, 1H), 1.75-1.59 (m, 2H), 1.37-1.29 (m, 2H), 0.98-0.92 (m, 2H).

The product was converted into a hydrochloric acid salt. Product as a yellow solid. ESI-MS: 542.3 [M+H]$^+$ $^1$H NMR (400 MHz, Methanol-d$_4$) δ 8.24 (d, 1H), 8.19 (d, 1H), 7.95 (s, 1H), 7.92-7.86 (m, 2H), 7.53 (d, 1H), 7.52-7.47 (m, 2H), 7.44-7.42 (m, 1H), 4.12-3.89 (m, 7H), 3.85-3.74 (m, 2H), 3.56-3.49 (m, 1H), 3.10-3.00 (m, 2H), 2.92-2.82 (m, 1H), 2.56 (s, 3H), 2.43 (s, 3H), 2.23-2.15 (m, 1H), 2.01-1.94 (m, 1H), 1.82-1.62 (m, 2H), 1.38-1.32 (m, 2H), 1.01-0.96 (m, 2H).

Example 46. 1-cyclopropyl-6-fluoro-7-[(3R)-3-methylpiperazin-1-yl]-3-({[(3S)-1-(6-methylpyridin-3-yl)piperidin-3-yl][(2-methylpyridin-4-yl)methyl]amino}methyl)-1,4-dihydroquinolin-4-one

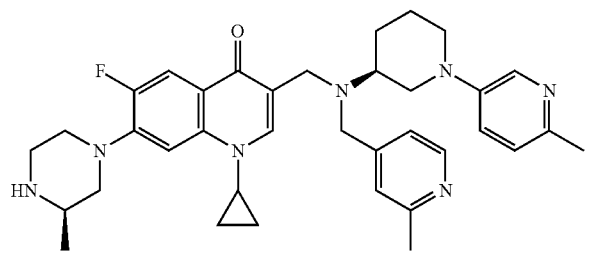 [SMILES: Cc1ccc(N2CCC[C@H](N(Cc3ccnc(C)c3)Cc3cn(C4CC4)c4cc(N5CCN[C@H](C)C5)c(F)cc4c3=O)C2)cn1]

Preparation of tert-butyl(2R)-4-[1-cyclopropyl-6-fluoro-3-({[(3S)-1-(6-methyl pyridin-3-yl)piperidin-3-yl][(2-methylpyridin-4-yl)methyl]amino}methyl)-4-oxo-1,4-dihydroquinolin-7-yl]-2-methylpiperazine-1-carboxylate The title compound was synthesized according to Procedure 23. The residue was purified by FCC (SiHP deactivated with NH$_3$:DCM, DCM:MeOH 9:1) to give the product (0.055 g, 0.077 mmol, yield 42%) as a yellow solid. ESI-MS: 710.9 [M+H]$^+$ Preparation of 1-cyclopropyl-6-fluoro-7-[(3R)-3-methylpiperazin-1-yl]-3-({[(3S)-1-(6-methylpyridin-3-yl)piperidin-3-yl][(2-methylpyridin-4-yl)methyl]amino}methyl)-1,4-dihydroquinolin-4-one The title compound was synthesized following the approach outlined in Procedure 1b substituting tert-butyl N-[(3S)1-(pyridin-3-yl)piperidin-3-yl]carbamate with tert-butyl (2R-4-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]-2-methyl piperazine-1-carboxylate. The residue after evaporation was basified with NH$_3$ solution in MeOH and purified by prep-H PLC to give the product (0.026 g, 0.043 mmol, yield 55%) as a white solid. ESI-MS: 610.8 [M+H]$^+$ The product was converted into a hydrochloric acid salt. Product as a pale yellow solid. ESI-MS: 610.3 [M+H]$^+$ $^1$H NMR (400 MHz, Deuterium Oxide) δ 8.34-8.29 (m, 1H), 8.12 (s, 1H), 8.07 (d, J=2.9 Hz, 1H), 7.92 (dd, J=9.1, 2.9 Hz, 1H), 7.75-7.71 (m, 1H), 7.69 (d, J=12.9 Hz, 1H), 7.53 (d, J=9.1 Hz, 1H), 7.45 (d, J=7.2 Hz, 1H), 4.67-4.50 (m, 2H), 4.48-4.27 (m, 2H), 4.02-3.94 (m, 1H), 3.84-3.75 (m, 2H), 3.75-3.66 (m, 1H), 3.65-3.57 (m, 1H), 3.57-3.41 (m, 4H), 3.41-3.30 (m, 1H), 3.29-3.19 (m, 1H), 3.16-2.99 (m, 2H), 2.51 (s, 3H), 2.42 (s, 3H), 2.32-2.23 (m, 1H), 2.15-1.98 (m, 2H), 1.82-1.72 (m, 1H), 1.35 (d, J=6.6 Hz, 3H), 1.32-1.25 (m, 2H), 0.98-0.90 (m, 2H).

Example 47. 1-cyclopropyl-6-fluoro-3-({[(3S)-1-(6-methylpyridin-3-yl)piperidin-3-yl][(2-methylpyridin-4-yl)methyl]amino}methyl)-7-(piperazin-1-yl)-1,4-dihydroquinolin-4-one

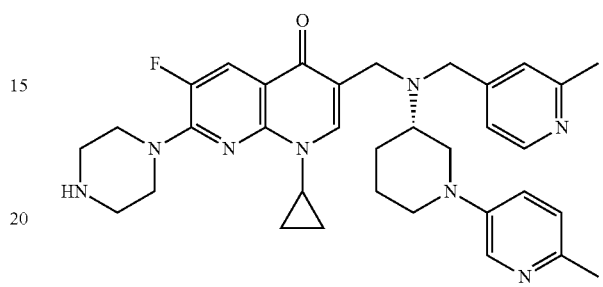

The title compound was synthesized according to Procedure 24. The residue was purified by FCC (SiHP, DCM:MeOH 9:1) and re-purified by prep-HPLC. The product was obtained as a free base after extraction using DCM/aq. NaHCO$_3$, drying the organic layer over anhydrous Na$_2$SO$_4$ and evaporation. The titled compound was isolated as a light yellow solid (0.019 g, 0.032 mmol, yield 17%). ESI-MS: 596.8 [M+H]$^+$ The product was converted into a hydrochloric acid salt. ESI-MS: 596.4 [M+H]$^+$ $^1$H NMR (400 MHz, Deuterium Oxide) δ 8.02 (s, 1H), 7.82 (d, J=5.2 Hz, 1H), 7.74-7.58 (m, 2H), 7.35-7.22 (m, 2H), 7.05 (d, J=8.6 Hz, 1H), 6.86 (d, J=5.3 Hz, 1H), 6.73 (s, 1H), 3.75-3.47 (m, 5H), 3.44-3.17 (m, 10H), 2.94-2.77 (m, 1H), 2.69-2.54 (m, 1H), 2.55-2.42 (m, 1H), 2.36-2.20 (m, 3H), 2.06-1.96 (m, 1H), 1.93-1.75 (m, 4H), 1.65-1.38 (m, 2H), 1.24-1.06 (m, 2H), 0.75-0.56 (m, 2H).

Example 48. 1-cyclopropyl-7-[4-(2,2-difluoroethyl)piperazin-1-yl]-6-fluoro-3-({[(3S)-1-(6-methylpyridin-3-yl)piperidin-3-yl][(2-methylpyridin-4-yl)methyl]amino}methyl)-1,4-dihydroquinolin-4-one

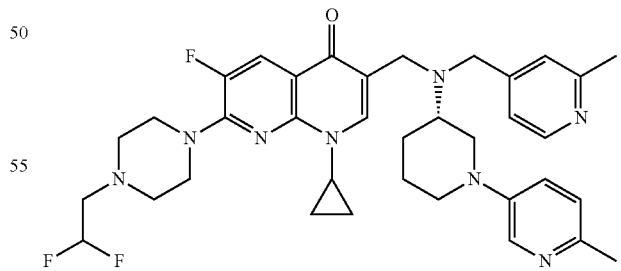

The title compound was synthesized following the approach outlined in Procedure 24 substituting piperazine with 1-(2,2-difluoroethyl)piperazine. Stirring in DCM with MPA scavenger was used after the residue was purified by FCC (SiHP, DCM:MeOH). The sample was then re-purified by prep-HPLC to give the product (0.053 g, 0.08 mmol, yield 44%) as a yellow solid. ESI-MS: 660.9 [M+H]$^+$ ¹H NMR (400 MHz, DMSO-d₅) δ 8.28 (d, J=5.1 Hz, 1H), 8.12 (d, J=3.0 Hz, 1H), 7.82 (s, 1H), 7.71 (d, J=13.5 Hz, 1H), 7.34 (d, J=7.4 Hz, 1H), 7.23-7.18 (m, 2H), 7.16 (d, J=5.2 Hz, 1H), 7.01 (d, J=8.5 Hz, 1H), 6.18 (tt, J=55.6, 4.2 Hz, 1H), 3.81-3.76 (m, 1H), 3.76-3.72 (m, 2H), 3.60 (s, 2H), 3.58-3.55 (m, 1H), 3.52-3.46 (m, 1H), 3.22-3.16 (m, 4H), 2.88-2.77 (m, 2H), 2.77-2.72 (m, 6H), 2.62-2.54 (m, 1H), 2.37 (s, 3H), 2.32 (s, 3H), 2.00-1.92 (m, 1H), 1.79-1.72 (m, 1H), 1.58-1.43 (m, 2H), 1.25-1.17 (m, 2H), 0.93-0.82 (m, 2H).

The product was converted into a hydrochloric acid salt. ESI-MS: 660.3 [M+H]⁺. Product as a yellow solid.

¹H NMR (400 MHz, Pyridine-d₅) δ 8.58 (d, J=5.0 Hz, 1H), 8.55 (d, J=3.0 Hz, 1H), 8.41 (d, J=13.4 Hz, 1H), 7.95 (s, 1H), 7.36-7.33 (m, 2H), 7.28 (dd, J=8.5, 3.0 Hz, 1H), 7.23 (d, J=7.4 Hz, 1H), 7.03 (d, J=8.5 Hz, 1H), 6.22 (tt, J=55.9, 4.3 Hz, 1H), 4.14-4.05 (m, 1H), 4.03 (s, 2H), 3.92-3.77 (m, 2H), 3.58-3.45 (m, 1H), 3.34-3.25 (m, 1H), 3.25-3.16 (m, 4H), 3.15-3.03 (m, 1H), 2.90-2.76 (m, 3H), 2.76-2.70 (m, 4H), 2.56-2.50 (m, 4H), 2.48 (s, 3H), 2.13-2.01 (m, 1H), 1.72-1.62 (m, 1H), 1.60-1.43 (m, 2H), 1.18-1.03 (m, 2H), 0.95-0.80 (m, 2H).

Example 49. 1-methyl-3-({[(3S)-1-(6-methylpyridin-3-yl)piperidin-3-yl][(2-methylpyridin-4-yl)methyl]amino}methyl)-7-(2-oxopiperazin-1-yl)-1,4-dihydroquinolin-4-one

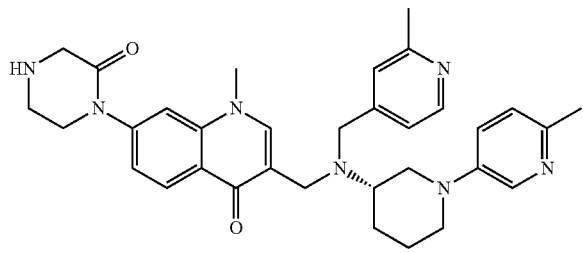 [SMILES: Cc1ccc(N2CCC[C@H](N(Cc3ccnc(C)c3)Cc3cn(C)c4cc(N5CCNCC5=O)ccc4c3=O)C2)cn1]

Preparation of tert-butyl 4-[1-methyl-3-({[(3S)-1-(6-methylpyridin-3-yl)piperidin-3-yl][(2-methylpyridin-4-yl)methyl]amino}methyl)-4-oxo-1,4-dihydroquinolin-7-yl]-3-oxopiperazine-1-carboxylate The title compound was synthesized according to Procedure 25a. The residue was purified by FCC (SiHP; DCM: MeOH 9:1). The obtained sample was dissolved in DCM and stirred with MPA scavenger for 10 min. The scavenger was filtered off and the filtrate was evaporated under reduced pressure to give the product (0.047 g, 0.068 mmol, yield 37%) as a beige powder. ESI-MS: 666.8 [M+H]⁺

¹H NMR (400 MHz, DMSO-d₆) δ 8.31-8.28 (m, 1H), 8.18 (d, J=8.7 Hz, 1H), 8.15 (d, J=3.0 Hz, 1H), 8.02 (s, 1H), 7.62 (d, J=2.0 Hz, 1H), 7.38 (dd, J=8.7, 1.8 Hz, 1H), 7.27-7.19 (m, 3H), 7.02 (d, J=8.5 Hz, 1H), 4.17-4.10 (m, 2H), 3.88-3.79 (m, 6H), 3.78-3.69 (m, 4H), 3.68-3.56 (m, 2H), 3.44-3.35 (m, 1H), 3.34-3.25 (m, 1H), 2.83-2.70 (m, 2H), 2.64-2.54 (m, 1H), 2.39 (s, 3H), 2.33 (s, 3H), 2.03-1.96 (m, 1H), 1.79-1.72 (m, 1H), 1.56-1.48 (m, 1H), 1.46 (s, 9H).

Preparation of 1-methyl-3-({[(3S)-1-(6-methylpyridin-3-yl)piperidin-3-yl][(2-methylpyridin-4-yl)methyl]amino}methyl)-7-(2-oxopiperazin-1-yl)-1,4-dihydroquinolin-4-one The title compound was synthesized according to Procedure 25b. The residue was purified by FCC (SiHP; DCM: MeOH 95:5) to give the product (0.023 g, 0.038 mmol, yield 56%) as an off-white powder. ESI-MS: 566.3 [M+H]⁺

¹H NMR (400 MHz, DMSO-d₆) δ 8.31-8.27 (m, 1H), 8.16 (d, J=8.7 Hz, 1H), 8.14 (d, J=3.1 Hz, 1H), 8.01 (s, 1H), 7.56 (d, J=1.9 Hz, 1H), 7.36 (dd, J=8.7, 1.8 Hz, 1H), 7.26-7.19 (m, 3H), 7.01 (d, J=8.5 Hz, 1H), 3.88-3.80 (m, 4H), 3.79-3.68 (m, 4H), 3.67-3.54 (m, 3H), 3.43 (s, 2H), 3.09-3.01 (m, 2H), 2.85-2.69 (m, 3H), 2.62-2.54 (m, 1H), 2.38 (s, 3H), 2.32 (s, 3H), 2.03-1.93 (m, 1H), 1.79-1.70 (m, 1H), 1.60-1.38 (m, 2H).

Example 50. 3-({[(3S)-1-(6-methylpyridin-3-yl)piperidin-3-yl][(2-methylpyridin-4-yl)methyl]amino}methyl)-1-(oxetan-3-yl)-1,4-dihydroquinolin-4-one

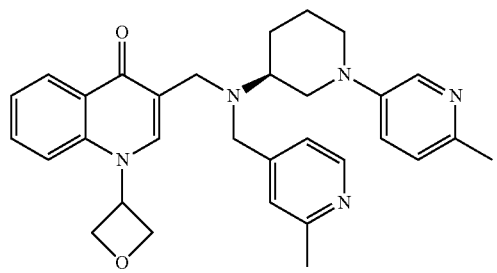 [SMILES: Cc1ccc(N2CCC[C@H](N(Cc3ccnc(C)c3)Cc3cn(C4COC4)c4ccccc4c3=O)C2)cn1]

Preparation of 1-(oxetan-3-yl)-4-oxo-1,4-dihydroquinoline-3-carbaldehyde

The title compound was synthesized according to Procedure 26a. The residue was purified by FCC (SiHP; DCM: MeOH 9:1) and re-purified by RP-FCC (SiC18; H₂O: MeCN) to give the product (0.037 g, 0.139 mmol, yield 21%) as a beige solid. ESI-MS: 230.1 [M+H]⁺

¹H NMR (400 MHz, DMSO-d₆) δ 10.20 (s, 1H), 8.47 (s, 1H), 8.34 (dd, J=8.0, 1.6 Hz, 1H), 7.83 (ddd, J=8.7, 7.1, 1.7 Hz, 1H), 7.60-7.55 (m, 1H), 7.51 (d, J=8.5 Hz, 1H), 5.82 (p, J=6.9 Hz, 1H), 5.13-5.06 (m, 2H), 5.00-4.94 (m, 2H).

Preparation of 3-({[(3S)-1-(6-methylpyridin-3-yl)piperidin-3-yl][(2-methylpyridin-4-yl)methyl]amino}methyl)-1-(oxetan-3-yl)-1,4-dihydroquinolin-4-one The title compound was synthesized according to Procedure 26b. The residue was purified by prep-HPLC to give the product (0.037 g, 0.073 mmol, yield 36%) as a white solid. ESI-MS: 510.3 [M+H]⁺

¹H NMR (400 MHz, Methanol-d₄) δ 8.38 (dd, J=8.2, 1.5 Hz, 1H), 8.21 (s, 1H), 8.20-8.18 (m, 1H), 8.10 (d, J=3.0 Hz, 1H), 7.77-7.71 (m, 1H), 7.47 (ddd, J=8.0, 7.0, 1.0 Hz, 1H), 7.39 (d, J=8.9 Hz, 1H), 7.36 (dd, J=8.6, 3.0 Hz, 1H), 7.32-7.29 (m, 1H), 7.29-7.25 (m, 1H), 7.12 (d, J=8.6 Hz, 1H), 5.80-5.72 (m, 1H), 5.20 (td, J=7.2, 2.5 Hz, 2H), 4.86 (t, J=6.7 Hz, 2H), 3.96-3.87 (m, 5H), 3.66-3.56 (m, 1H), 3.08-2.95 (m, 1H), 2.89 (t, J=11.1 Hz, 1H), 2.77-2.66 (m, 1H), 2.41 (s, 3H), 2.34 (s, 3H), 2.23-2.13 (m, 1H), 2.03-1.89 (m, 1H), 1.78-1.63 (m, 2H).

Example 51. 2-[3-({[(3S)-1-(6-Methylpyridin-3-yl)piperidin-3-yl][(2-methylpyridin-4-yl)methyl]amino}methyl)-4-oxo-1,4-dihydroquinolin-1-yl]acetic acid

Example 52. 1-cyclopropyl-7-{4,7-diazaspiro[2.5]octan-7-yl}-6-fluoro-3-({[(3S)-1-(6-methylpyridin-3-yl)piperidin-3-yl][(2-methylpyridin-4-yl)methyl]amino}methyl)-1,4-dihydroquinolin-4-one

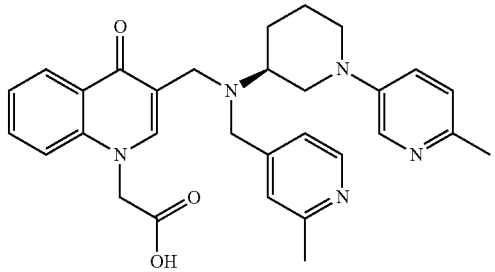 [SMILES: Cc1ccc(N2CCC[C@H](N(Cc3ccnc(C)c3)Cc3cn(CC(=O)O)c4ccccc4c3=O)C2)cn1]

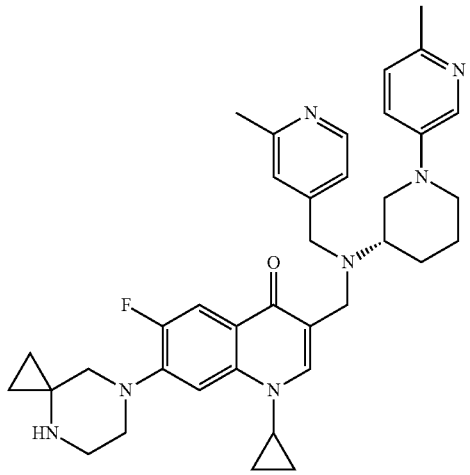 [SMILES: Cc1ccc(N2CCC[C@H](N(Cc3ccnc(C)c3)Cc3cn(C4CC4)c4cc(N5CCNC6(CC6)C5)c(F)cc4c3=O)C2)cn1]

Preparation of methyl 2-(3-formyl-4-oxo-1,4-dihydroquinolin-1-yl)acetate

The title compound was synthesized according to Procedure 27a. The residue was purified by FCC (SiHP; hexane:DCM:EtOAc) to afford the product (0.073 g, 0.294 mmol) as a white solid.

ESI-MS: 246.3 [M+H]$^+$ $^1$H NMR (300 MHz, DMSO-d$_6$) δ 10.21 (s, 1H), 8.66 (s, 1H), 8.31 (dd, J=8.0, 1.6 Hz, 1H), 7.81 (ddd, J=8.6, 7.1, 1.7 Hz, 1H), 7.63 (d, J=8.5 Hz, 1H), 7.55 (ddd, J=8.0, 7.1, 0.9 Hz, 1H), 5.43 (s, 2H), 3.72 (s, 3H).

Preparation of methyl 2-[3-({[(3S)-1-(6-methylpyridin-3-yl)piperidin-3-yl][(2-methylpyridin-4-yl)methyl]amino}methyl)-4-oxo-1,4-dihydroquinolin-1-yl]acetate The title compound was synthesized according to Procedure 27b. The residue was purified by FCC (SiHP; DCM:MeOH 9:1) to afford the product (0.043 g, 0.076 mmol, yield 26%) as a light yellow glass. ESI-MS: 526.7 [M+H]$^+$ Preparation of 2-[3-({[(3S)-1-(6-methylpyridin-3-yl)piperidin-3-yl][(2-methylpyridin-4-yl)methyl]amino}methyl)-4-oxo-1,4-dihydroquinolin-1-yl]acetic acid The title compound was synthesized according to Procedure 27c. The residue was purified by FCC (C18HP; H$_2$O:MeCN) to afford the product (0.030 g, 0.058 mmol, yield 71%) as an off-white solid. ESI-MS: 512.3 [M+H]$^+$ $^1$H NMR (400 MHz, Methanol-d$_4$) δ 8.33 (dd, J=8.2, 1.6 Hz, 1H), 8.21 (dd, J=5.1, 0.9 Hz, 1H), 8.10-8.01 (m, 2H), 7.70 (ddd, J=8.6, 6.9, 1.6 Hz, 1H), 7.53 (d, J=8.7 Hz, 1H), 7.44-7.33 (m, 2H), 7.33-7.27 (m, 2H), 7.11 (d, J=8.6 Hz, 1H), 4.78 (s, 2H), 3.94-3.76 (m, 5H), 3.65-3.55 (m, 1H), 2.99-2.80 (m, 2H), 2.75-2.62 (m, 1H), 2.40 (s, 6H), 2.20-2.09 (m, 1H), 1.94-1.83 (m, 1H), 1.71-1.55 (m, 2H).

Preparation of tert-butyl 7-[1-cyclopropyl-6-fluoro-3-({[(3S)-1-(6-methylpyridin-3-yl)piperidin-3-yl][(2-methylpyridin-4-yl)methyl]amino}methyl)-4-oxo-1,4-dihydroquinolin-7-yl]-4,7-diazaspiro[2.5]octane-4-carboxylate The title compound was synthesized following the approach outlined in Procedure 24 substituting piperazine with tert-butyl 4,7-diazaspiro[2.5]octane-4-carboxylate (2.09 eq.) and using 2.2 eq. of Cs$_2$CO$_3$. Stirring in DCM with MPA scavenger was used after the residue was purified by FCC (SiHP, DCM:MeOH). The product (0.087 g, 0.120 mmol, yield 57%) was isolated as a yellow oil.

AP-MS: 722.9 [M+H]$^+$

Preparation of 1-cyclopropyl-7-{4,7-diazaspiro[2.5]octan-7-yl}-6-fluoro-3-({[(3S)-1-(6-methylpyridin-3-yl)piperidin-3-yl][(2-methylpyridin-4-yl)methyl]amino}methyl)-1,4-dihydroquinolin-4-one The title compound was synthesized according to Procedure 28. The residue was purified by FCC (SiHP, DCM:MeOH 9:1) to give the product (0.034 g, 0.055 mmol, yield 45%) as a white solid.

ESI-MS: 622.7 [M+H]$^+$ $^1$H NMR (400 MHz, DMSO-d$_6$) δ 8.31-8.27 (m, 1H), 8.13 (d, J=3.0 Hz, 1H), 7.81 (s, 1H), 7.69 (d, J=13.7 Hz, 1H), 7.28 (d, J=7.5 Hz, 1H), 7.24-7.20 (m, 2H), 7.20-7.15 (m, 1H), 7.04-7.00 (m, 1H), 3.83-3.56 (m, 6H), 3.54-3.45 (m, 1H), 3.16-3.11 (m, 2H), 2.98 (d, J=24.0 Hz, 4H), 2.75 (d, J=7.8 Hz, 2H), 2.63-2.54 (m, 1H), 2.38 (s, 3H), 2.33 (s, 3H), 2.01-1.93 (m, 1H), 1.81-1.72 (m, 1H), 1.59-1.44 (m, 2H), 1.27-1.16 (m, 3H), 0.94-0.82 (m, 2H), 0.54-0.50 (m, 4H).

The product was converted into a hydrochloric acid salt. ESI-MS: 622.4 [M+H]$^+$. Product as a white solid.

$^1$H NMR (400 MHz, DMSO-d$_6$) δ 8.29 (d, J=5.0 Hz, 1H), 8.13 (d, J=3.0 Hz, 1H), 7.82 (s, 1H), 7.71 (d, J=13.6 Hz, 1H), 7.30 (d, J=7.5 Hz, 1H), 7.24-7.20 (m, 2H), 7.20-7.15 (m, 1H), 7.02 (d, J=8.5 Hz, 1H), 3.83-3.72 (m, 3H), 3.62-3.56 (m, 3H), 3.55-3.46 (m, 1H), 3.26-3.18 (m, 2H), 3.12-3.03 (m, 4H), 2.81-2.70 (m, 2H), 2.64-2.55 (m, 1H), 2.38 (s, 3H), 2.33 (s, 4H), 2.02-1.93 (m, 1H), 1.80-1.72 (m, 1H), 1.59-1.43 (m, 2H), 1.28-1.18 (m, 2H), 0.93-0.83 (m, 2H), 0.71-0.59 (m, 4H).

Example 53. 1-methyl-3-({[(3S)-1-(5-methyl-1,3,4-oxadiazol-2-yl)piperidin-3-yl][(2-methylpyridin-4-yl)methyl]amino}methyl)-1,4-dihydroquinolin-4-one

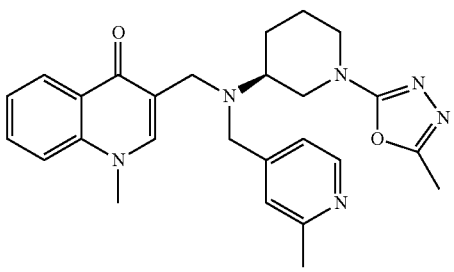 [SMILES: Cc1cc(CN(Cc2cn(C)c3ccccc3c2=O)[C@H]2CCCN(c3nnc(C)o3)C2)ccn1]

Preparation of tert-butyl(3S)-3-{[(1-methyl-4-oxo-1,4-dihydroquinolin-3-yl)methyl]amino}piperidine-1-carboxylate The title compound was synthesized according to Procedure 29a. The residue was purified by FCC (Al$_2$O$_3$; DCM:MeOH 9:1) to give the product (5.6 g, 15.1 mmol, yield 94%) as a yellow solid.
AP-MS: 372.4 [M+H]$^+$ Preparation of tert-butyl(3S)-3-{[(1-methyl-4-oxo-1,4-dihydroquinolin-3-yl)methyl][(2-methylpyridin-4-yl)methyl]amino}piperidine-1-carboxylate The title compound was synthesized according to Procedure 29b. The residue was purified by FCC (SiHP, DCM/MeOH) to give the product (2.4 g, 5.0 mmol, yield 62%) as a yellow oil.
ESI-MS: 477.6 [M+H]$^+$ Preparation of 1-methyl-3-({[(2-methylpyridin-4-yl)methyl][(3S)-piperidin-3-yl]amino}methyl)-1,4-dihydroquinolin-4-one The title compound was synthesized according to Procedure 29c. The product (1.6 g, 4.2 mmol, yield 83%) as a yellow oil.
ESI-MS: 377.5 [M+H]$^+$
$^1$H NMR (400 MHz, DMSO-d6) δ 8.29-8.23 (m, 1H), 8.18 (dd, J=8.1, 1.6 Hz, 1H), 7.93 (s, 1H), 7.71 (ddd, J=8.6, 6.9, 1.7 Hz, 1H), 7.63-7.59 (m, 1H), 7.36 (ddd, J=8.0, 6.9, 1.0 Hz, 1H), 7.24-7.15 (m, 2H), 3.82 (s, 3H), 3.66 (s, 2H), 3.63-3.49 (m, 5H), 3.11-3.00 (m, 1H), 2.80-2.72 (m, 1H), 2.35 (s, 3H), 2.34-2.24 (m, 1H), 2.01-1.88 (m, 1H), 1.63 (d, J=12.3 Hz, 1H), 1.51-1.36 (m, 1H), 1.33-1.18 (m, 1H).

Preparation 1-methyl-3-({[(3S)-1-(5-methyl-1,3,4-oxadiazol-2-yl)piperidin-3-yl][(2-methylpyridin-4-yl)methyl]amino}methyl)-1,4-dihydroquinolin-4-one The title compound was synthesized following the approach outlined in Procedure 5 substituting 3-({[(2-methoxypyridin-4-yl)methyl](piperidin-3-yl)amino}methyl)-1-methyl-1,4-dihydroquinolin-4-one with 1-methyl-3-({[(2-methylpyridin-4-yl)methyl][(3$_S$)-piperidin-3-yl]amino}methyl)-1,4-dihydroquinolin-4-one, 3-bromopyridazine with 2-bromo-5-methyl-1,3,4-oxadiazole (1 eq.) and shortening time of the reaction to overnight heating. After filtration through celite, MPA scavenger was added and the resulting mixture was stirred for 15 min. Subsequently, the mixture was filtered and evaporated. The residue was purified by FCC (SiHP; DCM:MeOH 9:1) to give the product (0.025 g, 0.06 mmol, yield 41%) as a white powder. ESI-MS: 459.2 [M+H]$^+$ $^1$H NMR (400 MHz, DMSO-d6) δ 8.27 (d, J=5.0 Hz, 1H), 8.20 (dd, J=8.0, 1.6 Hz, 1H), 7.98 (s, 1H), 7.75-7.70 (m, 1H), 7.62 (d, J=8.6 Hz, 1H), 7.38 (ddd, J=8.0, 6.9, 1.0 Hz, 1H), 7.21 (s, 1H), 7.19 (dd, J=5.1, 1.5 Hz, 1H), 3.96-3.90 (m, 1H), 3.83 (s, 3H), 3.79-3.56 (m, 5H), 3.15-3.07 (m, 1H), 2.96-2.87 (m, 1H), 2.77-2.69 (m, 1H), 2.36 (s, 3H), 2.28 (s, 3H), 2.05-1.97 (m, 1H), 1.82-1.74 (m, 1H), 1.67-1.55 (m, 1H), 1.50-1.38 (m, 1H).

Example 54. 3-({[(3S)-1-(2-chloropyrimidin-4-yl)piperidin-3-yl][(2-methylpyridin-4-yl)methyl]amino}methyl)-1-methyl-1,4-dihydroquinolin-4-one

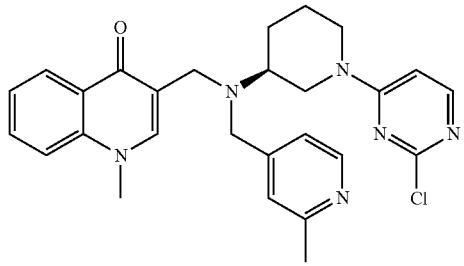 [SMILES: Cc1cc(CN(Cc2cn(C)c3ccccc3c2=O)[C@H]2CCCN(c3ccnc(Cl)n3)C2)ccn1]

Preparation of 3-({[(3S)-1-(2-chloropyrimidin-4-yl)piperidin-3-yl][(2-methylpyridin-4-yl)methyl]amino}methyl)-1-methyl-1,4-dihydroquinolin-4-one The title compound was synthesized according to Procedure 30. The residue was purified by FCC (SiHP: DCM/MeOH) to give the product (0.076 g, 0.1 mmol, yield 48%) as a yellowish solid. 0.026 g of the sample was re-purified by prep-HPLC affording formic acid salt of the compound (0.013 g, 0.03 mmol, yield 8%) as a yellowish solid.
ESI-MS: 489.2 [M+H]$^+$
$^1$H NMR (400 MHz, DMSO-d6) δ 8.28 (d, J=5.0 Hz, 1H), 8.19 (dd, J=8.1, 1.6 Hz, 1H), 8.15 (s, 1H), 8.03-7.97 (m, 2H), 7.71 (ddd, J=8.6, 6.9, 1.7 Hz, 1H), 7.64-7.60 (m, 1H), 7.37 (ddd, J=8.0, 6.9, 1.0 Hz, 1H), 7.25-7.19 (m, 2H), 6.89-6.83 (m, 1H), 4.63-4.11 (m, 2H), 3.84 (s, 3H), 3.82-3.71 (m, 2H), 3.69-3.57 (m, 2H), 3.14-3.03 (m, 1H), 2.91-2.80 (m, 1H), 2.61-2.54 (m, 1H), 2.36 (s, 3H), 2.02-1.95 (m, 1H), 1.80-1.65 (m, 2H), 1.37-1.22 (m, 1H).

Example 55. 1-methyl-3-({[(3S)-1-(pyridin-3-yl)piperidin-3-yl][(1,2-thiazol-5-yl)methyl]amino}methyl)-1,4-dihydroquinolin-4-one

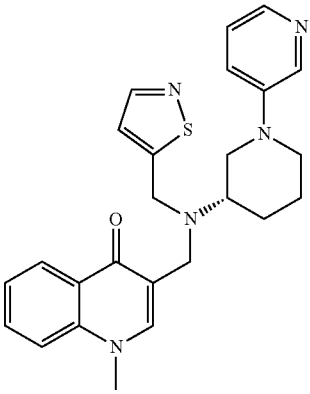 [SMILES: Cn1cc(CN(Cc2ccns2)[C@H]2CCCN(c3cccnc3)C2)c(=O)c2ccccc21]

Preparation of 1-methyl-3-({[(3S)-1-(pyridin-3-yl)piperidin-3-yl][(1,2-thiazol-5-yl)methyl]amino}methyl)-1,4-dihydroquinolin-4-one The title compound was synthesized following the approach outlined in Procedure 18 substituting 2,6-dimethylpyridine-4-carbaldehyde with 1,2-thiazole-5-carbaldehyde (1.2 eq.). The residue was purified by prep-HPLC to give the product (0.032 g, 0.07 mmol, yield 50%) as a beige solid.

ESI-MS: 446.2 [M+H]$^+$ $^1$H NMR (300 MHz, Methanol-d4) δ 8.39-8.33 (m, 1H), 8.31 (d, J=1.7 Hz, 1H), 8.20 (d, J=3.0 Hz, 1H), 8.18 (s, 1H), 7.89 (dd, J=4.6, 1.3 Hz, 1H), 7.78 (ddd, J=8.5, 6.8, 1.6 Hz, 1H), 7.74-7.67 (m, 1H), 7.47 (ddd, J=8.1, 6.8, 1.2 Hz, 1H), 7.38 (ddd, J=8.6, 3.0, 1.3 Hz, 1H), 7.25-7.16 (m, 2H), 4.27-4.15 (m, 2H), 4.02-3.81 (m, 6H), 3.75-3.59 (m, 1H), 3.01-2.85 (m, 2H), 2.81-2.66 (m, 1H), 2.20-2.08 (m, 1H), 1.96-1.83 (m, 1H), 1.76-1.53 (m, 2H).

Example 56. 7-chloro-1-cyclopropyl-3-({[(3S)-1-(6-methylpyridin-3-yl)piperidin-3-yl][(2-methylpyridin-4-yl)methyl]amino}methyl)-1,4-dihydro-1,6-naphthyridin-4-one

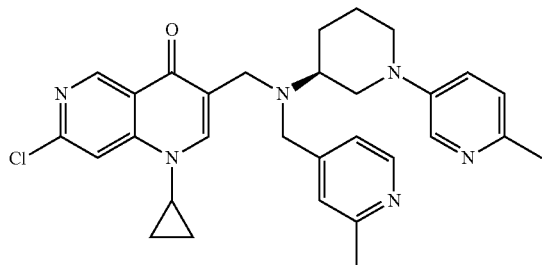 [SMILES: Cc1ccc(N2CCC[C@H](N(Cc3ccnc(C)c3)Cc3cn(C4CC4)c4cc(Cl)ncc4c3=O)C2)cn1]

Preparation of 4,6-dichloropyridine-3-carbonyl chloride

The title compound was synthesized according to Procedure 31a. The product was obtained (1.1 g, 5.2 mmol, yield 99%) as a yellow oil and was used in the next step without further purification.

Preparation of ethyl 7-chloro-1-cyclopropyl-4-oxo-1,4-dihydro-1,6-naphthyridine-3-carboxylate The title compound was synthesized according to Procedure 31b. The residue was purified by FCC (SiHP; Hex:AcOEt 0-100%) to give the product (0.38 g, 1.3 mmol, yield 25%) as a yellow solid.

ESI-MS: 293.8 [M+H]$^+$ $^1$H NMR (300 MHz, DMSO-d6) δ 9.07 (s, 1H), 8.50 (s, 1H), 8.01 (s, 1H), 4.24 (q, J=7.1 Hz, 2H), 3.62 (tt, J=7.2, 3.9 Hz, 1H), 1.32-1.21 (m, 5H), 1.15-1.08 (m, 2H).

Preparation of 7-chloro-1-cyclopropyl-4-oxo-1,4-dihydro-1,6-naphthyridine-3-carboxylic acid The title compound was synthesized according to Procedure 31c. The product (0.14 g, 0.5 mmol, yield 99%) was obtained as a white solid.

ESI-MS: 265.8 [M+H]$^+$

Preparation of 7-chloro-1-cyclopropyl-1,2,3,4-tetrahydro-1,6-naphthyridin-4-one

The title compound was synthesized according to Procedure 31d. The residue was purified by FCC (SiHP; Hex:AcOEt 4:1) to give the product (0.05 g, 0.2 mmol, yield 42%) as a white solid.

ESI-MS: 223.0 [M+H]$^+$

Preparation of 7-chloro-1-cyclopropyl-4-oxo-1,2,3,4-tetrahydro-1,6-naphthyridine-3-carbaldehyde The title compound was synthesized according to Procedure 31e. The crude product (0.053 g, 0.2 mmol, yield 94%) was obtained as a yellow solid and was used directly in the next step.

ESI-MS: 250.9 [M+H]$^+$

Preparation of 7-chloro-1-cyclopropyl-4-oxo-1,4-dihydro-1,6-naphthyridine-3-carbaldehyde The title compound was synthesized according to Procedure 31f. The residue was purified by FCC (SiHP; DCM:MeOH 95:5) to give the product (0.036 g, 0.2 mmol, yield 68%) as a light yellow solid.

ESI-MS: 249.9 [M+H]$^+$

Preparation of 7-chloro-1-cyclopropyl-3-({[(3S)-1-(6-methylpyridin-3-yl)piperidin-3-yl][(2-methylpyridin-4-yl)methyl]amino}methyl)-1,4-dihydro-1,6-naphthyridin-4-one The title compound was synthesized following the approach outlined in Procedure 15 substituting (3S)—N-[(2-methylpyridin-4-yl)methyl]-1-(pyridin-3-yl)piperidin-3-amine with (3S)-1-(6-methylpyridin-3-yl)-N-[(2-methylpyridin-4-yl)methyl]piperidin-3-amine and 7-chloro-1-cyclopropyl-6-fluoro-4-oxo-1,4-dihydroquinoline-3-carbaldehyde with 7-chloro-1-cyclopropyl-4-oxo-1,4- dihydro-1,6-naphthyridine-3-carbaldehyde. Time of the first and second stage of the procedure was expanded to over-weekend and 24 hours stirring respectively. After dilution of with DCM, the reaction mixture was washed with NaHCO₃, brine, dried over anh. Na₂SO₄ and evaporated. The residue was purified by FCC (SiHP; DCM:MeOH 9:1) and re-purified by FCC (SiHP; AcOEt:MeOH 9:1) give the product (0.04 g, 0.08 mmol, yield 34%) as a yellow solid.

AP-MS: 529.7 [M+H]⁺

The product was converted into a hydrochloric acid salt. Product as a yellow solid.

ESI-MS: 529.2 [M+H]⁺

¹H NMR (300 MHz, Methanol-d4) δ 9.14 (s, 1H), 8.26 (d, J=5.6 Hz, 1H), 8.18 (d, J=3.0 Hz, 1H), 7.98 (s, 1H), 7.95-7.85 (m, 2H), 7.57-7.47 (m, 2H), 7.47-7.41 (m, 1H), 4.11-4.02 (m, 1H), 3.97 (s, 2H), 3.91-3.67 (m, 3H), 3.51-3.38 (m, 1H), 3.07-2.76 (m, 3H), 2.57 (s, 3H), 2.46 (s, 3H), 2.21-2.10 (m, 1H), 1.99-1.92 (m, 1H), 1.77-1.60 (m, 2H), 1.37-1.24 (m, 2H), 1.02-0.90 (m, 2H).

Example 57. 7-(cyclohex-1-en-1-yl)-1-cyclopropyl-6-fluoro-3-({[(3S)-1-(6-methylpyridin-3-yl)piperidin-3-yl][(2-methylpyridin-4-yl)methyl]amino}methyl)-1,4-dihydroquinolin-4-one

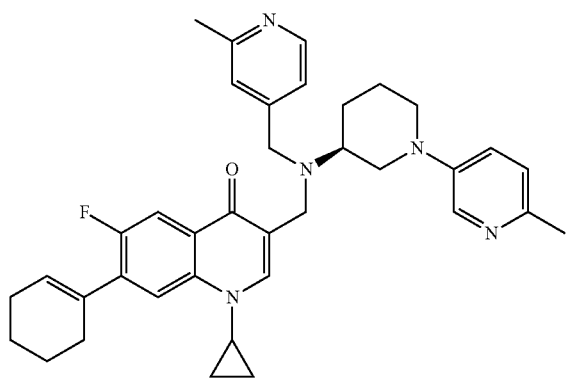 [SMILES: Cc1ccc(N2CCC[C@H](N(Cc3ccnc(C)c3)Cc3cn(C4CC4)c4cc(C5=CCCCC5)c(F)cc4c3=O)C2)cn1]

The title compound was synthesized according to Procedure 32. The filtrate was evaporated with silica and purified by FCC (SiHP deactivated with NH3:DCM; DCM:MeOH 8:2) and re-purified by prep-HPLC to give the product (0.031 g, 0.05 mmol, yield 47%) as a white solid.

ESI-MS: 592.7 [M+H]⁺

The product was converted into a hydrochloric acid salt. Product as a pale yellow solid.

ESI-MS: 592.9 [M+H]⁺

¹H NMR (400 MHz, DMSO-d6) δ 8.29 (d, J=5.1 Hz, 1H), 8.14 (d, J=3.0 Hz, 1H), 7.89 (s, 1H), 7.82 (d, J=6.4 Hz, 1H), 7.76 (d, J=11.3 Hz, 1H), 7.31 (dd, J=8.6, 3.0 Hz, 1H), 7.24 (s, 1H), 7.20 (d, J=5.1 Hz, 1H), 7.08 (d, J=8.6 Hz, 1H), 6.15-6.10 (m, 1H), 3.88-3.72 (m, 3H), 3.68-3.58 (m, 3H), 3.57-3.51 (m, 1H), 2.85-2.69 (m, 2H), 2.66-2.57 (m, 1H), 2.43-2.38 (m, 2H), 2.36 (s, 3H), 2.34 (s, 3H), 2.27-2.18 (m, 2H), 2.07-1.88 (m, 1H), 1.82-1.70 (m, 3H), 1.70-1.62 (m, 2H), 1.61-1.39 (m, 2H), 1.25-1.17 (m, 2H), 0.95-0.84 (m, 2H).

Example 58. 3-({[(3S)-1-(6-methylpyridin-3-yl)piperidin-3-yl][(2-methylpyridin-4-yl)methyl]amino}methyl)-1,4-dihydroquinolin-4-one

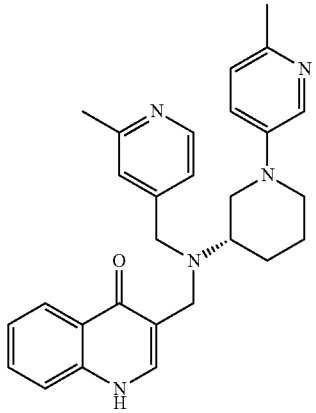 [SMILES: Cc1ccc(N2CCC[C@H](N(Cc3ccnc(C)c3)Cc3c[nH]c4ccccc4c3=O)C2)cn1]

Preparation of 3-({[(3S)-1-(6-methylpyridin-3-yl)piperidin-3-yl][(2-methylpyridin-4-yl)methyl]amino}methyl)-1,4-dihydroquinolin-4-one The title compound was synthesized according to Procedure 33. The residue was suspended in water and freeze-dried to give the product (0.08 g, 0.2 mmol, yield 14%) as a beige powder.

ESI-MS: 454.2 [M+H]⁺

¹H NMR (400 MHz, DMSO-d6) δ 11.68 (s, 1H), 8.30 (d, J=5.1 Hz, 1H), 8.12 (d, J=3.1 Hz, 1H), 8.11-8.09 (m, 1H), 7.94 (s, 1H), 7.60 (ddd, J=8.5, 6.9, 1.6 Hz, 1H), 7.50 (d, J=8.3 Hz, 1H), 7.32-7.17 (m, 4H), 7.01 (d, J=8.5 Hz, 1H), 3.84-3.70 (m, 3H), 3.66-3.54 (m, 3H), 2.79-2.69 (m, 2H), 2.60-2.55 (m, 1H), 2.39 (s, 3H), 2.32 (s, 3H), 2.00-1.92 (m, 1H), 1.80-1.71 (m, 1H), 1.59-1.39 (m, 2H).

Example 59. 1-cyclopropyl-6-fluoro-7-hydroxy-3-({[(3S)-1-(6-methylpyridin-3-yl)piperidin-3-yl][(2-methylpyridin-4-yl)methyl]amino}methyl)-1,4-dihydroquinolin-4-one

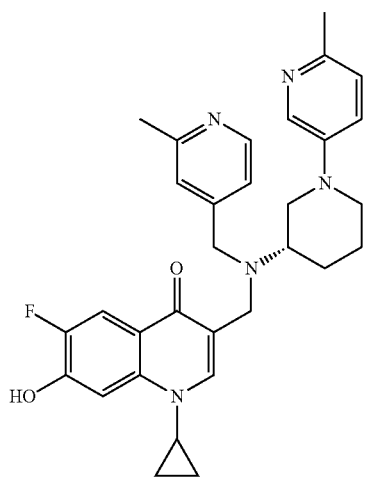 [SMILES: Cc1ccc(N2CCC[C@H](N(Cc3ccnc(C)c3)Cc3cn(C4CC4)c4cc(O)c(F)cc4c3=O)C2)cn1]

Preparation of 1-cyclopropyl-6-fluoro-7-hydroxy-3-({[(3S)-1-(6-methylpyridin-3-yl)piperidin-3-yl][(2-methylpyridin-4-yl)methyl]amino}methyl)-1,4-dihydroquinolin-4-one The title compound was synthesized according to Procedure 34. The residue was purified by FCC (SiHP; DCM: MeOH 9:1) the give the product (0.06 g, 0.1 mmol, yield 57%) as a beige solid.
ESI-MS: 528.3 [M+H]+
1H NMR (300 MHz, DMSO-d6) δ 10.97 (s, 1H), 8.28 (d, J=5.0 Hz, 1H), 8.13 (d, J=2.9 Hz, 1H), 7.78 (s, 1H), 7.74 (d, J=11.5 Hz, 1H), 7.44 (d, J=7.5 Hz, 1H), 7.28-7.12 (m, 3H), 7.02 (d, J=8.5 Hz, 1H), 3.89-3.50 (m, 6H), 3.47-3.37 (m, 1H), 2.83-2.65 (m, 2H), 2.64-2.54 (m, 1H), 2.37 (s, 3H), 2.32 (s, 3H), 2.04-1.90 (m, 1H), 1.83-1.67 (m, 1H), 1.60-1.38 (m, 2H), 1.23-1.08 (m, 2H), 0.95-0.81 (m, 2H).

Example 60. 8-bromo-1-methyl-3-({[(3S)-1-(6-methylpyridin-3-yl)piperidin-3-yl][(2-methylpyridin-4-yl)methyl]amino}methyl)-1,4-dihydroquinolin-4-one

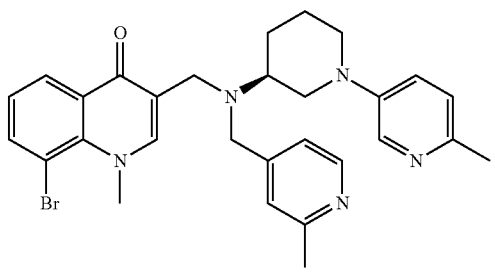 [SMILES: Cc1ccc(N2CCC[C@H](N(Cc3ccnc(C)c3)Cc3cn(C)c4c(Br)cccc4c3=O)C2)cn1]

Preparation of 3-[(2-bromophenyl)amino]propanoic acid

The title compound was synthesized according to Procedure 35a. The crude product (2.7 g, 11.1 mmol, yield 95%) was obtained as a yellow solid which was used in the next step without further purification.

Preparation of 8-bromo-1,2,3,4-tetrahydroquinolin-4-one

The title compound was synthesized according to Procedure 35b. The residue was purified by FCC (SiHP; Hex: AcOEt 8:2) to give the product (0.52 g, 2.3 mmol, yield 21%) as a yellow sticky solid.
ESI-MS: 225.9 [M+H]+
1H NMR (300 MHz, Chloroform-d) δ 7.82 (dd, J=7.9, 1.5 Hz, 1H), 7.56 (dd, J=7.9, 1.5 Hz, 1H), 6.62 (t, J=7.9 Hz, 1H), 4.99 (s, 1H), 3.66 (td, J=7.1, 2.2 Hz, 2H), 2.79-2.64 (m, 2H).

Preparation of 8-bromo-1-methyl-1,2,3,4-tetrahydroquinolin-4-one

The title compound was synthesized according to Procedure 35c. The residue was purified by FCC (SiHP; Hex: AcOEt 50-80%) to give the product (0.1 g, 0.4 mmol, yield 25%) as a yellow oil.
ESI-MS: 239.9 [M+H]+

Preparation of 8-bromo-1-methyl-4-oxo-1,4-dihydroquinoline-3-carbaldehyde

The title compound was synthesized according to Procedure 35d. The residue was purified by FCC (SiHP; DCM: MeOH 95:5) to give the product (0.03 g, 0.1 mmol, yield 23%) as a brown solid.
ESI-MS: 265.9 [M+H]+

Preparation of 8-bromo-1-methyl-3-({[(3S)-1-(6-methylpyridin-3-yl)piperidin-3-yl][(2-methylpyridin-4-yl)methyl]amino}methyl)-1,4-dihydroquinolin-4-one The title compound was synthesized according to Procedure 35e. The residue was purified by FCC (SiHP; DCM: MeOH 93:7) followed by RP-FCC (Si—C18; H2O/ACN) to give the product (0.012 g, 0.02 mmol, yield 9%) as a colorless oil.
ESI-MS: 546.3 [M+H]+
The product was converted into a hydrochloric acid salt. Product as a yellow solid.
ESI-MS: 547.6 [M+H]+
1H NMR (400 MHz, Methanol-d4) δ 8.65-8.57 (m, 1H), 8.41 (d, J=3.0 Hz, 1H), 8.38-8.33 (m, 1H), 8.31 (dd, J=8.0, 1.6 Hz, 1H), 8.26-8.22 (m, 1H), 8.22-8.17 (m, 2H), 8.15 (dd, J=7.6, 1.6 Hz, 1H), 7.70 (d, J=9.1 Hz, 1H), 7.44-7.29 (m, 1H), 4.81 (s, 2H), 4.67-4.57 (m, 1H), 4.57-4.41 (m, 2H), 4.31 (s, 3H), 3.92-3.81 (m, 1H), 3.73-3.57 (m, 1H), 3.52-3.40 (m, 1H), 3.11-2.95 (m, 1H), 2.69 (s, 3H), 2.64 (s, 3H), 2.58-2.48 (m, 1H), 2.17-2.00 (m, 2H), 1.89-1.69 (m, 1H).

Example 61. 7-chloro-6-fluoro-3-({[(3S)-1-(6-methylpyridin-3-yl)piperidin-3-yl][(2-methylpyridin-4-yl)methyl]amino}methyl)-1-(propan-2-yl)-1,4-dihydro-1,8-naphthyridin-4-one

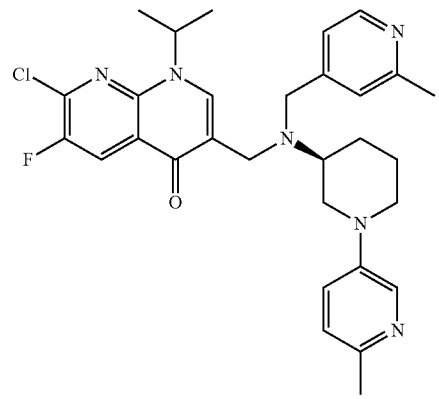 [SMILES: Cc1ccc(N2CCC[C@H](N(Cc3ccnc(C)c3)Cc3cn(C(C)C)c4nc(Cl)c(F)cc4c3=O)C2)cn1]

Preparation of ethyl 2-(2,6-dichloro-5-fluoropyridine-3-carbonyl)-3-(dimethylamino)prop-2-enoate The title compound was synthesized according to Procedure 36a. The residue was purified by FCC (SiHP; Hex/AcOEt) to give the product (2.8 g, 8.4 mmol, yield 32%) as an orange oil.
ESI-MS: 335.0 [M+H]+
1H NMR (400 MHz, DMSO-d6) δ 8.04 (d, J=7.9 Hz, 1H), 7.95 (s, 1H), 3.91 (q, J=7.1 Hz, 2H), 3.39 (s, 3H), 2.93 (s, 3H), 0.94 (t, J=7.1 Hz, 3H).

Preparation of ethyl 2-(2,6-dichloro-5-fluoropyridine-3-carbonyl)-3-[(propan-2-yl)amino]prop-2-enoate The title compound was synthesized according to Procedure 36b. The crude product (1.2 g, 3.4 mmol, yield 99%) was obtained as an orange oil and was used in next step without further purification.

Preparation of ethyl 7-chloro-6-fluoro-4-oxo-1-(propan-2-yl)-1,4-dihydro-1,8-naphthyridine-3-carboxylate The title compound was synthesized according to Procedure 36c. The product (0.8 g, 2.6 mmol) was obtained as an off-white solid.

ESI-MS: 313.9 [M+H]$^+$ $^1$H NMR (400 MHz, DMSO-d6) δ 8.71 (s, 1H), 8.48 (d, J=7.9 Hz, 1H), 5.47 (hept, J=6.5 Hz, 1H), 4.26 (q, J=7.1 Hz, 2H), 1.50 (d, J=6.8 Hz, 6H), 1.29 (t, J=7.1 Hz, 3H).

Preparation of 7-chloro-6-fluoro-4-oxo-1-(propan-2-yl)-1,4-dihydro-1,8-naphthyridine-3-carboxylic acid The title compound was synthesized according to Procedure 36d. The product (0.67 g, 0.2 mmol, yield 90%) was obtained as an off-white solid and was used in the next step without further purification.

$^1$H NMR (400 MHz, DMSO-d6) δ 14.40 (s, 1H), 9.01 (s, 1H), 8.73 (d, J=7.6 Hz, 1H), 5.61 (hept, J=6.4 Hz, 1H), 1.56 (d, J=6.7 Hz, 6H).

Preparation of 7-chloro-6-fluoro-1-(propan-2-yl)-1,2,3,4-tetrahydro-1,8-naphthyridin-4-one and 6-fluoro-7-methoxy-1-(propan-2-yl)-1,2,3,4-tetrahydro-1,8-naphthyridin-4-one The title compound was synthesized according to Procedure 36e. The residue was purified by FCC (SiHP; Hex: AcOEt 1:1) to give the product (0.46 g, 0.1 mmol, yield 81%) as a yellow solid.

ESI-MS: 243.1 [M+H]$^+$ $^1$H NMR (400 MHz, DMSO-d6) δ 7.88 (d, J=8.0 Hz, 1H), 4.88 (hept, J=6.7 Hz, 1H), 3.52-3.44 (m, 2H), 2.67-2.59 (m, 2H), 1.17 (d, J=6.8 Hz, 7H).

and 6-fluoro-7-methoxy-1-(propan-2-yl)-1,2,3,4-tetrahydro-1,8-naphthyridin-4-one (0.074 g, 0.02 mmol, yield 13%) as a yellow solid.

ESI-MS: 239.3 [M+H]$^+$ $^1$H NMR (400 MHz, DMSO-d6) δ 7.66 (d, J=10.3 Hz, 1H), 4.99-4.88 (m, 1H), 3.96 (s, 3H), 3.46-3.39 (m, 2H), 2.55-2.51 (m, 2H), 1.18 (d, J=6.8 Hz, 6H).

Preparation of 7-chloro-6-fluoro-4-oxo-1-(propan-2-yl)-1,2,3,4-tetrahydro-1,8-naphthyridine-3-carbaldehyde and 7-chloro-6-fluoro-4-oxo-1-(propan-2-yl)-1,4-dihydro-1,8-naphthyridine-3-carbaldehyde The title compound was synthesized according to Procedure 36f. The residue was purified by FCC (SiHP; DCM: AcOEt 9:1) to the product (0.29 g, 1.0 mmol, yield 57%) as a yellow solid.

AP-MS: 269.0 [M+H]$^+$ $^1$H NMR (400 MHz, DMSO-d6) δ 10.14 (s, 1H), 8.68 (s, 1H), 8.58 (d, J=7.7 Hz, 1H), 5.51 (hept, J=6.7 Hz, 1H), 1.52 (d, J=6.8 Hz, 6H).

Preparation of 7-chloro-6-fluoro-3-({[(3S)-1-(6-methylpyridin-3-yl)piperidin-3-yl][(2-methylpyridin-4-yl)methyl]amino}methyl)-1-(propan-2-yl)-1,4-dihydro-1,8-naphthyridin-4-one The title compound was synthesized according to Procedure 36g. The residue was purified by FCC (SiHP; DCM: MeOH 9:1). Product was re-purified by FCC (SiHP; DCM/MeOH/NH$_3$) and RP-FCC (Si—C18; H$_2$O/ACN) to give the product (0.40 g, 0.7 mmol, yield 70%) as a white solid.

ESI-MS: 549.4 [M+H]$^+$ $^1$H NMR (400 MHz, Methanol-d4) δ 8.42-8.34 (m, 1H), 8.24-8.15 (m, 2H), 8.06 (d, J=3.0 Hz, 1H), 7.34 (dd, J=8.6, 3.0 Hz, 1H), 7.30 (s, 1H), 7.27-7.22 (m, 1H), 7.11 (d, J=8.6 Hz, 1H), 5.75-5.59 (m, 1H), 3.96-3.76 (m, 5H), 3.64-3.53 (m, 1H), 3.02-2.92 (m, 1H), 2.90-2.82 (m, 1H), 2.77-2.64 (m, 1H), 2.48-2.35 (m, 6H), 2.22-2.07 (m, 1H), 2.00-1.85 (m, 1H), 1.77-1.57 (m, 2H), 1.53-1.36 (m, 6H).

Example 62. 6-fluoro-7-methoxy-3-({[(3S)-1-(6-methylpyridin-3-yl)piperidin-3-yl][(2-methylpyridin-4-yl)methyl]amino}methyl)-1-(propan-2-yl)-1,4-dihydro-1,8-naphthyridin-4-one

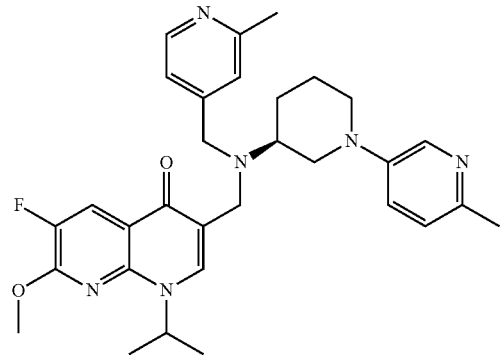 [SMILES: COc1nc2c(cc1F)c(=O)c(CN(Cc1ccnc(C)c1)[C@H]1CCCN(c3ccc(C)nc3)C1)cn2C(C)C]

Preparation of 6-fluoro-7-methoxy-4-oxo-1-(propan-2-yl)-1,4-dihydro-1,8-naphthyridine-3-carbaldehyde The title compound was synthesized following the approach outlined in Procedure 36f substituting 7-Chloro-6-fluoro-1-(propan-2-yl)-1,2,3,4-tetrahydro-1,8-naphthyridin-4-one with 6-fluoro-7-methoxy-1-(propan-2-yl)-1,2,3,4-tetrahydro-1,8-naphthyridin-4-one and using 6.1 eq. of MnO$_2$.

The residue was purified by FCC (SiHP; DCM:MeOH 9:1) to give the product (0.09 g, 0.3 mmol) as a yellow solid.

ESI-MS: 265.4 [M+H]$^+$ $^1$H NMR (400 MHz, DMSO-d6) δ 10.15 (s, 1H), 8.57 (s, 1H), 8.28 (d, J=9.8 Hz, 1H), 5.59-5.48 (m, 1H), 4.13 (s, 3H), 1.54 (d, J=6.8 Hz, 6H).

Preparation of 6-fluoro-7-methoxy-3-({[(3S)-1-(6-methylpyridin-3-yl)piperidin-3-yl][(2-methylpyridin-4-yl)methyl]amino}methyl)-1-(propan-2-yl)-1,4-dihydro-1,8-naphthyridin-4-one The title compound was synthesized following the approach outlined in Procedure 36g substituting 7-chloro- 6-fluoro-4-oxo-1-(propan-2-yl)-1,4-dihydro-1,8-naphthyridine-3-carbaldehyde with 6-fluoro-7-methoxy-4-oxo-1-(propan-2-yl)-1,4-dihydro-1,8-naphthyridine-3-carbaldehyde. The residue was purified by FCC (SiHP; DCM:MeOH 9:1) re-purified by prep-HPLC to give the product (0.022 g, 0.04 mmol, yield 12%) as a white solid.

ESI-MS: 545.3 [M+H]$^+$ $^1$H NMR (400 MHz, Methanol-d4) δ 8.19 (d, J=5.2 Hz, 1H), 8.14 (d, J=9.9 Hz, 1H), 8.09 (s, 1H), 8.07 (d, J=2.9 Hz, 1H), 7.34 (dd, J=8.6, 3.0 Hz, 1H), 7.30 (s, 1H), 7.25 (d, J=5.3 Hz, 1H), 7.11 (d, J=8.6 Hz, 1H), 5.68 (hept, J=6.5 Hz, 1H), 4.14 (s, 3H), 3.90-3.80 (m, 5H), 3.64-3.56 (m, 1H), 3.00-2.91 (m, 1H), 2.89-2.81 (m, 1H), 2.74-2.65 (m, 1H), 2.44-2.37 (m, 6H), 2.17-2.09 (m, 1H), 1.97-1.87 (m, 1H), 1.74-1.59 (m, 2H), 1.46 (d, J=6.8 Hz, 6H).

Example 63. 3-({[(1,3-dimethyl-1H-pyrazol-5-yl)methyl][(3S)-1-(pyridin-3-yl)piperidin-3-yl]amino}methyl)-1-methyl-1,4-dihydroquinolin-4-one

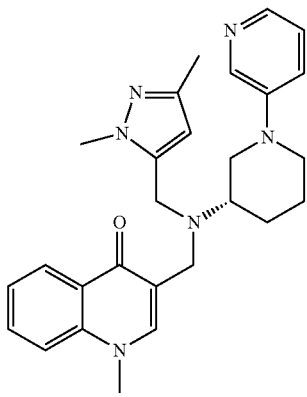 [SMILES: Cc1cc(CN(Cc2cn(C)c3ccccc3c2=O)[C@H]2CCCN(c3cccnc3)C2)n(C)n1]

Preparation of 3-({[(1,3-dimethyl-1H-pyrazol-5-yl)methyl][(3S)-1-(pyridin-3-yl)piperidin-3-yl]amino}methyl)-1-methyl-1,4-dihydroquinolin-4-one The title compound was synthesized according to Procedure 37. The residue was purified by FCC (SiHP; DCM:MeOH 9:1). The final compound was suspended in water and freeze-dried to the product (0.14 g, 0.3 mmol, yield 53%) as a light yellow powder.

ESI-MS: 457.5 [M+H]$^+$ $^1$H NMR (300 MHz, DMSO-d6) δ 8.30 (d, J=3.0 Hz, 1H), 8.20 (dd, J=8.0, 1.6 Hz, 1H), 7.92 (dd, J=4.5, 1.3 Hz, 1H), 7.87 (s, 1H), 7.72 (ddd, J=8.5, 6.8, 1.6 Hz, 1H), 7.64 (d, J=8.5 Hz, 1H), 7.38 (ddd, J=8.0, 6.8, 1.1 Hz, 1H), 7.29 (ddd, J=8.6, 3.1, 1.4 Hz, 1H), 7.21-7.10 (m, 1H), 5.97 (s, 1H), 4.03-3.49 (m, 12H), 2.93-2.80 (m, 1H), 2.80-2.68 (m, 1H), 2.68-2.56 (m, 1H), 2.07-1.91 (m, 4H), 1.83-1.69 (m, 1H), 1.68-1.35 (m, 2H).

Example 64. 1-Cyclopropyl-3-({[(3S)-1-(6-methylpyridin-3-yl)piperidin-3-yl][(2-methylpyridin-4-yl)methyl]amino}methyl)-7-(morpholin-3-yl)-1,4-dihydroquinolin-4-one

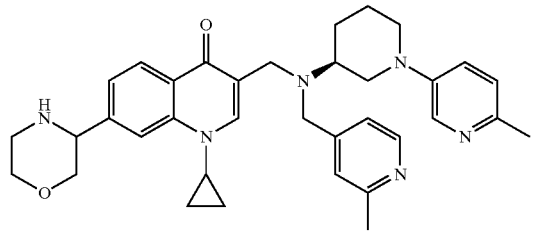 [SMILES: Cc1ccc(N2CCC[C@H](N(Cc3ccnc(C)c3)Cc3cn(C4CC4)c4cc(C5COCCN5)ccc4c3=O)C2)cn1]

Preparation of ethyl 2-[4-bromo-2-fluorobenzoyl]-3-(dimethylamino)prop-2-enoate

The title compound was synthesized according to Procedure 38a. The residue was purified by FCC (SiHP; Hex:AcOEt 2:3) to give the title product (1.24 g, 3.6 mmol, yield 81%) as a yellow oil.

ESI-MS: 344.0 [M+H]$^+$

Preparation of ethyl 7-bromo-1-cyclopropyl-4-oxo-1,4-dihydroquinoline-3-carboxylate The title compound was synthesized according to Procedure 38b. The residue was purified by FCC (SiHP; Hex:AcOEt 1:4) to give the title product (0.97 g, 3.3 mmol, yield 88%) as a yellow solid.

AP-MS: 336.0 [M+H]$^+$

Preparation of 7-bromo-1-cyclopropyl-4-oxo-1,4-dihydroquinoline-3-carboxylic acid The title compound was synthesized according to Procedure 38c. The product (0.8 g, 3.5 mmol, yield 92%) was obtained as a yellow solid.

ESI-MS: 308.0 [M+H]$^+$

Preparation of 7-bromo-1-cyclopropyl-1,2,3,4-tetrahydroquinolin-4-one

The title compound was synthesized according to Procedure 38d. The crude product was purified by FCC (SiHP; Hex:AcOEt 1:1) to give the title product (0.52 g, 2.0 mmol, yield 65%) as a yellow solid.

ESI-MS: 266.0 [M+H]$^+$

Preparation of 7-bromo-1-cyclopropyl-4-oxo-1,2,3,4-tetrahydroquinoline-3-carbaldehyde The title compound was synthesized according to Procedure 38e. The title compound (0.44 g, 1.4 mmol, yield 91%) was obtained as an orange solid.

AP-MS: 294.0 [M+H]$^+$

Preparation of 7-bromo-1-cyclopropyl-4-oxo-1,4-dihydroquinoline-3-carbaldehyde

The title compound was synthesized according to Procedure 38f. FCC purification (SiHP; DCM:MeOH 95:5) afforded the product (0.17 g, 0.6 mmol, yield 98%) as a yellow solid.

AP-MS: 292.0 [M+H]$^+$

Preparation of tert-butyl 3-(1-cyclopropyl-3-formyl-4-oxo-1,4-dihydroquinolin-7-yl)morpholine-4-carboxylate The title compound was synthesized according to Procedure 38g. The residue was purified by FCC (SiHP; Hex: AcOEt 1:1) to give the title product (0.024 g, 0.06 mmol, yield 56%) as a white solid.

ESI-MS: 399.6 [M+H]$^+$

Preparation of tert-butyl 3-[1-cyclopropyl-3-({[(3S)-1-(6-methylpyridin-3-yl)piperidin-3-yl][(2-methylpyridin-4-yl)methyl]amino}methyl)-4-oxo-1,4-dihydroquinolin-7-yl]morpholine-4-carboxylate The title compound was synthesized according to Procedure 38h. The residue was purified by FCC (RF-C18 column, ACN/H$_2$O) to give the title product: (0.017 g, 0.02 mmol, yield 42%) as a white solid.

Preparation of 1-cyclopropyl-3-({[(3S)-1-(6-methylpyridin-3-yl)piperidin-3-yl][(2-methylpyridin-4-yl)methyl]amino}methyl)-7-(morpholin-3-yl)-1,4-dihydroquinolin-4-one The title compound was synthesized according to Procedure 38i. The product (0.009 g, 0.02 mmol, yield 62%) was obtained as a white solid.

ESI-MS: 579.5 [M+H]$^+$ $^1$H NMR (400 MHz, Methanol-d4) δ 8.28 (d, J=8.3 Hz, 1H), 8.16 (d, J=5.1 Hz, 1H), 8.11-8.08 (m, 2H), 8.01 (s, 1H), 7.52-7.45 (m, 1H), 7.36 (dd, J=8.6, 3.0 Hz, 1H), 7.25-7.21 (m, 2H), 7.12 (d, J=8.6 Hz, 1H), 4.11 (dd, J=10.1, 3.3 Hz, 1H), 3.98-3.84 (m, 5H), 3.83 (s, 2H), 3.72-3.64 (m, 1H), 3.64-3.58 (m, 1H), 3.53-3.43 (m, 2H), 3.17-2.92 (m, 3H), 2.90-2.83 (m, 1H), 2.75-2.64 (m, 1H), 2.41 (s, 3H), 2.32 (s, 3H), 2.18-2.12 (m, 1H), 1.95-1.90 (m, 1H), 1.74-1.61 (m, 2H), 1.39-1.28 (m, 2H), 0.97-0.89 (m, 2H).

Biological Assays and Data:

As stated above, the compounds of the present invention are STING modulators and are useful in treating diseases by STING activity regulation. The biological activity of the compounds of the present invention can be determined by any appropriate test to determine the activity of the compound as STING modulator, as well as cell lines and in vivo models.

Fluorescence Thermal Shift Assay

Compounds of the present invention were tested for binding to human STING in Fluorescence Thermal Shift assay. STING was preincubated with the compounds for 20 minutes in 50 mM Hepes, 150 mM NaCl, pH 7.5 in 16 μl volume, following by adding 4 μl of SyproOrange dye dilution (ThermoFisher, cat no. S-6651). Final STING concentration was 0.1 mg/ml. Thermal unfolding was performed in Real-Time PCR QuantStudio 6 Flex System (Applied Biosystems), from 25 to 99° C., with continuous ramp mode and ramp rate 0.033° C./s. The data were analyzed using Protein Thermal Shift Software (ThermoFisher).

Using the Fluorescence Thermal Shift assay described above, Examples 1-64 exhibited ΔTm [° C.] values in the following ranges: +=ΔTm<10° C.; ++=ΔTm>10° C. For example, ΔTm [° C.] of FTS assay for following examples are:

| Examples | hSTING FTS binding assay (ΔT C.°) |
|---|---|
| 1 | ++ |
| 2 | ++ |
| 3 | + |
| 4 | + |
| 5 | ++ |
| 6 | ++ |
| 7 | ++ |
| 8 | + |
| 9 | ++ |
| 10 | ++ |
| 11 | ++ |
| 12 | ++ |
| 13 | + |
| 14 | + |
| 15 | + |
| 16 | + |
| 17 | + |
| 18 | ++ |
| 19 | + |
| 20 | + |
| 21 | + |
| 22 | ++ |
| 23 | ++ |
| 24 | + |
| 25 | ++ |
| 26 | ++ |
| 27 | + |
| 28 | ++ |
| 29 | ++ |
| 30 | + |
| 31 | ++ |
| 32 | + |
| 33 | ++ |
| 34 | + |
| 35 | ++ |
| 36 | + |
| 37 | ++ |
| 38 | + |
| 39 | ++ |
| 40 | ++ |
| 41 | + |
| 42 | ++ |
| 43 | ++ |
| 44 | ++ |
| 45 | ++ |
| 46 | ++ |
| 47 | ++ |
| 48 | ++ |
| 49 | + |
| 50 | ++ |
| 51 | ++ |
| 52 | ++ |
| 53 | + |
| 54 | + |
| 55 | + |
| 56 | + |
| 57 | NA |
| 58 | ++ |
| 59 | ++ |
| 60 | NA |
| 61 | NA |
| 62 | NA |
| 63 | NA |
| 64 | NA |

NA—not available

THP-1 Dual Reporter Assay

Compounds of the present invention were tested for their activity using THP-1 dual cells (Invivogen, cat no. thpd-nfis) allowing for simultaneous study of NF-κB pathway and the interferon regulatory factor (IRF) pathway. THP-1 dual cells contain luciferase reporter gene under the control of an ISG54 (interferon-stimulated gene) minimal promoter in conjunction with five interferon-stimulated response elements and a secreted embryonic alkaline phosphatase reporter gene under the control an IFN (interferon)-β minimal promoter fused to five copies of the NF-κB consensus transcriptional response element with three copies of the c-Rel binding site. Following 18 h of stimulation with STING agonist, medium was collected and transferred onto fresh cell culture plate. To verify activity of the IRF pathway, luminescence activity was measured with standard laboratory plate reader immediately after addition 10 μl of the medium to 50 μl (or 40 μl) of luminescence reagent (Invivogen, cat. No. rep-qlc2). To verify activity of NF-κB pathway, 20 μl (or 10 μl) of the medium was mixed with 80 μl of a detection medium (Invivogen, cat. No. rep-qb2) and incubated for 2 hours (or 1 hour) at 37° C. in a humidified atmosphere containing 5% $CO_2$. Next, absorbance at 630 nm (or 655 nm) was recorded using standard laboratory plate reader.

Compounds of the present disclosure, as exemplified in Examples 1-64, showed EC50 values in the following ranges: +=$EC_{50} \geq 10$ μM; ++=$1$ μM<$EC_{50}$<$10$ μM; +++=$EC_{50} \leq 1$ μM.

| Examples | Structure | THP1 Dual EC50 (μM) IRF | THP1 Dual EC50 (μM) NFkB |
|---|---|---|---|
| 1 | 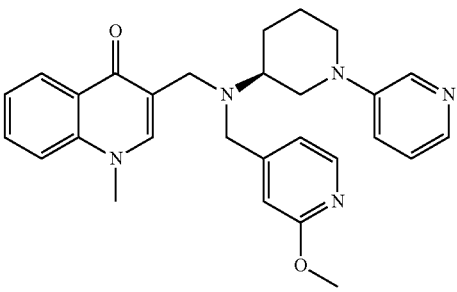 [SMILES: COc1cc(CN(Cc2cn(C)c3ccccc3c2=O)[C@H]2CCCN(c3cccnc3)C2)ccn1] | +++ | +++ |
| 2 | 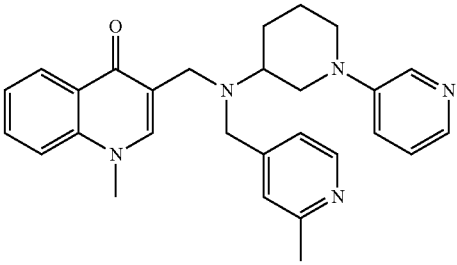 [SMILES: Cc1cc(CN(Cc2cn(C)c3ccccc3c2=O)C2CCCN(c3cccnc3)C2)ccn1] | +++ | +++ |
| 3 | 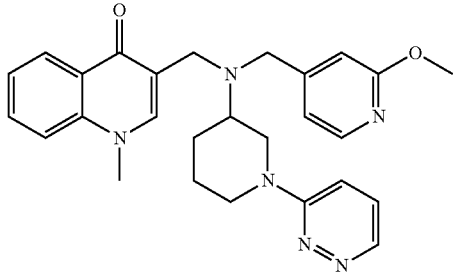 [SMILES: COc1cc(CN(Cc2cn(C)c3ccccc3c2=O)C2CCCN(c3cccnn3)C2)ccn1] | + | + |
| 4 | 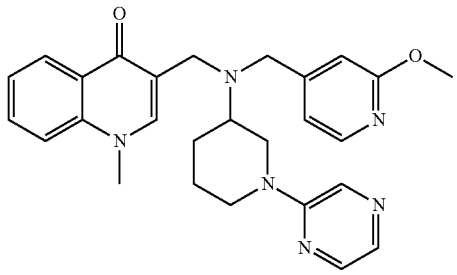 [SMILES: COc1cc(CN(Cc2cn(C)c3ccccc3c2=O)C2CCCN(c3cnccn3)C2)ccn1] | ++ | ++ |

-continued
| Examples | Structure | THP1 Dual EC50 (μM) IRF | THP1 Dual EC50 (μM) NFkB |
|---|---|---|---|
| 5 | 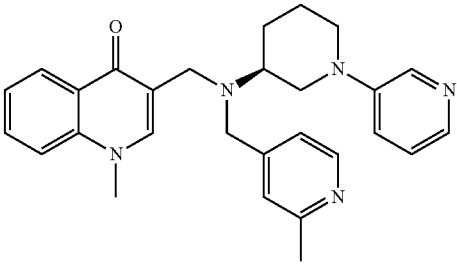 [SMILES: Cc1cc(CN(Cc2cn(C)c3ccccc3c2=O)[C@H]2CCCN(c3cccnc3)C2)ccn1] | +++ | +++ |
| 6 | 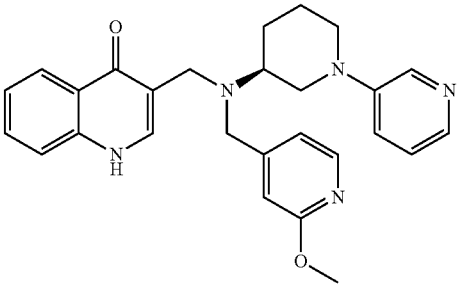 [SMILES: COc1cc(CN(Cc2c[nH]c3ccccc3c2=O)[C@H]2CCCN(c3cccnc3)C2)ccn1] | +++ | +++ |
| 7 | 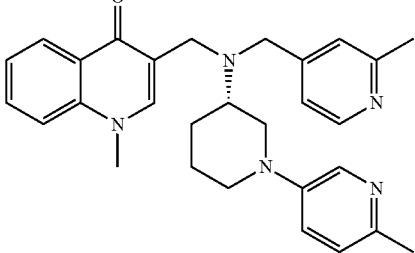 | +++ | +++ |
| 8 | 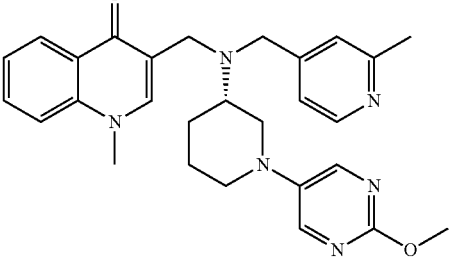 | + | + |
| 9 | 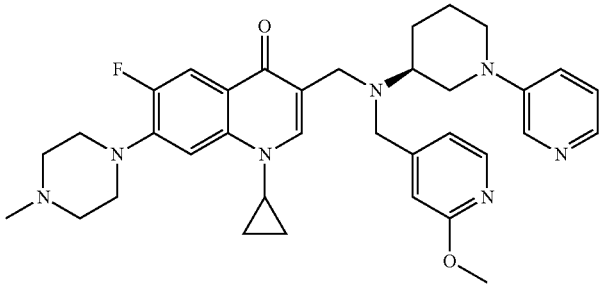 [SMILES: COc1cc(CN(Cc2cn(C3CC3)c3cc(N4CCN(C)CC4)c(F)cc3c2=O)[C@H]2CCCN(c3cccnc3)C2)ccn1] | +++ | +++ |

-continued

| Examples | Structure | THP1 Dual EC50 (μM) IRF | THP1 Dual EC50 (μM) NFkB |
|---|---|---|---|
| 10 | 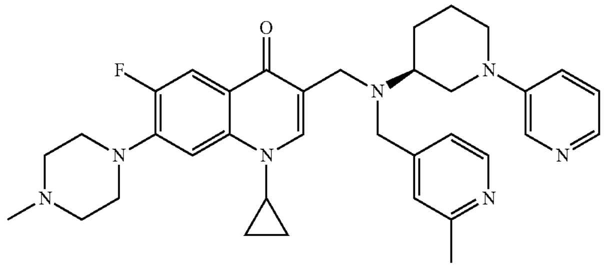 [SMILES: Cc1cc(CN(Cc2cn(C3CC3)c3cc(N4CCN(C)CC4)c(F)cc3c2=O)[C@H]2CCCN(c3cccnc3)C2)ccn1] | +++ | +++ |
| 11 | 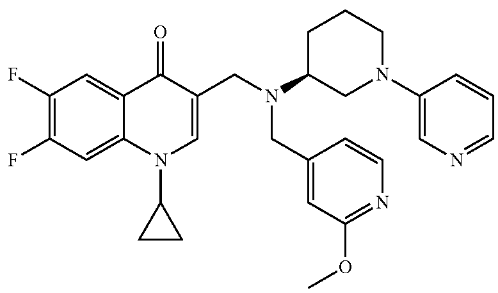 [SMILES: COc1cc(CN(Cc2cn(C3CC3)c3cc(F)c(F)cc3c2=O)[C@H]2CCCN(c3cccnc3)C2)ccn1] | +++ | +++ |
| 12 | 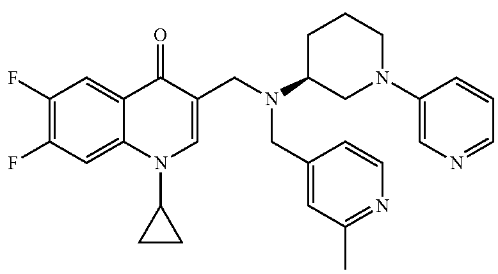 [SMILES: Cc1cc(CN(Cc2cn(C3CC3)c3cc(F)c(F)cc3c2=O)[C@H]2CCCN(c3cccnc3)C2)ccn1] | +++ | +++ |
| 13 | 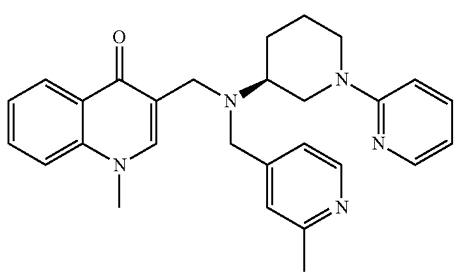 [SMILES: Cc1cc(CN(Cc2cn(C)c3ccccc3c2=O)[C@H]2CCCN(c3ccccn3)C2)ccn1] | ++ | ++ |
| 14 | 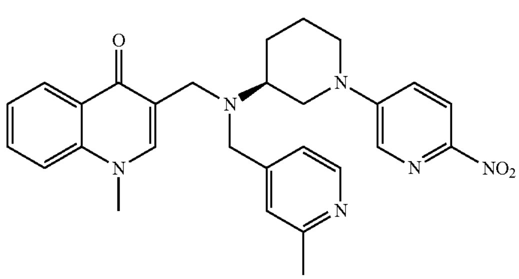 [SMILES: Cc1cc(CN(Cc2cn(C)c3ccccc3c2=O)[C@H]2CCCN(c3ccc([N+](=O)[O-])nc3)C2)ccn1] | ++ | + |

| Examples | Structure | THP1 Dual EC50 (μM) IRF | THP1 Dual EC50 (μM) NFkB |
|---|---|---|---|
| 15 | 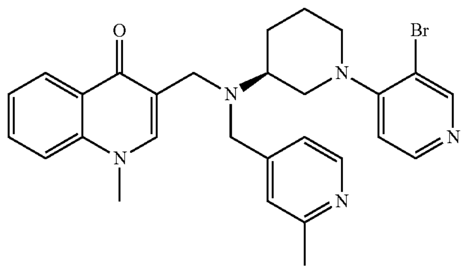 [SMILES: Cc1cc(CN(Cc2cn(C)c3ccccc3c2=O)[C@H]2CCCN(c3ccncc3Br)C2)ccn1] | ++ | ++ |
| 16 | 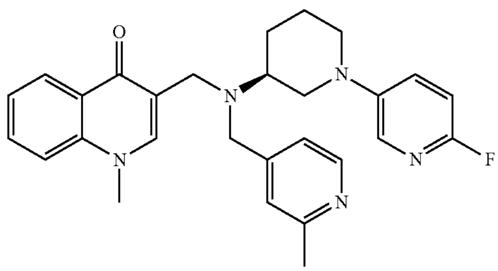 [SMILES: Cc1cc(CN(Cc2cn(C)c3ccccc3c2=O)[C@H]2CCCN(c3ccc(F)nc3)C2)ccn1] | ++ | ++ |
| 17 | 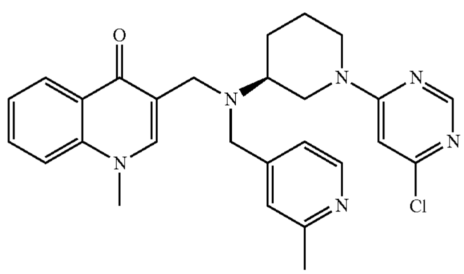 [SMILES: Cc1cc(CN(Cc2cn(C)c3ccccc3c2=O)[C@H]2CCCN(c3cc(Cl)ncn3)C2)ccn1] | ++ | ++ |
| 18 | 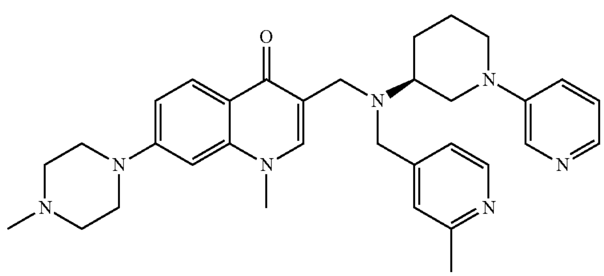 [SMILES: Cc1cc(CN(Cc2cn(C)c3cc(N4CCN(C)CC4)ccc3c2=O)[C@H]2CCCN(c3cccnc3)C2)ccn1] | +++ | +++ |
| 19 | 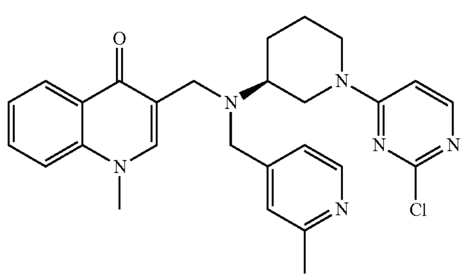 [SMILES: Cc1cc(CN(Cc2cn(C)c3ccccc3c2=O)[C@H]2CCCN(c3ccnc(Cl)n3)C2)ccn1] | ++ | ++ |

-continued

| Examples | Structure | THP1 Dual EC50 (μM) IRF | THP1 Dual EC50 (μM) NFkB |
|---|---|---|---|
| 20 | 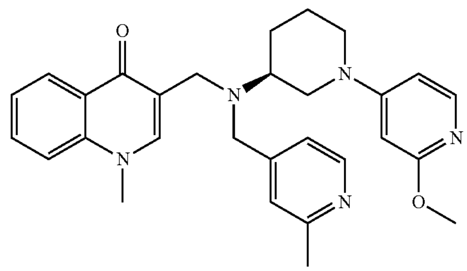 | + | + |
| 21 | 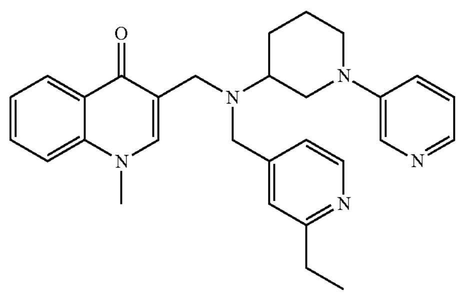 [SMILES: CCc1cc(CN(Cc2cn(C)c3ccccc3c2=O)C2CCCN(c3cccnc3)C2)ccn1] | + | + |
| 22 | 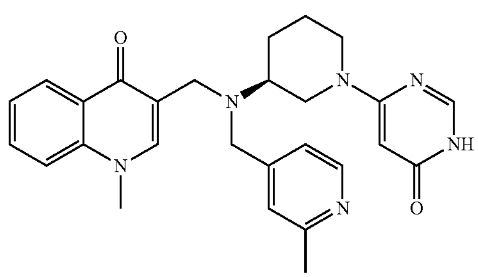 [SMILES: Cc1cc(CN(Cc2cn(C)c3ccccc3c2=O)[C@H]2CCCN(c3cc(=O)[nH]cn3)C2)ccn1] | + | + |
| 23 | 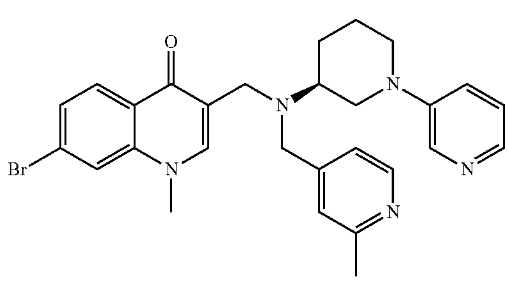 [SMILES: Cc1cc(CN(Cc2cn(C)c3cc(Br)ccc3c2=O)[C@H]2CCCN(c3cccnc3)C2)ccn1] | +++ | +++ |
| 24 | 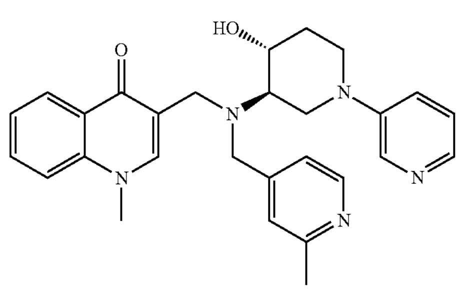 [SMILES: Cc1cc(CN(Cc2cn(C)c3ccccc3c2=O)[C@@H]2CN(c3cccnc3)CC[C@H]2O)ccn1] | + | + |

-continued

| Examples | Structure | THP1 Dual EC50 (μM) IRF | THP1 Dual EC50 (μM) NFkB |
|---|---|---|---|
| 25 | 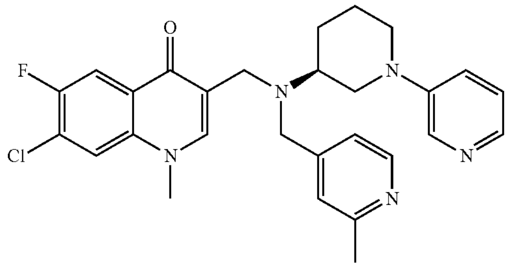 [SMILES: Cc1cc(CN(Cc2cn(C)c3cc(Cl)c(F)cc3c2=O)[C@H]2CCCN(c3cccnc3)C2)ccn1] | +++ | +++ |
| 26 | 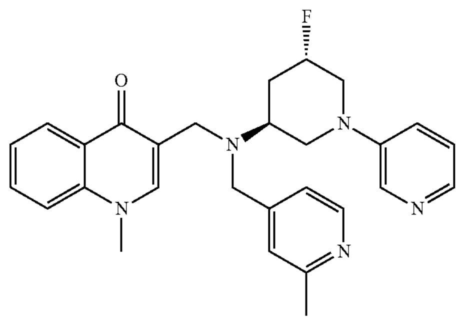 [SMILES: Cc1cc(CN(Cc2cn(C)c3ccccc3c2=O)[C@H]2C[C@H](F)CN(c3cccnc3)C2)ccn1] | +++ | +++ |
| 27 | 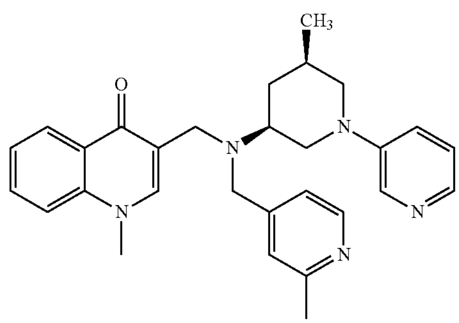 [SMILES: Cc1cc(CN(Cc2cn(C)c3ccccc3c2=O)[C@H]2C[C@@H](C)CN(c3cccnc3)C2)ccn1] | + | + |
| 28 | 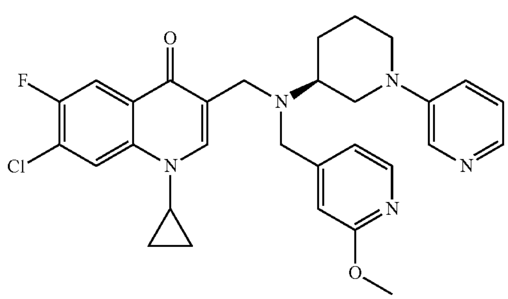 [SMILES: COc1cc(CN(Cc2cn(C3CC3)c3cc(Cl)c(F)cc3c2=O)[C@H]2CCCN(c3cccnc3)C2)ccn1] | +++ | +++ |
| 29 | 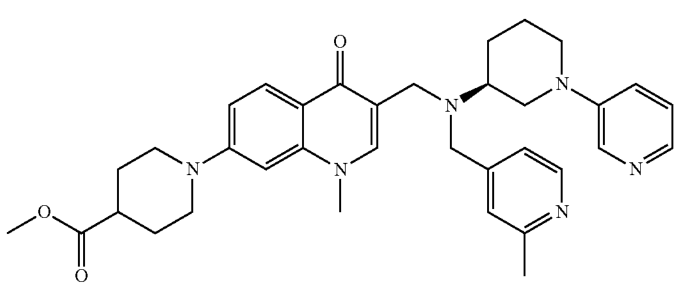 [SMILES: COC(=O)C1CCN(c2ccc3c(=O)c(CN(Cc4ccnc(C)c4)[C@H]4CCCN(c5cccnc5)C4)cn(C)c3c2)CC1] | +++ | +++ |

-continued

| Examples | Structure | THP1 Dual EC50 (μM) IRF | THP1 Dual EC50 (μM) NFkB |
|---|---|---|---|
| 30 | 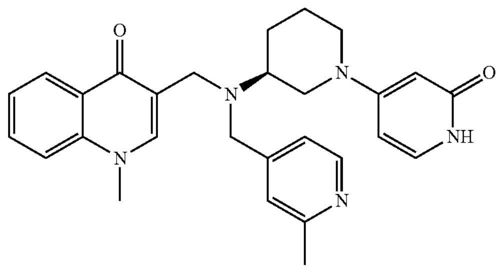 [SMILES: Cc1cc(CN(Cc2cn(C)c3ccccc3c2=O)[C@H]2CCCN(c3cc[nH]c(=O)c3)C2)ccn1] | + | + |
| 31 | 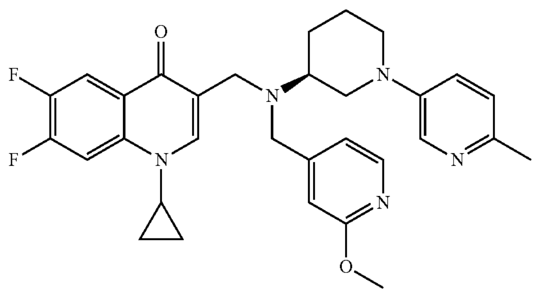 [SMILES: COc1cc(CN(Cc2cn(C3CC3)c3cc(F)c(F)cc3c2=O)[C@H]2CCCN(c3ccc(C)nc3)C2)ccn1] | +++ | +++ |
| 32 | 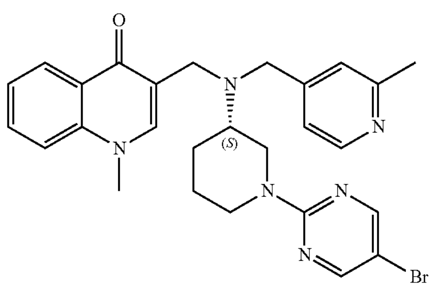 | ++ | ++ |
| 33 | 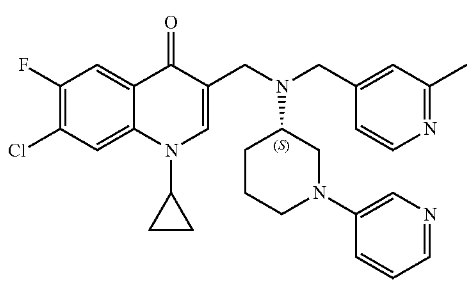 | +++ | +++ |
| 34 | 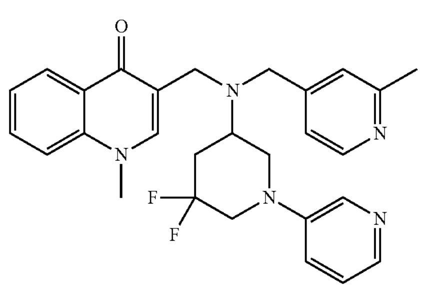 [SMILES: Cc1cc(CN(Cc2cn(C)c3ccccc3c2=O)C2CN(c3cccnc3)CC(F)(F)C2)ccn1] | + | + |

-continued

| Examples | Structure | THP1 Dual EC50 (μM) IRF | THP1 Dual EC50 (μM) NFkB |
|---|---|---|---|
| 35 | 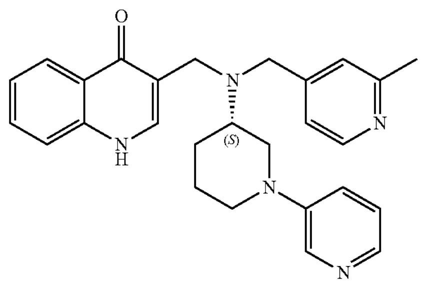 | +++ | ++ |
| 36 | 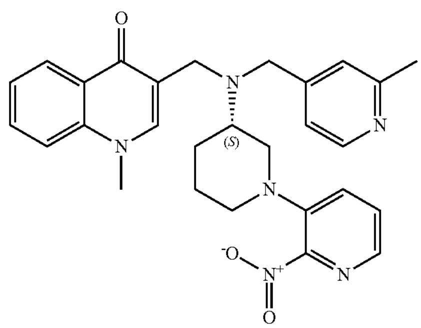 | + | + |
| 37 | 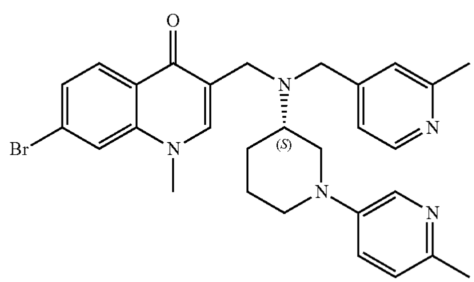 | +++ | +++ |
| 38 | 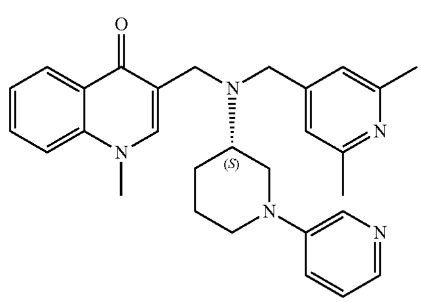 | + | + |
| 39 | 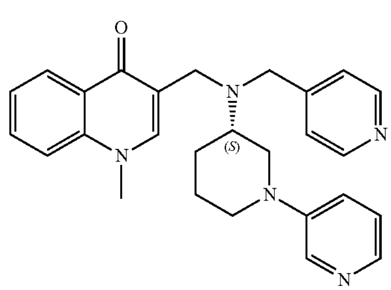 | +++ | ++ |

-continued
| Examples | Structure | THP1 Dual EC50 (μM) IRF | THP1 Dual EC50 (μM) NFkB |
|---|---|---|---|
| 40 | 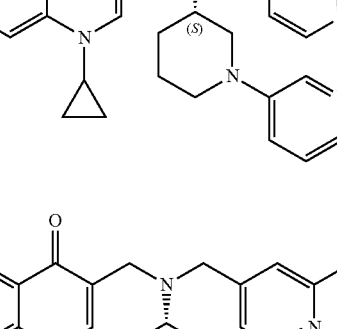 | +++ | +++ |
| 41 | 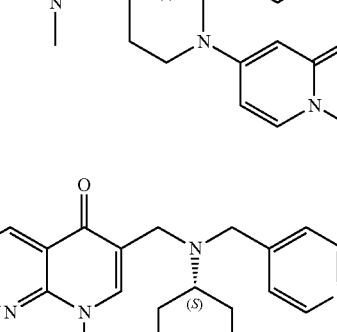 | + | + |
| 42 | 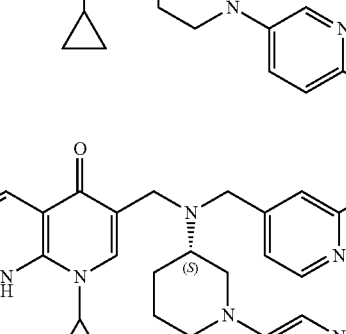 | +++ | +++ |
| 43 | 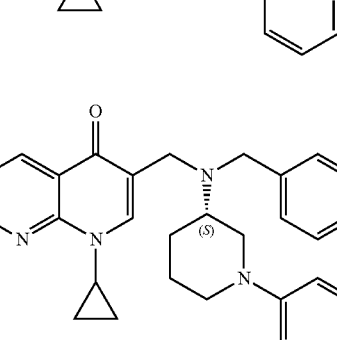 | + | + |
| 44 | 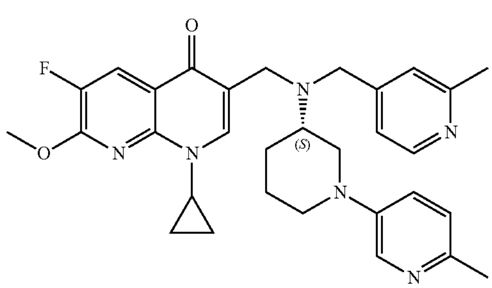 | +++ | +++ |

| Examples | Structure | THP1 Dual EC50 (µM) IRF | THP1 Dual EC50 (µM) NFkB |
|---|---|---|---|
| 45 | 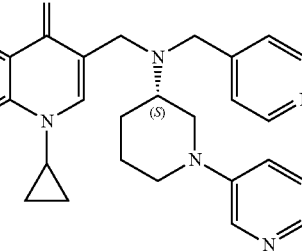 | +++ | +++ |
| 46 | 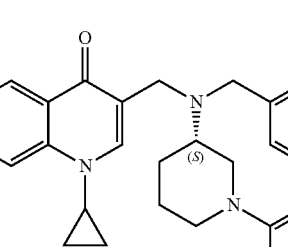 | +++ | +++ |
| 47 | 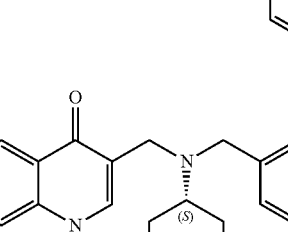 | +++ | +++ |
| 48 | 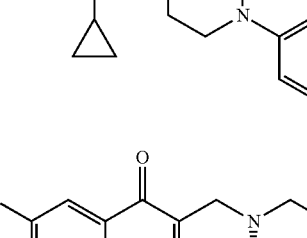 | +++ | +++ |
| 49 | 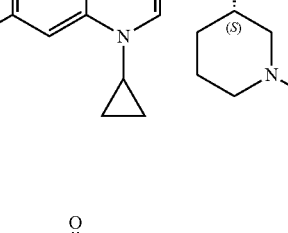 | + | + |

| Examples | Structure | THP1 Dual EC50 (μM) IRF | THP1 Dual EC50 (μM) NFkB |
|---|---|---|---|
| 50 | 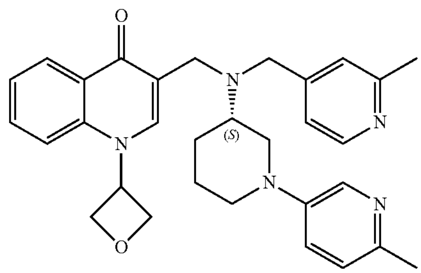 | +++ | +++ |
| 51 | 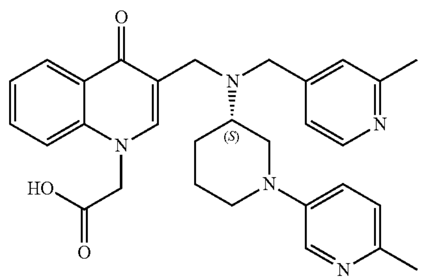 | + | + |
| 52 | 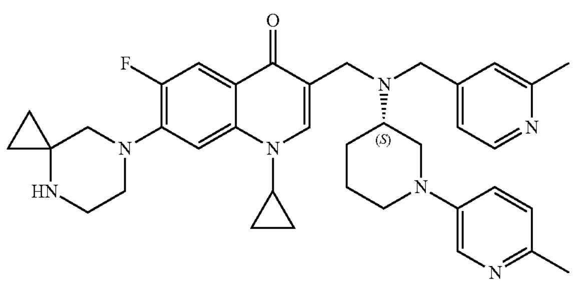 | +++ | +++ |
| 53 | 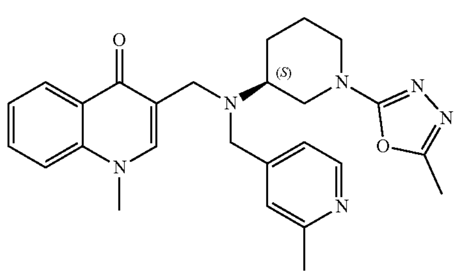 | + | ++ |
| 54 | 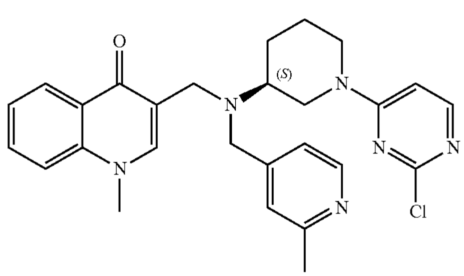 | ++ | ++ |

-continued
| Examples | Structure | THP1 Dual EC50 (μM) IRF | THP1 Dual EC50 (μM) NFkB |
|---|---|---|---|
| 55 | 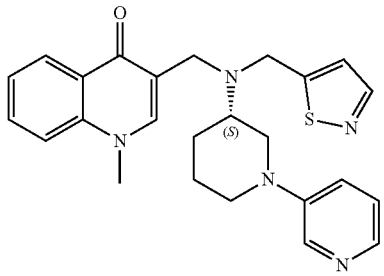 | + | + |
| 56 | 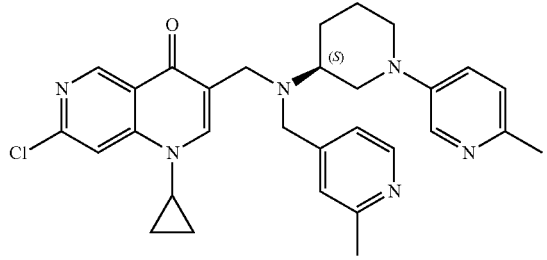 | +++ | ++ |
| 57 | 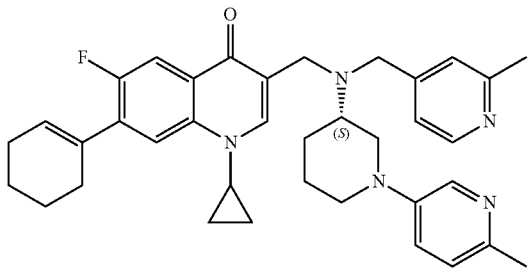 | +++ | +++ |
| 58 | 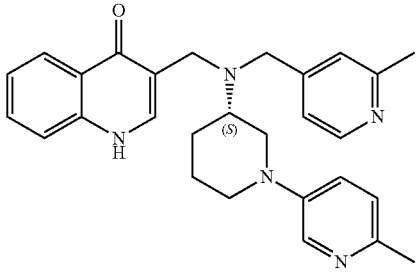 | +++ | +++ |
| 59 | 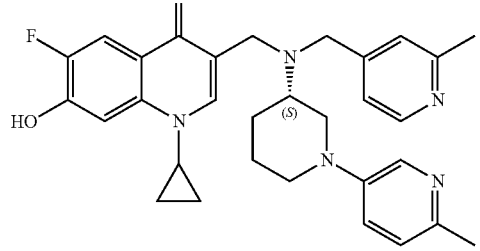 | +++ | ++ |

| Examples | Structure | THP1 Dual EC50 (µM) IRF | THP1 Dual EC50 (µM) NFkB |
|---|---|---|---|
| 60 | 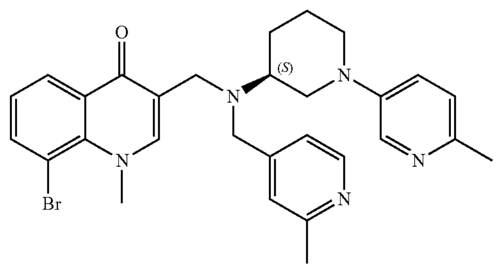 | +++ | +++ |
| 61 | 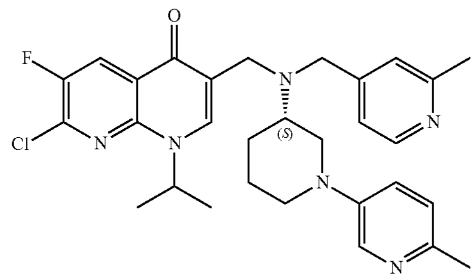 | +++ | +++ |
| 62 | 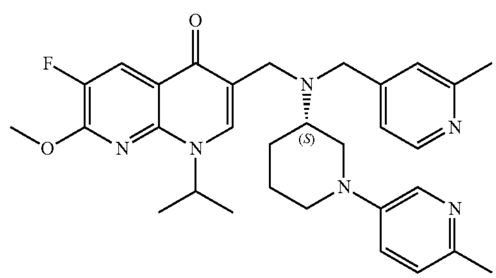 | +++ | +++ |
| 63 | 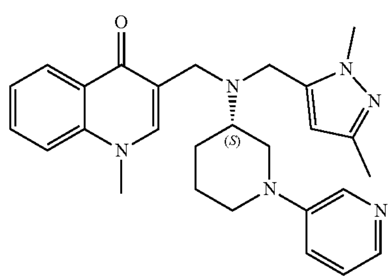 | ++ | + |
| 64 | 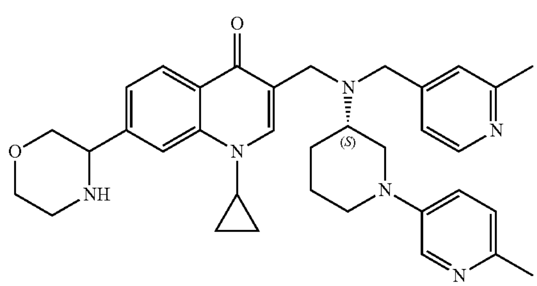 | +++ | +++ |

In Vivo Anti-Tumor Efficacy

Figure 1:
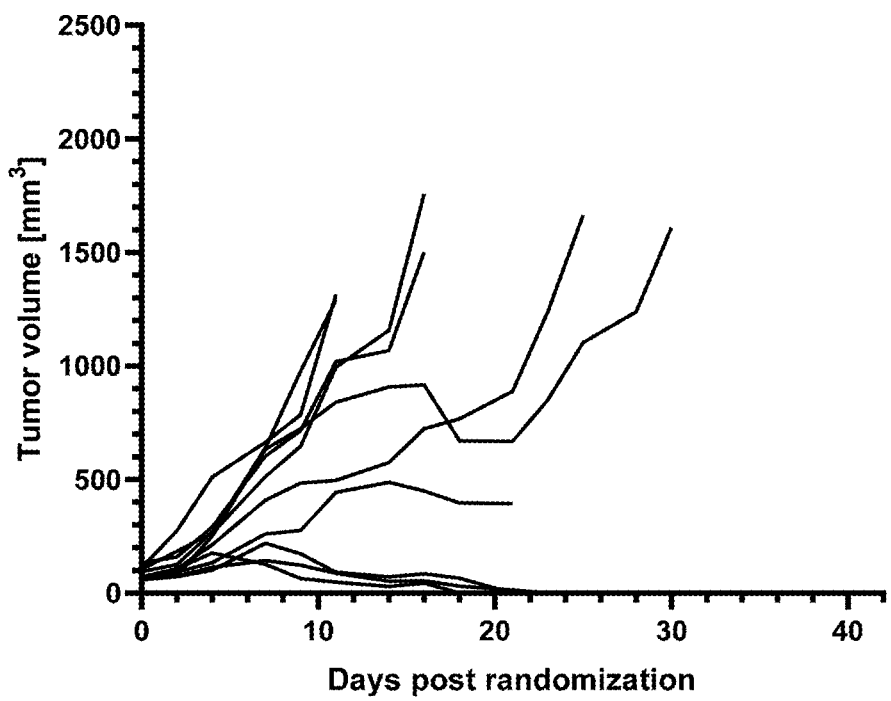
Figure 2:
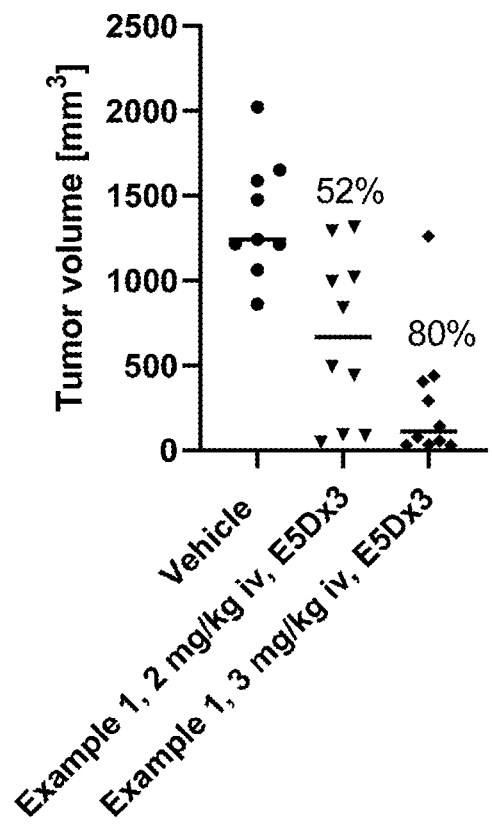
FIG. 2 shows the in vivo anti-tumor efficacy of a compound according to Example 1 in CT26 murine colon carcinoma allograft in Balb/C female mice by depicting a dot plot presenting individual tumor volumes and % TGI (tumor growth inhibition) for day 11 for different doses of the compound according to Example 1 in comparison to the vehicle.

The efficacy of Example 1 was evaluated in established CT26 murine colon carcinoma allografts in female Balb/C mice. Example 1 was formulated in 10% Captisol in PBS and administered intravenously, once every fifth day on three occasions. The solution was prepared fresh prior to each administration. CT26 tumors responded prominently to the treatment with Example 1, with moderately efficacious dose at 2 mg/kg and full efficacious dose at 3 mg/kg (see FIGS. 1(*i*) to (*iii*)). In both treatment groups tumor growth delay was observed when compared to the control group. By the end of the study, on day 42, there were 3 and 6 complete responses recorded for mice treated at 2 and 3 mg/kg E5Dx3, respectively. TGI on 11th day for these groups (the last day when at least 90% animals in each group were in the study) reached 52% and 80%, respectively (see FIG. 2).

Figure 3I:
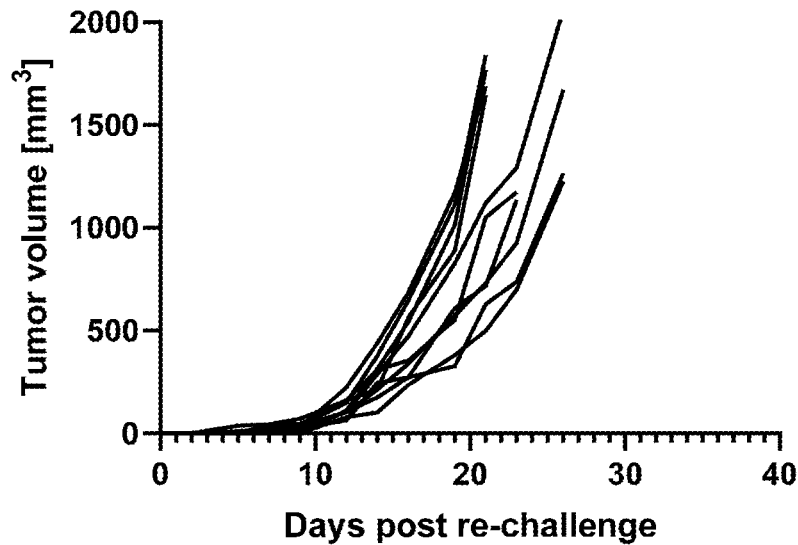
FIGS. 3(i) to (iii) show the in vivo anti-tumor immune memory toward CT26 murine colon carcinoma allograft in Balb/C female mice in a re-challenge study by depicting the tumor volume over time in mice treated previously at different doses of the compound according to Example 1 in comparison to nave mice.
Figure 3:
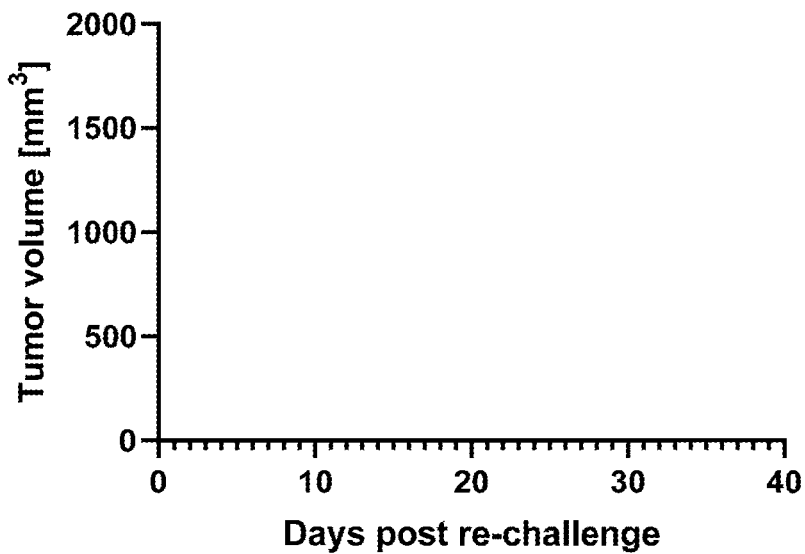

Mice with complete responses were subjected to a re-challenge study. CT26 cells were injected into the flank opposite to an original site of inoculation. Naïve mice were included into the re-challenge study as a control of the tumor growth kinetics. Out of three mice with complete responses dosed previously at 2 mg/kg, none of them developed tumors. In the case of six mice with complete responses dosed previously at 3 mg/kg, two of them developed a tumor, however a substantial delay in the tumor growth was observed (see FIGS. 3(i) to (iii)).

In particular, the present invention relates to the following items:

1. A compound of formula (I)

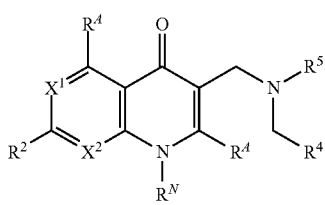

(I)

or a salt, stereoisomer, tautomer, or N-oxide thereof, wherein $X^1$ is $CR^1$ or N;

$X^2$ is $CR^3$ or N;

$R^1$, $R^2$ and $R^3$ are independently H, OH, CN, halogen, $C_1$-$C_4$-alkyl, $C_1$-$C_4$-alkoxy, aryloxy, benzyloxy, $C(=O)R^E$, $NR^FC(=O)R^E$, $NR^F$—($C_1$-$C_4$-alkylene)-$C(=O)R^E$, or 4- to 6-membered saturated, partially or fully unsaturated, or aromatic carbocyclyl, carbocyclyl-$C_1$-$C_2$-alkyl, heterocyclyl, heterocyclyloxy or heterocyclyl-$C_1$-$C_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^X$;

$R^4$ is a 5- or 6-membered aromatic carbocyclic or heterocyclic ring, or a 9- or 10-membered aromatic carbobicyclic or heterobicyclic ring, wherein the heterocyclic or heterobicyclic ring comprises at least one nitrogen atom and optionally one or more, same or different additional heteroatoms selected from O, N or S, wherein said N- and/or S-atoms are independently oxidized or non-oxidized, and wherein each substitutable carbon or heteroatom in the aforementioned cyclic rings is independently unsubstituted or substituted with one or more same or different substituents $R^X$;

$R^5$ is a 5- or 6-membered saturated heterocyclic ring, wherein said heterocyclic ring comprises one or more, same or different heteroatoms selected from O, N or S, wherein said N and/or S-atoms are independently oxidized or non-oxidized, and wherein each substitutable carbon or heteroatom is independently unsubstituted or substituted with one or more, same or different substituents $R^Y$;

and wherein $R^N$ is H, $CH_3$, $HO(C=O)$—$C_1$-$C_4$-alkyl, or a 3- or 4-membered saturated carbocyclyl or heterocyclyl, wherein said heterocyclic ring comprises one or more, same or different heteroatoms selected from O, N or S, wherein said N and/or S-atoms are independently oxidized or non-oxidized, and wherein each substitutable carbon or heteroatom in the aforementioned groups is independently unsubstituted or substituted with one or more, same or different substituents $R^X$;

$R^A$ is H, halogen, CN, OH, $C_1$-$C_3$-alkyl, $C_1$-$C_3$-alkoxy, or 3- to 6-membered saturated, partially or fully unsaturated, or aromatic carbocyclyl, or heterocyclyl, wherein the aforementioned heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^C$ and $R^D$ are independently H, or $C_1$-$C_2$-alkyl; or $R^C$ and $R^D$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^E$ is H, $C_1$-$C_2$-alkyl, phenyl, benzyl, $OR^G$, or $NR^HR^I$; or a 5- or 6-membered saturated, partially or fully unsaturated heterocyclyl, wherein said heterocyclic ring comprises one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents $R^F$;

$R^F$ is H, $C_1$-$C_2$-alkyl, $C_3$-$C_6$-cycloalkyl, phenyl, benzyl, or $C(=O)NR^HR^I$;

$R^G$ is H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N-atoms are independently oxidized or non-oxidized;

$R^H$ and $R^I$ are independently H, $C_1$-$C_2$-alkyl, or 5- or 6-membered aromatic carbocyclyl, carbocyclyl-$C_1$-$C_2$-alkyl, heterocyclyl, or heterocyclyl-$C_1$-$C_2$-alkyl, wherein the aforementioned heterocyclic rings comprise one or more, same or different heteroatoms selected from O, N or S, wherein said N-atoms are independently oxidized or non-oxidized; or $R^H$ and $R^I$ together with the nitrogen atom to which they are bonded form a 5- or 6-membered saturated, partially or fully unsaturated, or aromatic heterocyclic ring, wherein said heterocyclic ring comprises one or more, same or different heteroatoms selected from O, N or S, wherein said N- and/or S-atoms are independently oxidized or non-oxidized, and wherein each substitutable carbon or heteroatom in the heterocyclic ring is independently unsubstituted or substituted with one or more, same or different substituents $R^X$;

$R^X$ is halogen, CN, NO$_2$, C$_1$-C$_2$-alkyl, C$_1$-C$_2$-alkoxy, C(=O)R$^E$, or two R$^X$ form =O;

$R^Y$ is halogen, CN, OH, C$_1$-C$_2$-alkyl, C$_1$-C$_2$-alkyl-OH, C$_3$-C$_6$-cycloalkyl, C$_1$-C$_2$-alkoxy, NR$^C$R$^D$, S(=O)$_2$NR$^C$R$^D$, C(=O)R$^E$, or 5- or 6-membered saturated, partially or fully unsaturated, or aromatic carbocyclyl, carbocyclyl-C$_1$-C$_2$-alkyl, heterocyclyl, and heterocyclyl-C$_1$-C$_2$-alkyl, wherein the aforementioned heterocyclic rings comprise one or more, same or different heteroatoms selected from O, N or S, wherein said N- and/or S-atoms are independently oxidized or non-oxidized, and wherein each substitutable carbon or heteroatom in the aforementioned groups is independently unsubstituted or substituted with one or more, same or different substituents R$^X$; or two R$^Y$ form =O; or two R$^Y$ attached to identical or neighboring carbon atoms may form a 3-membered carbocyclic ring.

2. The compound according to item 1, wherein R$^A$ is H.

3. The compound according to item 1 or 2, wherein R$^N$ is H, CH$_3$ or cyclopropyl, preferably CH$_3$.

4. The compound according to any one of items 1 to 3, wherein R$^1$, R$^2$ and R$^3$ are H.

5. The compound according to any one of items 1 to 4, wherein R$^5$ is a 6-membered saturated heterocyclic ring, wherein said heterocyclic ring comprises one or more, same or different heteroatoms selected from O, N or S, wherein said N and/or S-atoms are independently oxidized or non-oxidized, and wherein each substitutable carbon or heteroatom is independently unsubstituted or substituted with one or more, same or different substituents R$^Y$.

6. The compound according to any one of items 1 to 5, wherein R$^5$ is piperidine, wherein each substitutable carbon or heteroatom in the piperidine ring is independently unsubstituted or substituted by one or more, same or different substituents R$^Y$.

7. The compound according to any one of items 1 to 6, wherein R$^5$ is piperidine, wherein each substitutable carbon atom in the piperidine ring is independently unsubstituted or substituted by one or more, same or different substituents R$^Y$; and wherein the nitrogen atom in the piperidine ring is preferably substituted with R$^Y$ being pyridinyl.

8. The compound according to any one of items 1 to 7, wherein R$^4$ is pyridinyl, wherein each substitutable carbon or heteroatom in the cyclic ring is independently unsubstituted or substituted by one or more, same or different substituents R$^X$.

9. The compound according to any one of items 1 to 8, wherein X$^1$ is CR$^1$; and X$^2$ is CR$^3$; and wherein R$^1$ and R$^3$ are preferably H.

10. The compound according to any one of items 1 to 9, wherein the compound according to formula (I) is selected from the group consisting of 3-({[(2-methoxypyridin-4-yl)methyl][(3S)-1-(pyridin-3-yl)piperidin-3-yl]amino}methyl)-1-methyl-1,4-dihydroquinolin-4-one, 1-methyl-3-({[(2-methylpyridin-4-yl)methyl][1-(pyridin-3-yl)piperidin-3-yl]amino}methyl)-1,4-dihydroquinolin-4-one, 3-({[(2-methoxypyridin-4-yl)methyl][1-(pyridazin-3-yl)piperidin-3-yl]amino}methyl)-1-methyl-1,4-dihydroquinolin-4-one, 3-({[(2-methoxypyridin-4-yl)methyl][1-(pyrazin-2-yl)piperidin-3-yl]amino}methyl)-1-methyl-1,4-dihydroquinolin-4-one, 1-methyl-3-({[(2-methylpyridin-4-yl)methyl][(3S)-1-(pyridin-3-yl)piperidin-3-yl]amino}methyl)-1,4-dihydroquinolin-4-one, 3-({[(2-methoxypyridin-4-yl)methyl][(3S)-1-(pyridin-3-yl)piperidin-3-yl]amino}methyl)-1,4-dihydroquinolin-4-one, 1-methyl-3-({[(3S)-1-(6-methylpyridin-3-yl)piperidin-3-yl][(2-methylpyridin-4-yl)methyl]amino}methyl)-1,4-dihydroquinolin-4-one, 3-({[(3S)-1-(2-methoxypyrimidin-5-yl)piperidin-3-yl][(2-methylpyridin-4-yl)methyl]amino}methyl)-1-methyl-1,4-dihydroquinolin-4-one, 1-cyclopropyl-6-fluoro-3-({[(2-methoxypyridin-4-yl)methyl][(3S)-1-(pyridin-3-yl)piperidin-3-yl]amino}methyl)-7-(4-methylpiperazin-1-yl)-1,4-dihydroquinolin-4-one, 1-cyclopropyl-6-fluoro-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-methoxypyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-methylpyridin-4-yl)methyl][(3S)-1-(pyridin-3-yl)piperidin-3-yl]amino}methyl)-1,4-dihydroquinolin-4-one, 1-methyl-3-({[(2-methylpyridin-4-yl)methyl][(3S)-1-(pyridin-2-yl)piperidin-3-yl]amino}methyl)-1,4-dihydroquinolin-4-one, 1-methyl-3-({[(2-methylpyridin-4-yl)methyl][(3S)-1-(6-nitropyridin-3-yl)piperidin-3-yl]amino}methyl)-1,4-dihydroquinolin-4-one, 3-({[(3S)-1-(3-bromopyridin-4-yl)piperidin-3-yl][(2-methylpyridin-4-yl)methyl]amino}methyl)-1-methyl-1,4-dihydroquinolin-4-one, 3-({[(3S)-1-(6-fluoropyridin-3-yl)piperidin-3-yl][(2-methylpyridin-4-yl)methyl]amino}methyl)-1-methyl-1,4-dihydroquinolin-4-one, 3-({[(3S)-1-(6-chloropyrimidin-4-yl)piperidin-3-yl][(2-methylpyridin-4-yl)methyl]amino}methyl)-1-methyl-1,4-dihydroquinolin-4-one, 1-methyl-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one, 3-({[(3S)-1-(2-chloropyrimidin-4-yl)piperidin-3-yl][(2-methylpyridin-4-yl)methyl]amino}methyl)-1-methyl-1,4-dihydroquinolin-4-one, 3-({[(3S)-1-(2-methoxypyridin-4-yl)piperidin-3-yl][(2-methylpyridin-4-yl)methyl]amino}methyl)-1-methyl-1,4-dihydroquinolin-4-one, 3-({[(2-ethylpyridin-4-yl)methyl][1-(pyridin-3-yl)piperidin-3-yl]amino}methyl)-1-methyl-1,4-dihydroquinolin-4-one, 1-methyl-3-({[(2-methylpyridin-4-yl)methyl][(3S)-1-(6-oxo-1,6-dihydropyrimidin-4-yl)piperidin-3-yl]amino}methyl)-1,4-dihydroquinolin-4-one, 7-bromo-1-methyl-3-({[(2-methylpyridin-4-yl)methyl][(3S)-1-(pyridin-3-yl)piperidin-3-yl]amino}methyl)-1,4-dihydroquinolin-4-one, 3-({[(3R,4/i)-4-hydroxy-1-(pyridin-3-yl)piperidin-3-yl][(2-methylpyridin-4-yl)methyl]amino}methyl)-1-methyl-1,4-dihydroquinolin-4-one, 7-chloro-6-fluoro-1-methyl-3-({[(2-methylpyridin-4-yl)methyl][(3S)-1-(pyridin-3-yl)piperidin-3-yl]amino}methyl)-1,4-dihydroquinolin-4-one, 3-({[(3S,5S)-5-fluoro-1-(pyridin-3-yl)piperidin-3-yl][(2-methylpyridin-4-yl)methyl]amino}methyl)-1-methyl-1,4-dihydroquinolin-4-one, 1-methyl-3-({[(3S, 5R)-5-methyl-1-(pyridin-3-yl)piperidin-3-yl][(2-methylpyridin-4-yl)methyl]amino}methyl)-1,4-dihydroquinolin-4-one, 7-chloro-1-cyclopropyl-6-fluoro-3-({[(2-methoxypyridin-4-yl)methyl][(3S)-1-(pyridin-3-yl)piperidin-3-yl]amino}methyl)-1,4-dihydroquinolin-4-one, methyl 1-[1-methyl-3-({[(2-methylpyridin-4-yl)methyl][(3S)-1-(pyridin-3-yl)piperidin-3-yl]amino}methyl)-4-oxo-1,4-dihydroquinolin-7-yl]piperidine-4-carboxylate, 1-methyl-3-({[(2-methylpyridin-4-yl)methyl][(3S)-1-(2-oxo-1,2-dihydropyridin-4-yl)piperidin-3-yl]amino}methyl)-1,4-dihydroquinolin-4-one and 1-cyclopropyl-6,7-difluoro-3-({[(2-methoxypyridin-4-yl)methyl][(3S)-1-(6-methylpyridin-3-yl)piperidin-3-yl]amino}methyl)-1,4-dihydroquinolin-4-one.

11. The compound according to any one of items 1 to 10, wherein the compound according to formula (I) is preferably selected from the group consisting of 3-({[(2-methoxypyridin-4-yl)methyl][(3S)-1-(pyridin-3-yl)piperidin-3-yl]amino}methyl)-1-methyl-1,4-dihydroquinolin-4-one, 1-methyl-3-({[(2-methylpyridin-4-yl)methyl][(3S)-1-(pyridin-3-yl)piperidin-3-yl]amino}methyl)-1,4-dihydroquinolin-4-one, 1-methyl-3-({[(3S)-1-(6-methylpyridin-3-yl)piperidin-3-yl][(2-methylpyridin-4-yl)methyl]amino}methyl)-1,4-dihydroquinolin-4-one, 1-cyclopropyl-6-fluoro-3-({[(2-methoxypyridin-4-yl)methyl][(3S)-1-(pyridin-3-yl)piperidin-3-yl]amino}methyl)-7-(4-methylpiperazin-1-yl)-1,4-dihydroquinolin-4-one, 1-cyclopropyl-6-fluoro-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-methoxypyridin-4-yl)methyl][(3S)-1-(pyridin-3-yl)piperidin-3-yl]amino}methyl)-1,4-dihydroquinolin-4-one, 1-cyclopropyl-6,7-difluoro-3-({[(2-methylpyridin-4-yl)methyl][(3S)-1-(pyridin-3-yl)piperidin-3-yl]amino}methyl)-1,4-dihydroquinolin-4-one, 1-methyl-7-(4-methylpiperazin-1-yl)-3-({[(2-methylpyridin-4-yl)methyl][(3S)-1-(pyridin-3-yl)piperidin-3-yl]amino}methyl)-1,4-dihydroquinolin-4-one, 7-bromo-1-methyl-3-({[(2-methylpyridin-4-yl)methyl][(3S)-1-(pyridin-3-yl)piperidin-3-yl]amino}methyl)-1,4-dihydroquinolin-4-one, 7-chloro-6-fluoro-1-methyl-3-({[(2-methylpyridin-4-yl)methyl][(3S)-1-(pyridin-3-yl)piperidin-3-yl]amino}methyl)-1, 4-dihydroquinolin-4-one, 3-({[(3S,5S)-5-fluoro-1-(pyridin-3-yl)piperidin-3-yl][(2-methylpyridin-4-yl)methyl]amino}methyl)-1-methyl-1,4-dihydroquinolin-4-one, 7-chloro-1-cyclopropyl-6-fluoro-3-({[(2-methoxypyridin-4-yl)methyl][(3S)-1-(pyridin-3-yl)piperidin-3-yl]amino}methyl)-1,4-dihydroquinolin-4-one and 1-cyclopropyl-6,7-difluoro-3-({[(2-methoxypyridin-4-yl)methyl][(3S)-1-(6-methylpyridin-3-yl)piperidin-3-yl]amino}methyl)-1,4-dihydroquinolin-4-one.

12. A pharmaceutical composition comprising a pharmaceutically effective amount of the compound according to any one of items 1 to 11 and optionally a pharmaceutically acceptable carrier, diluent or excipient.

13. A compound according to any one of items 1 to 11 or a pharmaceutical composition according to item 12 for use in medicine.

14. A compound according to any one of items 1 to 11 or a pharmaceutical compositions according to item 12 for use in the treatment of a disease selected from the group consisting of cancer, pre-cancerous syndromes, and infectious diseases; or for use in an immunogenic composition or as vaccine adjuvant.

15. A compound according to any one of items 1 to 11 or a pharmaceutical composition according to item 12 for use in the treatment of a disease selected from the group consisting of inflammatory diseases, allergic diseases, and autoimmune diseases.

The invention claimed is:

1. A compound which is
3-({[(2-methoxypyridin-4-yl)methyl][(3S)-1-(pyridin-3-yl) piperidin-3-yl]amino}methyl)-1-methyl-1,4-dihydroquinolin-4-one,
1-methyl-3-({[(2-methylpyridin-4-yl)methyl][1-(pyridin-3-yl) piperidin-3-yl]amino}methyl)-1,4-dihydroquinolin-4-one,
1-methyl-3-({[(2-methylpyridin-4-yl)methyl][(3S)-1-(pyridin-3-yl) piperidin-3-yl]amino}methyl)-1,4-dihydroquinolin-4-one,
3-({[(2-methoxypyridin-4-yl)methyl][(3S)-1-(pyridin-3-yl) piperidin-3-yl]amino}methyl)-1,4-dihydroquinolin-4-one,
1-methyl-3-({[(3S)-1-(6-methylpyridin-3-yl) piperidin-3-yl][(2-methylpyridin-4-yl)methyl]amino}methyl)-1,4-dihydroquinolin-4-one,
1-cyclopropyl-6,7-difluoro-3-({[(2-methoxypyridin-4-yl)methyl][(3S)-1-(pyridin-3, yl) piperidin-3-yl]amino}methyl)-1,4-dihydroquinolin-4-one,
7-bromo-1-methyl-3-({[(2-methylpyridin-4-yl)methyl][(3S)-1-(pyridin-3-yl) piperidin-3-yl]amino}methyl)-1, 4-dihydroquinolin-4-one,
7-chloro-6-fluoro-1-methyl-3-({[(2-methylpyridin-4-yl)methyl][(3S)-1-(pyridin-3-yl) piperidin-3-yl]amino}methyl)-1,4-dihydroquinolin-4-one,
3-({[(3S,5S)-5-fluoro-1-(pyridin-3-yl) piperidin-3-yl][(2-methylpyridin-4-yl)methyl]amino}methyl)-1-methyl-1,4-dihydroquinolin-4-one,
7-chloro-1-cyclopropyl-6-fluoro-3-({[(2-methoxypyridin-4-yl)methyl][(3S)-1-(pyridin-3-yl) piperidin-3-yl]amino}methyl)-1,4-dihydroquinolin-4-one,
1-cyclopropyl-6,7-difluoro-3-({[(2-methoxypyridin-4-yl)methyl][(3S)-1-(6-methylpyridin-3-yl) piperidin-3-yl]amino}methyl)-1,4-dihydroquinolin-4-one,
7-chloro-1-cyclopropyl-6-fluoro-3-({(2-methylpyridin-4-yl)methyl][(3S)-1-(pyridin-3-yl)piperidin-3-yl]amino}methyl)-1,4-dihydroquinolin-4-one,
3-({[(2-methylpyridin-4-yl)methyl][(3S)-1-(pyridin-3-yl) piperidin-3-yl]amino}methyl)-1,4-dihydroquinolin-4-one,
7-bromo-1-methyl-3-({[(3S)-1-(6-methylpyridin-3-yl) piperidin-3-yl][(2-methylpyridin-4-yl)methyl]amino}methyl)-1,4-dihydroquinolin-4-one,
1-methyl-3-({[(3S)-1-(pyridin-3-yl) piperidin-3-yl][(pyridin-4-yl)methyl]amino}methyl)-1,4-dihydroquinolin-4-one,
7-chloro-1-cyclopropyl-6-fluoro-3-({[(3S)-1-(6-methylpyridin-3-yl) piperidin-3-yl][(2-methylpyridin-4-yl)methyl]amino}methyl)-1,4-dihydroquinolin-4-one,
7-chloro-1-cyclopropyl-6-fluoro-3-({[(3S)-1-(6-methylpyridin-3-yl) piperidin-3-yl][(2-methylpyridin-4-yl)methyl]amino}methyl)-1,4-dihydro-1,8-naphthyridin-4-one,
1-cyclopropyl-6-fluoro-7-methoxy-3-({[(3S)-1-(6-methylpyridin-3-yl) piperidin-3-yl][(2-methylpyridin-4-yl)methyl]amino}methyl)-1,4-dihydro-1,8-naphthyridin-4-one, 1-cyclopropyl-6-fluoro-7-methoxy-3-({[(3S)-1-(6-methylpyridin-3-yl) piperidin-3-yl][(2-methylpyridin-4-yl)methyl]amino}methyl)-1,4-dihydroquinolin-4-one, 3-({[(3S)-1-(6-methylpyridin-3-yl) piperidin-3-yl][(2-methylpyridin-4-yl)methyl]amino}methyl)-1-(oxetan-3-yl)-1,4-dihydroquinolin-4-one, 7-chloro-1-cyclopropyl-3-({[(3S)-1-(6-methylpyridin-3-yl) piperidin-3-yl][(2-methylpyridin-4-yl)methyl]amino}methyl)-1,4-dihydro-1,6-naphthyridin-4-one, 7-(cyclohex-1-en-1-yl)-1-cyclopropyl-6-fluoro-3-({[(3S)-1-(6-methylpyridin-3-yl) piperidin-3-yl][(2-methylpyridin-4-yl)methyl]amino}methyl)-1,4-dihydroquinolin-4-one, 3-({[(3S)-1-(6-methylpyridin-3-yl) piperidin-3-yl][(2-methylpyridin-4-yl)methyl]amino}methyl)-1,4-dihydroquinolin-4-one, 1-cyclopropyl-6-fluoro-7-hydroxy-3-({[(3S)-1-(6-methylpyridin-3-yl) piperidin-3-yl][(2-methylpyridin-4-yl)methyl]amino}methyl)-1,4-dihydroquinolin-4-one, 8-bromo-1-methyl-3-({[(3S)-1-(6-methylpyridin-3-yl) piperidin-3-yl][(2-methylpyridin-4-yl)methyl]amino}methyl)-1,4-dihydroquinolin-4-one, 7-chloro-6-fluoro-3-({[(3S)-1-(6-methylpyridin-3-yl) piperidin-3-yl][(2-methylpyridin-4-yl)methyl]amino}methyl)-1-(propan-2-yl)-1,4-dihydro-1,8-naphthyridin-4-one, 6-fluoro-7-methoxy-3-({[(3S)-1-(6-methylpyridin-3-yl) piperidin-3-yl][(2-methylpyridin-4-yl)methyl]amino}methyl)-1-(propan-2-yl)-1,4-dihydro-1,8-naphthyridin-4-one, or 1-cyclopropyl-3-({[(3S)-1-(6-methylpyridin-3-yl) piperidin-3-yl][(2-methylpyridin-4-yl)methyl]amino}methyl)-7-(morpholin-3-yl)-1,4-dihydroquinolin-4-one;

or a salt, stereoisomer, or N-oxide thereof.

2. The compound according to claim 1, wherein the compound is selected from the group consisting of 3-({[(3S)-1-(6-methylpyridin-3-yl) piperidin-3-yl][(2-methylpyridin-4-yl)methyl]amino}methyl)-1,4-dihydroquinolin-4-one, 1-cyclopropyl-6-fluoro-7-hydroxy-3-({[(3S)-1-(6-methylpyridin-3-yl) piperidin-3-yl][(2-methylpyridin-4-yl)methyl]amino}methyl)-1,4-dihydroquinolin-4-one, 6-fluoro-7-methoxy-3-({[(3S)-1-(6-methylpyridin-3-yl) piperidin-3-yl][(2-methylpyridin-4-yl)methyl]amino}methyl)-1-(propan-2-yl)-1,4-dihydro-1,8-naphthyridin-4-one, and 1-cyclopropyl-3-({[(3S)-1-(6-methylpyridin-3-yl) piperidin-3-yl][(2-methylpyridin-4-yl)methyl]amino}methyl)-7-(morpholin-3-yl)-1,4-dihydroquinolin-4-one, or a salt, stereoisomer, tautomer, or N-oxide thereof.

3. A pharmaceutical composition comprising a pharmaceutically effective amount of the compound according to claim 1, or a salt, stereoisomer, or N-oxide thereof, and optionally a pharmaceutically acceptable carrier, diluent or excipient.

4. A method of treating a cancerous or pre-cancerous solid tumor or a bacterial or viral infection in a patient in need thereof, comprising administering to said patient a pharmaceutically effective amount of a compound according to claim 1 or a salt, stereoisomer, or N-oxide thereof.

5. The method of claim 4, wherein the cancerous or pre-cancerous solid tumor is selected from the group consisting of prostate cancer, renal carcinoma, melanoma, pancreatic cancer, cervical cancer, ovarian cancer, colon cancer, head and neck cancer, lung cancer, fibrosarcoma, and breast cancer.

6. A method of treating a disease selected from the group consisting of inflammatory diseases, allergic diseases, and autoimmune diseases in a patient in need thereof, comprising administering to said patient a pharmaceutically effective amount of a compound according to claim 1 or a salt, stereoisomer, or N-oxide thereof.

7. A method of treating a cancerous or pre-cancerous solid tumor or a bacterial or viral infection in a patient in need thereof, comprising administering to said patient a pharmaceutically effective amount of a pharmaceutical composition according to claim 3.

8. The method of claim 7, wherein the cancerous or pre-cancerous solid tumor is selected from the group consisting of prostate cancer, renal carcinoma, melanoma, pancreatic cancer, cervical cancer, ovarian cancer, colon cancer, head and neck cancer, lung cancer, fibrosarcoma, and breast cancer.

9. A method of treating a disease selected from the group consisting of inflammatory diseases, allergic diseases, and autoimmune diseases in a patient in need thereof, comprising administering to said patient a pharmaceutically effective amount of a pharmaceutical composition according to claim 3.

10. A method of enhancing response to an immunogenic composition or vaccine composition in a patient in need thereof, comprising administering to said patient a pharmaceutically effective amount of a compound according to claim 1 or a salt, stereoisomer, or N-oxide thereof, together with said immunogenic composition or vaccine composition.

11. A method of enhancing response to an immunogenic composition or vaccine composition in a patient in need thereof, comprising administering to said patient a pharmaceutically effective amount of a pharmaceutical composition according to claim 3, together with said immunogenic composition or vaccine composition.

* * * * *